(12) United States Patent
Blouse et al.

(10) Patent No.: US 12,116,606 B2
(45) Date of Patent: Oct. 15, 2024

(54) COMPLEMENT FACTOR I-RELATED COMPOSITIONS AND METHODS

(71) Applicant: Vertex Pharmaceuticals Incorporated, Boston, MA (US)

(72) Inventors: Grant E. Blouse, Burlingame, CA (US); Brajesh Kumar, Fremont, CA (US); Tom Knudsen, Burlingame, CA (US); Jan Kristian Jensen, Randers (DK); Emil Oldenburg, Aarhus (DK); Christine René Schar, Randers (DK); Matthew John Traylor, Boulder, CO (US); Eric Steven Furfine, Lincoln, MA (US); Jeffrey Charles Way, Cambridge, MA (US); Agnieszka Jendroszek, Risskov (DK); Arzu Sandikci, Berkeley, CA (US); Jim McGuire, South San Francisco, CA (US); Shyam Rajan Iyer, Woodside, CA (US); Natacha Le Moan, South San Francisco, CA (US)

(73) Assignee: Vertex Pharmaceuticals Incorporated, Boston, MA (US)

(*) Notice: Subject to any disclaimer, the term of this patent is extended or adjusted under 35 U.S.C. 154(b) by 377 days.

(21) Appl. No.: 17/347,442

(22) Filed: Jun. 14, 2021

(65) Prior Publication Data
US 2023/0038638 A1    Feb. 9, 2023

Related U.S. Application Data

(60) Provisional application No. 63/179,160, filed on Apr. 23, 2021, provisional application No. 63/124,698, filed on Dec. 11, 2020, provisional application No. 63/122,437, filed on Dec. 7, 2020, provisional application No. 63/038,874, filed on Jun. 14, 2020.

(51) Int. Cl.
*C12N 9/64* (2006.01)
*A61K 38/00* (2006.01)

(52) U.S. Cl.
CPC ............ *C12N 9/6424* (2013.01); *A61K 38/00* (2013.01); *C07K 2319/31* (2013.01)

(58) Field of Classification Search
None
See application file for complete search history.

(56) References Cited

U.S. PATENT DOCUMENTS

| | | | |
|---|---|---|---|
| 4,883,784 A | 11/1989 | Kaneko | |
| 6,248,365 B1 | 6/2001 | Romisch et al. | |
| 8,765,915 B2 | 7/2014 | Weimer et al. | |
| 9,066,941 B2 | 6/2015 | Lachmann | |
| 9,295,713 B2 | 3/2016 | Smith et al. | |
| 9,573,984 B2 | 2/2017 | Garred et al. | |
| 9,649,357 B2 | 5/2017 | Smith et al. | |
| 9,782,460 B2 | 10/2017 | Lachmann | |
| 9,862,757 B2 | 1/2018 | Hu et al. | |
| 10,155,983 B2 | 12/2018 | Ero et al. | |
| 10,378,005 B2 | 8/2019 | Schmidt et al. | |
| 10,774,116 B2 | 9/2020 | Barlow et al. | |
| 10,940,186 B2 | 3/2021 | Lachmann | |
| 10,975,131 B2 | 4/2021 | Ram et al. | |
| 10,988,519 B2 | 4/2021 | Song et al. | |
| 11,007,254 B2 | 5/2021 | Tomlinson et al. | |
| 11,045,544 B2 | 6/2021 | Cummings et al. | |
| 11,136,380 B2 | 10/2021 | Patz, Jr. et al. | |
| 11,168,120 B2 | 11/2021 | Hageman | |
| 2004/0180046 A1 | 9/2004 | Himawan | |
| 2005/0175608 A1 | 8/2005 | Tamura et al. | |
| 2009/0042787 A1 | 2/2009 | Metzner et al. | |
| 2009/0298760 A1 | 12/2009 | Weimer et al. | |
| 2013/0078245 A1 | 3/2013 | Holers et al. | |
| 2015/0182588 A1 | 7/2015 | Kahvejian et al. | |
| 2016/0326231 A1 | 11/2016 | Hu et al. | |
| 2016/0333082 A1 | 11/2016 | Wiestner et al. | |
| 2017/0209549 A1 | 7/2017 | Holers et al. | |
| 2018/0021416 A1 | 1/2018 | Lachmann | |

(Continued)

FOREIGN PATENT DOCUMENTS

| | | |
|---|---|---|
| EP | 2 032 607 B2 | 2/2017 |
| EP | 3 262 066 B1 | 2/2018 |

(Continued)

OTHER PUBLICATIONS

Banda, N.K. et al. (2009). "Targeted inhibition of the complement alternative pathway with complement receptor 2 and factor H attenuates collagen antibody-induced arthritis in mice," J. Immunol. 183:5928-5937.

Buchberger, A. (2016). "The therapeutic utility of Factor I in the treatment of complement dependent pathophysiological processes," University of Leicester, Department of Infection, Immunity and Inflammation, Dissertation, 207 total pages.

(Continued)

*Primary Examiner* — Sudhakar Katakam
*Assistant Examiner* — Zachary J Miknis
(74) *Attorney, Agent, or Firm* — Cooley LLP

(57) ABSTRACT

Provided herein are Complement Factor I (CFI) variants that exhibit at least one improved characteristic relative to a wild type CFI. CFI variants of the disclosure can exhibit tunable specificity and activity. Also included are CFI-containing fusion constructs comprising at least one domain of CFI, for example, wild type full length CFI fused to human serum albumin. Also included are methods of making and using such CFI variants and fusion constructs. The CFI variants and fusion constructs provided herein may be useful for treating a disease or condition associated with dysregulation of the complement system or a deficiency of CFI.

20 Claims, 36 Drawing Sheets

Specification includes a Sequence Listing.

(56) References Cited

U.S. PATENT DOCUMENTS

| | | |
|---|---|---|
| 2018/0200346 A1 | 7/2018 | Ballance et al. |
| 2018/0271910 A1 | 9/2018 | Mata-Fink et al. |
| 2019/0071477 A1 | 3/2019 | Bao et al. |
| 2019/0202878 A1 | 7/2019 | Schmidt et al. |
| 2020/0031888 A1* | 1/2020 | Kavanagh ............ C07K 19/00 |
| 2020/0147240 A1 | 5/2020 | Lachmann et al. |
| 2020/0181249 A1 | 6/2020 | Curtis et al. |
| 2020/0270614 A1 | 8/2020 | Strapps et al. |
| 2020/0291427 A1 | 9/2020 | Strapps et al. |
| 2020/0325481 A1 | 10/2020 | Strapps et al. |

FOREIGN PATENT DOCUMENTS

| | | |
|---|---|---|
| EP | 1 984 503 B2 | 8/2018 |
| EP | 3 363 454 A2 | 8/2018 |
| EP | 3 454 910 A1 | 3/2019 |
| EP | 3 793 586 A1 | 11/2019 |
| EP | 3 615 559 A1 | 3/2020 |
| EP | 3 634 985 A1 | 4/2020 |
| EP | 3 697 920 A1 | 8/2020 |
| EP | 3 360 890 B1 | 10/2020 |
| EP | 3 359 561 B1 | 12/2020 |
| EP | 3 287 142 B1 | 8/2021 |
| WO | WO-94/00571 A1 | 1/1994 |
| WO | WO-99/44625 A1 | 9/1999 |
| WO | WO-2005/063815 A2 | 7/2005 |
| WO | WO-2005/063815 A3 | 7/2005 |
| WO | WO-2007/149567 A2 | 12/2007 |
| WO | WO-2007/149567 A3 | 12/2007 |
| WO | WO-2014099997 A1 * 6/2014 ........... A61K 31/713 | |
| WO | WO-2015/023972 A1 | 2/2015 |
| WO | WO-2018/170152 A1 | 9/2018 |
| WO | WO-2018/197873 A1 | 11/2018 |
| WO | WO-2018/224663 A1 | 12/2018 |
| WO | WO-2019/079718 A1 | 4/2019 |
| WO | WO-2019/218009 A1 | 11/2019 |
| WO | WO-2020/086735 A1 | 4/2020 |
| WO | WO-2020/102680 A1 | 5/2020 |
| WO | WO-2020/123662 A2 | 6/2020 |
| WO | WO-2020/123662 A3 | 6/2020 |
| WO | WO-2020/128516 A2 | 6/2020 |
| WO | WO-2020/128516 A3 | 6/2020 |
| WO | WO-2020/128535 A1 | 6/2020 |
| WO | WO-2021/011903 A1 | 1/2021 |
| WO | WO-2021/081348 A1 | 4/2021 |
| WO | WO-2021/081395 A1 | 4/2021 |
| WO | WO-2021/081401 A1 | 4/2021 |
| WO | WO-2021/257480 A2 | 12/2021 |
| WO | WO-2021/257480 A3 | 12/2021 |
| WO | WO-2021/260394 A1 | 12/2021 |
| WO | WO-2022/003357 A1 | 1/2022 |
| WO | WO-2022/254182 A1 | 12/2022 |
| WO | WO-2023/079297 A1 | 5/2023 |
| WO | WO-2023/079301 A1 | 5/2023 |

OTHER PUBLICATIONS

Hebecker, M. et al. (2013). "An Engineered Construct Combining Complement Regulatory and Surface-Recognition Domains Represents a Minimal-Size Functional Factor H," J. Immunol. 191:912-921.

International Search Report mailed on Jan. 17, 2022, for PCT Application No. PCT/US2021/037278, filed on Jun. 14, 2021, 7 pages.

International Search Report mailed on Oct. 19, 2018, for PCT Application No. PCT/EP2018/065199, filed on Jun. 8, 2018, 5 pages.

International Search Report mailed on Jun. 16, 2020, for PCT Application No. PCT/US2019/065741, filed on Dec. 11, 2019, 7 pages.

International Search Report mailed on Jul. 3, 2018, for PCT Application No. PCT/US2018/022471, filed on Mar. 14, 2018, 6 pages.

International Search Report mailed on Apr. 20, 2020, for PCT Application No. PCT/GB2019/053698, filed on Dec. 23, 2019, 5 pages.

Lachmann, P.J. (2019). "The story of complement factor I," Immunobiology 224:511-517.

Nilsson, S.C. et al. (2010). "Analysis of Binding Sites on Complement Factor I That Are Required for Its Activity," 285:6235-6245.

Renner, B. et al. (2011). "Binding of factor H to tubular epithelial cells limits interstitial complement activation in ischemic injury," Kidney international 80:165-173.

Rohrer, B. et al. (2012). "Systemic human CR2-targeted complement alternative pathway inhibitor ameliorates mouse laser-induced choroidal neovascularization," J. Ocul. Pharmacol. Ther. 28:402-409.

Roversi, P. et al. (2011). "Structural basis for complement factor I control and its disease-associated sequence polymorphisms," PNAS 108:12839-12844.

Ruseva, M.M. et al. (2016). "Efficacy of Targeted Complement Inhibition in Experimental C3 Glomerulopathy," J. Am. Soc. Nephrol. 27:405-416.

Sanchez-Gallego, J.I. et al. (2012). "Analysis of binding sites on complement factor I using artificial N-Linked glycosylation," J. Biol. Chem. 287:13572-13583.

Takeda, K. et al. (2012). "The critical role of complement alternative pathway regulator factor H in allergen-induced airway hyperresponsiveness and inflammation," J. Immunol. 188:661-667.

Written Opinion of the International Searching Authority mailed on Jan. 17, 2022, for PCT Application No. PCT/US2021/037278, filed on Jun. 14, 2021, 12 pages.

Written Opinion of the International Searching Authority mailed on Oct. 19, 2018, for PCT Application No. PCT/EP2018/065199, filed on Jun. 8, 2018, 7 pages.

Written Opinion of the International Searching Authority mailed on Apr. 20, 2020, for PCT Application No. PCT/GB2019/053698, filed on Dec. 23, 2019, 6 pages.

Written Opinion of the International Searching Authority mailed on Jul. 3, 2018, for PCT Application No. PCT/US2018/022471, filed on Mar. 14, 2018, 5 pages.

Written Opinion of the International Searching Authority mailed on Jun. 16, 2020, for PCT Application No. PCT/US2019/065741, filed on Dec. 11, 2019, 11 pages.

Nilsen, J. et al. (2020). "An intact C-terminal end of albumin is required for its long half-life in humans," Comm. Biol. 3:181, 11 pages.

* cited by examiner

COMPLEMENT FACTOR I-RELATED COMPOSITIONS AND METHODS

CROSS REFERENCE TO RELATED APPLICATION

This application claims priority to U.S. Provisional Application No. 63/038,874 filed on Jun. 14, 2020, U.S. Provisional Application No. 63/122,437 filed on Dec. 7, 2020, U.S. Provisional Application No. 63/124,698 filed on Dec. 11, 2020, and U.S. Provisional Application No. 63/179,160 filed on Apr. 23, 2021, the contents of which are incorporated herein by reference in their entireties.

REFERENCE TO SEQUENCE LISTING

An electronic version of the Sequence Listing is filed herewith, the contents of which are incorporated by reference in their entirety. The electronic file was created on Jun. 14, 2021, is 92 kilobytes in size, and is titled CTBI_001_04US_SeqList_ST25.txt.

BACKGROUND

The complement system includes the classical, lectin and alternative pathways, and is tightly controlled by a number of regulators. Complement Factor I (CFI) is one such regulator, and acts to regulate the complement system by cleaving C4b and C3b proteins, thereby inactivating these proteins. Such cleavage results in inhibition of the classical, lectin and alternative pathways, respectively, thus ultimately preventing the assembly of the C3 and C5 convertase enzymes. CFI is encoded as a proenzyme and is then activated by proteolytic cleavage into a heterodimeric glycoprotein having a heavy chain and a light chain that are connected by a disulfide linkage. The light chain (also referred to as the B chain) comprises the serine protease domain (SPD) responsible for the cleavage of C3b and C4b, and contains a catalytic triad (His362, Asp411, and Ser507) within a region referred to as the active site. The heavy chain (also referred to as the A chain) comprises four domains: the FI membrane attack complex (FIMAC) domain, the scavenger receptor cysteine-rich domain SRCR (also called the CD5 domain) domain, the low density lipoprotein receptor 1 domain (LDLr1), and the low density lipoprotein receptor 2 domain (LDLr2). CFI is processed into its active form post-translationally by the addition of six Asn-linked glycans and proteolytic activation by furin, thereby excising a RRKR linker to generate the two chain mature protein.

With respect to its ability to cleave C3b or C4b, CFI is proteolytically active when it forms ternary complexes with its cofactors; Factor H (FH) or Complement Receptor 1 (CR1, also called CD35) and its physiological substrates, C3b and C4b. FH is an example of a soluble member of the group of proteins called regulators of complement activation (RCA). The formation of the complex made by CFI and FH and subsequent cleavage of C3b together act to regulate the alternative pathway of the complement system. Continuous regulation of C3b levels by CFI acts to maintain the balance between the classical and alternative pathways. For instance, removal of CFI has been shown to cause an immediate activation, resulting in over-activity, of the alternative pathway. CR1 is an example of a monomeric single-pass type I membrane glycoprotein that is a member of the group of proteins called regulators of complement activation (RCA). Formation of the complex made between CFI and CR1 and the subsequent cleavage of C3b and C4b act to regulate the alternative or the classical and lectin pathways, respectively.

Dysregulated CFI, mutated and dysfunctional CFI, or CFI deficiency have been implicated in diseases involving the complement system, and needed are methods for modulating or inhibiting particular points of regulation within the complement system. Provided here are compositions and methods to address the dysfunction and/or dysregulation in the complement system.

SUMMARY

In one aspect, the disclosure provides a complement factor I (CFI) variant comprising at least one modification with respect to a wild type CFI, wherein the CFI variant is capable of modulating the complement system, and wherein the CFI variant has at least one improved characteristic as compared to the wild type CFI. In some embodiments, the improved characteristic is selected from an increase in half-life or bioavailability, or increase or decrease in any one or more of activity, substrate specificity, potency, substrate affinity, cofactor affinity and catalytic capability In some embodiments, the improved characteristic is an increase in activity. In some embodiments, the improved characteristic is a change in substrate specificity.

In some embodiments, the increase in activity comprises an increase in the cleavage of C3b and/or C4b, as compared to wild type CFI or a fusion construct comprising wild type CFI. In some embodiments, the increase in activity comprises an increase in the cleavage of C3b, and does not comprise an increase in the cleavage of C4b. In some embodiments, the increase in the cleavage of C3b is increased by at least or about 1.5-fold, at least or about 2-fold, at least or about 3-fold, at least or about 4-fold, at least or about 5-fold, at least or about 10-fold, at least or about 20-fold, at least or about 30-fold, at least or about 40-fold, at least or about 50-fold, at least or about 100-fold, at least or about 150-fold, at least or about 500-fold, or at least or about 1000-fold as compared to the wild type CFI or a fusion construct comprising wild type CFI.

In some embodiments, the increase in activity comprises an increase in the cleavage of C4b as compared to the wild type CFI or a fusion construct comprising wild type CFI, and does not comprise an increase in the cleavage of C3b. In some embodiments, the increase in the cleavage of C4b is increased by at least or about 1.5-fold, at least or about 2-fold, at least or about 3-fold, at least or about 4-fold, at least or about 5-fold, at least or about 10-fold, at least or about 20-fold, at least or about 30-fold, at least or about 40-fold, at least or about 50-fold, at least or about 100-fold, at least or about 150-fold, at least or about 500-fold, or at least or about 1000-fold as compared to the wild type CFI or a fusion construct comprising wild type CFI.

In some embodiments, the increase in the cleavage of C3b and C4b each is increased by at least or about at least or about 1.5-fold, at least or about 2-fold, at least or about 3-fold, at least or about 4-fold, at least or about 5-fold, at least or about 10-fold, at least or about 20-fold, at least or about 30-fold, at least or about 40-fold, at least or about 50-fold, at least or about 100-fold, at least or about 150-fold, at least or about 500-fold, or at least or about 1000-fold as compared to the wild type CFI or a fusion construct comprising wild type CFI.

In some embodiments, the increase in activity comprises an increase in the generation of iC3b. In some embodiments, an increase in activity comprises an increase in the generation of C3dg and/or C3c from iC3b.

In some embodiments, the increase in activity comprises a reduction in the levels of C3b Δ-chain In some embodiments, the increase in activity comprises an increase in the proteolysis of a peptide substrate. In some embodiments, an increase in activity comprises a reduction in the levels or function of membrane attack complex (MAC). In some embodiments, the increase in activity results in a reduction of an amplification of the complement system. In some embodiments, the improved characteristic is a decrease in activity for C3b and/or C4b.

In some embodiments, the improved characteristic is an increase in specificity for a substrate. In some embodiments, the increase in specificity comprises an increase in the specificity for C3b or C4b, as compared to wild type CFI or a fusion construct comprising wild type CFI. In some embodiments, the increase in specificity comprises an increase in the specificity for C3b and/or C4b, as compared to wild type CFI or a fusion construct comprising wild type CFI. In some embodiments, the increase in specificity comprises an increase in the specificity for C3b, as compared to wild type CFI or a fusion construct comprising wild type CFI.

In some embodiments, the increase in specificity comprises an increase in the specificity for C3b, as compared to wild type CFI or a fusion construct comprising wild type CFI. In some embodiments, the increase in the specificity for C3b is increased by at least or about 1.5-fold, at least or about 2-fold, at least or about 3-fold, at least or about 4-fold, at least or about 5-fold, at least or about 10-fold, at least or about 20-fold, at least or about 30-fold, at least or about 40-fold, at least or about 50-fold, at least or about 100-fold, at least or about 150-fold, at least or about 500-fold, or at least or about 1000-fold as compared to the wild type CFI or a fusion construct comprising wild type CFI.

In some embodiments, the increase in specificity comprises an increase in the specificity for C4b, as compared to wild type CFI or a fusion construct comprising wild type CFI. In some embodiments, the increase in the specificity for C4b is increased by at least or about 1.5-fold, at least or about 2-fold, at least or about 3-fold, at least or about 4-fold, at least or about 5-fold, at least or about 10-fold, at least or about 20-fold, at least or about 30-fold, at least or about 40-fold, at least or about 50-fold, at least or about 100-fold, at least or about 150-fold, at least or about 500-fold, or at least or about 1000-fold as compared to the wild type CFI or a fusion construct comprising wild type CFI.

In some embodiments, the modification with respect to a wild type CFI comprises any one or more of: a deletion of one or more amino acid residues, a deletion of one or more CFI domains, a substitution of one or more amino acid residues, an insertion of one or more amino acid residues, an insertion of one or more CFI domains, and a swapping of one or more CFI domains. In some embodiments, the CFI variant comprises any one or more of the modifications presented in Tables 2-9 and 13.

In some embodiments, the CFI variant comprises any one or more domains of CFI selected from: the serine protease domain (SPD), the Factor I membrane attack complex (FIMAC) domain, the SRCR domain, the low density lipoprotein receptor 1 (LDLr1) domain, and the low density lipoprotein receptor 2 (LDLr2) domain.

In some embodiments, the CFI variant comprises at least one modification corresponding to a wild type human CFI. In some embodiments, the CFI variant comprises at least one modification corresponding to a wild type non-human CFI. In some embodiments, the CFI variant comprises at least one modification corresponding to a wild type CFI having the amino acid sequence set forth in SEQ ID NO: 1 or SEQ ID NO: 5.

In some embodiments, the CFI variant is a chimera comprising one or more domains from a human CFI, and wherein the human CFI further comprises a substitution of one or more amino acid residues for amino acid residues of a corresponding region from a non-human species CFI. In some embodiments, the non-human species is mouse. In some embodiments, the CFI variant is a chimera, and wherein the modification comprises the substitution of one or more amino acid residues of the CFI with amino acid residues from a corresponding region of a non-CFI serine protease. In some embodiments, the non-CFI serine protease is trypsin.

In some embodiments, the CFI variant comprises an A chain and a B chain, wherein the CFI variant comprises one or more modifications at the interface of the A chain and the B chain.

In some embodiments, the CFI variant comprises one or more of the modifications presented in Table 2. In some embodiments, the CFI variant comprises a modification at any one or more positions corresponding to positions K14, Y20, D26, F29, R35, E38, M220, K221, S250, L304, P305, K306, L307, and S308 in a CFI having the amino acid sequence set forth in SEQ ID NO: 5. In some embodiments, the CFI variant comprises a substitution in a 200 loop of the CFI (SEQ ID NO: 13) for a 200 loop of trypsin having amino acid residues NG, wherein the 200 loop occurs between positions corresponding to position 514 and position 520 in a CFI having the amino acid sequence set forth in SEQ ID NO: 5. In some embodiments, the CFI variant comprises one or more of the substitutions selected from K14A, Y20A, Y20F, D26A, F29A, R35A, E38A, M220A, K221Q, S250A, S250L, L304G, P305G, K306G, L307G, and S308G, wherein the positions correspond to positions in a CFI having the amino acid sequence set forth in SEQ ID NO: 5. In some embodiments, the CFI variant comprises one or more of the combination of substitutions M220A; K221Q, and L304G; P305G; K306G; L307G; S308G, wherein the positions correspond to positions in a CFI having the amino acid sequence set forth in SEQ ID NO: 5.

In some embodiments, the CFI variant comprises one or more modifications at a C-terminal region of the CFI variant. In some embodiments, the CFI variant comprises one or more of the modifications presented in Table 3. In some embodiments, the CFI variant comprises a modification at any one or more positions corresponding to positions T377, W381, P384, Y403, A405, G406, Y408, Q409, D425, G556, R557, P558, P559, I560, and Y563 in a CFI having the amino acid sequence set forth in SEQ ID NO: 5. In some embodiments, the CFI variant comprises one or more modifications at a C-terminal region is a deletion of amino acid residues (PFISQYNV, SEQ ID NO: 14) between positions corresponding to positions 558 to 565 in a CFI having the amino acid sequence set forth in SEQ ID NO: 5. In some embodiments, the CFI variant comprises amino acid residues (DGNK, SEQ ID NO: 15) between positions corresponding to positions 420 to 424 in a CFI having the amino acid sequence set forth in SEQ ID NO: 5 are substituted for a linker. In some embodiments, the CFI variant comprises one or more of the substitutions selected from T377G, W381A, P384A, P384G, Y403F, A405S, G406R, G406A, Y408L, Q409D, Q409H, D425A, D425K, D425R, G556A, G556S, R557A, R557K, P558G, P558L, P558S, F559L, I560V, and Y563H, and/or a deletion of P384, wherein the positions correspond to positions in a CFI having the amino acid sequence set forth in SEQ ID NO: 5.

In some embodiments, the CFI variant comprises one or more modifications at one or more N-linked glycosylation sites of the CFI. In some embodiments, the CFI variant comprises one or more modifications is a removal of an N-linked glycosylation site. In some embodiments, the CFI variant comprises one or more of the modifications presented in Table 4. In some embodiments, the CFI variant comprises a modification at any one or more positions corresponding to positions N52, N85, N159, N446, N476, and N518 in a CFI having the amino acid sequence set forth in SEQ ID NO: 5. In some embodiments, the CFI variant comprises one or more of the substitutions selected from N52Q, N85Q, N159Q, N446Q, N476Q, and N518Q, wherein the positions correspond to positions in a CFI having the amino acid sequence set forth in SEQ ID NO: 5. In some embodiments, the CFI variant comprises one or more of combination of substitutions selected from N52Q; N85Q; N159Q, N446Q; N476Q; N518Q, wherein the positions correspond to positions in a CFI having the amino acid sequence set forth in SEQ ID NO: 5.

In some embodiments, the CFI variant comprises one or more modifications in the SPD domain of the CFI. In some embodiments, the CFI variant comprises one or more of the modifications presented in Table 5. In some embodiments, the CFI variant comprises one or more modifications at any one or more of the autolysis loop, the 99 loop, the S1 pocket entrance, or the activation loop of SPD, or any one or more of the domains presented in FIG. 1. In some embodiments, the CFI variant comprises a modification at any one or more positions corresponding to positions K14, K312, R314, I322, V323, K326, R327, A328, K340, D341, G344, I345, T346, A361, L364, Y372, W381, P384, V390, N402, N404, G406, Y408, Q409, E416, K418, N422, D425, E457, K458, R456, E461, R462, F464, S465, Q467, W468, G469, T495, Y496, D497, S499, I500, A502, K504, D506, S507, E530, N531, E530, N531, G533, K534, P535, E536, and F537 in a CFI having the amino acid sequence set forth in SEQ ID NO: 5.

In some embodiments, the CFI variant comprises a substitution of an autolysis loop of the CFI (REKDNERVFS, SEQ ID NO: 9) for an autolysis loop of trypsin (NTASSGADYPDE, SEQ ID NO: 10), wherein the autolysis loop occurs between positions corresponding to position 456 and position 465 in a CFI having the amino acid sequence set forth in SEQ ID NO: 5. In some embodiments, the CFI variant comprises a substitution of an autolysis loop of the CFI (REKDNERVFS, SEQ ID NO: 9) for an autolysis loop of a mouse CFI (RGKDNQKVYS, SEQ ID NO: 11), wherein the autolysis loop occurs between positions corresponding to position 456 and position 465 in a CFI having the amino acid sequence set forth in SEQ ID NO: 5.

In some embodiments, the CFI variant comprises one or more of the substitutions selected from K14A, K312A, R314A, I322T, I322Y, I322V, V323I, V323G, V323A, K326A, R327A, R327P, R327N, A328C, K340G, D341A, G344R, G344K, G344Y, I345G, T346R, T346K, T346H, A361G, L364G, Y372G, W381K, W381G, P384A, P384G, V390G, N402E, N404G, G406D, G406E, G406F, G406H, G406I, G406K, G406L, G406M, G406N, G406P, G406Q, G406S, G406T, G406V, G406W, G406Y, Y408L, Y408F, Y408G, Y408P, Y408D, Y408A, Y408N, Y408T, Y408K, Y408R, Y408H, Y408I, Y408E, Y408M, Y408Q, Y408S, Y408W, Y408V, Q409G, E416A, K418G, N422K, D425A, D425K, D425R, D425G, R456A, R456N, E457G, E457A, E457D, E457F, E457H, E457I, E457K, E457L, E457M, E457N, E457P, E457Q, E457R, E457S, E457T, E457W, E457Y, E457V, K458A, E461Q, E461K, E461R, E461H, E461G, E461A, E461D, E461F, E461I, E461L E461M, E461N, E461P, E461S, E461T, E461W, E461Y, E461V, R462K, R462A, R462D, F464Y, S465G, Q467K, Q467R, W468C, G469L, T495F, Y496L, D497E, S499G, I500K, A502S, K504Q, K504E, K504R, K504A, K504G, K504L, K504P, K504H, K504D, K504F, K504I, K504M, K504N, K504S, K504T, K504V, K504W, K504Y, D506A, D506V, D506E, D506G, S507A, E530D, E530G, E530F, E530Y, N531G, N531A, E530D, E530G, E530F, E530Y, E530R, E530K, N531D, N531E, N531F, N531H, N531I, N531K, N531L, N531M, N531P, N531Q, N531R, N531S, N531T, N531V, N531W, N531Y, G533A, K534Q, P535A, P535K, E536N, E536A, F537K and F537R, wherein the positions correspond to positions in a CFI having the amino acid sequence set forth in SEQ ID NO: 5.

In some embodiments, the CFI variant comprises one or more of the combination substitutions selected from K326A; R327A, N531G; P535A, E457G; E461Q; R462K; F464Y, Y408L; N531G; E457G, Y408L; N531G; E457G; E461Q, Y408L; N531G; E457G; E461Q-R462K; F464Y, Y408L; N531G; P535A, K14A; D425R, E530D; N531G; G533A; K534Q; P535K; E536N, A502S; K504Q; F537K, T495F; Y496L; D497E; S499G; I500K, G533A; K534Q; P535K; E536N; F537K, T495F; Y496L; D497E; S499G; I500K; G533A; K534Q; P535K; E536N; F537K, Q467K; F537K, E530G; N531G; E530D; F537K, E457G; E461Q; E457G; E461G, Y408L; N531G; E457G; E461Q, N531G; E457G; E461Q, I322V; V323I, I322V; V323I; R327P, A328C; W468C, A328C; W468C; K326Y; R327N, Y408L; N531G; E461Q, Y408L; N531G; E457G; E461Q; R462K, Y408L; N531G; E457G; E461Q F464Y, Y408L; N531G; E457G; R462K; F464Y, Y408L; N531G; E461Q; R462K; F464Y, Y408L; E457G; E461Q; R462K; F464Y, E457G; N531G; E461Q; R462K; F464Y, Y408L; E457G; E461Q; R462K, N531G; E457G; E461Q; F464Y, E416A; D425R, Y408L; N531G; E457G; E461Q; R462K; F464Y; S507A, E457G; E461G, K312A; R314A, G469L; R456N; E457T; K458A, G469L; R456N; K458A, G469L; R456N; K458A; E461G, G469L R456N; K458A; E461G; F537K, G406D; Y408L, G406D; N531G, G406D; P535A, G406D Y408L; N531G, G406D; Y408L; P535A, G406D; N531G; P535A, G406D; Y408L; N531G; P535A, G406D; Y408L; N531G; P535A, K340G; I345G, L364G; Y372G, W381G; V390G, W381G; P384A; V390G, W381G; P384G; V390G, N404G; Q409G, K418G; D425G, T346R; K504E; E530R, T346K K504D; E530K, G344R; Y408L; N531G, G344K; Y408L; N531G, T346R; Y408L; N531G, T346K; Y408L; N531G; K504D; Y408L; N531G; K504E; Y408L; N531G, Y408L E530R; N531G, Y408L; E530K; N531G, T346R; Y408L; K504E; E530R; N531G, T346K Y408L; K504D; E530K; N531G, Y408L; S507A; N531G, Y408L; N531G; E457G; E461Q; R462K; F464Y; S507A, E457G; S507A, and N531G; P535A; S507A, wherein the positions correspond to positions in a CFI having the amino acid sequence set forth in SEQ ID NO: 5.

In some embodiments, the CFI variant comprises one or more modifications at an active site of the CFI. In some embodiments, the CFI variant comprises any modification presented in Table 6. In some embodiments, the CFI variant comprises a modification at a position corresponding to position S507 in a CFI having the amino acid sequence set forth in SEQ ID NO: 5. In some embodiments, the CFI variant comprises a substitution S507A, wherein the position corresponds to position S507 in a CFI having the amino acid sequence set forth in SEQ ID NO: 5.

In some embodiments, the CFI variant comprises an A chain and a B chain, wherein the CFI variant comprises a structural arrangement from N-terminus to C-terminus as (A chain)-(optional linker)-(B chain). In some embodiments, the CFI variant comprises an A chain and a B chain, wherein the CFI variant comprises a structural arrangement from N-terminus to C-terminus as (B chain)-(optional linker)-(A chain). In some embodiments, the CFI variant comprises modifications at one or more of C309 and C435, wherein the positions correspond to positions in a CFI having the amino acid sequence set forth in SEQ ID NO: 5.

In some embodiments, the CFI variant comprises substitutions C309S; C435S, wherein the positions correspond to positions in a CFI having the amino acid sequence set forth in SEQ ID NO: 5. In some embodiments, the B chain and the A chain are further linked by a disulfide bond. In some embodiments, the CFI variant comprises the amino acid sequence set forth in SEQ ID NO: 17 or SEQ ID NO: 18. In some embodiments, the B chain and the A chain are not further linked by a disulfide bond. In some embodiments, the CFI variant comprises the amino acid sequence set forth in SEQ ID NO: 19 or SEQ ID NO: 20.

In some embodiments, the CFI variant comprises one or more modifications presented in Table 7. In some embodiments, the CFI variant is more easily activated as compared to the wild type CFI. In some embodiments, the CFI variant comprises a modification at any one or more positions corresponding to positions I317, R318, R319, K320, and R321 in a CFI having the amino acid sequence set forth in SEQ ID NO: 5. In some embodiments, the CFI variant comprises one or more of the substitutions selected from I317D, R318D, R319D, K320D, and R321K, wherein the positions correspond to positions in a CFI having the amino acid sequence set forth in SEQ ID NO: 5.

In some embodiments, the CFI variant comprises substitutions I317D, R318D, R319D, K320D, and R321K, wherein the positions correspond to positions in a CFI having the amino acid sequence set forth in SEQ ID NO: 5.

In some embodiments, the CFI variant comprises two or more modifications described herein. In some embodiments, the CFI variant comprises any one or more of the modifications presented in Table 9. In some embodiments, the CFI variant comprises one or more of the combination of substitutions selected from Y408; N531G, E38A; D425R, Y20F; D425R, S250A; D425R, Y408F; N531G, Y408L; N531G; E457G; E461Q; R462K; F464Y, K14A; Y20F, K14A; E38A, K14A; S250A, K14A; D425A, Y20F; E38A, Y20F; S250A, Y20F; D425A, E38A; S250A, E38A; D425A, S250A; D425A, K14A; N531G; P535A, Y20F; N531G; P535A, E38A; N531G; P535A, S250A; N531G; P535A, D425A; N531G; P535A, Y20F; Y408L; N531G; E457G; E461Q; R462K; F464Y, E38A; Y408L; N531G; E457G; E461Q; R462K; F464Y, S250A; Y408L; N531G; E457G; E461Q; R462K; F464Y, D425R; Y408L; N531G; E457G; E461Q; R462K; F464Y, Y20F; E38A; S250A; D425A, Y20F; E38A; S250A; D425A; Y408L; N531G; E457G; E461Q; R462K; F464Y, Y20F; E38A; S250A; D425A; Y408L; N531G; E457G; E461Q, I317D; R318D; R319D; K320D; R321K; E457G; E461Q-R462K; F464Y, I317D; R318D; R319D; K320D; R321K; E457G; E461Q-R462K; F464Y, I317D; R318D; R319D; K320D; R321K; Y408L; N531G; E457G; E461Q; R462K; F464Y, K504D; Y408L; N531G; K504E; N531G; E457G; D425K, Y408F; N531G; Y408L; E457G; N531G; D425K, Y408L; E457G; P535G; D425K, Y408L; E457G; N531G; K534Q, Y408L; N531G, R462K; F464Y, and Y408L; P535G; D425K, wherein the positions correspond to positions in a CFI having the amino acid sequence set forth in SEQ ID NO: 5.

In some embodiments, the CFI variant comprises each one of the SPD, the FIMAC domain, the SRCR domain, the LDLr1 domain, and the LDLr2 domain, and any other domains presented in FIG. 1. In some embodiments, the CFI variant does not comprise all of the SPD, the FIMAC domain, the SRCR domain, the LDLr1 domain, and the LDLr2 domain. In some embodiments, the CFI variant comprises the SPD. In some embodiments, the CFI variant comprises the amino acid sequence set forth in SEQ ID NO: 12.

In some embodiments, the CFI variant comprises or consists of any one or more of the modifications presented in Table 13, wherein the positions correspond to positions in a CFI having the amino acid sequence set forth in SEQ ID NO: 5.

In some embodiments, the CFI variant is sialylated. In some embodiments, the CFI variant is further sialylated as compared to a wild type CFI.

In some embodiments, the CFI variant is in an activated form. In some embodiments, the CFI variant is activated by furin or variant thereof. In some embodiments, the CFI variant is activated by furin or variant thereof in vitro. In some embodiments, the CFI variant is activated by furin or variant thereof during recombinant production in a host cell. In some embodiments, the activation by furin or variant thereof during production in a host cell is by overexpression of furin or a variant thereof. In some embodiments, the CFI variant is activated by furin or variant thereof after production and secretion by a host cell, optionally in the media.

In some embodiments, the CFI variant is a first component of a fusion construct comprising a first component and a second component, and the CFI variant is fused to the second component; the fusion construct may comprise further components. In some embodiments, the second component is a protein. In some embodiments, the second component is not a protein. In some embodiments, the second component is a half-life extender. In some embodiments, the half-life extender comprises peptide repeats.

In some embodiments, the second component is a half-life extender selected from albumin, PEG, a non-biodegradable polymer, a biodegradable polymer, and Fc. In some embodiments, the half-life extender is a modified albumin or albumin derivative. In some embodiments, the half-life extender is a wild type albumin. In some embodiments, the half-life extender is a human serum albumin, or a variant thereof.

In some embodiments, the CFI variant comprises an A chain and a B chain, and wherein the fusion construct comprises a structural arrangement from N-terminus to C-terminus, or C-terminus to N-terminus, as (Second Component)-(optional linker)-(A chain)-(optional linker)-(B chain). In some embodiments, the CFI variant comprises an A chain and a B chain, and wherein the fusion construct comprises a structural arrangement from N-terminus to C-terminus, or C-terminus to N-terminus, as (Second Component)-(optional linker)-(B chain)-(optional linker)-(A chain). In some embodiments, the fusion construct comprises or consists of the amino acid sequence set forth in SEQ ID NO: 21, or a sequence with at least 80% sequence identity thereto.

In some embodiments, the second component is at least one domain, or part of a domain of Factor H. In some embodiments, the at least one Factor H domain comprises any one or more of complement control protein (CCP)

domains 1-20 of Factor H. In some embodiments, the amino acid sequence of the at least one Factor H domain is, or is derived from, the sequence set forth in SEQ ID NO: 4. In some embodiments, the at least one Factor H domain comprises each of the CCP domains 1-20 of Factor H. In some embodiments, the at least one Factor H domain comprises CCP1, CCP 2, CCP3, and CCP4. In some embodiments, the at least one Factor H domain comprises CCP2, CCP3, and CCP4. In some embodiments, the at least one Factor H domain comprises CCP2 and CCP3. In some embodiments, the amino acid sequence of the at least one domain of Factor H is, or is derived from, the sequence set forth in SEQ ID NO: 8. In some embodiments, the at least one Factor H domain comprises CCP domains 1-4 and 19-20 of Factor H.

In some embodiments, the second component is at least one domain, or part of a domain of Complement Receptor 1 (CR1). In some embodiments, the at least one domain of CR1 is any one or more of CR1 CCP domains 15-17. In some embodiments, the second component comprises at least one domain, or part of a domain of a Complement Receptor I (CRI) and at least one domain, or part of a domain of Factor H.

In some embodiments, the fusion construct further comprises a third component. In some embodiments, the third component is a protein. In some embodiments, the third component is not a protein.

In some embodiments, the CFI variant comprises a third component, wherein the third component is a half-life extender, optionally selected from selected from albumin, PEG, a non-biodegradable polymer, a biodegradable polymer, and Fc. In some embodiments, the half-life extender is a repetitive peptide sequence. In some embodiments, the CFI variant comprises at least one modification with respect to a wild type CFI, wherein the CFI variant is not activatable. In some embodiments, the CFI variant comprises a modification at a position corresponding to position R321 of a CFI having the amino acid sequence set forth in SEQ ID NO: 5. In some embodiments, the CFI variant comprises a substitution R321A, wherein the position corresponds to a position in a CFI having the amino acid sequence set forth in SEQ ID NO: 5.

In another aspect, the disclosure provides a fusion construct comprising a first component and a second component, wherein the first component comprises a wild type CFI or variant thereof (CFI variant), and wherein the second component comprises a half-life extender. In some embodiments, the first component comprises a wild type CFI, comprising an amino acid sequence set forth in SEQ ID NO: 5.

In some embodiments, the second component is albumin. In some embodiments, the second component is human serum albumin. In some embodiments, the second component comprises a human serum albumin comprising an amino acid sequence set forth in SEQ ID NO: 7.

In some embodiments, the fusion construct comprises an amino acid sequence set forth in SEQ ID NO: 21, or an amino acid sequence comprising at least 80% identity thereto. In some embodiments, the fusion construct consists of an amino acid sequence set forth in SEQ ID NO: 21. In some embodiments, the fusion construct comprises the amino acid sequence of SEQ ID NO: 5 and SEQ ID NO: 7.

In some embodiments, the fusion construct comprises the amino acid sequence of SEQ ID NO: 5 and SEQ ID NO: 7 wherein the fusion construct comprises a structural arrangement from N-terminus to C-terminus (SEQ ID NO: 7)-(optional linker)-(SEQ ID NO: 5). In some embodiments, the fusion construct comprises the amino acid sequence of SEQ ID NO: 5 and SEQ ID NO: 7 wherein the fusion construct comprises a structural arrangement from N-terminus to C-terminus (SEQ ID NO: 7)-(linker)-(SEQ ID NO: 5). In some embodiments, the fusion construct comprises the amino acid sequence of SEQ ID NO: 5, SEQ ID NO: 6, and SEQ ID NO: 7, wherein the fusion construct comprises a structural arrangement from N-terminus to C-terminus (SEQ ID NO: 7)-(SEQ ID NO: 6)-(SEQ ID NO: 5). In some embodiments, the fusion construct comprises the amino acid sequence of SEQ ID NO: 5 and SEQ ID NO: 7 wherein the fusion construct comprises a structural arrangement from N-terminus to C-terminus (SEQ ID NO: 5)-(optional linker)-(SEQ ID NO: 7). In some embodiments, the fusion construct comprises the amino acid sequence of SEQ ID NO: 5 and SEQ ID NO: 7 wherein the fusion construct comprises a structural arrangement from N-terminus to C-terminus (SEQ ID NO: 5)-(linker)-(SEQ ID NO: 7). In some embodiments, the fusion construct comprises the amino acid sequence of SEQ ID NO: 5, SEQ ID NO: 6, and SEQ ID NO: 7, wherein the fusion construct comprises a structural arrangement from N-terminus to C-terminus (SEQ ID NO: 5)-(SEQ ID NO: 6)-(SEQ ID NO: 7).

In some embodiments, the first component comprises a CFI variant. In some embodiments, the CFI variant is any CFI variant described herein. In some embodiments, the CFI variant comprises or consists of any one or more of the modifications presented in Table 13, wherein the positions correspond to positions in a CFI having the amino acid sequence set forth in SEQ ID NO: 5.

In some embodiments, the fusion construct has at least one improved characteristic as compared to a free wild type CFI (not part of a fusion construct), or as compared to a fusion construct comprising a wild type CFI. In some embodiments, the improved characteristic is selected from an increase in half-life or bioavailability, or an increase or decrease in any one or more of activity, substrate specificity, potency, substrate affinity, cofactor affinity and catalytic capability. In some embodiments, the improved characteristic is an increase in activity. In some embodiments, the increase in activity comprises an increase in the cleavage of C3b and/or C4b. In some embodiments, the improved characteristic is an increase in substrate specificity.

In some embodiments, the increase in activity comprises an increase in the cleavage of C3b as compared to a wild type CFI not part of a fusion construct, or compared to a fusion construct comprising a wild type CFI. In some embodiments, the increase in activity comprises an increase in the cleavage of C3b and does not comprise an increase in the cleavage of C4b, as compared to a wild type CFI not part of a fusion construct, or compared to a fusion construct comprising a wild type CFI. In some embodiments, the increase in the cleavage of C3b is increased at least or about 1.5-fold, at least or about 2-fold, at least or about 3-fold, at least or about 4-fold, at least or about 5-fold, at least or about 10-fold, at least or about 20-fold, at least or about 30-fold, at least or about 40-fold, at least or about 50-fold, at least or about 100-fold, at least or about 150-fold, at least or about 500-fold, or at least or about 1000-fold as compared to a wild type CFI not part of a fusion construct, or compared to a fusion construct comprising a wild type CFI.

In some embodiments, the increase in activity comprises an increase in the cleavage of C4b as compared to a wild type CFI not part of a fusion construct, or compared to a fusion construct comprising a wild type CFI., In some embodiments, the increase in activity comprises an increase in the cleavage of C4b as compared to a wild type CFI not part of a fusion construct, or compared to a fusion construct comprising a wild type CFI and does not comprise an increase in the cleavage of C3b. In some embodiments, the increase in the cleavage of C4b is increased at least or about 1.5-fold, at least or about 2-fold, at least or about 3-fold, at least or about 4-fold, at least or about 5-fold, at least or about 10-fold, at least or about 20-fold, at least or about 30-fold, at least or about 40-fold, at least or about 50-fold, at least or about 100-fold, at least or about 150-fold, at least or about 500-fold, or at least or about 1000-fold as compared to a wild type CFI not part of a fusion construct, or compared to a fusion construct comprising a wild type CFI.

In some embodiments, the increase in activity comprises an increase in generation of iC3b. In some embodiments, the increase in activity comprises an increase in the generation of C3dg from iC3b. In some embodiments, the increase in activity comprises a reduction in the levels of C3b α-chain In some embodiments, the increase in activity comprises an increase in the hydrolysis of a peptide substrate or proteolysis of a macromolecular protein substrate.

In some embodiments, the improved characteristic is a decrease in activity with respect to C4b or C3b substrates.

In some embodiments, the fusion construct has at least one improved characteristic as compared to a free wild type CFI, without the presence of Factor H and/or without the presence of CR1. In some embodiments, the fusion construct has at least one improved characteristic as compared to a free wild type CFI, and wherein the at least one improved characteristic is further improved by the presence of exogenous Factor H and/or exogenous CR1.

In one aspect, the disclosure provides a pharmaceutical composition comprising any one of the CFI variants described herein, or any one of the fusion constructs described herein, and optionally a pharmaceutically acceptable excipient.

In another aspect, the disclosure provides a method of modulating the complement system, comprising contacting a sample in vitro or contacting a tissue in vivo with any one of the CFI variants described herein, or any one of the fusion constructs described herein. In some embodiments, the method is in vitro. In some embodiments, the method is in vivo.

In some embodiments, the method results in the increase in the cleavage of C3b, C4b, generation of iC3b, generation of C3dg, and/or C4c. In some embodiments, the method results in a decrease in hemolysis. In some embodiments, the method results in the reduction or level of MAC. In some embodiments, the method results in the reduction of the amplification of the complement system. In some embodiments, the method results in the increase in the hydrolysis of a peptide substrate, or an increase in the proteolysis of a macromolecular protein substrate.

In another aspect, the disclosure provides a method of treating a non-ocular condition in a subject in need thereof, the method comprising administering to the subject a therapeutically effective amount of any one of the CFI variants described herein, or any one of the fusion constructs described herein, or any one of the pharmaceutical compositions described herein. Such treatment as contemplated herein includes both administration of a CFI variant of the disclosure or fusion construct of the disclosure, as well as administration of one or more nucleic acids encoding for a CFI variant of the disclosure or a fusion construct of the disclosure. Accordingly, provided herein are pharmaceutical compositions comprising the CFI variants of the disclosure, CFI fusion constructs of the disclosure, as well as pharmaceutical compositions comprising one or more nucleic acids encoding for CFI variants of the disclosure and encoding for fusion constructs of the disclosure.

In some embodiments, the non-ocular condition is characterized by a deficiency of CFI. In some embodiments, the non-ocular condition is characterized by dysregulation of the complement system.

In some embodiments, the non-ocular condition is a systemic acute indication. In some embodiments, the non-ocular condition is a systemic acute indication selected from the group consisting of: acute glomerulonephritis, acute renal injury, acute respiratory distress syndrome, bacterial meningitis, brain hemorrhage, burns, coronavirus infection, Epstein-Barr virus infection, hematopoietic stem cell transplantation, ischemia reperfusion injury, Lyme disease, myocardial infarction, organ transplantation, periodontitis, pneumonia, pre-eclampsia, schistosomiasis, sepsis, stroke, thromboembolism, ischemia-reperfusion injury and traumatic brain injury.

In some embodiments, the non-ocular condition is a systemic chronic indication. In some embodiments, the non-ocular condition is a systemic chronic indication selected from the group consisting of: Alzheimer's disease, anti-neutrophil cytoplasmic antibody (ANCA)-associated vasculitis, antiphospholipid syndrome, asthma, atherosclerosis, atypical hemolytic uremic syndrome (aHUS), autoimmune hemolytic anemia, bullous pemphigoid (BP), C3 glomerulopathy, chronic kidney failure, chronic obstructive pulmonary disease, Crohn's disease, diabetic neuropathy, generalized myasthenia gravis (gMG), Granulomatosis with Polyangiitis (GPA), Guillain-Barré Syndrome (GBS), hereditary angioedema (HAE), hidradenitis suppurativa (HS), IgA nephropathy, lupus nephritis (LN), membranous glomerulonephritis (MN), microscopic polyangiitis (MPA), motor neuron disease, multifocal motor neuropathy (MMN), multiple sclerosis (MS), non-insulin dependent diabetes, osteoarthritis, pancreatitis, Parkinson's disease, paroxysmal nocturnal hemoglobinuria, post-transplant lymphoproliferative disease, protein losing enteropathy, psoriasis, pyoderma gangrenosum, rheumatoid arthritis, schizophrenia (SZ), systemic lupus erythematosus (SLE), immune thrombocytopenia (ITP), ulcerative colitis, Amyotrophic lateral sclerosis (ALS), warm autoimmune hemolytic anemia (wAIHA), cold agglutinin disease (CAD), and Immune-Complex Membranoproliferative Glomerulonephritis (IC-MPGN), Lampert-Eaton myasthenic syndrome (LEMS), CHAPLE syndrome (CD55 deficiency), thrombotic microangiography (TMA), Huntington's disease and chronic inflammatory demyelinating polyneuropathy (CIDP).

In some embodiments, the non-ocular condition is non-oncological.

In some embodiments, the non-ocular condition is oncological. In some embodiments, the non-ocular condition is characterized by solid tumors, or by liquid tumors. In some embodiments, the non-ocular condition is characterized by solid tumors, and is selected from the group consisting of: colorectal tumors, hormone-refractory prostate cancer, melanoma, metastatic breast cancer, metastatic colorectal cancer, metastatic esophageal cancer, metastatic pancreas cancer, metastatic stomach cancer, nasopharyngeal carcinoma, non-small cell lung cancer, pancreas tumors, squamous cell carcinoma, and stomach tumors. In some embodiments, the non-ocular condition is characterized by liquid tumors, and is selected from the group consisting of: acute myelogenous leukemia, B-cell lymphoma, and Hodgkin's disease.

In some embodiments, the CFI variant, the fusion construct, or the pharmaceutical composition is administered to the subject subcutaneously, or intravenously. In some embodiments, the administration is a subcutaneous administration. In some embodiments, the subcutaneous administration is a daily, twice a week, or weekly, or every other week.

In another aspect, the disclosure provides a method of treating an ocular condition in a subject in need thereof, the method comprising administering to the subject a therapeutically effective amount of any one of the CFI variants described herein, or any one of the fusion constructs described herein, or any one of the pharmaceutical compositions described herein. Such treatment as contemplated herein includes both administration of a CFI variant of the disclosure or fusion construct of the disclosure, as well as administration of one or more nucleic acids encoding for a CFI variant of the disclosure or a fusion construct of the disclosure. Accordingly, provided herein are pharmaceutical compositions comprising the CFI variants of the disclosure, CFI fusion constructs of the disclosure, as well as pharmaceutical compositions comprising one or more nucleic acids encoding for CFI variants of the disclosure and encoding for fusion constructs of the disclosure.

In some embodiments, the ocular condition is characterized by a deficiency of CFI. In some embodiments, the ocular condition is characterized by dysregulation of the complement system. In some embodiments, the ocular condition is selected from the group consisting of: diabetic macular edema (DME), diabetic retinopathy, dry age-related macular degeneration (AMD), glaucoma, keratoconjunctivitis, neuromyelitis optica spectrum disorder (NMOSD), open angle glaucoma, polypoidal choroidal vasculopathy, Stargardt Disease, uveitis, and vitreoretinopathy. In some embodiments, the ocular condition is non-oncological.

In another aspect, the disclosure provides a cell comprising one or more nucleic acids encoding a wild type CFI or variant thereof, and comprising one or more a nucleic acids encoding furin.

In another aspect, the disclosure provides a method of generating a wild type CFI or a variant thereof, in an activated state, the method comprising producing the CFI or a variant thereof recombinantly in a cell comprising one or more nucleic acids encoding the CFI or variant thereof, and comprising one or more nucleic acids encoding furin.

DETAILED DESCRIPTION

The disclosure provides compositions and methods useful for modulating the signaling and amplification of the complement system. By providing complement factor I (CFI) variants and CFI-containing fusion constructs that are more or less active on one or more physiological substrates of CFI, and/or more stable than plasma-derived CFI, a modulation of the complement system is observed. Such modulation includes an increased amount of C3b cleavage and/or C4b cleavage, thus reducing complement activation, and reducing the amplification of the complement pathways. For example, some CFI variants can alter levels of regulators within the complement system. In some embodiments, the CFI variants and fusion constructs provided herein can act on the classical and lectin pathways of the complement system, on the alternative pathway of the complement system, or on both pathways. The disclosure also provides methods of making and using these variants and constructs, for example in treating a disease or condition associated with complement dysregulation, e.g. treating an overactive complement response.

I. Complement Factor I Proteins Useful for Modulation of the Complement System

A. Complement Factor I Variants

Provided herein are Complement Factor I variants (CFI), such variants comprising one or more modifications with respect to a wild type CFI, referred to herein as "CFI variants." As used herein, a "modification" to a wild type CFI includes: a deletion of one or more amino acid residues, a deletion of one or more domains, a substitution of one or more amino acid residues, an insertion (i.e. addition) of one or more amino acid residues, an insertion (i.e. addition) of one or more domains, an inversion of or one or more domains, and a substitution of one or more domains.

The CFI variants of the disclosure do not directly act on C3, for example, the variants of the disclosure do not directly cleave C3, do not directly inhibit C3, do not directly inhibit the activation of C3, and do not directly reduce the activation of C3.

As used herein, a wild type CFI refers to any naturally occurring full-length CFI that is not a disease-causing CFI, with or without a signal sequence, and which may be of any species.

In some embodiments, a wild type CFI is plasma-derived. In some embodiments, a wild type CFI is a human wild type CFI. In some embodiments, a wild type, human CFI having a signal sequence comprises the amino acid sequence set forth in SEQ ID NO: 1 (as shown in Table 1 below). In some embodiments, a wild type CFI is a human CFI. In some embodiments, a wild type, human CFI does not include a signal sequence. In some embodiments, a wild type CFI without a signal sequence comprises the amino acid sequence set forth in SEQ ID NO: 5 (as shown in Table 1 below).

Figure 1:
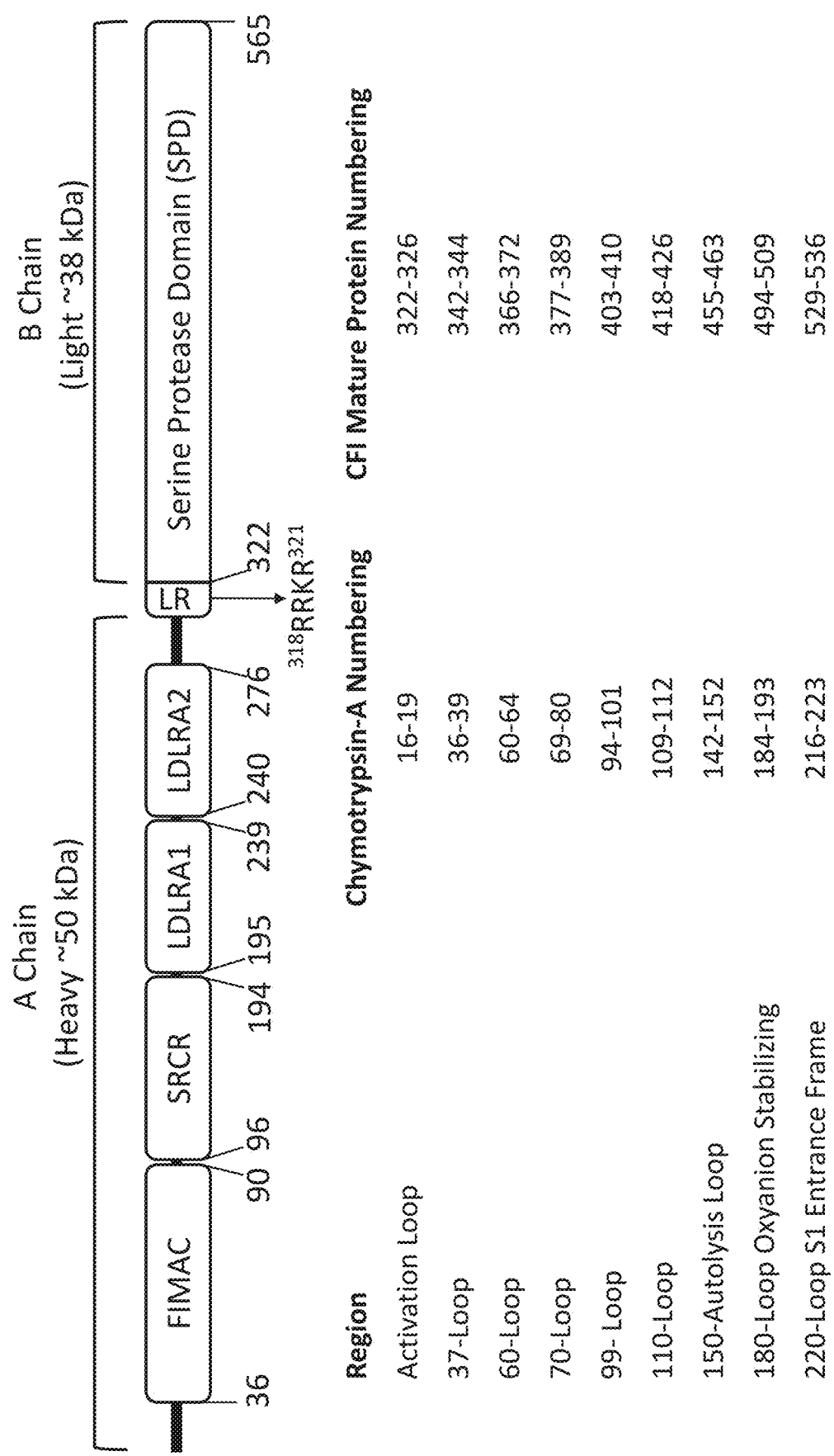
FIG. 1 is a schematic representation of the domains of a wild type Complement Factor I (CFI), showing a heavy chain and a light chain The heavy chain (A Chain) includes the FIMAC, SRCR, LDLr1, LDLr2 domains, and a linker. The light chain (B Chain) includes the serine protease domain. Regions of the light chain include the activation loop, 37-Loop, 60-Loop, 70-Loop, 99-Loop, 110-Loop, 150-Autolysis Loop, 190-Loop, Oxyanion Stabilizing, and/or 220-Loop S1 Entrance Frame.

A wild type CFI comprises a heavy chain and a light chain, which are also referred to as the A-chain and B-chain, respectively. FIG. 1 depicts a schematic diagram of CFI showing the two chains. The heavy chain (A-chain) has four domains: the FI membrane attack complex (FIMAC) domain (residues 36 to 90 of SEQ ID NO: 5), the SRCR domain is further composed of a plurality of scavenger receptor cysteine-rich (SRCR) domains, a low density lipoprotein 1 domain (LDLr1), and a low density lipoprotein 2 domain (LDLr2). The light chain (B-chain) consists of a serine protease domain (SPD). The interface between these chains is referred to as the A:B chain interface.

A CFI variant of the disclosure includes one or more of a deletion of one or more amino acid residues of a wild type CFI, a deletion of one or more CFI domains of a wild type CFI, a substitution of one or more amino acid residues of a wild type CFI, an insertion of one or more amino acid residues to a wild type CFI, an inversion of one or more CFI domains of a wild type CFI, and an insertion of one or more domains to a wild type CFI.

The CFI variants of the disclosure may be generated by the introduction of one or more modifications to a CFI base molecule, wherein the domains of the CFI base molecule correspond to those domains found in a wild type CFI, e.g. as put forth in FIG. 1. A CFI base molecule may therefore be a wild type CFI of any species, or a CFI base molecule may comprise only portions of a wild type CFI, having only some of the domains of a wild type CFI of any species (e.g. already a CFI variant). In some embodiments, a CFI base molecule is a wild type, mouse CFI. In some embodiments, a CFI base molecule is a wild type, human CFI. In some embodiments, a CFI base molecule is a wild type, non-human primate CFI. In some embodiments, a CFI base molecule comprises only some domains of a wild type, human CFI.

In some embodiments, the CFI variants provided herein modulate the activity of the complement system and have at least one improved characteristic as compared to a wild type CFI. Such improved characteristics include, but are not limited to an increase or decrease in any one or more of bioavailability, half-life, activity, potency, catalytic capability, cofactor affinity (e.g. affinity for Factor H and/or CR1), substrate specificity and substrate affinity (e.g. affinity for C3b and/or C4b). In some embodiments, the improved characteristic is increased half-life. In some embodiments, the improved characteristic is an increase in activity, discussed further in detail, in subsequent sections below. In other embodiments, the improved characteristic is a change in substrate specificity for C3b and/or C4b, allowing for tunability of the CFI variant.

Provided in Table 1 are exemplary base molecules that may be used for the generation of any of the CFI variants. The base molecules of Table 1 were used to generate the CFI variants disclosed herein, having any one or more of the modifications discussed further herein. The base molecules provided herein may be useful for modulation of the complement system without further modification, or may be useful for modulation of the complement system with further modification. For example, any one of the base molecules provided in Table 1 may be further modified to include one or more modifications, such as a deletion of one or more amino acid residues, a deletion of one or more CFI domains, a substitution of one or more amino acid residues, or an addition of one or more amino acid residues or CFI domains The base molecules of Table 1 may be further part of a fusion construct, further described below.

TABLE 1

| Base Molecules for Generation of CFI Variants | | |
|---|---|---|
| Description of CFI Base Molecule | Nomenclature of Base Molecule | Amino Acid Sequence |
| Plasma derived, wild type human CFI (wt hCFI), with signal sequence underlined) | CFI-PD | MKLLHVFLLFLCFHLRFCKVTYTSQE DLVEKKCLAKKYTHLSCDKVFCQPW QRCIEGTCVCKLPYQCPKNGTAVCAT NRRSFPTYCQQKSLECLHPGTKFLNN GTCTAEGKFSVSLKHGNTDSEGIVEV KLVDQDKTMFICKSSWSMREANVAC LDLGFQQGADTQRRFKLSDLSINSTEC LHVHCRGLETSLAECTFTKRRTMGYQ DFADVVCYTQKADSPMDDFFQCVNG KYISQMKACDGINDCGDQSDELCCKA CQGKGFHCKSGVCIPSQYQCNGEVDC ITGEDEVGCAGFASVTQEETEILTADM DAERRRIKSLLPKLSCGVKNRMHIRR KRIVGGKRAQLGDLPWQVAIKDASGI TCGGIYIGGCWILTAAHCLRASKTHR YQIWTTVVDWIHPDLKRIVIEYVDRII FHENYNAGTYQNDIALIEMKKDGNK KDCELPRSIPACVPWSPYLFQPNDTCI VSGWGREKDNERVFSLQWGEVKLIS NCSKFYGNRFYEKEMECAGTYDGSID ACKGDSGGPLVCMDANNVTYVWGV VSWGENCGKPEFPGVYTKVANYFDW ISYHVGRPFISQYNV (SEQ ID NO: 1) |
| wt hCFI, no signal sequence | hCFI | KVTYTSQEDLVEKKCLAKKYTHLSC DKVFCQPWQRCIEGTCVCKLPYQCPK NGTAVCATNRRSFPTYCQQKSLECLH PGTKFLNNGTCTAEGKFSVSLKHGNT DSEGIVEVKLVDQDKTMFICKSSWSM REANVACLDLGFQQGADTQRRFKLS DLSINSTECLHVHCRGLETSLAECTFT KRRTMGYQDFADVVCYTQKADSPM DDFFQCVNGKYISQMKACDGINDCG DQSDELCCKACQGKGFHCKSGVCIPS QYQCNGEVDCITGEDEVGCAGFASVT QEETEILTADMDAERRRIKSLLPKLSC GVKNRMHIRRKRIVGGKRAQLGDLP |

TABLE 1-continued

Base Molecules for Generation of CFI Variants

| Description of CFI Base Molecule | Nomenclature of Base Molecule | Amino Acid Sequence |
|---|---|---|
| | | WQVAIKDASGITCGGIYIGGCWILTAA HCLRASKTHRYQIWTTVVDWIHPDLK RIVIEYVDRIIFHENYNAGTYQNDIALI EMKKDGNKKDCELPRSIPACVPWSPY LFQPNDTCIVSGWREKDNERVFSLQ WGEVKLISNCSKFYGNRFYEKEMECA GTYDGSIDACKGDSGGPLVCMDANN VTYVWGVVSWGENCGKPEFPGVYTK VANYFDWISYHVGRPFISQYNV (SEQ ID NO: 5) |
| Δ(K1-P305), deletion of A-chain | ΔA-chain (CFI-SPD) | KLSCGVKNRMHIRRKRIVGGKRAQL GDLPWQVAIKDASGITCGGIYIGGCWI LTAAHCLRASKTHRYQIWTTVVDWI HPDLKRIVIEYVDRIIFHENYNAGTYQ NDIALIEMKKDGNKKDCELPRSIPACV PWSPYLFQPNDTCIVSGWGREKDNER VFSLQWGEVKLISNCSKFYGNRFYEK EMECAGTYDGSIDACKGDSGGPLVC MDANNVTYVWGVVSWGENCGKPEF PGVYTKVANYFDWISYHVGRPFISQY NV (SEQ ID NO: 12) |
| Wild type mouse CFI (https://www.uniprot.org/uniprot/Q61129) | Mouse CFI (mCFI) | MKLAHLSLFLLALHLSSSRSPSASDLP QEELVDQKCLLQKYTHRSCNKVFCQP WQRCIEGTCICKLPYQCPRAGTPVCA MNGRSYPTYCHQKSFECLHPEIKFSH NGTCAAEGKFNVSLIYGRTKTEGLVQ VKLVDQDERMFICKNSWSMAEANVA CVDLGFPLGVRDIQGSFNISGNLHIND TECLHVHCRGVETSLAECAFTKRRTE LSNGLAGVVCYKQDADFPTSLSFQCV NGKHIPQEKACNGVNDCGDQSDELC CKGCRGNASLCKSGVCIPDQYKCNGE VDCITGEDESRCEEDRQQNIPKGLARS AQGEAEIETEETEMLTPGMDNERKRI KSLLPKLSCGVKRNTHTRRKRVIGGK PANVGDYPWQVAIKDGQRITCGGIYI GGCWILTAAHCVRPSRAHSYQVWTA LLDWLKPNSQLGIQTVKRVIVHEKYN GATFQNDIALIEMKMHTGKKECELPN SVPACVPWSPYLFQPNDRCIISGWGR GKDNQKVYSLRWGEVDLIGNCSQFY PDRYYEKEMQCAGTRDGSIDACKGD SGGPLVCEDINNVTYVWGIVSWGENC GKPEFPGVYTRVANYFDWISYHVGRS LVSQHNV (SEQ ID NO: 23) |
| wt hCFI + GSSGG (linker) + wt hCFI | hCFI-hCFI fusion | KVTYTSQEDLVEKKCLAKKYTHLSC DKVFCQPWQRCIEGTCVCKLPYQCPK NGTAVCATNRRSFPTYCQQKSLECLH PGTKFLNNGTCTAEGKFSVSLKHGNT DSEGIVEVKLVDQDKTMFICKSSWSM REANVACDLGFQQGADTQRRFKLS DLSINSTECLHVHCRGLETSLAECTFT KRRTMGYQDFADVVCYTQKADSPM DDFFQCVNGKYISQMKACDGINDCG DQSDELCCKACQGKGFHCKSGVCIPS QYQCNGEVDCITGEDEVGCAGFASVT QEETEILTADMDAERRRIKSLLPKLSC GVKNRMHIRRKRIVGGKRAQLGDLP WQVAIKDASGITCGGIYIGGCWILTAA HCLRASKTHRYQIWTTVVDWIHPDLK RIVIEYVDRIIFHENYNAGTYQNDIALI EMKKDGNKKDCELPRSIPACVPWSPY LFQPNDTCIVSGWREKDNERVFSLQ WGEVKLISNCSKFYGNRFYEKEMECA GTYDGSIDACKGDSGGPLVCMDANN VTYVWGVVSWGENCGKPEFPGVYTK VANYFDWISYHVGRPFISQYNVGSSG GKVTYTSQEDLVEKKCLAKKYTHLS CDKVFCQPWQRCIEGTCVCKLPYQCP KNGTAVCATNRRSFPTYCQQKSLECL HPGTKFLNNGTCTAEGKFSVSLKHGN |

TABLE 1-continued

Base Molecules for Generation of CFI Variants

| Description of CFI Base Molecule | Nomenclature of Base Molecule | Amino Acid Sequence |
|---|---|---|
| | | TDSEGIVEVKLVDQDKTMFICKSSWS<br>MREANVACLDLGFQQGADTQRRFKL<br>SDLSINSTECLHVHCRGLETSLAECTF<br>TKRRTMGYQDFADVVCYTQKADSPM<br>DDFFQCVNGKYISQMKACDGINDCG<br>DQSDELCCKACQGKGFHCKSGVCIPS<br>QYQCNGEVDCITGEDEVGCAGFASVT<br>QEETEILTADMDAERRRIKSLLPKLSC<br>GVKNRMHIRRKRIVGGKRAQLGDLP<br>WQVAIKDASGITCGGIYIGGCWILTAA<br>HCLRASKTHRYQIWTTVVDWIHPDLK<br>RIVIEYVDRIIFHENYNAGTYQNDIALI<br>EMKKDGNKKDCELPRSIPACVPWSPY<br>LFQPNDTCIVSGWGREKDNERVFSLQ<br>WGEVKLISNCSKFYGNRFYEKEMECA<br>GTYDGSIDACKGDSGGPLVCMDANN<br>VTYVWGVVSWGENCGKPEFPGVYTK<br>VANYFDWISYHVGRPFISQYNV<br>(SEQ ID NO: 16) |

In some embodiments, a base molecule itself may be a CFI variant, for example in some embodiments, a CFI variant comprising only the serine protease domain (CFI-SPD) itself is a CFI variant. In some embodiments, the CFI variants are derived from any base molecule of Table 1, and comprise modifications to loops corresponding to the loops of an unmodified CFI. In some embodiments, the CFI variants are derived from any base molecule of Table 1, and comprise substitution mutations. In some embodiments, the CFI variants are derived from any base molecule of Table 1, and comprise a deletion of one or more domains of CFI. In some embodiments, the CFI variants are derived from any base molecule of Table 1, and comprise an inversion of the A-chain and the B-chain of the CFI. Examples of such inversions are provided in Table 9, and include, but are not limited to, SEQ ID NOs: 17, 18, 19, and 20.

In some embodiments, provided herein are CFI variants comprising at least one CFI domain, wherein the at least one CFI domain corresponds to those of a wild type CFI of any species. For example, the amino acid sequence of the at least one CFI domain may comprise the amino acid sequence derived from a wild type human CFI as set forth in SEQ ID NO: 5. The CFI variants provided herein comprising an amino acid sequence derived from SEQ ID NO: 5 may comprise one or more modifications with respect to the sequence set forth in SEQ ID NO: 5. For example, the one or more modifications may include a deletion of one or more amino acid residues, substitution mutations of one or more amino acid residues, an addition of one or more amino acid residues, the deletion of one or more domains of CFI, the substitution of one or more domains of CFI, or the addition of one or more domains of CFI.

In some embodiments, provided herein are CFI variants comprising at least one CFI domain of any species, wherein the at least one CFI domain comprises any one or more CFI domains selected from: a serine protease domain (SPD), a Factor I membrane attack complex (FIMAC) domain, a scavenger receptor cysteine-rich domain (SRCR), a low density lipoprotein receptor 1 (LDLr1), and low density lipoprotein receptor 2 (LDLr2) domains. In some embodiments, the any one or more CFI domains are that of a human CFI. In some embodiments, the any one or more CFI domains comprise an amino acid sequence derived from the sequence set forth in SEQ ID NO: 5.

In some embodiments, the CFI variants comprise all domains of a wild type CFI, i.e., each one of the SPD, the FIMAC domain, the SRCR domain, the LDLr1 domain, and the LDLr2 domain, and comprises a modification in any one or more of these domains with respect to the wild type CFI.

In some embodiments, the CFI variants do not comprise all of the domains corresponding to that of the wild type CFI. In some embodiments, the CFI variants comprise the SPD. In some embodiments, the CFI variants comprise only the SPD, wherein the A-chain of the CFI has been deleted, referred to herein as "CFI-SPD." In some embodiments, the CFI-SPD comprises the amino acid sequence set forth in SEQ ID NO: 12 (as shown in Table 1), which is the SPD of a human CFI. In some embodiments, the CFI-SPD comprises no further modifications with respect to that of a wild type CFI SPD. In some embodiments, the CFI-SPD comprises one or more modifications with respect to that of a wild type CFI SPD. In some embodiments, the CFI-SPD comprises at least one modification with respect to the amino acid sequence set forth in SEQ ID NO: 12.

Exemplary variants of CFI are described in further detail below. Exemplary CFI variants comprise one or more substitutions of amino acid residues with respect to a CFI having the amino acid sequence set forth in SEQ ID NO: 5. For example, a CFI variant that includes substitutions at positions N531 and P535 will have substitutions at positions N531 and P535 in the amino acid sequence set forth in SEQ ID NO: 5.

Exemplary CFI Variants

Provided herein are CFI variants comprising or consisting of at least one modification with respect to a wild type CFI, wherein the CFI variant is capable of increasing complement system inhibition, and wherein the CFI variant has at least one improved characteristic as compared to the wild type CFI. Examples of improved characteristic include, but are not limited to, an increase in half-life, an increase in bioavailability or an increase or decrease in any one or more of activity, substrate specificity, potency, substrate affinity, cofactor affinity and catalytic capability. In exemplary embodiments, an improved characteristic is increased half-life. In other exemplary embodiments, an improved characteristic is increased, or altered substrate specificity.

Without limitation, the disclosure contemplates the exemplary CFI variants described in Table 13. The variants of Table 13 include modified CFIs, as well as CFI fusion constructs, described herein. For avoidance of doubt, unless otherwise indicated, where a residue number is indicated, it refers to SEQ ID NO: 5 (wild type human CFI), or a sequence corresponding thereto. For avoidance of doubt, by way of example a variant whose description is K14A indicates that the disclosure provides a CFI variant comprising a K14A substitution, e.g. a CFI variant comprising a K14A substitution in SEQ ID NO: 5 (or a sequence corresponding thereto); the disclosure also provides for a CFI variant consisting of a K14A substitution, e.g. a CFI variant, wherein SEQ ID NO: 5 has a K14A substitution.

In some embodiments, a CFI variant of the disclosure comprises or consists of any one or more of the modifications presented in Table 13, wherein the positions correspond to positions in a CFI having the amino acid sequence set forth in SEQ ID NO: 5.

CFI variants of the disclosure can have at least one, at least two, at least three, at least four, at least five, at least six, at least seven, or more modifications, e.g. substitutions, deletions, insertions and fusions. Modification, e.g. substitutions, for a given variant may be represented in one of many ways recognized by the skilled artisan. For example, a hCFI variant having substitutions at T377G and N422K may be referred to as having substitutions: "T377G and N422K", "T377G-N422K", "T377G+N422K", "T377G/N422K", or "T377G; N422K" and are used interchangeably herein. In some instances, a CFI variant having substitutions at T377G and N422K may be referred to as "hCFI; T377G; N422K" or CFI variant (T377G; N422K)." As described herein, variants with other modifications, such as deletions, or combinations of modifications, such as deletions, fusions and substitutions, can conform to similar styles of nomenclature. Tables disclosing variants (e.g. Tables 13, 7.1, and 7.2) include the following symbols and abbreviations and associated meanings: HSA=human serum albumin; CFI=complement factor I; Δ=Deletion of the amino acid range noted; →=Deletion of noted sequence and replaced with noted amino acids; Cr1=CR1 fusion; Fh=FH fusion; G(#) denotes a linker of sequence GGSSGG (SEQ ID NO: 6) repeated the indicated number of instances.

TABLE 13

Exemplary CFI Variants

| Variant Description | Variant Description |
|---|---|
| Wild type HSA-CFI | Δ(K1-P305); GGSSGG (SEQ ID NO: 6); fH_CCP2-4 |
| K14A | |
| Y20A | Δ(K1-P305); GGSSGG (SEQ ID NO: 6); fH_CCP2-3 |
| Y20F | |
| D26A | N531G |
| F29A | N531A |
| R35A | P535A |
| E38A | Y408F |
| M220A; K221Q | Y408F; N531G |
| S507A | Y408L; N531G; E457G; E461Q; R462K; F464Y |
| S250A | |
| S250L | E530D |
| Δ(K1-P305) | E457G |
| D425A | E461Q |
| D425K | R462K |
| D425R | F464Y |
| 514-MDANNVT (SEQ ID NO: 13)-520 → NG | I317D; R318D; R319D; K320D; R321K |
| | Δ(K1-P305); N531G |
| ΔC-term (Δ558-PFISQYNV (SEQ ID NO: 14)-565) | Δ(K1-P305); Y408L; N531G |
| | Δ(K1-P305); N531G; P535A |
| R557A | WT hCFI; GGSSGG (SEQ ID NO: 6); CCP_1-4 |
| K326A; R327A | |
| Y408L; N531G | WT hCFI; GGSSGG (SEQ ID NO: 6); CCP_2-4 |
| L307G | |
| fH_CCP1-8; GGGGGGGGGGGG (SEQ ID NO: 25); ΔHSA | P535G |
| | Y408L; N531G; E457G |
| fH_CCP1-4; 19-20; 5-8; GGGGGGGGGGGG (SEQ ID NO: 25); ΔHSA | Y408L; N531G; E457G; E461Q |
| | Δ(K1-P305); Y408L; N531G; E457G; E461Q; R462K; F464Y |
| N531G; P535A | Y408L; N531G; P535A |
| Y408L | Δ(K1-P305); |
| 456-REKDNERVF5 (SEQ ID NO: 9)-465 → NTASSGADYPDE (SEQ ID NO: 10) | I317D; R318D; R319D; K320D; R321K |
| | K14A; D425R |
| E457G; E461Q; R462K; F464Y | Y408G |
| E38A; D425R | Y408P |
| Y20F; D425R | Y408D |
| S250A; D425R | Y408A |
| Δ(K1-P305); GGSSGG (SEQ ID NO: 6); fH_CCP1-4 | Y408N |
| | Y408T |
| Y408K | E457G; E461Q |
| Y408R | WT hCFI; GGSSGG (SEQ ID NO: 6); CCP_1-4; GGSS(6)+G; compstatin |
| Y408H | |
| Y408I | WT hCFI; GGSSGG (SEQ ID NO: 6); CCP_1-5; GGSS(3)+GGG; compstatin |
| P535K | |
| K534Q | WT hCFI; GGSSGG (SEQ ID NO: 6); CR1(ccp15-17); GGSSGG (SEQ ID NO: 6); fH(ccp1-4) |
| E530D; N531G; G533A; K534Q; P535K; E536N | |

TABLE 13-continued

Exemplary CFI Variants

| Variant Description | Variant Description |
|---|---|
| R321A | WT hCFI; GGSSGG (SEQ ID NO: 6); |
| WT mouse CFI | CR1(ccp15-17) |
| fH_CCP1-4; GGGGSS(7); WT hCFI | R462A |
| fH_CCP1-4; GGSS(11); WT hCFI | R462D |
| fH_CCP1-4; GGGGSS(9); WT hCFI | E457G; E461G |
| fH_CCP1-4; GGSS(13); WT hCFI | N531G; E457G; E461Q |
| N402E | W381K |
| N422K | N404G |
| A502S; K504Q; F537K | D506A |
| A502S | D506V |
| K504Q | D506E |
| K504E | D506G |
| K504R | I322V |
| K504A | I322V; V323I |
| K504G | R327P |
| K504L | I322V; V323I; R327P |
| K504P | V323A |
| K504H | A328C; W468C |
| A361G | A328C; W468C; K326Y; R327N |
| T495F; Y496L; D497E; S499G; I500K | Y408L; N531G; E461Q |
| T495F; Y496L; D497E; S499G; I500K; G533A; K534Q; P535K; E536N; F537K | D425R; Y408L; N531G; E457G; E461Q; R462K; F464Y |
| F537K | Y20F; E38A; S250A; D425A |
| F537R | Y20F; E38A; S250A; D425A; Y408L; |
| Q467K | N531G; E457G; E461Q; R462K; F464Y |
| Q467R | (HSA-GS); V311-V565 - G(13) - K1-G310 |
| Q467K; F537K | (HSA-GS)-V311-V565 - G(10) - K1-G310; |
| E530G | C309S; C435S |
| E530G; N531G | (HSA-G5)-V311-V565 - G(13) - K1-G310; |
| E530F | C309S; C435S |
| E530Y | Y408L; N531G; E457G; E461Q; R462K |
| E530D; F537K | Y408L; N531G; E457G; E461Q; F464Y |
| R557K | Y408L; N531G; E457G; R462K; F464Y |
| P558L | Y408L; N531G; E461Q; R462K; F464Y |
| N531G; E457G; E461Q; F464Y | Y408L; E457G; E461Q; R462K; F464Y |
| E416A | E457G; N531G; E461Q; R462K; F464Y |
| Y408L; N531G; E457G; E461Q; R462K; F464Y; S507A | Y408L; E457G; E461Q; R462K |
| H370A | E461A |
| P384A | E461D |
| P384G | E461F |
| 420-DGNK (SEQ ID NO: 15)-424 → GG | E461G |
| E536A | E461H |
| N85Q | E461I |
| N159Q | E461L |
| N476Q | E461M |
| N518Q | E461N |
| N52Q; N85Q; N159Q | E461P |
| N446Q; N476Q; N518Q | E461S |
| E457A | E461T |
| E457D | E461W |
| E457F | E461Y |
| E457H | E461V |
| E457I | R456A |
| E457K | I317D-R318D-R319D-K320D-R321K; |
| E457L | Y408L; N531G; E457G; E461Q; R462K; |
| E457M | F464Y |
| E457N | K312A |
| E457P | R314A |
| E457Q | K312A; R314A |
| E457R | P558S |
| E457S | F559L |
| E457T | I560V |
| E457W | Y563H |
| E457Y | P558S; F559L; I560V; Y563H |
| E457V | P558G |
| Y408E | L304G; P305G; K306G; L307G; S308G |
| K14A; Y20F; D26A; R35A; E38A | N531D |
| K14A; Y20F; D26A; R35A; E38A; L304G; P305G; K306G; L307G; S308G | N531E |
| Y408M | N531F |
| Y408Q | N531H |
| Y408S | N531I |
| Y408W | N531K |
| D341A | N531L |
| Y408V | N531M |
| | I322T |
| | N531P |

TABLE 13-continued

Exemplary CFI Variants

| Variant Description | Variant Description |
|---|---|
| N531T | N531Q |
| N531V | N531R |
| N531W | N531S |
| N531Y | G406E |
| Y403F | G406F |
| A405S | G406H |
| G406R | G406I |
| Q409D | G406K |
| A405S; G406R; Y408L; Q409D | G406L |
| A405S; G406A; Y408L; Q409D | G406M |
| Q409Y | G406N |
| Q409H | G406P |
| G406A | G406Q |
| G406A; Y408L | G406S |
| T377G | G406T |
| W381A | G406V |
| W381A; P384A | G406W |
| W381A; ΔP384 | G406Y |
| G469L | G406D; Y408L |
| R456N | G406D; N531G |
| K458A | G406D; P535A |
| G469L; R456N; E457T; K458A | G406D; Y408L; N531G) |
| G469L; R456N; K458A | G406D; Y408L; P535A) |
| G469L; R456N; K458A; E461G | G406D; N531G; P535A |
| G469L; R456N; K458A; E461G; F537K | G406D; Y408L; N531G; P535A |
| Y408L; N531G; GGSSGG (SEQ ID NO: 6); CCP_1-4 | K340G |
| | I345G |
| Y408L; N531G; E457G; GGSSGG (SEQ ID NO: 6); CCP_1-4 | K340G; I345G |
| | Y372G |
| Y408L; N531G; E457G; E461Q; R462K; F464Y; GGSSGG (SEQ ID NO: 6); CCP_1-4 | P384A |
| | P384G |
| | W381G |
| K504D | V390G |
| K504F | W381G; V390G |
| K504I | W381G; P384A; V390G |
| K504M | W381G; P384G; V390G |
| K504N | N404G |
| K504S | Q409G |
| K504T | K418G |
| K504V | D425G |
| K504W | K418G; D425G |
| K504Y | S465G |
| G406D | WT hCFI; GGSSGG (SEQ ID NO: 6); CR1(ccp15); fH(ccp2); fH(ccp3); fH(ccp4) |
| WT hCFI; GGSSGG (SEQ ID NO: 6); fH(ccp1); CR1(ccp16); fH(ccp3); fH(ccp4) | |
| WT hCFI; GGSSGG (SEQ ID NO: 6); CR1(ccp15); CR1(ccp16); fH(ccp3); fH(ccp4) | N531G; P535A; 5507A; GGSSGG (SEQ ID NO: 6); CCP_1-4 |
| | WT hCFI; GGSSGGSSGG (SEQ ID NO: 26); CCP_1-4 |
| WT hCFI; GGSSGG (SEQ ID NO: 6); fH(ccp1); CR1(ccp16); CR1(ccp17); fH(ccp4) | WT hCFI; GGSSGGSSGG (SEQ ID NO: 26); CCP_2-4 |
| WT hCFI; GGSSGG (SEQ ID NO: 6); CR1(ccp15); CR1(ccp16); CR1(ccp17); fH(ccp4) | WT hCFI; GGSSGGSSGG (SEQ ID NO: 26); CR1(ccp15); fH(ccp2); fH(ccp3); fH(ccp4) |
| G344R | WT hCFI; GGSSGGSSGG (SEQ ID NO: 26); fH(ccp1); CR1(ccp16); fH(ccp3); fH(ccp4) |
| G344K | |
| G344Y | |
| T346R | WT hCFI; GGSSGGSSGG (SEQ ID NO: 26); CR1(ccp15); CR1(ccp16); fH(ccp3); fH(ccp4) |
| T346K | |
| T346H | |
| K504E | WT hCFI; GGSSGGSSGG (SEQ ID NO: 26); fH(ccp1); CR1(ccp16); CR1(ccp17); fH(ccp4) |
| K504D | |
| E530R | |
| E530K | WT hCFI; GGSSGGSSGG (SEQ ID NO: 26); CR1(ccp15); CR1(ccp16); CR1(ccp17); fH(ccp4) |
| T346R; K504E; E530R | |
| T346K; K504D; E530K | WT hCFI; GGSSGGSSGG; CR1(ccp15-17) |
| G344R; Y408L; N531G | Y408L; N531G; GGSSGGSSGG (SEQ ID NO: 26); fH(ccp1-4) |
| G344K; Y408L; N531G | |
| T346R; Y408L; N531G | Y408L; N531G; E457G; GGSSGGSSGG (SEQ ID NO: 26); fH(ccp1-4) |
| T346K; Y408L; N531G | |
| K504D; Y408L; N531G | |
| K504E; Y408L; N531G | Y408L; N531G; E457G; E461Q; R462K; F464Y; GGSSGGSSGG (SEQ ID NO: 26); fH(ccp1-4) |
| Y408L; E530R; N531G | |
| Y408L; E530K; N531G | F208Y |
| T346R; Y408L; K504E; E530R; N531G | F246Y |
| T346K; Y408L; K504D; E530K; N531G | F480Y |

TABLE 13-continued

Exemplary CFI Variants

| Variant Description | Variant Description |
|---|---|
| Y408L; S507A; N531G | F537Y |
| Y408L; N531G; E457G; E461Q; R462K; F464Y; S507A | F208Y; F246Y; F480Y; F537Y |
| E457G; S507A | H362T; V463S; R456I; D459W; S343R |
| N531G; P535A; S507A | H362T; V463S; R456I; D459W; S343K |
| S507A; GGSSGG (SEQ ID NO: 6); CCP_1-4 | H362T; V463S; R456F; D459W; S343R |
| Y408L; S507A; N531G; GGSSGG (SEQ ID NO: 6); CCP_1-4 | H362T; V463S; R456I; S343R |
| E457G; A507A; GGSSGG (SEQ ID NO: 6); CCP_1-4 | H362T; R456I; D459W; S343R |
| Y408L; N531G; E461Q; R462K | H362T; R456I; S343R |
| Y408L; N531G; E461Q; F464Y | H362T; R456I; S343K |
| Y408L; N531G; R462K; F464Y | K14A; D425R; Y408L-N531G |
| Y408L; E457G; E461Q; F464Y | Y408L; E457G; S507A; N531G |
| Y408L; E457G; R462K; F464Y | E457G; N531G |
| Y408L; E461Q; R462K; F464Y | E457G; Y408L |
| N531G; E457G; E461Q; R462K | Y408L; N531G; E457G; R462K |
| N531G; E457G; R462K; F464Y | Y408L; N531G; E457G; F464Y |
| N531G; E461Q; R462K; F464Y | N531G; N422K |
| Y408L; N531G; R462K | P535G; N422K |
| Y408L; N531G; F464Y | Y408L; P535G; N422K |
| Y408L; E457G; E461Q | E457G; P535G; N422K |
| Y408L; E457G; R462K | N531G; P535G; N422K |
| Y408L; E457G; F464Y | Y408L; E457G; N422K |
| Y408L; E461Q; R462K | Y408L; N531G; N422K |
| Y408L; E461Q; F464Y | E457G; N531G; N422K |
| Y408L; R462K; F464Y | Y408L; E457G; N531G; N422K |
| N531G; E457G; R462K | Y408L; E457G; P535G; N422K |
| N531G; E457G; F464Y | E457G; N531G; P535G; N422K |
| N531G; E461Q; R462K | Y408L; E457G; N531G; P535G; N422K |
| N531G; E461Q; F464Y | E457G; GGSSGG (SEQ ID NO: 6); CR1(ccp1-3) |
| N531G; R462K; F464Y | E457G; E461Q; R462K; F464Y; N531G; GGSSGG (SEQ ID NO: 6); CR1(ccp15-17) |
| E457G; E461Q; R462K | N531G; P535A; GGSSGG (SEQ ID NO: 6); CR1(ccp15-17) |
| E457G; E461Q; F464Y | S507A; GGSSGG (SEQ ID NO: 6); CR1(ccp15-17) |
| E457G; R462K; F464Y | S507A; GGSSGG (SEQ ID NO: 6); CR1(ccp1-3) |
| E461Q; R462K; F464Y | |
| Y408L; N531G | Y408L; E416A |
| Y408L; E461Q | E457G; E416A |
| Y408L; R462K | N531G; E416A |
| Y408L; F464Y | P535G; E416A |
| N531G; E461Q | Y408L; D425R; E416A |
| N531G; R462K | E457G; D425R; E416A |
| N531G; F464Y | N531G; D425R; E416A |
| E457G; R462K | Y408L; E457G; E416A |
| E457G; F464Y | Y408L; N531G; E416A |
| E461Q; R462K | E457G; N531G; E416A |
| E461Q; F464Y | Y408L; E457G; N531G; E416A |
| R462K; F464Y | Y408L; E457G; D425R; E416A |
| (Wild Type or any variant CFI); GGSSGG (SEQ ID NO: 6); CR1(ccp15-17) | Y408L; N531G; D425R; E416A |
| Y408L; N422K | E457G; N531G; D425R; E416A |
| E457G; N422K | D425R; Y408L; N531G; E457G; E461Q; R462K; F464Y; E416A |
| Y408L; D425R; E530Y | E457G; N531G; E461Q; R462K; F464Y; E416A |
| E457G; D425R; E530Y | |
| N531G; D425R; E530Y | Y408L; E530Y |
| Y408L; E457G; E530Y | E457G; E530Y |
| Y408L; N531G; E530Y | N531G; E530Y |
| E457G; N531G; E530Y | P535G; E530Y |
| Y408L; E457G; N531G; E530Y | R365K |
| Y408L; E457G; D425R; E530Y | R365D |
| Y408L; N531G; D425R; E530Y | R365E |
| E457G; N531G; D425R; E530Y | A366G |
| Y408L; E457G; N531G; D425R; E530Y | K368G |
| D425R; Y408L; N531G; E457G; E461Q; R462K; F464Y; E530Y | K368E |
| E457G; N531G; E461Q; R462K; F464Y; E530Y | K424A |
| E457G; N531G; E461Q; R462K; F464Y; E530Y; GGSSGG (SEQ ID NO: 6); CR1(ccp15-17) | K424V |
| | K424I |
| | K424L |
| | K424M |
| E457G; E461Q; N531G; GGSSGG (SEQ ID NO: 6); CR1 (ccp15-17) | K424F |
| | K424Y |
| | K424W |
| Y408L; E457G; E461Q; R462K; N531G; GGSSGG (SEQ ID NO: 6); CR1 (ccp15-17) | K424G |
| | K424P |
| Y408L; E457G; R462K; F464Y; N531G; | K424S |

TABLE 13-continued

Exemplary CFI Variants

| Variant Description | Variant Description |
|---|---|
| GGSSGG (SEQ ID NO: 6); CR1 (ccp15-17) E457G; N531G; E461Q; R462K; F464Y; | K424T |
| GGSSGG (SEQ ID NO: 6); CR1 (ccp15-17) E457G; N531G; E461Q; R462K; F464Y; | K424N |
| GGSSGG (SEQ ID NO: 6); CR1 (ccp1-3) E457G; E461Q; F464Y; N531G; GGSSGG (SEQ ID NO: 6); CR1 (ccp15-17) | K424Q |
| | K424R |
| | K424H |
| | K424D |
| | K424E |
| R365A | K423G |
| R365V | K423A |
| R365I | K423E |
| R365L | K423D |
| R365M | D549A |
| R365F | D549V |
| R365Y | D549L |
| R365W | D549M |
| R365G | D549F |
| R365P | D549Y |
| R365S | D549W |
| R365T | D549T |
| R365N | D549N |
| R365Q | D549Q |
| R365H | D549G |
| D549K | D549P |
| Y553A | D549R |
| Y553V | D549H |
| Y553I | Y408L; E457G; E461Q; R462K; N531G; R557K |
| Y553L | |
| Y553S | Y408L; N531G; ΔC-term (Δ558-PFISQYNV (SEQ ID NO: 14)-565) |
| Y553N | |
| Y553Q | N531G; P535A; ΔC-term (Δ558-PFISQYNV (SEQ ID NO: 14)-565) |
| Y553R | |
| Y553H | N531G; E457G; E461Q; ΔC-term (Δ558-PFISQYNV (SEQ ID NO: 14)-565) |
| Y553K | |
| Y553E | Y408L; E457G; E461Q; R462K; N531G; ΔC-term (Δ558-PFISQYNV (SEQ ID NO: 14)-565) |
| R557V | |
| R557I | |
| R557L | ΔC-term (Δ557-RPFISQYNV (SEQ ID NO: 27)-565) |
| R557M | |
| R557F | Q69G |
| R557Y | L73G |
| R557W | L76G |
| R557S | H362G |
| R557T | H370G |
| R557N | F399G |
| R557Q | E401G |
| R557G | A405G |
| R557P | R456G |
| R557H | D459G |
| R557D | R484G |
| R557E | D501G |
| T377G; N531G | A502G |
| T377G; E457G | V526G |
| T377G; E461Q | S527G |
| T377G; E457G; E461Q | W528G |
| T377G; E457G; E461Q; N531G | F537G |
| Y408L; N531G; R557A | P538G |
| N531G; P535A; R557A | V540G |
| E457G; E461Q; R557A | Y553G |
| N531G; E457G; E461Q; R557A | A342G |
| Y408L; E457G; E461Q; R462K; N531G; R557A | R371G |
| | R327G |
| N531G; P535A; R557K | S343G |
| E457G; E461Q; R557K | Q373G |
| N531G; E457G; E461Q; R557K | W375G |
| I389G | I382G |
| I391G | H383G |
| E392G | L386G |
| Y393G | K387G |
| K419G | R388G |
| D420G | Y408F; E416A; E457G; E461Q; R462K; N531G |
| N422G | |
| N460G | E416A; E457G; E461Q; F464Y; N531G |
| R462G | T377G; E457G; E461Q; R462K; F464Y; N531G |
| V463G | |
| WT mouse CFI; His tag | T377G; Y408L; E457G; E461Q; R462K; N531G |
| Y408F; E457G; E461Q; N531G | |

TABLE 13-continued

Exemplary CFI Variants

| Variant Description | Variant Description |
|---|---|
| Y408F; E457G; E461Q; R462K; F464Y; N531G | T377G; E457G; E461Q; F464Y; N531G |
| Y408F; E457G; E461Q; R462K; N531G | T377G; E416A; K504H |
| Y408F; E457G; E461Q; F464Y; N531G | E416A; K504H |
| E457G; E461Q; R462K; F464Y; N531G; R557K | T377G; K504H |
| E457G; E461Q; F464Y; N531G; R557K | N422K; E457G; E461Q; N531G |
| E530F; P558S | N422K; E457G; E461Q; Q467K; N531G |
| E530Y; P558S | E416A; N422K; E457G; E461Q; Q467K; N531G |
| E457G; E461Q; E530F; N531G; P558S | K504R; E530F; D425K; P558S |
| E457G; E461Q; R462K; F464Y; E530F; N531G; P558S | K504R; E530F; D425R; P558S |
| Y408L; E457G; E461Q; R462K; E530F; N531G; P558S | K504R; E530F; D425R; P558G |
| E457G; E461Q; F464Y; E530F; N531G; P558S | K504R; E530F; D425K; P558G |
| E457G; E461Q; E530Y; N531G; P558S | K504R; E530F; D425K; P558S; E457G; E461Q; N531G |
| E457G; E461Q; R462K; F464Y; E530Y; N531G; P558S | K504R; E457G; E461Q; N531G |
| Y408L; E457G; E461Q; R462K; E530Y; N531G; P558S | E530F; E457G; E461Q; N531G |
| Y408F; E457G; E461Q; R462K; E530Y; N531G; P558S | D425R; E457G; E461Q; N531G |
| E457G; E461Q; F464Y; E530Y; N531G; P558S | D425K; E457G; E461Q; N531G |
| E457G; E461Q; K504H; N531G | P558S; E457G; E461Q; N531G |
| E457G; E461Q; R462K; F464Y; K504H; N531G | P558G; E457G; E461Q; N531G |
| Y408L; E457G; E461Q; R462K; K504H; N531G | K504R; E530F; E457G; E461Q; N531G |
| E457G; E461Q; F464Y; K504H; N531G | K504R; D425R; E457G; E461Q; N531G |
| E416A; E457G; E461Q; N531G | K504R; P558S; E457G; E461Q; N531G |
| Y408L; E416A; E457G; E461Q; R462K; N531G | E530F; P558S; E457G; E461Q; N531G |
| R557A; N531D; Y403F; K504Y | D425R; P558S; E457G; E461Q; N531G |
| R557A; N531M; Y403F; K504Y; E457G; E461Q | D425R; E530F; E457G; E461Q; N531G |
| R557A; N531G; Y403F; K504Y; E457G; E461Q | D425K; E530F; E457G; E461Q; N531G |
| R557A; N531D; Y403F; K504Y; E457G; E461Q | D425R; E530F; P558G; E457G; E461Q; N531G |
| R557A; N531M; Y403F; K504Y; E457G; E461L | K504R; E530F; P558G; E457G; E461Q; N531G |
| R557A; N531M; Y403F; K504Y; E457G; E461T | K504R; D425R; P558G; E457G; E461Q; N531G |
| R557A; N531M; Y403F; K504Y; E457G; E461V | K504R; D425R; E530F; E457G; E461Q; N531G |
| R557A; N531M; Y403F; K504Y; E457N; E461Q | R557A; N531M |
| R557A; N531M; Y403F; K504Y; E457N; E461L | R557K; N531M |
| R557A; N531M; Y403F; K504Y; E457N; E461T | R557A; N531M; Y403F; K504Y |
| R557A; N531M; Y403F; K504Y; E457N; E461V | E530F; P558S |
| N531M; Y403F; K504Y; E457G; E461Q | F537K; K504R |
| N422K; E461Q | F537K; P558S |
| T377G; N422K | K504R; P558S |
| N531G; E457G; T377G | D425K; Y408M; F537K |
| N531G; E461Q; N422K | D425K; Y408M; K504R |
| N531G; E461Q; T377G | D425K; Y408M; E530F; F537K |
| N531G; N422K; T377G | D425K; E530F; F537K; K504R |
| E457G; E461Q; N422K | Y408M; E530F; F537K; K504R |
| E457G; N422K; T377G | Y408M; F537K; K504R; P558S |
| E461Q; N422K; T377G | D425K; Y408M; E530F; F537K; K504R |
| N531G; E457G; N422K; T377G | D425K; Y408M; E530F; F537K; P558S |
| N531G; E461Q; N422K; T377G | D425K; Y408M; E530F; K504R; P558S |
| E457G; E461Q; N422K; T377G | D425K; Y408M; F537K; K504R; P558S |
| T377G; N422K; E457G; E461Q; N531G | D425K; E530F; F537K; K504R; P558S |
| D425K; Y408M | D425K; Y408M; E530F; F537K; K504R; P558S |
| D425K; E530F | D425K; E457G; E461Q; K504R; N531G |
| D425K; F537K | D425K; E457G; E461Q; N531G; P558S |
| D425K; K504R | T377G; Y408M; N422K; E457G; E461Q; E530F; N531G |
| D425K; P558S | T377G; N422K; D425K; E457G; E461Q; E530F; N531G |
| Y408M; E530F | E457G; E461Q; N531G; S507A |
| Y408M; K504R | N531G; S507A |
| | E457G; S507A |
| | E461Q; S507A |
| | N422K; S507A |
| | T377G; S507A |
| | D425K; S507A |
| | Y408M; S507A |
| | P558S; S507A |
| | E530F; S507A |
| | F537K; S507A |
| | K504R; S507A |
| | Y408F; S507A |
| | R557A; S507A |

TABLE 13-continued

| Exemplary CFI Variants | |
|---|---|
| Variant Description | Variant Description |
| Y408M; P558S | E416A; E457G; E461Q; R462K; F464Y; N531G |
| E530F; F537K | N52Q; N159Q |
| E530F; K504R | N476Q; N518Q |
| Y408F; K504Y | Y408F; N531M |
| G406A; Y403F | Y403F; G406A; D425K; E457G; E461Q; K504Y; N531G |
| D425K | D425K; E457G; E461Q; N531G |
| Y403F; D425K; E457G; N531G | D425K; E457G; E461Q; N531G; R557A |
| G406A; D425K; E457G; E461Q; N531G | R557A |
| Y403F; G406A; D425K; E457G; E461Q; N531G | Δ(V565) |
| Y403F; D425K; E457G; E461Q; K504Y; N531G | F559Y |
| | Δ(S308) |

The activity and specificity of the CFI variants provided herein can be tuned for particular applications and therapeutic indications. For example, activity and specificity can be tuned by selection of C3b degraders, or C4b degraders, or degraders of both C3b and C4b. As used herein, protease activity for a substrate refers to the ability of a CFI variant of the disclosure to cleave its substrates, C4b and C3b. This can be expressed as an increase in C4b degrader activity, protease activity towards C4b, C3b degrader activity, protease activity towards C3b and the like.

As used herein a C3b degrader is a CFI variant that is capable of cleaving C3b; likewise, a C4b degrader is a CFI variant that is capable of cleaving C4b. The use of C3b degrader does not imply that it does not degrade C4b. A CFI variant can be both a C3b degrader, and a C4b degrader, and can show specificity for one over the other.

The CFI variants provided herein have modified characteristics that include increases or decreases in protease activity for a substrate as well increases or decreases in substrate specificity.

As used herein, specificity for a substrate, also referred to as substrate specificity, refers to the specificity for one over the other that a CFI variant demonstrates. If a substrate specificity of a CFI variant is about 1, then the specificity for both C4b and C3b are equal. If the specificity of a CFI variant is 2-fold higher for C4b, then it is deemed to demonstrate increased specificity of cleavage for C4b, as compared to C3b. Specificity for C4b in the examples provided herein, is expressed as a ratio of the percent maximum cleavage of C4b divided by the ratio of percent maximum cleavage of C3b. Likewise, specificity for C3b in the examples provided herein, is expressed as a ratio of the percent maximum cleavage of C3b divided by the ratio of percent maximum cleavage of C4b. An increase in protease activity for one substrate by a greater fold increase as compared to another substrate is an example of an increase in specificity for that substrate.

In some embodiments amino acids modifications (e.g. substitutions) either increase activity, confer specificity or both. In some embodiments, an increase in C4b degrader activity comprises an increase in the cleavage of C4b, (and the generation of a cleavage product such as C4c) and an increase in the specificity towards C4b comprises an increase in the cleavage of C4b and a decrease in the cleavage of C3b (and the generation of a cleavage product such as iC3b), as compared to wild type CFI or a fusion construct comprising wild type CFI.

In some embodiments the combination of two or more modifications (e.g. substitutions) confers unexpected increases in activity that are synergistic or additive.

In some embodiments the combination of one or more modifications confers unexpected increases or decreases in activity that are synergistic when C4b is the substrate and additive or less than additive when C3b is the substrate.

In some embodiments the combination of one or more modifications confers unexpected increases or decreases in activity that are synergistic when C3b is the substrate and additive or less than additive when C4b is the substrate.

Accordingly, a modified characteristic can be achieved by selection of one or more modifications that confer increased C3b degrader activity and decrease C4b degrader activity (increase in C3b substrate specificity) or, alternatively, confer increased C4b degrader activity and decrease C3b degrader activity (increase in C4b substrate specificity) or, alternatively, provide increased activity as degraders of both C3b and C4b (no change in specificity, but increase in activity for both substrates).

Accordingly, a modified characteristic can be achieved by selection of one or more modifications that confer increased C3b degrader activity and no change in C4b degrader activity (increase in C3b substrate specificity) or, alternatively, confer increased C4b degrader activity and no change in C3b degrader activity (increase in C4b substrate specificity).

Accordingly, a modified characteristic can be achieved by selection of one or more modifications that confer a decrease in C3b degrader activity and no change in C4b degrader activity (increase in C4b substrate specificity) or, alternatively, confer a decrease in C4b degrader activity and no change in C3b degrader activity (increase in C3b substrate specificity).

Modifications providing increased activity and specificity are typically concentrated in, but not bound by limitation, to structural regions critical in for CFI function. Exemplary structural regions where modifications (e.g. substitutions) lead to at least one improved characteristic are the C-terminal extension, the A:B interface, the surface representing an interface with cofactors and modifications (e.g. substitutions) within the active site of the SPD including surface loops that provide an interface with the C3b and C4b substrates and the CR1 and FH cofactors (FIG. 1).

Without being bound to theory or mechanism, provided herein are CFI variants having one or more combinations of any of the amino acid modifications detailed below, wherein the CFI variants have at least one improved characteristic. CFI variants with combined modifications (e.g. substitutions) comprise two or more modifications in one or more regions of CFI selected from, but not limited to the structural regions of the C-terminal extension, the A:B interface, the interface with cofactors and the active site, including surface loops that provide an interface with cofactors and the C3b or C4b substrates.

In some embodiments CFI variants comprising two or more substitutions exhibit changes in activity, substrate specificity, or both. In some embodiments, an increase in activity comprises an increase in the cleavage of C4b, and/or the generation of C4c and specificity comprises a limited increase or a decrease in the cleavage of C3b, and/or the generation of iC3b as compared to wild type CFI (or compared to a fusion construct comprising wild type CFI, e.g. SEQ ID NO: 21). In some embodiments the combination of two or more substitutions confers unexpected increases in activity that are synergistic when C4b is the substrate and additive or less than additive when C3b is the substrate.

In some embodiments amino acids substitutions either increase activity, confer specificity or both and may switch between C3b selectivity and C4b selectivity. In some embodiments, an increase in activity comprises an increase in the cleavage of C4b, and/or the generation of C4c and selectivity comprises a decrease in the cleavage of C3b, and/or the generation of iC3b as compared to wild type CFI. In some embodiments, an increase in activity comprises an increase in the cleavage of C3b, and/or the generation of iC3b and specificity comprises a decrease in the cleavage of C4b, and/or the generation of C4c as compared to wild-type CFI. In some embodiments the nature of the amino acid substitution defines whether the CFI variant displays characteristics of specificity for C3b or specificity for C4b.

Exemplary variants of the disclosure are tested for differences in activity, and for differences in specificity. Exemplary data are provided in at least Table 7.2.

In some embodiments, the CFI variant exhibits increased activity, wherein the increase in activity comprises an increase in the C3b degrader activity by a CFI variant of the disclosure (with a concomitant increase in a C3b cleavage product). In some embodiments, a CFI variant of the disclosure exhibits increase C3b degrader activity by at least or about 1.5-fold, at least or about 2-fold, at least or about 3-fold, at least or about 4-fold at least or about 5-fold, at least or about 6-fold, at least or about 7-fold at least or about 8-fold, at least or about 9-fold, at least or about 10-fold at least or about 15-fold, at least or about 20-fold, at least or about 25-fold at least or about 30-fold, at least or about 40-fold, at least or about 50-fold at least or about 75-fold, at least or about 100-fold, at least or about 150-fold at least or about 200-fold, at least or about 250-fold, at least or about 300-fold, at least or about 350-fold at least or about 400-fold, at least or about 450-fold, at least or about 500-fold, at least or about 550-fold at least or about 600-fold, at least or about 650-fold, at least or about 700-fold, at least or about 750-fold at least or about 800-fold, at least or about 850-fold, at least or about 900-fold, at least or about 950-fold at least or even at least about 1000-fold, as compared to a wild type CFI, or a fusion construct comprising a wild type CFI, e.g. SEQ ID NO: 21. In some embodiments, this increase in C3b degrader activity is accompanied by an increase also in C4b degrader activity. In some embodiments, this increase in C3b degrader activity is not accompanied by an increase also in C4b degrader activity, and there may even be a decrease in C4b degrader activity.

In some embodiments, the CFI variant exhibits increased activity, wherein the increase in activity comprises an increase in the C4b degrader activity by a CFI variant of the disclosure (with a concomitant increase in a C4b cleavage product). In some embodiments, a CFI variant of the disclosure exhibits increase C4b degrader activity by at least or about 1.5-fold, at least or about 2-fold, at least or about 3-fold, at least or about 4-fold at least or about 5-fold, at least or about 6-fold, at least or about 7-fold at least or about 8-fold, at least or about 9-fold, at least or about 10-fold at least or about 15-fold, at least or about 20-fold, at least or about 25-fold at least or about 30-fold, at least or about 40-fold, at least or about 50-fold at least or about 75-fold, at least or about 100-fold, at least or about 150-fold at least or about 200-fold, at least or about 250-fold, at least or about 300-fold, at least or about 350-fold at least or about 400-fold, at least or about 450-fold, at least or about 500-fold, at least or about 550-fold at least or about 600-fold, at least or about 650-fold, at least or about 700-fold, at least or about 750-fold at least or about 800-fold, at least or about 850-fold, at least or about 900-fold, at least or about 950-fold at least or even at least about 1000-fold, as compared to a wild type CFI, or a fusion construct comprising a wild type CFI, e.g. SEQ ID NO: 21. In some embodiments, this increase in C4b degrader activity is accompanied by an increase also in C3b degrader activity. In some embodiments, this increase in C4b degrader activity is not accompanied by an increase also in C3b degrader activity, and there may even be a decrease in C3b degrader activity.

In some embodiments, the CFI variant exhibits increased activity, wherein the increase in activity comprises an increase in both C3b and C4b degrader activity. In some embodiments, a CFI variant of the disclosure exhibits both increased C3b and increased C4b degrader activity by at least or about 1.5-fold, at least or about 2-fold, at least or about 3-fold, at least or about 4-fold at least or about 5-fold, at least or about 6-fold, at least or about 7-fold at least or about 8-fold, at least or about 9-fold, at least or about 10-fold at least or about 15-fold, at least or about 20-fold, at least or about 25-fold at least or about 30-fold, at least or about 40-fold, at least or about 50-fold at least or about 75-fold, at least or about 100-fold, at least or about 150-fold at least or about 200-fold, at least or about 250-fold, at least or about 300-fold, at least or about 350-fold at least or about 400-fold, at least or about 450-fold, at least or about 500-fold, at least or about 550-fold at least or about 600-fold, at least or about 650-fold, at least or about 700-fold, at least or about 750-fold at least or about 800-fold, at least or about 850-fold, at least or about 900-fold, at least or about 950-fold at least or even at least about 1000-fold, as compared to a wild type CFI, or a fusion construct comprising a wild type CFI, e.g. SEQ ID NO: 21. The increase in degrader activity of one substrate may be the same, but need not be.

In some embodiments, the CFI variant exhibits increased specificity for a substrate, wherein the increase in specificity is for C3b (over C4b). In some embodiments, a CFI variant of the disclosure exhibits increased specificity for C3b by at least or about 1.5-fold, at least or about 2-fold, at least or about 3-fold, at least or about 4-fold at least or about 5-fold, at least or about 6-fold, at least or about 7-fold at least or about 8-fold, at least or about 9-fold, at least or about 10-fold at least or about 15-fold, at least or about 20-fold, at least or about 25-fold at least or about 30-fold, at least or about 40-fold, at least or about 50-fold at least or about 75-fold, at least or about 100-fold, at least or about 150-fold at least or about 200-fold, at least or about 250-fold, at least or about 300-fold, at least or about 350-fold at least or about 400-fold, at least or about 450-fold, at least or about 500-fold, at least or about 550-fold at least or about 600-fold, at least or about 650-fold, at least or about 700-fold, at least or about 750-fold at least or about 800-fold, at least or about 850-fold, at least or about 900-fold, at least or about 950-fold at least or even at least about 1000-fold, as compared to a wild type CFI, or a fusion construct comprising a wild type CFI, e.g. SEQ ID NO: 21.

In some embodiments, the CFI variant exhibits increased specificity for a substrate, wherein the increase in specificity is for C4b (over C3b). In some embodiments, a CFI variant of the disclosure exhibits increased specificity for C4b by at least or about 1.5-fold, at least or about 2-fold, at least or about 3-fold, at least or about 4-fold at least or about 5-fold, at least or about 6-fold, at least or about 7-fold at least or about 8-fold, at least or about 9-fold, at least or about 10-fold at least or about 15-fold, at least or about 20-fold, at least or about 25-fold at least or about 30-fold, at least or about 40-fold, at least or about 50-fold at least or about 75-fold, at least or about 100-fold, at least or about 150-fold at least or about 200-fold, at least or about 250-fold, at least or about 300-fold, at least or about 350-fold at least or about 400-fold, at least or about 450-fold, at least or about 500-fold, at least or about 550-fold at least or about 600-fold, at least or about 650-fold, at least or about 700-fold, at least or about 750-fold at least or about 800-fold, at least or about 850-fold, at least or about 900-fold, at least or about 950-fold at least or even at least about 1000-fold, as compared to a wild type CFI, or a fusion construct comprising a wild type CFI, e.g. SEQ ID NO: 21 which has an about equal specificity for both C3b and C4b.

In some embodiments, the CFI variant exhibits decreased specificity for a substrate, wherein the decrease in specificity is for C3b (over C4b). In some embodiments, a CFI variant of the disclosure exhibits decreased specificity for C3b by at least or about 1.5-fold, at least or about 2-fold, at least or about 3-fold, at least or about 4-fold at least or about 5-fold, at least or about 6-fold, at least or about 7-fold at least or about 8-fold, at least or about 9-fold, at least or about 10-fold at least or about 15-fold, at least or about 20-fold, at least or about 25-fold at least or about 30-fold, at least or about 40-fold, at least or about 50-fold at least or about 75-fold, at least or about 100-fold, at least or about 150-fold at least or about 200-fold, at least or about 250-fold, at least or about 300-fold, at least or about 350-fold at least or about 400-fold, at least or about 450-fold, at least or about 500-fold, at least or about 550-fold at least or about 600-fold, at least or about 650-fold, at least or about 700-fold, at least or about 750-fold at least or about 800-fold, at least or about 850-fold, at least or about 900-fold, at least or about 950-fold at least or even at least about 1000-fold, as compared to a wild type CFI, or a fusion construct comprising a wild type CFI, e.g. SEQ ID NO: 21 which has an about equal specificity for both C3b and C4b.

In some embodiments, the CFI variant exhibits decreased specificity for a substrate, wherein the decrease in specificity is for C4b (over C3b). In some embodiments, a CFI variant of the disclosure exhibits decreased specificity for C4b by at least or about 1.5-fold, at least or about 2-fold, at least or about 3-fold, at least or about 4-fold at least or about 5-fold, at least or about 6-fold, at least or about 7-fold at least or about 8-fold, at least or about 9-fold, at least or about 10-fold at least or about 15-fold, at least or about 20-fold, at least or about 25-fold at least or about 30-fold, at least or about 40-fold, at least or about 50-fold at least or about 75-fold, at least or about 100-fold, at least or about 150-fold at least or about 200-fold, at least or about 250-fold, at least or about 300-fold, at least or about 350-fold at least or about 400-fold, at least or about 450-fold, at least or about 500-fold, at least or about 550-fold at least or about 600-fold, at least or about 650-fold, at least or about 700-fold, at least or about 750-fold at least or about 800-fold, at least or about 850-fold, at least or about 900-fold, at least or about 950-fold at least or even at least about 1000-fold, as compared to a wild type CFI, or a fusion construct comprising a wild type CFI, e.g. SEQ ID NO: 21 which has an about equal specificity for both C3b and C4b.

In some embodiments, exemplary amino acid residues where one or more substitutions may confer improved or unexpected characteristics compared include, but are not limited to, L307, T377, G406, Y408, E416, N422, D425, E457, E461, K504, E530, P535, R557, P558, and combinations thereof, wherein the positions correspond to positions in a CFI having the amino acid sequence set forth in SEQ ID NO: 5 (or a sequence corresponding thereto).

In some embodiments, exemplary CFI variants of the disclosure displaying one or more improved characteristics include CFI variants comprising two or more combinations of T377G, N422K, E457G, E461Q, or N531G as compared to wild type CFI (or compared to a fusion construct comprising wild type CFI, e.g. SEQ ID NO: 21), wherein the positions correspond to positions in a CFI having the amino acid sequence set forth in SEQ ID NO: 5.

In some embodiments, exemplary CFI variants comprising or consisting of a single amino acid substitution of T377G, E457G or E461Q show at least a 2-fold increase in protease activity towards both C4b and C3b as compared to wild type CFI (or compared to a fusion construct comprising wild type CFI, e.g. SEQ ID NO: 21), wherein the positions correspond to positions in a CFI having the amino acid sequence set forth in SEQ ID NO: 5.

In some embodiments, exemplary CFI variants comprising or consisting of a single substitution such as N531G show at least a 5-fold increased protease activity towards C4b and at least a 3-fold increased activity towards C3b, as compared to wild type CFI (or compared to a fusion construct comprising wild type CFI, e.g. SEQ ID NO: 21), wherein the positions correspond to positions in a CFI having the amino acid sequence set forth in SEQ ID NO: 5.

In some embodiments, exemplary CFI variants comprising or consisting of a single substitution such as N422K show little or no change in protease activity towards C4b but show at least a 2-fold increased protease activity towards C3b as compared to wild type CFI (or compared to a fusion construct comprising wild type CFI, e.g. SEQ ID NO: 21), wherein the positions correspond to positions in a CFI having the amino acid sequence set forth in SEQ ID NO: 5.

In some embodiments, as compared to wild type CFI (e.g. a wild type CFI of SEQ ID NO: 5, a fusion construct comprising SEQ ID NO: 5, or a fusion construct of SEQ ID NO: 21), exemplary CFI variants comprising or consisting of or consisting of two substitutions such as E457G and N531G show at least a 27-fold increase in activity towards C4b and an at least 4-fold increase in activity towards C3b.

In some embodiments, as compared to wild type CFI (e.g. a wild type CFI of SEQ ID NO: 5, a fusion construct comprising SEQ ID NO: 5, or a fusion construct of SEQ ID NO: 21), exemplary CFI variants comprising or consisting of two substitutions such as T377G and N531G show at least a 16-fold increase in activity towards C4b and an at least 4-fold increase in activity towards C3b.

In some embodiments, as compared to wild type CFI (e.g. a wild type CFI of SEQ ID NO: 5, a fusion construct comprising SEQ ID NO: 5, or a fusion construct of SEQ ID NO: 21), exemplary CFI variants comprising or consisting of two substitutions such as T377G and E457G show at least a 15-fold increase in activity towards C4b and an at least 4-fold increase in activity towards C3b.

In some embodiments, as compared to wild type CFI (e.g. a wild type CFI of SEQ ID NO: 5, a fusion construct comprising SEQ ID NO: 5, or a fusion construct of SEQ ID NO: 21), exemplary CFI variants comprising or consisting of two substitutions such as T377G and E457G show at least a 15-fold increase in activity towards C4b and an at least 4-fold increase in activity towards C3b.

In some embodiments, as compared to wild type CFI (e.g. a wild type CFI of SEQ ID NO: 5, a fusion construct comprising SEQ ID NO: 5, or a fusion construct of SEQ ID NO: 21), exemplary CFI variants comprising or consisting of two substitutions such as T377G and N422K or N422K and E457G show at least an 8-fold increase in activity towards C4b and an at least a 5-fold increase in activity towards C3b.

In some embodiments, as compared to wild type CFI (e.g. a wild type CFI of SEQ ID NO: 5, a fusion construct comprising SEQ ID NO: 5, or a fusion construct of SEQ ID NO: 21), exemplary CFI variants comprising or consisting of three substitutions such as T377G and E457G and N531G show at least a 100-fold increase in activity towards C4b and an at least 6-fold increase in activity towards C3b.

In some embodiments, as compared to wild type CFI (e.g. a wild type CFI of SEQ ID NO: 5, a fusion construct comprising SEQ ID NO: 5, or a fusion construct of SEQ ID NO: 21), exemplary CFI variants comprising or consisting of three substitutions such as T377G and E461Q and N531G show at least a 60-fold increase in activity towards C4b and an at least 5-fold increase in activity towards C3b.

In some embodiments, as compared to wild type CFI (e.g. a wild type CFI of SEQ ID NO: 5, a fusion construct comprising SEQ ID NO: 5, or a fusion construct of SEQ ID NO: 21), exemplary CFI variants comprising or consisting of three substitutions such as T377G and N422K and N531G show at least a 45-fold increase in activity towards C4b and an at least 8-fold increase in activity towards C3b.

In some embodiments, exemplary CFI variants of the disclosure displaying one or more improved characteristics are CFI variants comprising or consisting of N531G, P535A and R557A as compared to wild type CFI (or compared to a fusion construct comprising wild type CFI, e.g. SEQ ID NO: 21), wherein the positions correspond to positions in a CFI having the amino acid sequence set forth in SEQ ID NO: 5.

In some embodiments, exemplary CFI variants comprising or consisting of a single amino acid substitution of R557A show at least a wild-type activity towards C4b and a 20-fold reduction in C3b activity as compared to wild type CFI (or compared to a fusion construct comprising wild type CFI, e.g. SEQ ID NO: 21), wherein the positions correspond to positions in a CFI having the amino acid sequence set forth in SEQ ID NO: 5.

In some embodiments, exemplary CFI variants comprising or consisting of a single substitution such as N531G show at least a 5-fold increased activity towards C4b and at least a 3-fold increased activity towards C3b, as compared to wild type CFI (or compared to a fusion construct comprising wild type CFI, e.g. SEQ ID NO: 21), wherein the positions correspond to positions in a CFI having the amino acid sequence set forth in SEQ ID NO: 5.

In some embodiments, as compared to wild type CFI (e.g. a wild type CFI of SEQ ID NO: 5, a fusion construct comprising SEQ ID NO: 5, or a fusion construct of SEQ ID NO: 21), CFI variants comprising or consisting of two substitutions such as N531G and P535A show at least a 5-fold increased activity towards C4b and a 3-fold increase in C3b activity, wherein the positions correspond to positions in a CFI having the amino acid sequence set forth in SEQ ID NO: 5.

In some embodiments, as compared to wild type CFI (e.g. a wild type CFI of SEQ ID NO: 5, a fusion construct comprising SEQ ID NO: 5, or a fusion construct of SEQ ID NO: 21), variants comprising or consisting of three substitutions such as N531G and P535A and R557A show at least an 18-fold increase in activity towards C4b and 2.5-fold reduction in C3b activity, wherein the positions correspond to positions in a CFI having the amino acid sequence set forth in SEQ ID NO: 5.

In some embodiments, exemplary CFI variants of the disclosure displaying one or more improved characteristics are CFI variants comprising or consisting of D425R, E457G and E530Y, as compared to wild type CFI (or compared to a fusion construct comprising wild type CFI, e.g. SEQ ID NO: 21), wherein the positions correspond to positions in a CFI having the amino acid sequence set forth in SEQ ID NO: 5.

In some embodiments, exemplary CFI variants comprising or consisting of a single amino acid substitution of E457G or E530Y show at least a wild-type activity towards C3b and C4b. In some embodiments, as compared to wild type CFI (e.g. a wild type CFI of SEQ ID NO: 5, a fusion construct comprising SEQ ID NO: 5, or a fusion construct of SEQ ID NO: 21), variants comprising or consisting of three substitutions such as D425R and E457G and E530Y show at least an 8-fold increase in activity towards C3b and near wild type activity towards C4b, wherein the positions correspond to positions in a CFI having the amino acid sequence set forth in SEQ ID NO: 5.

In some embodiments, exemplary CFI variants of the disclosure displaying one or more improved characteristics are CFI variants comprising or consisting of R557A, R557M, R557P, and R557G, as compared to wild type CFI (or compared to a fusion construct comprising wild type CFI, e.g. SEQ ID NO: 21), wherein the positions correspond to positions in a CFI having the amino acid sequence set forth in SEQ ID NO: 5.

In some embodiments, as compared to wild type CFI (e.g. a wild type CFI of SEQ ID NO: 5, a fusion construct comprising SEQ ID NO: 5, or a fusion construct of SEQ ID NO: 21), an exemplary CFI variant such as one consisting or comprising a R557A substitution shows at least a wild-type activity towards C4b and a 20-fold reduction in C3b activity, wherein the positions correspond to positions in a CFI having the amino acid sequence set forth in SEQ ID NO: 5.

In some embodiments, as compared to wild type CFI (e.g. a wild type CFI of SEQ ID NO: 5, a fusion construct comprising SEQ ID NO: 5, or a fusion construct of SEQ ID NO: 21), a variants comprising or consisting of or consisting of R557M and R557P show at least a 3-fold increase in activity towards C4b and 5-fold to 10-fold reductions in C3b activity, respectively, wherein the positions correspond to positions in a CFI having the amino acid sequence set forth in SEQ ID NO: 5.

In some embodiments, as compared to wild type CFI (e.g. a wild type CFI of SEQ ID NO: 5, a fusion construct comprising SEQ ID NO: 5, or a fusion construct of SEQ ID NO: 21), a variant such as R557G shows at least a 2-fold activity towards C4b and a 20-fold reduction in C3b activity, wherein the positions correspond to positions in a CFI having the amino acid sequence set forth in SEQ ID NO: 5.

In some embodiments, exemplary CFI variants of the disclosure displaying one or more improved characteristics are CFI variants comprising or consisting of E457T, E457Q, E457G or E457A, as compared to wild type CFI (or compared to a fusion construct comprising wild type CFI, e.g. SEQ ID NO: 21), wherein the positions correspond to positions in a CFI having the amino acid sequence set forth in SEQ ID NO: 5.

In some embodiments, as compared to wild type CFI (e.g. a wild type CFI of SEQ ID NO: 5, a fusion construct comprising SEQ ID NO: 5, or a fusion construct of SEQ ID NO: 21), an exemplary CFI variant comprising or consisting of a substitution such as E457T shows at least 2.6-fold increased activity towards C3b and a 5-fold reduction in C4b activity, wherein the positions correspond to positions in a CFI having the amino acid sequence set forth in SEQ ID NO: 5.

In some embodiments, as compared to wild type CFI (e.g. a wild type CFI of SEQ ID NO: 5, a fusion construct comprising SEQ ID NO: 5, or a fusion construct of SEQ ID NO: 21), an exemplary CFI variant comprising or consisting of a substitutions E457Q or E457G show at least a wild-type activity towards both C3b and C4b, wherein the positions correspond to positions in a CFI having the amino acid sequence set forth in SEQ ID NO: 5.

In some embodiments, as compared to wild type CFI (e.g. a wild type CFI of SEQ ID NO: 5, a fusion construct comprising SEQ ID NO: 5, or a fusion construct of SEQ ID NO: 21), an exemplary CFI variant comprising or consisting of a substitution such as E457A shows at least 2.7-fold increased activity towards C4b and a 1.6-fold increase in C3b activity, wherein the positions correspond to positions in a CFI having the amino acid sequence set forth in SEQ ID NO: 5.

In some embodiments, exemplary CFI variants of the disclosure displaying one or more improved characteristics are CFI variants comprising or consisting of E530F, E530Y, or E530R substitutions, as compared to wild type CFI (or compared to a fusion construct comprising wild type CFI, e.g. SEQ ID NO: 21), wherein the positions correspond to positions in a CFI having the amino acid sequence set forth in SEQ ID NO: 5.

In some embodiments, as compared to wild type CFI (e.g. a wild type CFI of SEQ ID NO: 5, a fusion construct comprising SEQ ID NO: 5, or a fusion construct of SEQ ID NO: 21), an exemplary CFI variant comprising or consisting of a substitution such as E530Y shows at least a 1.6-fold increase in activity towards C3b and near wild type activity on C4b activity, wherein the positions correspond to positions in a CFI having the amino acid sequence set forth in SEQ ID NO: 5.

In some embodiments, as compared to wild type CFI (e.g. a wild type CFI of SEQ ID NO: 5, a fusion construct comprising SEQ ID NO: 5, or a fusion construct of SEQ ID NO: 21), an exemplary CFI variant comprising or consisting of a substitution such as E530F shows at least a 1.6-fold increase in activity towards C3b and 3-fold reduction in C4b activity, wherein the positions correspond to positions in a CFI having the amino acid sequence set forth in SEQ ID NO: 5.

In some embodiments, as compared to wild type CFI (e.g. a wild type CFI of SEQ ID NO: 5, a fusion construct comprising SEQ ID NO: 5, or a fusion construct of SEQ ID NO: 21), an exemplary CFI variant comprising or consisting of a substitution such as E530R shows at least 1.8-fold increased activity towards C3b and a 5-fold reduction of C4b activity, wherein the positions correspond to positions in a CFI having the amino acid sequence set forth in SEQ ID NO: 5

In some embodiments, exemplary CFI variants of the disclosure displaying one or more improved characteristics are CFI variants comprising or consisting of E457G, E461Q, N531G or R557A substitutions, as compared to wild type CFI (or compared to a fusion construct comprising wild type CFI, e.g. SEQ ID NO: 21), wherein the positions correspond to positions in a CFI having the amino acid sequence set forth in SEQ ID NO: 5.

Exemplary CFI variants comprising or consisting of a single amino acid substitution of E457G or E461Q show at least a 2-fold increased activity towards C4b and C3b as compared to wild type CFI (e.g. a wild type CFI of SEQ ID NO: 5, a fusion construct comprising SEQ ID NO: 5, or a fusion construct of SEQ ID NO: 21). Exemplary CFI variants comprising or consisting of a single substitution such as N531G show at least a 5-fold increased activity towards C4b and at least a 3-fold increased activity towards C3b. Exemplary CFI variants comprising or consisting of a single amino acid substitution of R557A show at least a wild-type activity towards C4b and a 20-fold reduction in C3b activity. In some embodiments, as compared to wild type CFI (e.g. a wild type CFI of SEQ ID NO: 5, a fusion construct comprising SEQ ID NO: 5, or a fusion construct of SEQ ID NO: 21), variants comprising or consisting of two substitutions such as E457G and N531G show at least a 27-fold increase in activity towards C4b and an at least 4-fold increase in activity towards C3b. In some embodiments, as compared to wild type CFI (e.g. a wild type CFI of SEQ ID NO: 5, a fusion construct comprising SEQ ID NO: 5, or a fusion construct of SEQ ID NO: 21), variants comprising or consisting of two substitutions such as E457G and E461Q show at least a 5-fold increase in activity towards C4b and C3b. In some embodiments, as compared to wild type CFI (e.g. a wild type CFI of SEQ ID NO: 5, a fusion construct comprising SEQ ID NO: 5, or a fusion construct of SEQ ID NO: 21), variants comprising or consisting of two substitutions such as E461Q and N531G show at least a 12-fold increase in activity towards C4b and an at least 5-fold increase in activity towards C3b. In some embodiments, as compared to wild type CFI (e.g. a wild type CFI of SEQ ID NO: 5, a fusion construct comprising SEQ ID NO: 5, or a fusion construct of SEQ ID NO: 21), variants comprising or consisting of two substitutions such as E457G and E461Q and N531G and R557A show at least a 12-fold increase in activity towards C4b and an at least 1.5-fold increase in activity towards C3b. These differences are as compared to wild type CFI (or compared to a fusion construct comprising wild type CFI, e.g. SEQ ID NO: 21).

In some embodiments, the CFI variant having has increased activity, wherein the increased activity comprises increased cleavage of C3b and/or specificity for C3b over C4b. In some embodiments, the CFI variant having increased cleavage of C3b and/or specificity for C3b over C4b comprises one or more substitutions in an amino acid positions set forth in SEQ ID NO: 5. In some embodiments, the amino acid position is selected from one or more of E392, E416, D420, N422, D425, P558, T346, E401, G406, E457, E461, and N531 in a CFI having the amino acid sequence set forth in SEQ ID NO: 5. In some embodiments, the amino acid position is a position within the cofactor interface region in a CFI having the amino acid sequence set forth in SEQ ID NO: 5. In some embodiments, the position within the cofactor interface region is selected from one or more of E392, D420, and N422. In some embodiments, the amino acid position is a position within the C-terminal extension region in a CFI having the amino acid sequence set forth in SEQ ID NO: 5. In some embodiments, the position within the c-terminal extension region is selected from one or more of E416, D425, and P558. In some embodiments, the amino acid position is a position within the active site; C3b interface region in a CFI having the amino acid sequence set forth in SEQ ID NO: 5. In some embodiments, the position within the active site; C3b interface region is selected from one or more of T346, E401, and N531. In some embodiments, the amino acid position is a position within the autolysis loop; cofactor interface in a CFI having an amino acid sequence set forth in SEQ ID NO: 5. In some embodiments, the position within the autolysis loop; cofactor interface is selected from one or more of E457 and E461. These differences are as compared to wild type CFI (or compared to a fusion construct comprising wild type CFI, e.g. SEQ ID NO: 21), wherein the positions correspond to positions in a CFI having the amino acid sequence set forth in SEQ ID NO: 5.

In some embodiments, the CFI variant having has increased activity, wherein in the increased activity comprises increased cleavage of C4b and/or specificity for C4b over C3b. In some embodiments, the CFI variant having an increase in the cleavage of C4b comprises one or more substitutions in an amino acid positions set forth in SEQ ID NO: 5. In some embodiments, the amino acid position is selected from one or more of L307, T377, D420, D425, Y553, R557, P558, E401, G406, E457, E461, E487, N531, and K534 in a CFI having the amino acid sequence set forth in SEQ ID NO: 5. In some embodiments, the amino acid position is a position within the A:B interface region in a CFI having the amino acid sequence set forth in SEQ ID NO: 5. In some embodiments, the position within the A:B interface region is selected from one or more of L307 and E487. In some embodiments, the amino acid position is a position within the cofactor interface region in a CFI having the amino acid sequence set forth in SEQ ID NO: 5. In some embodiments, the position within the cofactor interface region is selected from one or more of T377 and D420. In some embodiments, the amino acid position is a position within the C-terminal extension region in a CFI having the amino acid sequence set forth in SEQ ID NO: 5. In some embodiments, the position within the C-terminal extension region is selected from one or more of D425, R557, and P558. In some embodiments, the amino acid position is a position within the c-terminal extension; C4b interface region in a CFI having the amino acid sequence set forth in SEQ ID NO: 5. In some embodiments, the position within the C-terminal extension; C4b interface region is Y553. In some embodiments, the amino acid position is a position within the C4b interface region in a CFI having the amino acid sequence set forth in SEQ ID NO: 5. In some embodiments, the position within the C4b interface region is E401. In some embodiments, the amino acid position is a position within the active site; C4b interface region in a CFI having the amino acid sequence set forth in SEQ ID NO: 5. In some embodiments, the position within the active site; C4b interface region is G406. In some embodiments, the amino acid position is a position within the autolysis loop; cofactor interface region in a CFI having the amino acid sequence set forth in SEQ ID NO: 5. In some embodiments, the position within the autolysis loop; cofactor interface region is selected from one or more of E457 and E461. In some embodiments, the amino acid position is a position within the active site; S1 entrance frame region in a CFI having the amino acid sequence set forth in SEQ ID NO: 5. In some embodiments, the position within the active site; S1 entrance frame region is N531. In some embodiments, the amino acid position is a position within the S1 entrance frame region in a CFI having the amino acid sequence set forth in SEQ ID NO: 5. In some embodiments, the position within the S1 entrance frame region is K534. These differences are as compared to wild type CFI (or compared to a fusion construct comprising wild type CFI, e.g. SEQ ID NO: 21), wherein the positions correspond to positions in a CFI having the amino acid sequence set forth in SEQ ID NO: 5.

In some embodiments, the improved characteristic is an increase in activity, wherein the increase in activity comprises an increase in the cleavage of C3b and/or C4b. In some embodiments, the CFI variants provided herein are C3b degraders, referring to the ability of the CFI variants to increase C3b cleavage. In some embodiments, the CFI variants provided herein are C4b degraders, referring to the ability of the CFI variants to increase C4b cleavage. In some embodiments, the CFI variants provided herein are C3b and C4b degraders, referring to the ability of the CFI variants to increase cleavage of both C3b and C4b.

In some embodiments, the CFI variant having has increased activity, wherein the increased activity comprises increased cleavage of C3b and C4b. In some embodiments, the CFI variant having an increase in the cleavage of C3b and C4b comprises one or more substitutions in amino acid positions set forth in SEQ ID NO: 5. In some embodiments, the amino acid position is selected from one or more of E392, E420, E401, G406, D420, D425, P558, E457, D459, N460, E461, and N531 in a CFI having the amino acid sequence set forth in SEQ ID NO: 5. In some embodiments, the amino acid position is a position within the substrate interface region in a CFI having the amino acid sequence set forth in SEQ ID NO: 5. In some embodiments, the position within the substrate interface region is E401. In some embodiments, the amino acid position is a position within the active site; substrate interface region in a CFI having the amino acid sequence set forth in SEQ ID NO: 5. In some embodiments, the position within the active site; substrate interface region is G406. In some embodiments, the amino acid position is a position within the cofactor interface region in a CFI having the amino acid sequence set forth in SEQ ID NO: 5. In some embodiments, the position within the cofactor interface region is D420. In some embodiments, the amino acid position is a position within the C-terminal extension region in a CFI having the amino acid sequence set forth in SEQ ID NO: 5. In some embodiments, the position within the c-terminal extension region is selected from one or more of D425 and P558. In some embodiments, the amino acid position is a position within the autolysis loop; cofactor interface region in a CFI having the amino acid sequence set forth in SEQ ID NO: 5. In some embodiments, the position within the autolysis loop; cofactor interface region is selected from one or more of E457, D459, N460 and E461. In some embodiments, the amino acid position is a position within the active site; S1 entrance frame region in a CFI having the amino acid sequence set forth in SEQ ID NO: 5. In some embodiments, position within the active site; S1 entrance frame region is N531. These differences are as compared to wild type CFI (or compared to a fusion construct comprising wild type CFI, e.g. SEQ ID NO: 21), wherein the positions correspond to positions in a CFI having the amino acid sequence set forth in SEQ ID NO: 5.

In some embodiments, the CFI variant having has increased activity, wherein the increase in activity comprises an increase in the cleavage of C3b by a CFI variant of the disclosure and does not comprise or minimally comprises an increase in the cleavage of C4b. In some embodiments, the CFI variant having an increase in the cleavage of C3b and does not comprise or minimally comprises an increase in the cleavage of C4b comprises one or more substitutions at positions selected from T346, E392, N422, E416, and E401 in amino acid positions set forth in SEQ ID NO: 5. In some embodiments, the amino acid position is a position within the active site; C3b interface region in a CFI having the amino acid sequence set forth in SEQ ID NO: 5. In some embodiments, the position within the active site; C3b interface region is T346. In some embodiments, the amino acid position is a position within the cofactor interface region in a CFI having the amino acid sequence set forth in SEQ ID NO: 5. In some embodiments, the position within the cofactor interface region is selected from one or more of E392 and N422. In some embodiments, the amino acid position is a position within the c-terminal extension region in a CFI having the amino acid sequence set forth in SEQ ID NO: 5. In some embodiments, the position within the C-terminal extension region is E416. These differences are as compared to wild type CFI (or compared to a fusion construct comprising wild type CFI, e.g. SEQ ID NO: 21), wherein the positions correspond to positions in a CFI having the amino acid sequence set forth in SEQ ID NO: 5.

In some embodiments, the CFI variant has increased activity, wherein the increase in activity comprises an increase in the cleavage of C4b by a CFI variant of the disclosure and does not comprise or minimally comprises an increase in the cleavage of C3b. In some embodiments, the CFI variant having an increase in the cleavage of C4b and does not comprise or minimally comprises an increase in the cleavage of C3b comprises one or more substitutions in amino acid positions set forth in SEQ ID NO: 5. In some embodiments, the amino acid position is selected from L307, T377, E460, E487, K534, Y553, and R557. In some embodiments, the amino acid position is a position within the A:B interface region in a CFI having the amino acid sequence set forth in SEQ ID NO: 5. In some embodiments, the position within the A:B interface region is one or more positions selected from L307 and E487. In some embodiments, the amino acid position is a position within the cofactor interface region in a CFI having the amino acid sequence set forth in SEQ ID NO: 5. In some embodiments, the position within the cofactor interface region is T377. In some embodiments, the amino acid position is a position within the S1 entrance frame region in a CFI having the amino acid sequence set forth in SEQ ID NO: 5. In some embodiments, the position within the S1 entrance frame region is K534. In some embodiments, the amino acid position is a position within the c-terminal extension; C4b interface region in a CFI having the amino acid sequence set forth in SEQ ID NO: 5. In some embodiments, the position within the C-terminal extension; C4b interface region is Y553. In some embodiments, the amino acid position is a position within the C-terminal extension region in a CFI having the amino acid sequence set forth in SEQ ID NO: 5. In some embodiments, the position within the C-terminal extension region is R557. These differences are as compared to wild type CFI (or compared to a fusion construct comprising wild type CFI, e.g. SEQ ID NO: 21), wherein the positions correspond to positions in a CFI having the amino acid sequence set forth in SEQ ID NO: 5.

In some embodiments, the CFI variants of the disclosure that are specific C3b degraders are useful for the treatment of diseases.

In some embodiments, the CFI variants of the disclosure that are specific C4b degraders are useful for the treatment of diseases.

In some embodiments, the CFI variants of the disclosure that are both C4b and C3b degraders, and show an improved characteristic as compared to wild type CFI (e.g. increased activity for both C4b and C3b) are useful for the treatment of diseases.

For example, the diseases that may be treated by use of the C4b degraders include, but are not limited to a non-ocular condition. In some embodiments, the non-ocular condition is a systemic chronic indication. In some embodiments, the non-ocular condition is a systemic chronic indication selected from the group consisting of: Alzheimer's disease, Amyotrophic lateral sclerosis (ALS), anti-neutrophil cytoplasmic antibody (ANCA)-associated vasculitis, antiphospholipid syndrome, asthma, atherosclerosis, atypical hemolytic uremic syndrome (aHUS), autoimmune hemolytic anemia, bullous pemphigoid (BP), C3 glomerulopathy, chronic kidney failure, chronic obstructive pulmonary disease (COPD), Cold agglutinin disease (CAD), Crohn's disease, diabetic neuropathy, generalized myasthenia gravis (gMG), Granulomatosis with Polyangiitis (GPA), Guillain-Barré Syndrome (GBS), hereditary angioedema (HAE), hidradenitis suppurativa (HS), IgA nephropathy (IgAN), lupus nephritis (LN), membranous glomerulonephritis (MN), microscopic polyangiitis (MPA), motor neuron disease, multifocal motor neuropathy (MMN), multiple sclerosis (MS), non-insulin dependent diabetes, osteoarthritis, pancreatitis, Parkinson's disease, paroxysmal nocturnal hemoglobinuria (PNH), post-transplant lymphoproliferative disease, protein losing enteropathy, psoriasis, pyoderma gangrenosum, rheumatoid arthritis, schizophrenia (SZ), systemic lupus erythematosus (SLE), immune thrombocytopenia (ITP), warm Autoimmune hemolytic anemia (wAIHA), Immune-Complex Membranoproliferative Glomerulonephritis (IC-MPGN), and ulcerative colitis, Lampert-Eaton myasthenic syndrome (LEMS), CHAPLE syndrome (CD55 deficiency), thrombotic microangiopathy (TMA) and chronic inflammatory demyelinating polyneuropathy (CIDP), Huntington disease and ischemia reperfusion injuries.

In some embodiments, the CFI variants provided here are degraders of both C3b and C4b and are useful for the treatment of diseases.

In some embodiments, an increase in activity comprises an increase in the generation of C3dg and/or C3c from iC3b. Exemplary CFI variants of the disclosure displaying this improved characteristic are a CFI variant that comprises the substitutions N531G+P535A, D425A, or D425R, wherein the positions correspond to positions in a CFI having the amino acid sequence set forth in SEQ ID NO: 5.

In some embodiments, an increase in activity comprises a reduction in the levels of C3b Δ-chain. An exemplary variant of the disclosure displaying this improved characteristic is a CFI variant that comprises the N531G+P535A substitutions, wherein the positions correspond to positions in a CFI having the amino acid sequence set forth in SEQ ID NO: 5. Other variants that exhibit similar improved characteristics are provided in Table 13, and discussed in the examples.

In some embodiments, an increase in activity comprises hydrolysis of a peptide substrate or proteolysis of a macromolecular protein substrate. In some embodiments, the macromolecular protein substrate is C3b. In some embodiments, the macromolecular protein substrate is C4b. In some embodiments, the peptide substrate is a chromogenic substrate, e.g. such peptide substrates are useful in an assay format. Exemplary CFI variants of the disclosure displaying this improved characteristic are a CFI variant that comprises the modifications L307G, E457G, E461Q, E457G+E461Q+

R462K+F464Y, N531G, N531A, P535A, N531G+P535A, Y408L, Y408L+N531G, Y408F+N531G, Y408L+N531G+ E457G+E461Q+R462K+F464Y, A(K1-P305)+N531G, Δ(K1-P305)+N531G+P535A, or the autolysis loop swap of 456-REKDNERVFS (SEQ ID NO: 9)-465 →NTASSGADYPDE (SEQ ID NO: 10), wherein the positions correspond to positions in a CFI having the amino acid sequence set forth in SEQ ID NO: 5. Other variants that exhibit similar improved characteristics are provided in Table 13, and discussed in the examples.

In some embodiments, an increase in activity comprises a reduction in the levels or function of membrane attack complex (MAC). In some embodiments, a reduction or even inhibition of hemolysis is correlated with the reducing in the levels of MAC, and accordingly, in some embodiments, an increase in activity comprises a decrease (partial or complete) in the observed hemolysis.

In some embodiments, an increase in activity comprises a reduction in the amplification of the complement system for the production of C3b. An exemplary variant of the disclosure displaying this improved characteristic is a CFI variant that comprises the N531G+P535A substitutions, wherein the positions correspond to positions in a CFI having the amino acid sequence set forth in SEQ ID NO: 5. Other variants that exhibit similar improved characteristics are provided in Table 13, and discussed in the examples.

In some embodiments, the CFI variants are sialylated. In some embodiments, the CFI variants are further sialylated as compared to a wild type CFI. In some embodiments the CFI variants are sialylated by in vitro methods post-translationally.

In some embodiments, the CFI variants are activated variants (i.e. in an active two chain form). In some embodiments, the CFI variants are activated by furin (the term furin is inclusive of furin variants). In some embodiments, the CFI variants are activated by furin during production in a host cell. In some embodiments, the activation by furin during production in a host cell is achieved by overexpression of furin, e.g. by stable or transient transfection. In some embodiments, the CFI variant is activated by furin after production and secretion by a host cell, i.e. post-translationally.

References to modifications, such as substitutions, in the following sections are modifications with respect to the amino acid sequence of human CFI as set forth in SEQ ID NO: 5. However, it should be understood that modifications to corresponding amino acid residues of any non-human species may also be made.

A:B Chain Interface CFI Variants

Provided herein are CFI variants comprising one or more modifications at the interface of the heavy and light chains, also referred to as the A:B chain interface, and variants that cause a disruption to the A:B chain interface.

Without being bound to theory or mechanism, the serine protease domain (SPD) of CFI is thought to be kept in a zymogen-like state, via numerous interactions with its own A-chain Although naturally occurring CFI can cleave peptide or protein substrates at a relatively slow rate, the rate of cleavage by CFI is increased by disrupting the A:B chain interface.

Accordingly in some embodiments, provided herein are A:B chain interface CFI variants. Specifically, provided herein are exemplary CFI variants, comprising any one or more of the modifications presented in Table 2. Table 2 presents CFI variants comprising one or more modifications to the amino acid sequence set forth in SEQ ID NO: 5, wherein the one or more modifications are at the A:B chain interface or cause a disruption to the A:B chain interface. The base molecule for the CFI variants presented in Table 2 may be wild type human CFI. It is noted that not all of the A:B chain interface CFI variants of the disclosure are provided in Table 2, and additional variants may be provided in at least the Examples and/or Table 13.

TABLE 2

Exemplary A:B Chain Interface CFI Variants

| Alterations from WT hCFI | Description of variant |
| --- | --- |
| K14A | A:B chain interface |
| Y20A | |
| Y20F | |
| D26A | |
| F29A | |
| R35A | |
| E38A | |
| M220A + K221Q | |
| S250A | |
| S250L | |
| 514-MDANNVT (SEQ ID NO: 13)-520 → NG (→ represents a replacement as used herein) | A:B chain interface: hTrypsin 200-loop swap |
| L307G | A:B chain interface |
| L304G + P305G + K306G + L307G + S308G | A:B linker |

In some embodiments, the CFI variants comprise or consist of any one or more of the modifications presented in Table 2. In some embodiments, the CFI variants comprise a modification at any one or more positions corresponding to positions K14, Y20, D26, F29, R35, E38, M220, K221, S250, L304, P305, K306, L307, and S308 in a CFI having the amino acid sequence set forth in SEQ ID NO: 5.

In some embodiments, the CFI variants comprise or consist of a substitution in a 200 loop of the CFI (MDANNVT, SEQ ID NO: 13) for a 200 loop of trypsin having amino acid residues NG, wherein the 200 loop occurs between positions corresponding to position 514 and position 520 in a CFI having the amino acid sequence set forth in SEQ ID NO: 5.

In some embodiments, the CFI variants comprise or consist of any one or more of the substitutions selected from K14A, Y20A, Y20F, D26A, F29A, R35A, E38A, M220A, K221Q, S250A, S250L, L304G, P305G, K306G, L307G, and S308G, wherein the positions correspond to positions in a CFI having the amino acid sequence set forth in SEQ ID NO: 5.

In some embodiments, the CFI variants comprise or consist of any one or more of the combination of substitutions M220A and K221Q, and L304G+P305G+K306G+ L307G+S308G, wherein the positions correspond to positions in a CFI having the amino acid sequence set forth in SEQ ID NO: 5.

C-Terminal Region Variants

In the complex formed between CFI and C3b, the C-terminal extension region is positioned in a cavity between the A and B chain of the bound and slightly twisted CFI molecule. This suggests that the C-terminal extension of CFI could be an important regulatory region for the activation of CFI upon binding to C3b.

Accordingly, provided herein are C-terminal region CFI variants. Table 3 presents exemplary CFI variants comprising or consisting of one or more modifications to the amino acid sequence set forth in SEQ ID NO: 5, wherein the one or more modifications are at the C-terminal region or extension of CFI. The base molecule for the CFI variants presented in Table 3 may be a wild type human CFI. It is noted that not all of the C-terminal region CFI variants of the disclosure are provided in Table 3, and additional variants may be provided in at least the Examples and/or Table 13.

TABLE 3

Exemplary C-Terminus CFI Variants

| Alterations from WT hCFI | Description |
|---|---|
| D425A | C-term extension |
| D425K | |
| D425R | |
| ΔC-term (Δ558-PFISQYNV (SEQ ID NO: 14)-565) | |
| R557A | |
| R557K | C-terminal extension region |
| P558G | |
| P558L | |
| P384A | 60-loop (extra position not in chymotrypsinogen) |
| P384A | 70-loop (extra position not in chymotrypsinogen) |
| P384G | |
| 420-DGNK (SEQ ID NO: 15)-424 --> GG | 110-loop (extra position not in chymotrypsinogen) |
| P558S | C-terminal extension |
| F559L | |
| I560V | |
| Y563H | |
| P558S + F559L + I560V + Y563H | mCFI C-terminal extension |
| Y403F | 99-loop |
| A405S | |
| G406R | |
| Q409D | |
| A405S + G406R + Y408L + Q409D | |
| A405S + G406A + Y408L + Q409D | |
| Q409Y | |
| Q409H | |
| G406A | |
| G406A + Y408L | |
| T377G | 70-loop |
| W381A | |
| W381A + P384A | |
| W381A + ΔP384 | |
| G556A | |
| G556S | |

In some embodiments, the CFI variants comprise any one or more of the modifications presented in Table 3.

In some embodiments, the CFI variants comprise or consist of a modification at any one or more positions corresponding to positions T377, W381, P384, Y403, A405, G406, Y408, Q409, D425, G556, R557, P558, P559, I560, and Y563 in a CFI having the amino acid sequence set forth in SEQ ID NO: 5.

In some embodiments, the CFI variants comprise or consist of a deletion of amino acid residues (PFISQYNV, SEQ ID NO: 14) between positions corresponding to positions 558 to 565 in a CFI having the amino acid sequence set forth in SEQ ID NO: 5.

In some embodiments, amino acid residues, the CFI variants comprise or consist of a substitution in a 110 loop of the CFI (DGNK, SEQ ID NO: 15) between positions corresponding to positions 420 to 424 in a CFI having the amino acid sequence set forth in SEQ ID NO: 5 are substituted for a linker, e.g. GG.

In some embodiments, the CFI variants comprise or consist of any one or more of the substitutions selected from T377G, W381A, P384A, P384G, Y403F, A405S, G406R, G406A, Y408L, Q409D, Q409H, D425A, D425K, D425R, G556A, G556S, R557A, R557K, P558G, P558L, P558S, F559L, I560V, and Y563H, and/or a deletion of P384, wherein the positions correspond to positions in a CFI having the amino acid sequence set forth in SEQ ID NO: 5.

In some embodiments, the CFI variants comprise or consist of any one or more of the combination modifications selected from P558S+F559L+I560V+Y563H, A405S+G406R+Y408L+Q409D, A405S+G406A+Y408L+Q409D, G406A+Y408L, and W381A+ΔP384, wherein the positions correspond to positions in a CFI having the amino acid sequence set forth in SEQ ID NO: 5.

N-linked Glycosylation Site Variants

Provided herein are CFI variants comprising at least one CFI domain, wherein the at least one CFI domain comprises one or more modifications at N-linked glycosylation sites of CFI.

In some embodiments, the modification at the N-linked glycosylation site is a removal of one or more N-linked glycosylation sites of a CFI.

Accordingly, provided herein are N-linked glycosylation site CFI variants. Specifically, provided herein are exemplary CFI variants comprising or consisting of any one or more of the modifications presented in Table 4. Table 4 presents exemplary CFI variants comprising one or more modifications to the amino acid sequence set forth in SEQ ID NO: 5, wherein the one or more modifications are at the N-linked glycosylation site of CFI. The base molecule for the CFI variants presented in Table 4 may be wild type human CFI. It is noted that not all of the N-linked glycosylation site variants of the disclosure are provided in Table 4, and additional variants may be provided in at least the Examples and/or Table 13.

TABLE 4

Exemplary N-Linked Glycosylation Site CFI Variants

| Alterations from WT hCFI | Description |
|---|---|
| N52Q | A-chain (FIMAC), Remove N-linked glycosylation site |
| N85Q | |
| N159Q | A-chain (SRCR), Remove N-linked glycosylation site |
| N446Q | 130-loop, Remove N-linked glycosylation site |
| N476Q | 170-loop, Remove N-linked glycosylation site |
| N518Q | 200-loop, Remove N-linked glycosylation site |
| N52Q + N85Q + N159Q | A-chain glycosylations, Remove all N-linked glycosylation sites of A-chain |
| N446Q + N476Q + N518Q | B-chain glycosylations, Remove all N-linked glycosylation sites of B-chain (SPD) |
| N52Q + N85Q + N159Q + N446Q + N476Q + N518Q | CFI glycosylations, Remove all N-linked glycosylation sites in CFI |

Without being bound by any theory or mechanism, exemplary CFI variants comprising an N-linked glycosylation site modification may include the following variants.

In some embodiments, the CFI variants comprise any one or more of the modifications presented in Table 4.

In some embodiments, the CFI variants comprise or consist of a modification at any one or more positions corresponding to positions N52, N85, N159, N446, N476, and N518 in a CFI having the amino acid sequence set forth in SEQ ID NO: 5.

In some embodiments, the CFI variants comprise or consist of any one or more of the substitutions selected from N52Q, N85Q, N159Q, N446Q, N476Q, and N518Q, wherein the positions correspond to positions in a CFI having the amino acid sequence set forth in SEQ ID NO: 5.

In some embodiments, the CFI variants comprise or consist of any one or more of combination of substitutions selected from N52Q+N85Q+N159Q, N446Q+N476Q+N518Q, and N52Q+N85Q+N159Q+N446Q+N476Q+N518Q, wherein the positions correspond to positions in a CFI having the amino acid sequence set forth in SEQ ID NO: 5.

Serine Protease Domain Variants

Provided herein are CFI variants comprise or consist of at least one CFI domain, wherein the at least one CFI domain is the serine protease domain (SPD) of CFI, and wherein the CFI variant comprises one or more modifications at the SPD.

In the crystal structure of free CFI, cleavage of the activation loop did not result in the insertion of the newly formed N-terminal (Ile322), which is the next step in the classical activation of serine proteases. Instead, the crystal structure suggests that the C-terminal region of the cleaved activation loop remains in a tightly bent loop structure on the surface of CFI, in the same area that the uncleaved activation loop would have remained. This prevents the insertion into the activation pocket, and thus, maturation of the active site (referred to as classical serine protease activation via induced conformational rearrangements). Upon proteolytic activation of the SPD of CFI the new N-terminus of the activation loop is generally released and inserted into the activation pocket such that the cleaved activation loop forces a full activation of CFI in solution. Thus, mutations in the C-terminal region of the activation loop should not affect cleavage by furin, as the region is beyond the 3' positions relative to the scissile bond.

Accordingly, provided herein are SPD CFI variants. In some embodiments, the CFI variants comprising one or more modifications within regions of the SPD of CFI (FIG. 1) may comprise one or more modifications at any one or more of the activation loop (residues 322-326 of SEQ ID NO: 5), 37-Loop (residues 342-344 of SEQ ID NO: 5), 60-Loop (residues 366-372 of SEQ ID NO: 5), 70-Loop (residues 377-389 of SEQ ID NO: 5), 99-Loop (residues 403-410 of SEQ ID NO: 5), 110-Loop (residues 418-426 of SEQ ID NO: 5), 150-Autolysis Loop (residues 455-463 of SEQ ID NO: 5), 180-Loop Oxyanion Stabilizing (residues 494-509 of SEQ ID NO: 5), and/or 220-Loop S1 Entrance Frame (residues 529-536 of SEQ ID NO: 5). Specifically, provided herein are CFI variants comprising the SPD of CFI, and wherein the CFI variant comprises any one or more of the modifications presented in Table 5. Table 5 presents exemplary CFI variants comprising one or more modifications to the amino acid sequence set forth in SEQ ID NO: 5, wherein the one or more modifications are in the SPD. The base molecule for the CFI variants presented in Table 5 may be a wild type, human CFI, or a CFI-SPD, wherein the SPD corresponds to that of a wild type CFI (also referred to as Δ(K1-P305) or an A-chain deletion), or a CFI fused with another complement regulator such as Factor H (FH-CFI) or CR1 (CR1-CFI) which are discussed in further detail herein when referring to fusion constructs.

It is noted that not all of the SPD CFI variants of the disclosure are provided in Table 5, and additional variants may be provided in at least the Examples and/or Table 13.

TABLE 5

Exemplary Serine Protease Domain CFI Variants

| Alterations from WT hCFI | Base Molecule | Description |
|---|---|---|
| K326A-R327A | hCFI | SPD Activation loop |
| N531G + P535A | | SPD S1 entrance frame |
| Y408L | | SPD 99-position |
| 456-REKDNERVFS (SEQ ID NO: 9)-465 --> NTASSGADYPDE (SEQ ID NO: 10) | | SPD Autolysis loop, hTrypsin autolysis loop swap |
| E457G + E461Q-R462K + F464Y | | SPD Autolysis loop, mCFI autolysis loop swap |
| N531G | | SPD S1 entrance frame |
| N531A | | SPD S1 entrance frame |
| P535A | | SPD S1 entrance frame |
| Y408F | | SPD 99-loop |
| E530D | | SPD S1 entrance frame |
| E457G | | SPD Mouse autolysis loop |
| E461Q | | |
| R462K | | |
| F464Y | | |
| Δ(K1-P305) + N531G | CFI-SPD | HSA-SPD (ΔA-chain) + S1 entrance, combination |
| Δ(K1-P305) + N531G + P535A | | |

TABLE 5-continued

Exemplary Serine Protease Domain CFI Variants

| Alterations from WT hCFI | Base Molecule | Description |
| --- | --- | --- |
| Y408L + N531G + E457G | hCFI | 99-loop + S1 entrance frame + reduced mCFI autolysis loop |
| Y408L + N531G + E457G + E461Q | | |
| Δ(K1-P305) + Y408L + N531G + E457G + E461Q + R462K + F464Y | | ΔA-chain + 99-loop + S1 entrance frame + mCFI autolysis loop |
| Y408L + N531G + P535A | | 99-position + S1 entrance frame |
| K14A + D425R | | A-chain + SPD (110-loop) |
| FH_CCP1-8 + GGGGGGGGGGGG (SEQ ID NO: 25) + ΔHSA + Y408L + N531G + E457G + E461Q + R462K + F464Y | FH-CFI + Y408L + N531G + E457G + E461Q + R462K + F464Y | FH-CFI fusion (fusion #1) + 99-position + S1 entrance + mCFI autolysis loop |
| Y408G | hCFI | SPD 99-loop |
| Y408P | | |
| Y408D | | |
| Y408A | | |
| Y408N | | |
| Y408T | | |
| Y408K | | |
| Y408R | | |
| Y408H | | |
| Y408I | | |
| P535K | | SPD S1 entrance, Partial Trypsin S1 entrance frame |
| K534Q | | |
| E530D-N531G + G533A-K534Q-P535K-E536N | | SPD S1 entrance, Trypsin S1 entrance frame |
| N402E | | SPD (99-loop) |
| N422K | | SPD (110-loop) |
| E461K | | SPD (150-loop/autolysis loop) |
| A502S + K504Q + F537K | | SPD (S1-pocket), Trypsin S1 pocket |
| A502S | | |
| K504Q | | SPD (S1 pocket) |
| K504R | | |
| K504A | | |
| K504G | | |
| K504L | | |
| K504P | | |
| K504H | | |
| A361G | | SPD (active site) |
| T495F + Y496L + D497E + S499G + I500K + G533A + | | SPD (180 loop) |
| G533A + K534Q + P535K + E536N + F537K | | SPD (220 loop) |
| T495F + Y496L + D497E + S499G + I500K + G533A + K534Q + P535K + E536N + F537K | | SPD (180 and 220 loop) |
| F537K | | SPD (220-loop) |
| F537R | | |
| Q467K | | SPD (150-loop/autolysis loop region) |
| Q467R | | |
| Q467K + F537K | | SPD (150-loop/autolysis loop region and 220-loop) |
| E530G | | SPD |
| E530G + N531G | | S1 entrance frame |
| E530F | | SPD |
| E530Y | | S1 entrance frame |
| E530D + F537K | | S1 entrance frame + 220 loop |
| E457G + E461Q | | SPD (150-loop/autolysis loop) |
| E457A | | |
| E461K | | |
| E461R | | |
| E461H | | |
| E461G | | |

TABLE 5-continued

Exemplary Serine Protease Domain CFI Variants

| Alterations from WT hCFI | Base Molecule | Description |
|---|---|---|
| R462A | | |
| R462D | | |
| E457G + E461G | | |
| Y408L-N531G + E457G + E461Q | | SPD 99-position + S1 entrance + opt mCFI autolysis loop |
| N531G + E457G + E461Q | | 99-position + S1 entrance + opt mCFI autolysis loop |
| W381K | | SPD (70-loop) |
| I322Y | | SPD (Activation loop) |
| N404G | | SPD (99-loop region) |
| D506A | | SPD (N-terminal insertion) |
| D506V | | SPD (N-terminal insertion) |
| D506E | | SPD (N-terminal insertion) |
| D506G | | |
| I322V | | Activation loop region (N-terminal insertion), mCFI Activation loop |
| I322V + V323I | | |
| R327P | | |
| I322V + V323I + R327P | | |
| V323G | | Activation loop region (N-terminal insertion) |
| V323A | | Activation loop region (N-terminal insertion) |
| A328C + W468C | | Activation loop region (N-terminal insertion) |
| A328C + W468C + K326Y + R327N | | |
| Y408L + N531G + E461Q | | 99-loop + S1 entrance frame + reduced mCFI autolysis loop |
| Δ(K1-P305) + Y408L + N531G + E457G + E461Q | | ΔA-chain + 99-position + S1 entrance frame + mCFI autolysis loop |
| Y408L + N531G + E457G+ E461Q + R462K | | 99-loop + S1 entrance frame + mCFI autolysis loop |
| Y408L + N531G + E457G + E461Q + F464Y | | |
| Y408L + N531G + E457G + R462K + F464Y | | |
| Y408L + N531G+ E461Q + R462K + F464Y | | |
| Y408L + E457G + E461Q + R462K + F464Y | | |
| E457G + N531G + E461Q + R462K + F464Y | | |
| Y408L + E457G + E461Q + R462K | | 99-loop + S1 entrance frame + mCFI autolysis loop |
| N531G + E457G + E461Q + F464Y | | |
| E416A | | 110-loop |
| E416A + D425R | | |
| Y408L + N531G + E457G + E461Q + R462K + F464Y + S507A | | 99-loop + S1 entrance frame + mCFI autolysis loop + active site (S195A) |
| E536A | | S1 entrance frame region |
| E457A | | SPD (150-loop/autolysis loop) |
| E457D | | |
| E457F | | |
| E457H | | |
| E457I | | |
| E457K | | |
| E457L | | |
| E457M | | |
| E457N | | |
| E457P | | |
| E457Q | | |
| E457R | | |
| E457S | | |
| E457T | | |
| E457W | | |
| E457Y | | |
| E457V | | |
| Y408E | | SPD (99-loop) |
| Y408F | | |
| Y408L | | |
| Y408M | | |
| Y408Q | | |
| Y408S | | |

TABLE 5-continued

| Exemplary Serine Protease Domain CFI Variants | | |
|---|---|---|
| Alterations from WT hCFI | Base Molecule | Description |
| Y408W | | |
| Y408V | | |
| E461A | | SPD (150-loop/autolysis loop) |
| E461D | | |
| E461F | | |
| E461G | | |
| E461H | | |
| E461I | | |
| E461K | | |
| E461L | | |
| E461M | | |
| E461N | | |
| E461P | | |
| E461R | | |
| E461S | | |
| E461T | | |
| E461W | | |
| E461Y | | |
| E461V | | |
| E457G + E461G | | |
| D341A | | SPD (37 loop) |
| R456A | | SPD (150-loop/autolysis loop) |
| K312A | | Activation loop region |
| R314A | | |
| K312A + R314A | | |
| N531D | | S1 entrance frame |
| N531E | | |
| N531F | | |
| N531H | | |
| N531I | | |
| N531K | | |
| N531L | | |
| N531M | | |
| I322T | | SPD (Activation loop) |
| N531P | | S1 entrance frame |
| N531Q | | |
| N531R | | |
| N531S | | |
| N531T | | |
| N531V | | |
| N531W | | |
| N531Y | | |
| G469L | | Activation pocket |
| R456N | | Activation pocket/autolysis loop |
| K458A | | |
| G469L + R456N + E457T + K458A | | |
| G469L + R456N + K458A | | |
| G469L + R456N + K458A + E461G | | |
| G469L + R456N + K458A + E461G + F537K | | Activation pocket/autolysis loop + 220 loop |
| K504F | | |
| K504I | | |
| K504M | | |
| K504N | | |
| K504S | | |
| K504T | | |
| K504V | | |
| K504W | | |
| K504Y | | |
| G406D | | SPD (99-loop) |
| G406E | | |
| G406F | | |
| G406H | | |
| G406I | | |
| G406K | | |
| G406L | | |
| G406M | | |
| G406N | | |
| G406P | | |
| G406Q | | |
| G406S | | |
| G406T | | |
| G406V | | |

TABLE 5-continued

Exemplary Serine Protease Domain CFI Variants

| Alterations from WT hCFI | Base Molecule | Description |
|---|---|---|
| G406W | | |
| G406Y | | |
| G406D + Y408L | | SPD (99-loop), G406D combination |
| G406D + N531G | | |
| G406D + P535A | | |
| G406D + Y408L + N531G | | |
| G406D + N531G + P535A | | |
| G406D + Y408L + N531G + P535A | | |
| K340G | | SPD (37-loop) |
| I345G | | |
| K340G + I345G | | |
| L364G | | SPD (60-loop) |
| Y372G | | |
| L364G + Y372G | | |
| P384A | | SPD (80-loop) |
| P384G | | |
| W381G | | |
| V390G | | |
| W381G + V390G | | |
| W381G + P384A + V390G | | |
| W381G + P384G + V390G | | |
| Q409G | | SPD (99-loop) |
| N404G + Q409G | | |
| K418G | | SPD (110-loop) |
| D425G | | |
| K418G + D425G | | |
| S465G | | SPD (150/autolysis-loop) |
| G344R | | SPD (37-loop) |
| G344K | | |
| G344Y | | |
| T346R | | |
| T346K | | |
| T346H | | |
| K504E | | SPD (S1 entrance) |
| K504D | | |
| E530R | | SPD (220-loop) |
| E530K | | |
| T346R + K504E + E530R | | SPD (37-loop + S1 entrance frame + 220-loop) |
| T346K + K504D + E530K | | |
| G344R + Y408L + N531G | | |
| G344K + Y408L + N531G | | SPD (37-loop + 99-position + S1 entrance frame) |
| T346R + Y408L + N531G | | |
| T346K + Y408L + N531G | | |
| K504D + Y408L + N531G | | SPD (99-loop + S1 entrance) |
| K504E + Y408L + N531G | | |
| Y408L + E530R + N531G | | SPD (99-loop + 220-loop + S1 entrance frame) |
| Y408L + E530K + N531G | | |
| T346R + Y408L + K504E + E530R + N531G | | SPD (37-loop + 99-loop + 220-loop + S1 entrance frame) |
| T346K + Y408L + K504D + E530K + N531G | | |
| Y408L + S507A + N531G | | SPD (99-loop + S1 entrance frame + catalytic triad) |
| Y408L + N531G + E457G + E461Q + R462K + F464Y + S507A | | SPD (99-loop + S1 entrance frame + mCFI autolysis loop + catalytic triad) |
| E457G + S507A | | SPD (Autolysis loop + catalytic triad) |
| N531G + P535A + S507A | | SPD (S1 entrance frame + catalytic triad) |

In some embodiments, the CFI variants comprise any one or more modifications presented in Table 5.

In some embodiments, the CFI variants comprise an autolysis loop substitution. The autolysis loop of serine proteases is part of the activation domain and are involved in substrate specificity. Trypsin has a longer autolysis loop than CFI, and several key residues are unique between the autolysis loops of trypsin and CFI. Differences may also occur between the autolysis loops from different species, such as between mouse and human. The mouse CFI autolysis loop may include a large number of differences as compared to the CFI autolysis loop of human CFI. Exemplary CFI variants may include a CFI variant wherein the autolysis loop of human CFI is swapped with that of human trypsin or swapped with that of mouse CFI. Such autolysis loop variants may help to identify critical residues that are involved in C3b and/or C4b cleavage activity. Accordingly, in some embodiments, provided herein are CFI variants, wherein the CFI variant is a chimera comprising one or more domains from a human CFI, and wherein the human CFI further comprises a substitution of one or more amino acid residues for amino acid residues of a corresponding region from a non-human species CFI. In some embodiments, the non-human species CFI is mouse CFI. Provided also herein are CFI variants wherein the CFI variant is a chimera, and wherein the modification comprises the substitution of one or more amino acid residues of the CFI with amino acid residues from a corresponding region of a non-CFI serine protease. In some embodiments, the non-CFI serine protease is trypsin.

An exemplary autolysis loop CFI variant includes a trypsin autolysis loop substitution, comprising a substitution of an autolysis loop of the CFI (REKDNERVFS, SEQ ID NO: 9) for an autolysis loop of trypsin (NTASSGADYPDE, SEQ ID NO: 10), wherein the autolysis loop occurs between positions corresponding to position 456 and position 465 in a CFI having the amino acid sequence set forth in SEQ ID NO: 5.

Another exemplary autolysis loop CFI variant includes a mouse CFI autolysis loop swap, wherein $^{456}$REKD-NERVFS$^{465}$ (SEQ ID NO: 9) swapped to RGKDNQKVYS (SEQ ID NO: 11), wherein the autolysis loop occurs between positions corresponding to position 456 and position 465 in a CFI having the amino acid sequence set forth in SEQ ID NO: 5.

In some embodiments, the CFI variants comprise or consist of one or more modifications at any one or more of the activation loop (residues 322-326 of SEQ ID NO: 5), 37-Loop (residues 342-344 of SEQ ID NO: 5), 60-Loop (residues 366-372 of SEQ ID NO: 5), 70-Loop (residues 377-389 of SEQ ID NO: 5), 99-Loop (residues 403-410 of SEQ ID NO: 5), 110-Loop (residues 418-426 of SEQ ID NO: 5), 150-Autolysis Loop (residues 455-463 of SEQ ID NO: 5), 180-Loop Oxyanion Stabilizing (residues 494-509 of SEQ ID NO: 5), and/or 22-Loop S1 Entrance Frame (residues 529-536 of SEQ ID NO: 5) of SPD.

In some embodiments, the CFI variants comprise or consist of a modification at any one or more positions corresponding to positions K14, K312, R314, I322, V323, K326, R327, A328, K340, D341, G344, I345, T346, A361, L364, Y372, W381, P384, V390, N402, N404, G406, Y408, Q409, E416, K418, N422, D425, E457, K458, R456, E461, R462, F464, S465, Q467, W468, G469, T495, Y496, D497, S499, I500, A502, K504, D506, S507, E530, N531, E530, N531, G533, K534, P535, E536, and F537 in a CFI having the amino acid sequence set forth in SEQ ID NO: 5.

In some embodiments, the CFI variants comprise or consist of any one or more of the substitutions selected from K14A, K312A, R314A, I322T, I322Y, I322V, V323I, V323G, V323A, K326A, R327A, R327P, R327N, A328C, K340G, D341A, G344R, G344K, G344Y, I345G, T346R, T346K, T346H, A361G, L364G, Y372G, W381K, W381G, P384A, P384G, V390G, N402E, N404G, G406D, G406E, G406F, G406H, G406I, G406K, G406L, G406M, G406N, G406P, G406Q, G406S, G406T, G406V, G406W, G406Y, Y408L, Y408F, Y408G, Y408P, Y408D, Y408A, Y408N, Y408T, Y408K, Y408R, Y408H, Y408I, Y408E, Y408M, Y408Q, Y408S, Y408W, Y408V, Q409G, E416A, K418G, N422K, D425A, D425K, D425R, D425G, R456A, R456N, E457G, E457A, E457D, E457F, E457H, E457I, E457K, E457L, E457M, E457N, E457P, E457Q, E457R, E457S, E457T, E457W, E457Y, E457V, K458A, E461Q, E461K, E461R, E461H, E461G, E461A, E461D, E461F, E461I, E461L E461M, E461N, E461P, E461S, E461T, E461W, E461Y, E461V, R462K, R462A, R462D, F464Y, S465G, Q467K, Q467R, W468C, G469L, T495F, Y496L, D497E, S499G, I500K, A502S, K504Q, K504E, K504R, K504A, K504G, K504L, K504P, K504H, K504D, K504F, K504I, K504M, K504N, K504S, K504T, K504V, K504W, K504Y, D506A, D506V, D506E, D506G, S507A, E530D, E530G, E530F, E530Y, N531G, N531A, E530D, E530G, E530F, E530Y, E530R, E530K, N531D, N531E, N531F, N531H, N5311, N531K, N531L, N531M, N531P, N531Q, N531R, N531S, N53iT, N531V, N531W, N531Y, G533A, K534Q, P535A, P535K, E536N, E536A, F537K and F537R, wherein the positions correspond to positions in a CFI having the amino acid sequence set forth in SEQ ID NO: 5.

In some embodiments, the CFI variants comprise or consist of any one or more of the combination substitutions selected from K326A+R327A, N531G+P535A, E457G+E461Q+R462K+F464Y, Y408L+N531G+E457G, Y408L+N531G+E457G+E461Q, Y408L+N531G+E457G+E461Q, Y408L+N531G+E457G+E461Q-R462K+F464Y, Y408L+N531G+P535A, K14A+D425R, E530D+N531G+G533A+K534Q+P535K+E536N, A502S+K504Q+F537K, T495F+Y496L+D497E+S499G+I500K, G533A+K534Q+P535K+E536N+F537K, T495F+Y496L+D497E+S499G+I500K+G533A+K534Q+P535K+E536N+F537K, Q467K+F537K, E530G+N531G, E530D+F537K, E457G+E461Q, E457G+E461G, Y408L+N531G+E457G+E461Q, N531G+E457G+E461Q, I322V+V3231, 1322V+V323I+R327P, A328C+W468C, A328C+W468C+K326Y+R327N, Y408L+N531G+E461Q, Y408L+N531G+E457G+E461Q+R462K, Y408L+N531G+E457G+E461Q+F464Y, Y408L+N531G+E457G+R462K+F464Y, Y408L+N531G+E461Q+R462K+F464Y, Y408L+E457G+E461Q+R462K+F464Y, E457G+N531G+E461Q+R462K+F464Y, Y408L+E457G+E461Q+R462K, N531G+E457G+E461Q+F464Y, E416A+D425R, Y408L+N531G+E457G+E461Q+R462K+F464Y+S507A, E457G+E461G, K312A+R314A, G469L+R456N+E457T+K458A, G469L+R456N+K458A, G469L+R456N+K458A+E461G, G469L+R456N+K458A+E461G+F537K, G406D+Y408L, G406D+N531G, G406D+P535A, G406D+Y408L+N531G, G406D+Y408L+P535A, G406D+N531G+P535A, G406D+Y408L+N531G+P535A, K340G+I345G, L364G+Y372G, W381G+V390G, W381G+P384A+V390G, W381G+P384G+V390G, N404G+Q409G, K418G+D425G, T346R+K504E+E530R, T346K+K504D+E530K, G344R+Y408L+N531G, G344K+Y408L+N531G, T346R+Y408L+N531G, T346K+Y408L+N531G, K504D+Y408L+N531G, K504E+Y408L+N531G, Y408L+E530R+N531G, Y408L+E530R+N531G, T346R+Y408L+K504E+N531G, E530R+N531G, T346K+Y408L+K504D+E530K+N531G, Y408L+S507A+N531G, Y408L+N531G+E457G+E461Q+R462K+F464Y+S507A, E457G+S507A, and N531G+P535A+S507A, wherein the positions correspond to positions in a CFI having the amino acid sequence set forth in SEQ ID NO: 5.

Active Site Variants

Provided herein are CFI variants comprising or consisting one or more modifications at the active site of CFI. In some embodiments, provided herein are CFI variants comprising at least one CFI domain, wherein the at least one CFI domain comprises a modification to the amino acid sequence set forth in SEQ ID NO: 5, wherein the modification is at the active site of CFI. In some embodiments, the active site CFI variants may improve the catalytic potential of CFI. In some embodiments, the CFI active site variants may improve the catalytic potential of CFI by improving the active site (catalytic machinery) without affecting C3b or C4b binding or binding specificity, which is dominated by exosite and A-chain interactions.

Accordingly, provided herein are active site CFI variants. Specifically, provided herein are exemplary CFI variants comprising a modification presented in Table 6. Table 6 presents CFI variants comprising one or more modifications to the amino acid sequence set forth in SEQ ID NO: 5, wherein the one or more modifications are at the active site of CFI. The base molecule for the CFI variants presented in Table 6 may be wild type human CFI.

TABLE 6

Exemplary Active Site CFI Variants

| Alterations from WT hCFI | Description of variant, purpose of modification |
|---|---|
| S507A | Active site (S195A) |

In some embodiments, the CFI variants comprise or consist of modifications presented in Table 6.

In some embodiments, the CFI variants comprise or consist of a modification at a position corresponding to position S507 in a CFI having the amino acid sequence set forth in SEQ ID NO: 5.

In some embodiments, the CFI variants comprise or consist of a substitution S507A, wherein the position corresponds to position S507 in a CFI having the amino acid sequence set forth in SEQ ID NO: 5.

A-B Chain Inversion CFI Variants

Provided herein are CFI variants, wherein the CFI comprises an A chain and a B chain, and comprise an inversion of the A chain and the B chain. In some embodiments, the CFI variants without a chain inversion (the individual chains optionally comprising one or more modifications) comprise a structural arrangement from N-terminus to C-terminus, or C-terminus to N-terminus, as (A chain)-(optional linker)-(B chain). In some embodiments, the CFI variants comprise an inversion of the A chain and the B chain (the individual chains optionally comprising one or more modifications), such that the structural arrangement from N-terminus to C-terminus, or C-terminus to N-terminus, is (B chain)-(optional linker)-(A chain). The optional linkers may be of any suitable length, e.g. of at least one amino acid. A linker may be a flexible linker, and may be a peptide of about 1 to about 20 amino acid residues in length, wherein the amino acid residues may comprise glycine residues. The linker may also optionally comprise serine residues. Exemplary flexible linkers can include, but are not limited to, glycine polymers, glycine-serine polymers, glycine-alanine polymers, alanine-serine polymers, or any other suitable flexible linkers known in the art. An exemplary linker is GGSSGG" (SEQ ID NO: 6), wherein n is any number from about 1 to about 20. Exemplary linkers of can be 1-50, 5-50, 10-50, 15-50, 20-50, 25-50, 1-20, 2-20, 3-20, 4-20, 5-20, 6-20, 7-20, 8-20, 9-20, 10-20, 3-15, 3-10, 3-9, 3-8, 3-7, 3-6, 3-5, 4-15, 4-10, 4-9, 4-8, 4-7, 4-6, 4-5, 5-15, 5-10, 5-9, 5-8, 5-7, 5-6, 6-15, 6-10, 6-9, 6-8, or 6-7 amino acids in length.

Accordingly, provided herein are CFI variants, wherein the CFI comprises an A chain and a B chain, and wherein the structural arrangement from N-terminus to C-terminus, or C-terminus to N-terminus, is (B chain)-(optional linker)-(A chain). Such fusion constructs are presented in Table 7. Table 7 presents exemplary CFI variants comprising or consisting of one or more modifications relative to the amino acid sequence set forth in SEQ ID NO: 5, wherein the one or more modifications are an inversion of the A and B chains of CFI.

TABLE 7

Exemplary CFI Chain Inversion Variants

| Alterations from WT hCFI | Description | Amino Acid Sequence |
|---|---|---|
| V311-V565 - G(10) - K1-G310 | A:B inversion + Gly linker | VKNRMHIRRKRIVGGKRAQLGDLPWQVAIKD ASGITCGGIYIGGCWILTAAHCLRASKTHRYQI WTTVVDWIHPDLKRIVIEYVDRIIFHENYNAG TYQNDIALIEMKKDGNKKDCELPRSIPACVPW SPYLFQPNDTCIVSGWGREKDNERVFSLQWG EVKLISNCSKFYGNRFYEKEMECAGTYDGSID ACKGDSGGPLVCMDANNVTYVWGVVSWGE NCGKPEFPGVYTKVANYFDWISYHVGRPFISQ YNVGGGGGGGGGGKVTYTSQEDLVEKKCLA KKYTHLSCDKVFCQPWQRCIEGTCVCKLPYQ CPKNGTAVCATNRRSFPTYCQQKSLECLHPGT KFLNNGTCTAEGKFSVSLKHGNTDSEGIVEVK LVDQDKTMFICKSSWSMREANVACLDLGFQQ GADTQRRFKLSDLSINSTECLHVHCRGLETSL AECTFTKRRTMGYQDFADVVCYTQKADSPM DDFFQCVNGKYISQMKACDGINDCGDQSDEL CCKACQGKGFHCKSGVCIPSQYQCNGEVDCIT GEDEVGCAGFASVTQEETEILTADMDAERRRI KSLLPKLSCG (SEQ ID NO: 17) |
| V311-V565 - G(13) - K1-G310 | | VKNRMHIRRKRIVGGKRAQLGDLPWQVAIKD ASGITCGGIYIGGCWILTAAHCLRASKTHRYQI WTTVVDWIHPDLKRIVIEYVDRIIFHENYNAG TYQNDIALIEMKKDGNKKDCELPRSIPACVPW SPYLFQPNDTCIVSGWGREKDNERVFSLQWG EVKLISNCSKFYGNRFYEKEMECAGTYDGSID ACKGDSGGPLVCMDANNVTYVWGVVSWGE NCGKPEFPGVYTKVANYFDWISYHVGRPFISQ YNVGGGGGGGGGGGGKVTYTSQEDLVEKK CLAKKYTHLSCDKVFCQPWQRCIEGTCVCKL PYQCPKNGTAVCATNRRSFPTYCQQKSLECL HPGTKFLNNGTCTAEGKFSVSLKHGNTDSEGI VEVKLVDQDKTMFICKSSWSMREANVACLDL GFQQGADTQRRFKLSDLSINSTECLHVHCRGL ETSLAECTFTKRRTMGYQDFADVVCYTQKAD SPMDDFFQCVNGKYISQMKACDGINDCGDQS DELCCKACQGKGFHCKSGVCIPSQYQCNGEV |

TABLE 7-continued

Exemplary CFI Chain Inversion Variants

| Alterations from WT hCFI | Description | Amino Acid Sequence |
|---|---|---|
| | | DCITGEDEVGCAGFASVTQEETEILTADMDAE RRRIKSLLPKLSCG (SEQ ID NO: 18) |
| V311-V565 - G(10) - K1-G310 + C309S + C435S | A:B inversion + Gly linker + no interdomain disulfide | VKNRMHIRRKRIVGGKRAQLGDLPWQVAIKD ASGITCGGIYIGGCWILTAAHCLRASKTHRYQI WTTVVDWIHPDLKRIVIEYVDRIIFHENYNAG TYQNDIALIEMKKDGNKKDCELPRSIPASVPW SPYLFQPNDTCIVSGWGREKDNERVFSLQWG EVKLISNCSKFYGNRFYEKEMECAGTYDGSID ACKGDSGGPLVCMDANNVTYVWGVVSWGE NCGKPEFPGVYTKVANYFDWISYHVGRPFISQ YNVGGGGGGGGGKVTYTSQEDLVEKKCLA KKYTHLSCDKVFCQPWQRCIEGTCVCKLPYQ CPKNGTAVCATNRRSFPTYCQQKSLECLHPGT KFLNNGTCTAEGKFSVSLKHGNTDSEGIVEVK LVDQDKTMFICKSSWSMREANVACLDLGFQQ GADTQRRFKLSDLSINSTECLHVHCRGLETSL AECTFTKRRTMGYQDFADVVCYTQKADSPM DDFFQCVNGKYISQMKACDGINDCGDQSDEL CCKACQGKGFHCKSGVCIPSQYQCNGEVDCIT GEDEVGCAGFASVTQEETEILTADMDAERRRI KSLLPKLSSG (SEQ ID NO: 19) |
| V311-V565 - G(13) - K1-G310 + C309S + C435S | | VKNRMHIRRKRIVGGKRAQLGDLPWQVAIKD ASGITCGGIYIGGCWILTAAHCLRASKTHRYQI WTTVVDWIHPDLKRIVIEYVDRIIFHENYNAG TYQNDIALIEMKKDGNKKDCELPRSIPASVPW SPYLFQPNDTCIVSGWGREKDNERVFSLQWG EVKLISNCSKFYGNRFYEKEMECAGTYDGSID ACKGDSGGPLVCMDANNVTYVWGVVSWGE NCGKPEFPGVYTKVANYFDWISYHVGRPFISQ YNVGGGGGGGGGGGGKVTYTSQEDLVEKK CLAKKYTHLSCDKVFCQPWQRCIEGTCVCKL PYQCPKNGTAVCATNRRSFPTYCQQKSLECL HPGTKFLNNGTCTAEGKFSVSLKHGNTDSEGI VEVKLVDQDKTMFICKSSWSMREANVACLDL GFQQGADTQRRFKLSDLSINSTECLHVHCRGL ETSLAECTFTKRRTMGYQDFADVVCYTQKAD SPMDDFFQCVNGKYISQMKACDGINDCGDQS DELCCKACQGKGFHCKSGVCIPSQYQCNGEV DCITGEDEVGCAGFASVTQEETEILTADMDAE RRRIKSLLPKLSSG (SEQ ID NO: 20) |

Without being bound by theory or mechanism, exemplary CFI variants comprising an inversion of the A and B chains may comprise the amino acid sequences set forth in SEQ ID NOs: 17, 18, 19, or 20. The chains may be held together by optional linkers. The linkers between the A chain and the B chain of the inversion variants may be of any suitable length of at least one amino acid. A linker may be a flexible linker and may be a peptide of about 1 to about 10, 3-11 to about 20 or 1 to about 40 acid residues in length, wherein the amino acid residues may comprise glycine residues. The linker may also optionally comprise serine residues. Exemplary flexible linkers can include, but are not limited to, glycine polymers, glycine-serine polymers, glycine-alanine polymers, alanine-serine polymers, or any other suitable flexible linkers known in the art. It should be understood that, while the exemplary inversion variants shown in Table 7 include glycine polymer linkers, any suitable flexible linkers may be used for a CFI variant having an A-B chain inversion.

In some embodiments, the CFI variants comprise a substitution at C309 and/or C435, wherein the positions correspond to positions in a CFI having the amino acid sequence set forth in SEQ ID NO: 5.

In some embodiments, the CFI variants comprise substitutions C309S and C435S, wherein the positions correspond to positions in a CFI having the amino acid sequence set forth in SEQ ID NO: 5.

Additional CFI Variants—Useful for Modulation and/or Evaluation of the Complement System In some embodiments, there are CFI variants provided that, while useful for modulation of the complement system, may also be useful for evaluation of activity of the complement system, e.g. can be considered tool proteins, in addition to having therapeutic value.

For example, these other CFI variants may allow for various tests using the CFI fusion constructs. An exemplary such CFI variant may be non-activatable to serve as a control. Another exemplary such CFI variant may provide an easier activation of a fusion construct.

In some embodiments, such additional CFI variants provided herein comprise a modification to the amino acid sequence set forth in SEQ ID NO: 5. In some embodiments, the envisioned CFI variants provided herein are derived from a wild type mouse CFI. In some embodiments, the envisioned CFI variants provided herein are derived from a wild type human CFI. In some embodiments, the envisioned CFI variants provided herein are further derived from a CFI-SPD.

In exemplary embodiments, the CFI variants comprises any one or more of the exemplary modifications presented in Table 8. Such CFI variants may be useful for providing a control for or further study of any CFI variants provided herein. Such CFI variants may also provide therapeutic utility.

TABLE 8

Other Exemplary CFI Variants

| Alterations from WT hCFI | Base Molecule | Description |
|---|---|---|
| I317D-R318D-R319D-K320D-R321K | hCFI | Enterokinase activation loop |
| Δ(K1-P305) + I317D-R318D-R319D-K320D-R321K | CFI-SPD | ΔA-chain + Enterokinase activation site, Enterokinase activation of HSA-SPD construct |
| R321A | hCFI | Non-activatable, control variant |
| WT mouse CFI | wt mCFI | Mouse CFI |

Exemplary CFI variants may include a non-activatable CFI variant, which may serve as a control.

In some embodiments, the CFI variants comprise any one or more of the modifications presented in Table 8.

In some embodiments, the CFI variants comprise or consist of a modification at any one or more positions corresponding to positions I317, R318, R319, K320, and R321 in a CFI having the amino acid sequence set forth in SEQ ID NO: 5.

In some embodiments, the CFI variants comprise or consist of any one or more of the substitutions selected from I317D, R318D, R319D, K320D, and R321K, wherein the positions correspond to positions in a CFI having the amino acid sequence set forth in SEQ ID NO: 5.

In some embodiments, the CFI variants are more easily activated as compared to the wild type CFI. In some embodiments, the CFI variants are more easily activated as compared to the wild type CFI, and comprise or consist of substitutions I317D, R318D, R319D, K320D, and R321K, wherein the positions correspond to positions in a CFI having the amino acid sequence set forth in SEQ ID NO: 5.

In some embodiments, the CFI variants are not activatable, and comprise or consist of least one modification with respect to a wild type CFI. In some embodiments, the CFI variants are not activatable, and comprise a modification at a position corresponding to position R321 of a CFI having the amino acid sequence set forth in SEQ ID NO: 5. In some embodiments, the CFI variants comprise a substitution R321A, wherein the position corresponds to a position in a CFI having the amino acid sequence set forth in SEQ ID NO: 5.

CFI Combination Variants

Provided herein are CFI variants comprising or consisting of two or more modifications with respect to a wild type CFI. The modifications occur in the same or different domains of CFI. In some embodiments, the modifications include two or more substitutions. In some embodiments, the modifications include a substitution and a deletion. In some embodiments, the modifications include a substitution and an addition. In some embodiments, the modifications include a deletion and an addition. In some embodiments, the modifications include a substitution, a deletion, and an addition. As used herein, such variants collectively may be referred to as CFI combination variants.

Accordingly, provided herein are CFI combination variants. Specifically, provided herein are exemplary CFI variants comprising any one or more of the modifications presented in Table 9. Table 9 presents CFI variants comprising two or more modifications to the amino acid sequence set forth in SEQ ID NO: 5. The base molecule for the CFI variants presented in Table 9 may be a wild type human CFI or a CFI-SPD. It should be understood that any of the CFI variants provided herein may comprise any combination of any of the modifications provided herein, such as, for example, any of the modifications presented in Tables 2-8 and in Table 13.

TABLE 9

Exemplary Combination CFI Variants

| Alterations from WT hCFI | Base Molecule | Description |
|---|---|---|
| Y408L-N531G | hCFI | 99-loop + S1 entrance frame |
| K504D + Y408L + N531G | | |
| K504E + Y408L + N531G | | |
| E457G + N531G + D425K | | |
| Y408F + N531G | | |
| Y408L + E457G + N531G + D425K | | |
| Y408L + E457G + P535G + D425K | | |
| Y408L + E457G + N531G + K534Q | | |
| Y408L + N531G | | |
| E38A + D425R | | Interface + C-term extension |
| Y20F + D425R | | |
| S250A + D425R | | |
| Y408L + N531G + E457G + E461Q + R462K + F464Y | | 99-loop + S1 entrance frame + mCFI autolysis loop |
| K14A + Y20F | | A-chain |
| K14A + E38A | | |
| K14A + S250A | | |
| K14A + D425A | | A-chain + SPD (110-loop) |
| Y20F + E38A | | A-chain |
| Y20F + S250A | | |
| Y20F + D425A | | A-chain + SPD (110-loop) |
| E38A + S250A | | A-chain |
| E38A + D425A | | A-chain + SPD (110-loop) |
| S250A + D425A | | |
| K14A + N531G + P535A | | A-chain + S1 entrance frame |
| Y20F + N531G + P535A | | |

TABLE 9-continued

Exemplary Combination CFI Variants

| Alterations from WT hCFI | Base Molecule | Description |
|---|---|---|
| E38A + N531G + P535A | | |
| S250A + N531G + P535A | | |
| D425A + N531G + P535A | | |
| Y20F + Y408L + N531G + E457G + E461Q + R462K + F464Y | | Interface + 99-loop + S1 entrance frame + mCFI autolysis loop |
| E38A + Y408L + N531G + E457G + E461Q + R462K + F464Y | | |
| S250A + Y408L + N531G + E457G + E461Q + R462K + F464Y | | |
| D425R + Y408L + N531G + E457G + E461Q + R462K + F464Y | | C-term extension + 99-loop + S1 entrance frame + mCFI autolysis loop |
| Y20F + E38A + S250A + D425A | | Interface + C-term extension |
| Y20F + E38A + S250A + D425A + Y408L + N531G + E457G + E461Q + R462K + F464Y | | Interface + C-term extension + 99-loop + S1 entrance frame + mCFI autolysis loop |
| Y20F + E38A + S250A + D425A + Y408L + N531G + E457G + E461Q | | Interface + C-term extension + 99-loop + S1 entrance frame + mCFI autolysis loop |
| Δ(K1-P305) + Y408L + N531G + E457G + E461Q | CFI-SPD | ΔA-chain + 99-loop + S1 entrance frame + mCFI autolysis loop |
| Y408L + N531G + E457G + E461Q + R462K + F464Y + S507A | hCFI | 99-loop + S1 entrance frame + mCFI autolysis loop + active site (S195A) |
| I317D + R318D + R319D + K320D + R321K + Y408L + N531G | | Enterokinase activation loop + 99 position + S1 entrance frame |
| I317D + R318D + R319D + K320D + R321K + E457G + E461Q + R462K + F464Y | | Enterokinase activation loop + mCFI autolysis loop swap |
| I317D + R318D + R319D + K320D-R321K + Y408L + N531G + E457G + E461Q + R462K + F464Y | | Enterokinase activation loop + 99-loop + S1 entrance frame + mCFI autolysis loop |
| R462K + F464Y N531G + CR1(CCP15-17) | | CR1 co-fusion |
| Y408L + E457G + N531G + P535G + CR1(CCP15-17) | | |
| Y408L + P535G + D425K | | 99-loop, S1 entrance, C-terminal extension |

Without being bound by any theory or mechanism, exemplary combination CFI variants may include the following variants.

In some embodiments, the CFI variants comprise or consist of any one or more of the modifications presented in Table 9.

In some embodiments, the CFI variants comprise or consist of any one or more of the combination substitutions selected from Y408+N531G, E38A+D425R, Y20F+D425R, S250A+D425R, Y408F+N531G, Y408L+N531G+E457G+E461Q+R462K+F464Y, K14A+Y20F, K14A+E38A, K14A+S250A, K14A+D425A, Y20F+E38A, Y20F+S250A, Y20F+D425A, E38A+S250A, E38A+D425A, S250A+D425A, K14A+N531G+P535A, Y20F+N531G+P535A, E38A+N531G+P535A, S250A+N531G+P535A, D425A+N531G+P535A, Y20F+Y408L+N531G+E457G+E461Q+R462K+F464Y, E38A+Y408L+N531G+E457G+E461Q+R462K+F464Y, S250A+Y408L+N531G+E457G+E461Q+R462K+F464Y, D425R+Y408L+N531G+E457G+E461Q+R462K+F464Y, Y20F+E38A+S250A+D425A, Y20F+E38A+S250A+D425A+Y408L+N531G+E457G+E461Q+R462K+F464Y, Y20F+E38A+S250A+D425A+Y408L+N531G+E457G+E461Q, I317D+R318D+R319D+K320D+R321K+E457G+E461Q-R462K+F464Y, I317D+R318D+R319D+K320D+R321K+E457G+E461Q-R462K+F464Y, I317D+R318D+R319D+K320D+R321K+Y408L+N531G+E457G+E461Q+R462K+F464Y, K504D+Y408L+N531G, K504E+Y408L+N531G, E457G+N531G+D425K, Y408F+N531G, Y408L+E457G+N531G+D425K, Y408L+E457G+P535G+D425K, Y408L+E457G+N531G+K534Q, Y408L+N531G, R462K+F464Y, and Y408L+P535G+D425K, wherein the positions correspond to positions in a CFI having the amino acid sequence set forth in SEQ ID NO: 5.

Substitutions with Minimal Impact on Activity and Specificity

Certain CFI variants exhibit little or no differences compared to wild type CFI protease activity or substrate specificity. In some cases, the substitutions even decreased activity as compared to wild type CFI. Some substitutions that individually exhibited little or no difference in protease activity or substrate specificity as single site substitutions are provided in Table 15. However, it should be understood that the listing of the substitutions here do not indicate that one or more of these substitutions used in combination with another substitution my exhibit a different effect on CFI substrate specificity and CFI protease activity.

TABLE 15

Substitutions with little or no difference on activity or specificity

Substitution

Q69G
L73G
L76G
F208Y
F246Y
R319D
A342G
S343G
S343K
S343R
H362G
H362T
R365A
R365D
R365E
R365F
R365G
R365H
R365I
R365K
R365L
R365M
R365N
R365P
R365Q
R365S
R365T
R365V
R365W
R365Y
A366G
K368G
H370A
H370G
R371G
Q373G
W375G
I382G
H383G
L386G
K387G
R388G
I389G
I391G
F399G
T407G
K419G
D420G
K423A
K423D
K423E
K423G
K424A
K424D
K424E
K424F
K424G
K424H
K424I
K424L
K424M
K424N
K424P
K424Q
K424R

TABLE 15-continued

Substitutions with little or no difference on activity or specificity

Substitution

K424S
K424T
K424V
K424W
K424Y
V463G
V463S
N476Q
F480Y
R484G
K488E
D501G
V526G
S527G
W528G
P538G
V540G
D549A
D549F
D549G
D549H
D549K
D549L
D549M
D549N
D549P
D549Q
D549R
D549T
D549V
D549W
D549Y
S552G
F559L
F559Y
V565I
V565T

B. Fusion Constructs Comprising Complement Factor I

Provided herein are fusion constructs comprising at least a first component (CFI portion) comprising at least one domain of complement factor I, and a second component, wherein the first component and second component are fused (e.g. contiguous or separated by an optional linker). These fusion constructs are referred to herein as "CFI fusion constructs" or simply as "fusion constructs." In some embodiments, the fusion construct comprises additional components, e.g. a third component, a fourth component, etc.

In some embodiments, the first component comprises a wild type CFI of any species, either a full length or domain thereof. In some embodiments, the first component comprises a CFI variant of the disclosure, described in detail in the preceding section. It is noted that the second component may increase the activity or alter the specificity of the CFI portion (first component) or its half-life. The second component may also allow for CFI portion (first component) to act within the complement system without the presence of an exogenous cofactor (e.g. a cofactor such as Factor H (FH) or CR1). As used herein, an exogenous cofactor for CFI is one that is not fused to CFI. It should be understood that a fusion construct may act within the complement system without the presence of FH and/or CR1, but the activity of the fusion construct may also be further increased with the presence of FH, and/or CR1, either as a part of the fusion construct or provided exogenously.

Provided herein are fusion constructs comprising a first component comprising any one of the CFI variants provided herein. It should be understood that the CFI variant may be any one of the CFI variants presented in Tables 2-9 or Table 13, or may comprise any combination of the modifications that are presented in Tables 2-9 or Table 13.

In some embodiments, the second component of the fusion construct is a protein. In some embodiments, the second component is not a protein.

The components of the fusion constructs of the disclosure may be held together by optional linkers. They may be of any suitable length of at least one amino acid. A linker may be a flexible linker, and may be a peptide of about 1 to about 20 amino acid residues in length, wherein the amino acid residues may comprise glycine residues. The linker may also optionally comprise serine residues. Exemplary flexible linkers can include, but are not limited to, glycine polymers, glycine-serine polymers, glycine-alanine polymers, alanine-serine polymers, or any other suitable flexible linkers known in the art. An exemplary linker is GGSSGG" (SEQ ID NO: 6), wherein n is any number from about 1 to about 20. In some embodiments, the linkers are protease-sensitive cleavable linkers. Exemplary linkers linking the fusion constructs can be 1-50, 5-50, 10-50, 15-50, 20-50, 25-50, 1-20, 2-20, 3-20, 4-20, 5-20, 6-20, 7-20, 8-20, 9-20, 10-20, 3-15, 3-10, 3-9, 3-8, 3-7, 3-6, 3-5, 4-15, 4-10, 4-9, 4-8, 4-7, 4-6, 4-5, 5-15, 5-10, 5-9, 5-8, 5-7, 5-6, 6-15, 6-10, 6-9, 6-8, or 6-7 amino acids in length.

CFI+Half-Life Extender Fusion Constructs

In some embodiments, the fusion construct comprises a wild type CFI or CFI variant (first component), and a second component, and wherein the second component is a half-life extender. Because naturally occurring CFI has a relatively short half-life, it may be advantageous in some embodiments to increase the half-life of CFI. As used herein, "CFI" is used to connotate either the wild type CFI, or variants thereof. By using a second component that is a half-life extender, the activity of CFI may increase, or it may improve another characteristic of the CFI as compared to a wild type CFI. For example, a wild type CFI or a CFI variant may have their half-life extended by fusing the CFI to a half-life extender.

Exemplary half-life extenders include, but are not limited to albumin, such as human serum albumin, PEG, a non-biodegradable polymer, a biodegradable polymer, and Fc. In some embodiments, the second component is a protein, and is a half-life extender, such as albumin or Fc. In some embodiments, the second component is not a protein, and is a half-life extender, such as PEG. In some embodiments, the half-life extender is comprising peptide repeats.

In some embodiments, the second component is a half-life extender, and is albumin. It is noted that as used herein, albumin refers to any albumin such as any serum albumin, or an albumin variant, or albumin derivative. As an example, a variant of albumin includes any albumin comprising at least one modification corresponding to the amino acid sequence set forth in SEQ ID NO: 7 (wild type Human serum albumin (HSA)), or at least one modification corresponding to the amino acid sequence of an albumin of any non-human species. In exemplary embodiments, the albumin is human serum albumin (HSA) and is provided in SEQ ID NO: 7.

Exemplary fusion constructs comprising wild type CFI and HSA are referred to herein, as "CFI-HSA" and are discussed in further detail below.

In some embodiments, a fusion construct of the disclosure comprises albumin and a CFI variant of the disclosure.

Structural Arrangements of Fusion Constructs

In some embodiments, a wild type CFI or a CFI variant of the disclosure is the first component of a fusion construct, and wherein this CFI portion comprises an A chain and a B chain In some embodiments, the fusion construct comprises a structural arrangement from N-terminus to C-terminus (A chain)-(optional linker)-(B chain)-(optional linker)-(Second Component). In some embodiments, the fusion construct comprises an inversion of the A and B chains in its CFI component, such that the structural arrangement from N-terminus to C-terminus, is (B chain)-(optional linker)-(A chain)-(optional linker)-(Second Component).

In some embodiments, a wild type CFI or a CFI variant of the disclosure is the first component of a fusion construct, and wherein this CFI portion comprises an A chain and a B chain In some embodiments, the fusion construct comprises a structural arrangement from N-terminus to C-terminus, as (Second Component)-(optional linker)-(A chain)-(optional linker)-(B chain). In some embodiments, the fusion construct comprises an inversion of the A and B chains in its CFI component, such that the structural arrangement from N-terminus to C-terminus is (Second Component)-(optional linker)-(B chain)-(optional linker)-(A chain).

In some embodiments, provided herein are fusion constructs comprising at least a first component, wherein the first component is any of the wild type CFI or CFI variants provided herein (CFI portion), and a second component, wherein the first component and second component are fused, and wherein the second component is fused to the N-terminal end of the CFI portion. In some embodiments, the second component is fused to the C-terminal end of the CFI portion. In some embodiments, the second component is fused to the C-terminal end of the CFI portion, and a third component is further fused to the N-terminal end of the CFI portion. In some embodiments, the second component is fused to the N-terminal end of the CFI portion, and a third component is further fused to the C-terminal end of the CFI portion.

Figures 2A, 2B:
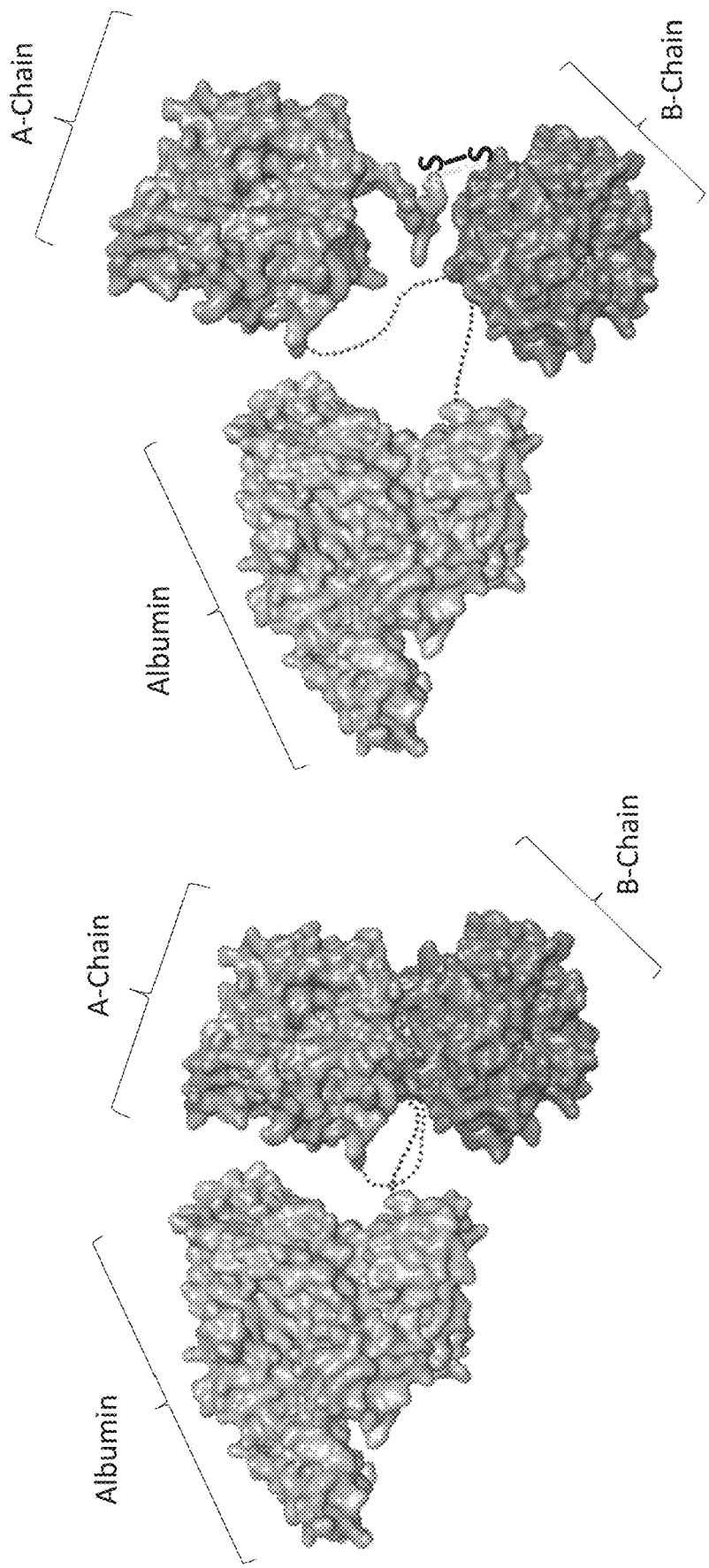
FIG. 2A, FIG. 2B, FIG. 2C, and FIG. 2D depict exemplary models of fusion constructs of the disclosure between albumin (e g serum albumin, e.g. human serum albumin (HSA)) and CFI comprising a CFI variant, wherein the CFI variant comprises an A-B chain inversion.
Figure 2D:
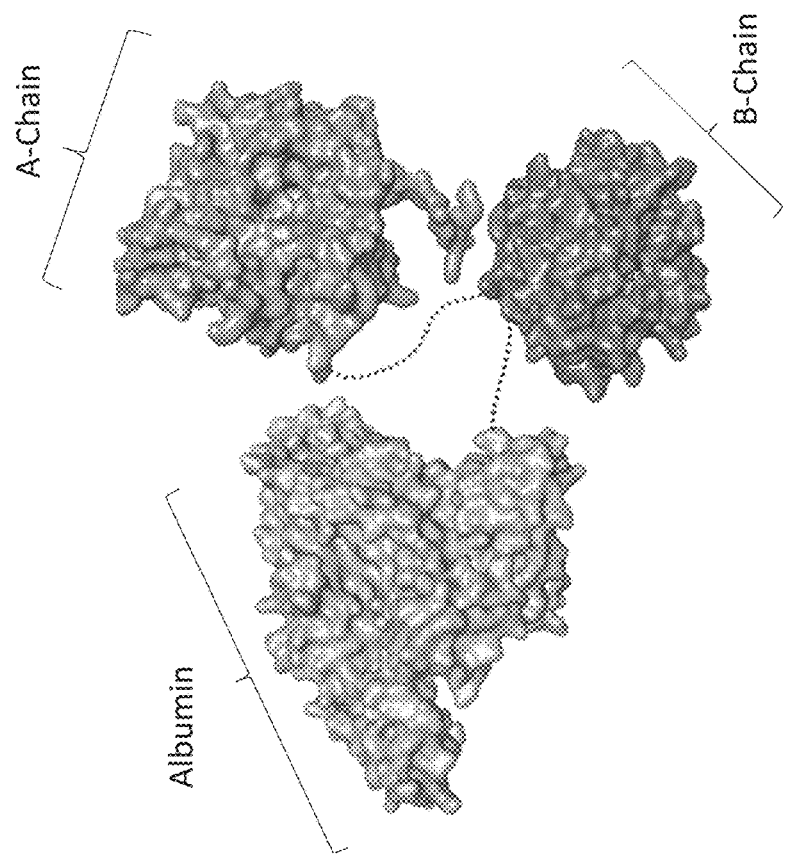
Figure 2C:
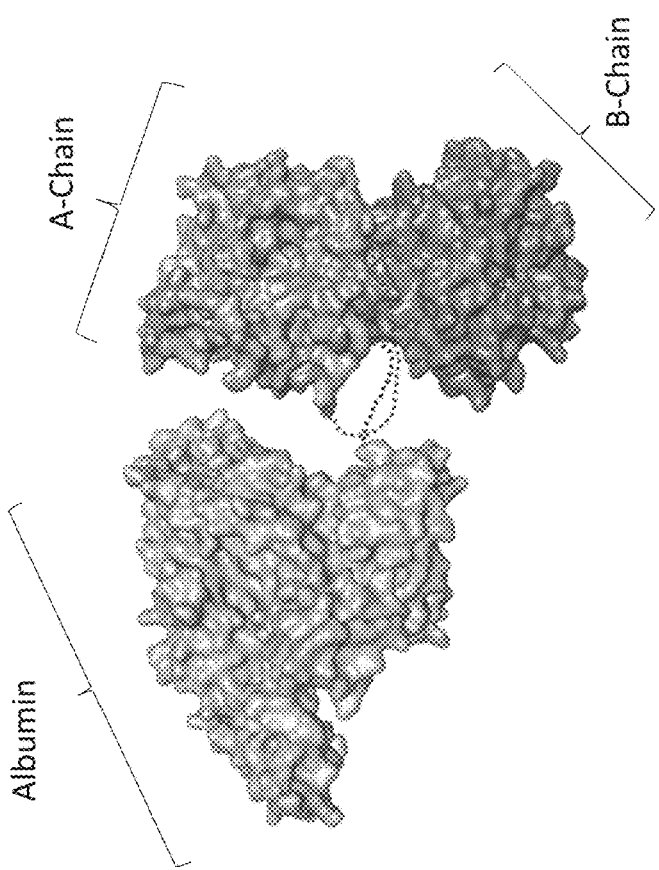

FIGS. 2A-2D depict models of a fusion construct comprising an albumin and a CFI variant, wherein the CFI variant comprises an A-B chain inversion. FIGS. 2A-2B depict a first version and FIGS. 2C-2D depict a second version of models of a fusion construct comprising human serum albumin (HSA) and the A and B chains of CFI, wherein the A and B chains comprise an inversion. The first version of an A-B chain inversion CFI variant comprises an inter-domain disulfide bond. The second version does not comprise the inter-domain disulfide bond. Both versions of the inversion variants may be constructed in a head-to-tail fashion as: (HSA)-(optional linker)-(B chain)-(optional linker)-(A chain).

Accordingly, provided herein are CFI variants, wherein the CFI variant is a first component of a fusion construct comprising a first component and a second component, and the CFI variant is fused to the second component, and wherein the CFI comprises an A chain and a B chain, and wherein the structural arrangement from N-terminus to C-terminus, or C-terminus to N-terminus, is (Second Component)-(optional linker)-(B chain)-(optional linker)-(A chain). Such chain inversions are presented in Table 7 above. Table 7 presents CFI variants comprising one or more modifications to the amino acid sequence set forth in SEQ ID NO: 5, wherein the one or more modifications are an inversion of the A and B chains of CFI.

FIGS. 2A-2B depict models of an exemplary CFI variant comprising an albumin fusion, and the inversion variant comprising the modifications V311-V565-G(13)-K1-G310.

In some embodiments, such a fusion construct comprising an albumin and a CFI comprising a chain inversion comprises the amino acid sequence set forth in SEQ ID NOs: 17 or 18.

FIGS. 2C-2D depict models of an exemplary CFI variant with an albumin fusion, and the inversion variant V311-V565-G(10)-K1-G310+C309S+C435S. In some embodiments, such a fusion construct comprising an albumin and a CFI comprising a chain inversion comprises the amino acid sequence set forth in SEQ ID NOs: 19 or 20.

In some embodiments, the CFI variants comprise a substitution at C309 and/or C435, wherein the positions correspond to positions in a CFI having the amino acid sequence set forth in SEQ ID NO: 5.

In some embodiments, the CFI variants comprise substitutions C309S and C435S, wherein the positions correspond to positions in a CFI having the amino acid sequence set forth in SEQ ID NO: 5. In some embodiments, the second component is at least one domain of Factor H. Fusion constructs comprising at least one CFI domain and Factor H are discussed in further detail below. In some embodiments, the second component is at least one domain of CR1. Fusion constructs comprising at least one CFI domain and Factor H are discuss in further detail below. In some embodiments, the second component comprises at least one domain of Factor H and at least one domain of CR1. Fusion constructs comprising at least one CFI domain, at least one Factor H domain, and at least one CR1 domain are discussed in further detail below.

Components of Fusion Constructs

Provided herein are fusion constructs comprising a first component and a second component. In some embodiments, the first component comprises a wild type CFI, whereas in some embodiments the first component comprises a CFI variant of the disclosure. In some embodiments, the second component comprises a half-life extender. In some embodiments, the second component comprises at least one domain of Factor H (FH), at least one domain of CR1, or a mixture of FH and CR1 domains. In some embodiments, the fusion construct further comprises a third component. In some embodiments, the first, second, and third (or more) components are any one or more of the components presented in Table 10. Table 10 presents various exemplary components and the amino acid sequences of the components that may be used to generate CFI fusion constructs provided herein.

Turning to Table 10, SEQ ID NO: 1 is the amino acid sequence of wild type plasma-derived human CFI, referred to as "CFI-PD", and has a leader sequence. Wild type CFI used for fusion with a second component may comprise the amino acid sequence of SEQ ID NO: 5, which does not include the leader sequence present in SEQ ID NO: 1. A mouse Ig kappa chain V-III region MOPC 63 leader sequence (SEQ ID NO: 2) may instead be used for the recombinant production of any of the CFI fusion constructs provided herein. In some embodiments, provided herein are CFI fusion constructs comprising at least one CFI domain, wherein the at least one CFI domain comprises the amino acid sequence set forth in SEQ ID NO: 5.

TABLE 10

Components of Exemplary CFI Fusion Constructs

| Description | Sequence |
|---|---|
| Wild type plasma-derived human CFI (CFI-PD) | MKLLHVFLLFLCFHLRFCKVTYTSQEDLVEKKCLAKKYTHLSC DKVFCQPWQRCIEGTCVCKLPYQCPKNGTAVCATNRRSFPTYC QQKSLECLHPGTKFLNNGTCTAEGKFSVSLKHGNTDSEGIVEVK LVDQDKTMFICKSSWSMREANVACLDLGFQQGADTQRRFKLS DLSINSTECLHVHCRGLETSLAECTFTKRRTMGYQDFADVVCY TQKADSPMDDFFQCVNGKYISQMKACDGINDCGDQSDELCCK ACQGKGFHCKSGVCIPSQYQCNGEVDCITGEDEVGCAGFASVT QEETEILTADMDAERRRIKSLLPKLSCGVKNRMHIRRKRIVGGK RAQLGDLPWQVAIKDASGITCGGIYIGGCWILTAAHCLRASKTH RYQIWTTVVDWIHPDLKRIVIEYVDRIIFHENYNAGTYQNDIALI EMKKDGNKKDCELPRSIPACVPWSPYLFQPNDTCIVSGWGREK DNERVFSLQWGEVKLISNCSKFYGNRFYEKEMECAGTYDGSID ACKGDSGGPLVCMDANNVTYVWGVVSWGENCGKPEFPGVYT KVANYFDWISYHVGRPFISQYNV (SEQ ID NO: 1) |
| Leader sequence (mouse leader for CFI-HSA) | METDTLLLWVLLLWVPGSTG (SEQ ID NO: 2) |
| Human CFI leader sequence | MKLLHVFLLFLCFHLRFC (SEQ ID NO: 3) |
| Human Factor H (FH) | MRLLAKIICLMLWAICVAEDCNELPPRRNTEILTGSWSDQTYPE GTQAIYKCRPGYRSLGNVIMVCRKGEWVALNPLRKCQKRPCG HPGDTPFGTFTLTGGNVFEYGVKAVYTCNEGYQLLGEINYREC DTDGWTNDIPICEVVKCLPVTAPENGKIVSSAMEPDREYHFGQA VRFVCNSGYKIEGDEEMHCSDDGFWSKEKPKCVEISCKSPDVIN GSPISQKIIYKENERFQYKCNMGYEYSERGDAVCTESGWRPLPS CEEKSCDNPYIPNGDYSPLRIKHRTGDEITYQCRNGFYPATRGN TAKCTSTGWIPAPRCTLKPCDYPDIKHGGLYHENMRRPYFPVA VGKYYSYYCDEHFETPSGSYWDHIHCTQDGWSPAVPCLRKCYF PYLENGYNQNYGRKFVQGKSIDVACHPGYALPKAQTTVTCME NGWSPTPRCIRVKTCSKSSIDIENGFISESQYTYALKEKAKYQCK LGYVTADGETSGSITCGKDGWSAQPTCIKSCDIPVFMNARTKND FTWFKLNDTLDYECHDGYESNTGSTTGSIVCGYNGWSDLPICY ERECELPKIDVHLVPDRKKDQYKVGEVLKFSCKPGFTIVGPNSV QCYHFGLSPDLPICKEQVQSCGPPPELLNGNVKEKTKEEYGHSE VVEYYCNPRFLMKGPNKIQCVDGEWTTLPVCIVEESTCGDIPEL EHGWAQLSSPPYYYGDSVEFNCSESFTMIGHRSITCIHGVWTQL |

TABLE 10-continued

Components of Exemplary CFI Fusion Constructs

| Description | Sequence |
| --- | --- |
| | PQCVAIDKLKKCKSSNLIILEEHLKNKKEFDHNSNIRYRCRGKE<br>GWIHTVCINGRWDPEVNCSMAQIQLCPPPPQIPNSHNMTTTLNY<br>RDGEKVSVLCQENYLIQEGEEITCKDGRWQSIPLCVEKIPCSQPP<br>QIEHGTINSSRSSQESYAHGTKLSYTCEGGFRISEENETTCYMGK<br>WSSPPQCEGLPCKSPPEISHGVVAHMSDSYQYGEEVTYKCFEGF<br>GIDGPAIAKCLGEKWSHPPSCIKTDCLSLPSFENAIPMGEKKDVY<br>KAGEQVTYTCATYYKMDGASNVTCINSRWTGRPTCRDTSCVN<br>PPTVQNAYIVSRQMSKYPSGERVRYQCRSPYEMFGDEEVMCLN<br>GNWTEPPQCKDSTGKCGPPPPIDNGDITSFPLSVYAPASSVEYQC<br>QNLYQLEGNKRITCRNGQWSEPPKCLHPCVISREIMENYNIALR<br>WTAKQKLYSRTGESVEFVCKRGYRLSSRSHTLRTTCWDGKLEY<br>PTCAKR (SEQ ID NO: 4) |
| Human mini<br>Factor H (mini<br>FH) | MRLLAKIICLMLWAICVAEDCNELPPRRNTEILTGSWSDQTYPE<br>GTQAIYKCRPGYRSLGNIIMVCRKGEWVALNPLRKCQKRPCGH<br>PGDTPFGTFTLTGGNVFEYGVKAVYTCNEGYQLLGEINYRECD<br>TDGWTNDIPICEVVKCLPVTAPENGKIVSSAMEPDREYHFGQAV<br>RFVCNSGYKIEGDEEMHCSDDGFWSKEKPKCVEISCKSPDVING<br>SPISQKIIYKENERFQYKCNMGYEYSERGDAVCTESGWRPLPSC<br>EEAGGGGGGGGGGGGKCGPPPPIDNGDITSFPLSVYAPASSVE<br>YQCQNLYQLEGNKRITCRNGQWSEPPKCLHPCVISREIMENYNI<br>ALRWTAKQKLYSRTGESVEFVCKRGYRLSSRSHTLRTTCWDGK<br>LEYPTCAKRENLYFQGHHHHHH (SEQ ID NO: 8) |
| Wild type CFI of<br>SEQ ID NO 1<br>without signal<br>sequence | KVTYTSQEDLVEKKCLAKKYTHLSCDKVFCQPWQRCIEGTCVC<br>KLPYQCPKNGTAVCATNRRSFPTYCQQKSLECLHPGTKFLNNG<br>TCTAEGKFSVSLKHGNTDSEGIVEVKLVDQDKTMFICKSSWSM<br>REANVACLDLGFQQGADTQRRFKLSDLSINSTECLHVHCRGLET<br>SLAECTFTKRRTMGYQDFADVVCYTQKADSPMDDFFQCVNGK<br>YISQMKACDGINDCGDQSDELCCKACQGKGFHCKSGVCIPSQY<br>QCNGEVDCITGEDEVGCAGFASVTQEETEILTADMDAERRRIKS<br>LLPKLSCGVKNRMHIRRKRIVGGKRAQLGDLPWQVAIKDASGI<br>TCGGIYIGGCWILTAAHCLRASKTHRYQIWTTVVDWIHPDLKRI<br>VIEYVDRIIFHENYNAGTYQNDIALIEMKKDGNKKDCELPRSIPA<br>CVPWSPYLFQPNDTCIVSGWGREKDNERVFSLQWGEVKLISNC<br>SKFYGNRFYEKEMECAGTYDGSIDACKGDSGGPLVCMDANNV<br>TYVWGVVSWGENCGKPEFPGVYTKVANYFDWISYHVGRPFIS<br>QYNV (SEQ ID NO: 5) |
| Linker | GGSSGG (SEQ ID NO: 6) |
| Human serum<br>albumin (HSA) | DAHKSEVAHRFKDLGEENFKALVLIAFAQYLQQCPFEDHVKLV<br>NEVTEFAKTCVADESAENCDKSLHTLFGDKLCTVATLRETYGE<br>MADCCAKQEPERNECFLQHKDDNPNLPRLVRPEVDVMCTAFH<br>DNEETFLKKYLYEIARRHPYFYAPELLFFAKRYKAAFTECCQAA<br>DKAACLLPKLDELRDEGKASSAKQRLKCASLQKFGERAFKAW<br>AVARLSQRFPKAEFAEVSKLVTDLTKVHTECCHGDLLECADDR<br>ADLAKYICENQDSISSKLKECCEKPLLEKSHCIAEVENDEMPAD<br>LPSLAADFVESKDVCKNYAEAKDVFLGMFLYEYARRHPDYSV<br>VLLLRLAKTYETTLEKCCAAADPHECYAKVFDEFKPLVEEPQN<br>LIKQNCELFEQLGEYKFQNALLVRYTKKVPQVSTPTLVEVSRNL<br>GKVGSKCCKHPEAKRMPCAEDYLSVVLNQLCVLHEKTPVSDR<br>VTKCCTESLVNRRPCFSALEVDETYVPKEFNAETFTFHADICTLS<br>EKERQIKKQTALVELVKHKPKATKEQLKAVMDDFAAFVEKCC<br>KADDKETCFAEEGKKLVAASQAALGL (SEQ ID NO: 7) |
| HSA linked with<br>CFI (CFI-HSA) | DAHKSEVAHRFKDLGEENFKALVLIAFAQYLQQCPFEDHVKLV<br>NEVTEFAKTCVADESAENCDKSLHTLFGDKLCTVATLRETYGE<br>MADCCAKQEPERNECFLQHKDDNPNLPRLVRPEVDVMCTAFH<br>DNEETFLKKYLYEIARRHPYFYAPELLFFAKRYKAAFTECCQAA<br>DKAACLLPKLDELRDEGKASSAKQRLKCASLQKFGERAFKAW<br>AVARLSQRFPKAEFAEVSKLVTDLTKVHTECCHGDLLECADDR<br>ADLAKYICENQDSISSKLKECCEKPLLEKSHCIAEVENDEMPAD<br>LPSLAADFVESKDVCKNYAEAKDVFLGMFLYEYARRHPDYSV<br>VLLLRLAKTYETTLEKCCAAADPHECYAKVFDEFKPLVEEPQN<br>LIKQNCELFEQLGEYKFQNALLVRYTKKVPQVSTPTLVEVSRNL<br>GKVGSKCCKHPEAKRMPCAEDYLSVVLNQLCVLHEKTPVSDR<br>VTKCCTESLVNRRPCFSALEVDETYVPKEFNAETFTFHADICTLS<br>EKERQIKKQTALVELVKHKPKATKEQLKAVMDDFAAFVEKCC<br>KADDKETCFAEEGKKLVAASQAALGLGGSSGGKVTYTSQEDL<br>VEKKCLAKKYTHLSCDKVFCQPWQRCIEGTCVCKLPYQCPKNG<br>TAVCATNRRSFPTYCQQKSLECLHPGTKFLNNGTCTAEGKFSVS<br>LKHGNTDSEGIVEVKLVDQDKTMFICKSSWSMREANVACLDLG<br>FQQGADTQRRFKLSDLSINSTECLHVHCRGLETSLAECTFTKRR<br>TMGYQDFADVVCYTQKADSPMDDFFQCVNGKYISQMKACDGI<br>NDCGDQSDELCCKACQGKGFHCKSGVCIPSQYQCNGEVDCITG |

TABLE 10-continued

Components of Exemplary CFI Fusion Constructs

| Description | Sequence |
|---|---|
| | EDEVGCAGFASVTQEETEILTADMDAERRRIKSLLPKLSCGVKN RMHIRRKRIVGGKRAQLGDLPWQVAIKDASGITCGGIYIGGCWI LTAAHCLRASKTHRYQIWTTVVDWIHPDLKRIVIEYVDRIIFHEN YNAGTYQNDIALIEMKKDGNKKDCELPRSIPACVPWSPYLFQPN DTCIVSGWGREKDNERVFSLQWGEVKLISNCSKFYGNRFYEKE MECAGTYDGSIDACKGDSGGPLVCMDANNVTYVWGVVSWGE NCGKPEFPGVYTKVANYFDWISYHVGRPFISQYNV (SEQ ID NO: 21) |

C. Complement Factor I and Albumin Fusion Constructs
Wild Type CFI+Albumin Fusion Constructs In some embodiments, provided herein are fusion constructs comprising a first component that is a wild type CFI, and second component that is albumin, e.g. serum albumin, e.g. human serum albumin.

In some embodiments, the albumin is human serum albumin (HSA), and the CFI is a wild type CFI, and such fusion constructs are referred to herein as "CFI-HSA."

In some embodiments, a CFI-HSA may have an extended half-life with respect to a CFI not part of a fusion construct. An exemplary CFI-HSA construct can be generated by linking an albumin with wild type CFI by a flexible linker. In some embodiments, the CFI-HSA comprises the amino acid sequence set forth in SEQ ID NO: 21, or comprises a sequence having at least 80%, 85%, 90%, 95%, 96%, 97%, 98%, or 99% sequence identity thereto.

Figure 3:
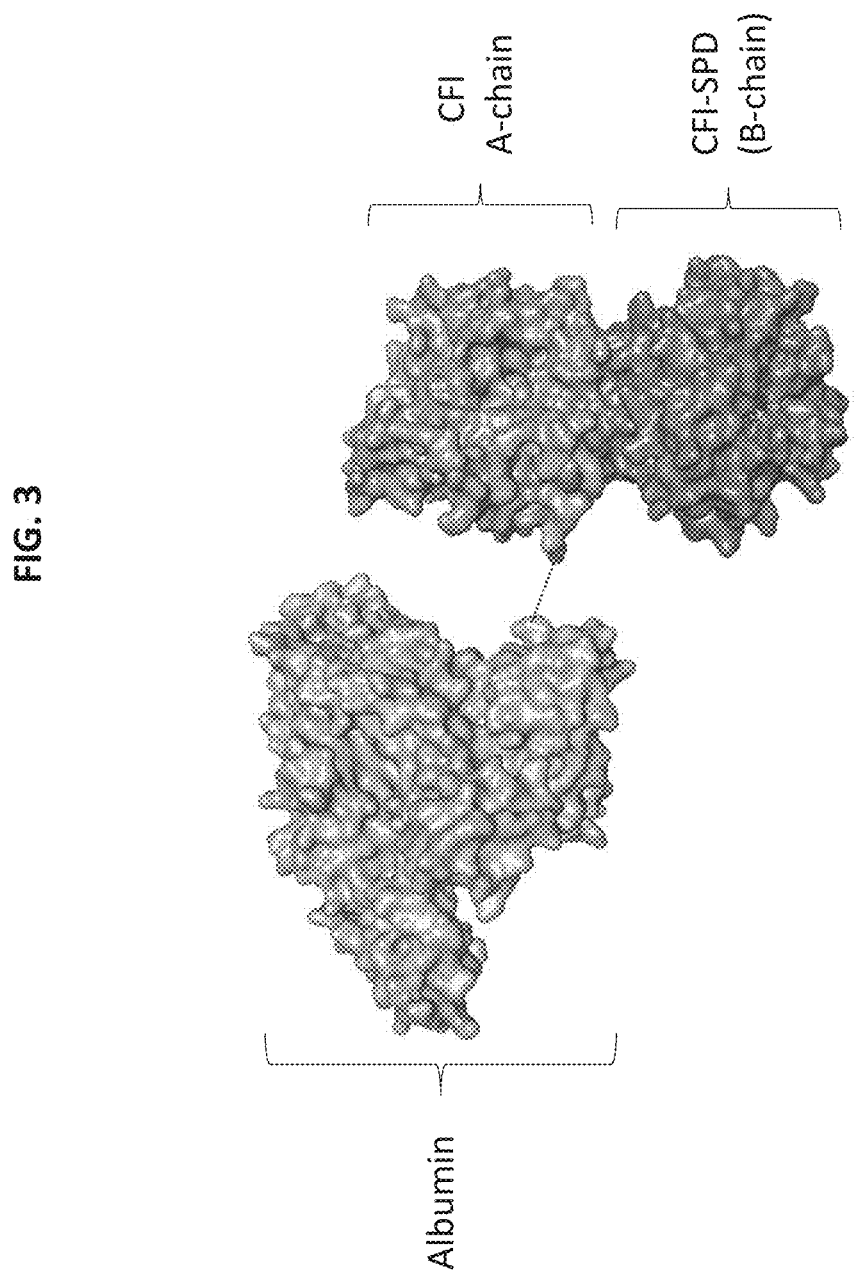
FIG. 3 depicts a model of an exemplary CFI-albumin (e.g. serum albumin, e.g. human serum albumin (HSA)) fusion construct comprising serum albumin fused with CFI, wherein the CFI comprises a wild type CFI.

FIG. 3 can depict a model of an exemplary CFI-HSA fusion construct comprising HSA fused with CFI, wherein the CFI comprises a wild type CFI.

In some embodiments, the fusion construct comprises a structural arrangement from N-terminus to C-terminus as (Albumin)-(optional linker)-(WT CFI A chain)-(optional linker)-(WT CFI B chain).

In some embodiments, the fusion construct comprises a structural arrangement from N-terminus to C-terminus as (WT CFI A chain)-(optional linker)-(WT CFI B chain)-(optional linker)-(Albumin).

In some embodiments, the fusion construct comprises the amino acid sequence of SEQ ID NO: 5 and SEQ ID NO: 7 wherein the fusion construct comprises a structural arrangement from N-terminus to C-terminus (SEQ ID NO: 7)-(optional linker)-(SEQ ID NO: 5). In some embodiments, the fusion construct comprises the amino acid sequence of SEQ ID NO: 5 and SEQ ID NO: 7 wherein the fusion construct comprises a structural arrangement from N-terminus to C-terminus (SEQ ID NO: 7)-(linker)-(SEQ ID NO: 5). In some embodiments, the fusion construct comprises the amino acid sequence of SEQ ID NO: 5, SEQ ID NO: 6, and SEQ ID NO: 7, wherein the fusion construct comprises a structural arrangement from N-terminus to C-terminus (SEQ ID NO: 7)-(SEQ ID NO: 6)-(SEQ ID NO: 5). In some embodiments, the fusion construct comprises the amino acid sequence of SEQ ID NO: 5 and SEQ ID NO: 7 wherein the fusion construct comprises a structural arrangement from N-terminus to C-terminus (SEQ ID NO: 5)-(optional linker)-(SEQ ID NO: 7). In some embodiments, the fusion construct comprises the amino acid sequence of SEQ ID NO: 5 and SEQ ID NO: 7 wherein the fusion construct comprises a structural arrangement from N-terminus to C-terminus (SEQ ID NO: 5)-(linker)-(SEQ ID NO: 7). In some embodiments, the fusion construct comprises the amino acid sequence of SEQ ID NO: 5, SEQ ID NO: 6, and SEQ ID NO: 7, wherein the fusion construct comprises a structural arrangement from N-terminus to C-terminus (SEQ ID NO: 5)-(SEQ ID NO: 6)-(SEQ ID NO: 7).

In some embodiments, the fusion construct comprises an amino acid sequence set forth in SEQ ID NO: 21, or an amino acid sequence comprising at least 80% identity thereto. In some embodiments, the fusion construct consists of an amino acid sequence set forth in SEQ ID NO: 21. In some embodiments, the fusion construct comprises the amino acid sequence of SEQ ID NO: 5 and SEQ ID NO: 7. In some embodiments it is noted that albumin fusion (e.g. N-terminal albumin fusion) to a wild type CFI provides solubility and facilitates activation of CFI-HSA. When activation of CFI to the mature two-chain protein with furin is carried out post translationally and activation is compared between CFI-HSA and a wild type CFI without an albumin (WT-CFI), it is observed that furin activates the CFI-HSA significantly better, and almost completely. It is observed that the CFI-HSA protein remains as a monomer with no evidence of aggregates. There is a significant and unexpected benefit of the amino terminal HSA fusion for maintaining solubility, monodispersity and efficient furin activation of a CFI-HSA construct. There is a significant improvement of bioavailability through, for example, improved half-life.

Accordingly provided herein are methods of increasing the activation of a CFI, comprising fusing a HSA to a wild type CFI, wherein the fusion is a N-terminal fusion prior to activation with furin; and activating with furin. In some embodiments the activation with furin is carried out in a cell during recombinant production of CFI variant, or CFI fusion construct of the dislcosure. In some embodiments the activation with furin is carried out in vitro.

CFI Variants+Albumin Fusion Constructs

In some embodiments, provided herein are fusion constructs comprising a first component that is a CFI variant of the disclosure, and second component that is albumin, e.g. serum albumin, e.g. human serum albumin.

In some embodiments, provided herein are fusion constructs comprising at least one CFI domain, and a second component, wherein the second component is HSA, and wherein the at least one CFI domain comprises any one or more domains of CFI selected from: the SPD, the FIMAC domain, the SRCR domain, the LDLr1, and the LDLr2 domains. In some embodiments, the any one or more domains of CFI comprise the amino acid sequence set forth in SEQ ID NO: 5, or comprise an amino acid sequence derived from SEQ ID NO: 5. In some embodiments, the any one or more domains of CFI correspond to the domains of a wild type CFI. In some embodiments, the at least one CFI domain comprises each one of the SPD, the FIMAC domain, the SRCR domain, and the LDLr1 and LDLr2 domains. In some embodiments, the at least one CFI domain of the CFI-HSA construct comprises only the SPD.

FIG. 3 can depict a model of an exemplary fusion construct comprising HSA fused with CFI, wherein the CFI comprises a CFI variant, comprising each one of the SPD, the FIMAC domain, the SRCR domain, and the LDLr1 and LDLr2 domains. Thus, the A-chain and B-chain are both included in the CFI in this model. The FIMAC domain, the SRCR domain, and the LDLr1 and LDLr2 domains together are the A-chain, or heavy chain, while the SPD is the B-chain, or light chain In some embodiments, the amino acid residues of any one or more of domains of the fusion construct may correspond to that of a wild type CFI. In some embodiments, the amino acid residues of any one or more of domains of the fusion construct may comprise one or more modifications with respect to the domains of a wild type CFI.

Figure 4:
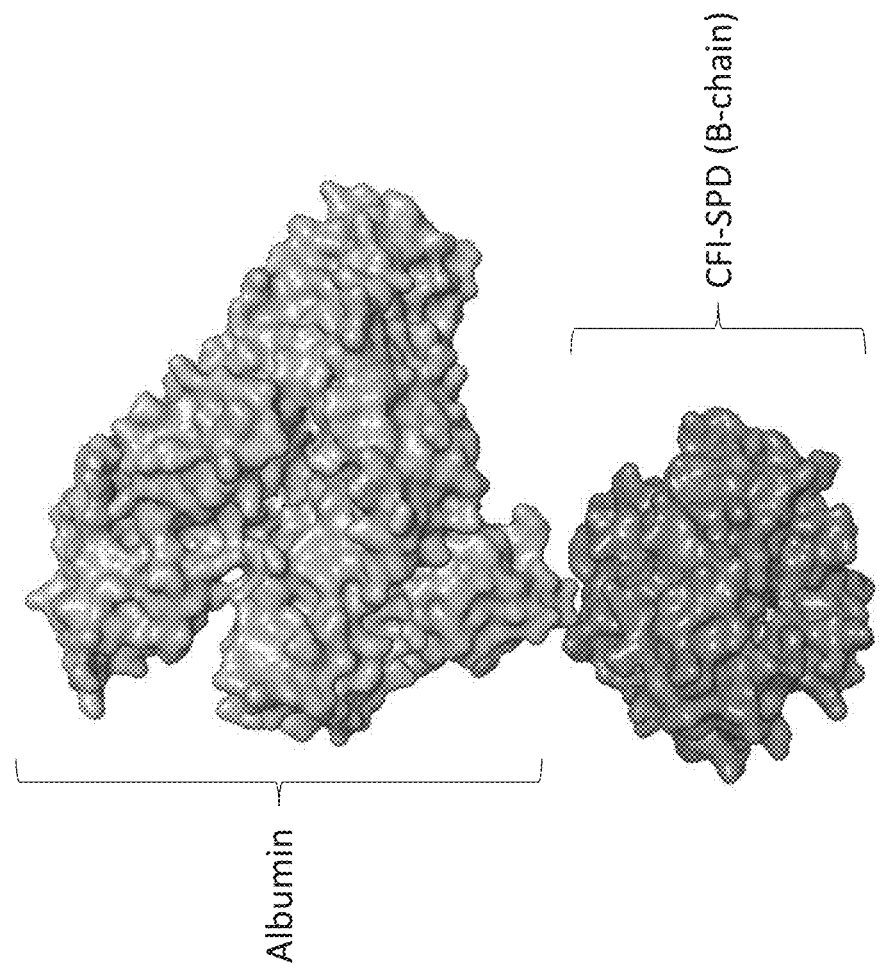
FIG. 4 depicts a model of an exemplary CFI-HSA fusion construct comprising HSA fused with the serine protein domain of a CFI.

FIG. 4 depicts a model of an exemplary fusion construct comprising HSA fused with a CFI portion, wherein the CFI comprises only the serine protease domain (SPD). The exemplary fusion construct depicted in FIG. 4 may be referred to as "HSA-SPD," and includes an activation loop at amino acid residues 322-326, an autolysis loop at amino acid residues 455-463, and an S1 entrance frame at amino acid residues 529-536. In some embodiments, the amino acid residues of any one or more of the activation loop, the autolysis loop, and the S1 entrance frame of the fusion construct may correspond to that of a wild type SPD of CFI. In some embodiments, the amino acid residues of any one or more of the activation loop, the autolysis loop, and the S1 entrance frame of the fusion construct may comprise one or more modifications with respect to a wild type SPD of CFI.

D. Complement Factor I and Factor H Fusion Constructs

Figure 5A:
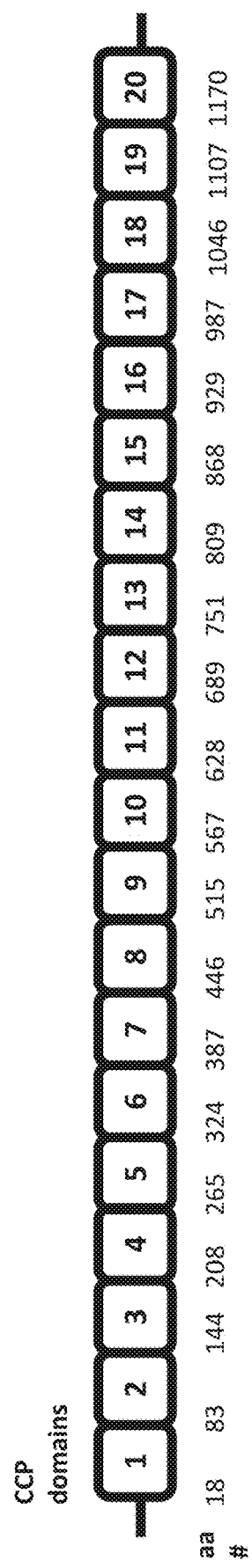
FIG. 5A depicts a schematic diagram of Factor H (FH) showing its 20 domains.

In some embodiments, provided herein are fusion constructs comprising a wild type CFI (or variant thereof) fused to at least one domain of Factor H. Factor H (FH), like CFI, is a protein involved in the complement pathway. FH is cofactor of CFI that forms a complex with CFI and C3b to catalyze C3b cleavage by CFI. As noted above, full-length FH comprises 20 domains. FIG. 5A depicts a schematic diagram of FH showing its 20 domains, each of which is a complement control protein (CCP) domain, and each of which are connected by short linkers, in a head-to-tail arrangement. The CCP domains are numbered 1-20 beginning at the N-terminus. CCPs 1-4 complex with C3b, and CCPs 19-20 complex with C3d. Without being bound to any theory or mechanism, FH is thought to be important for efficient C3b cleavage by CFI. Accordingly, in some embodiments, a fusion construct comprising specific domains of FH fused to at least one CFI domain may allow for C3b cleavage independent of exogenous FH. Exogenous FH may be defined as any FH that is not fused to any CFI domain, and may be a wild type FH. A wild type FH as used herein refers to any naturally occurring FH which is not a disease-causing FH. In some embodiments, the FH is a human FH. In some embodiments, the wild type FH comprises the amino acid sequence set forth in SEQ ID NO: 4.

In some embodiments, the second component of the fusion constructs of the disclosure is at least one Factor H domain, or part of a domain of FH. In some embodiments, the at least one FH domain comprises CCP domains 1-20 of FH. In some embodiments, the at least one domain of FH correspond to that of a wild type FH comprising the amino acid sequence set forth in SEQ ID NO: 4.

Figure 5B:
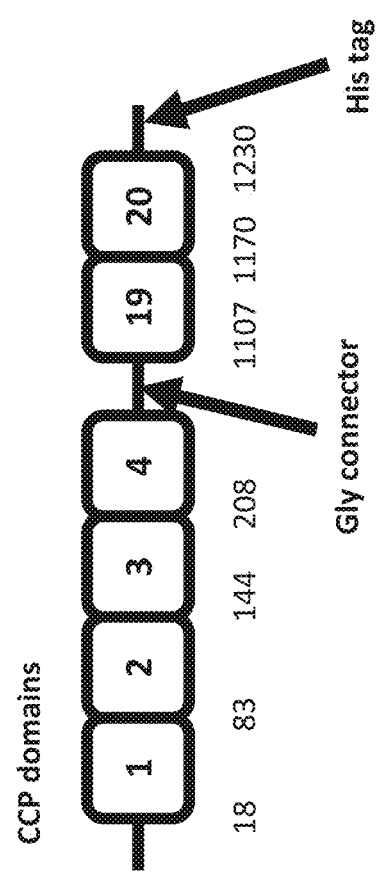
FIG. 5B depicts a schematic diagram of a mini Factor H showing domains 1-4 connected to domains 19-20 of FH.

In some embodiments, provided herein are fusion constructs comprising at least one CFI domain and a second component, wherein the second component is at least one Factor H domain, and wherein the at least one Factor H domain comprises complement control protein (CCP) domains 1-4 and 19-20 of Factor H. The CCP domains 1-4 and 19-20 are referred to as "mini Factor H" (mini FH). FIG. 5B depicts a schematic diagram of mini FH showing the CCP domains 1-4 connected by a Gly connector to domains 19-20, which include a His tag. In some embodiments, the mini FH is a human mini FH. In some embodiments, the amino acid sequence of mini FH comprises the amino acid sequence set forth in SEQ ID NO: 8.

Based on the structure of the complex formed by C3b-CFI and mini FH, several domains relevant for the function of FH were identified. The following types of exemplary FH-CFI fusion constructs were generated as base molecules in order to drive FH-independent CFI cleavage activity:

(a) FH domains 1-8 fused with CFI (Factor H-CPPs1-8+CFI)
(b) FH domains 1-4, 19-20, and 5-8 fused with CFI (Factor H-CPPs1-4+19-20+5-8+CFI)
(c) FH domains 1-8 fused with only the LDLr2 CFI domain (Factor H-CPPs1-8+LDLR2-CFI)
(d) FH domains 1-4, 19-20, and 5-8 fused with only the LDLr2 CFI domain (Factor H-CPPs1-4+19-20+5-8+LDLr2-CFI)
(e) FH domains 1-4 fused with human serum albumin (HSA) and the serine protease domain (SPD) of CFI (CFI-HSA(SPD)-factor H-CCP1-4)
(f) FH domains 2-4 fused with human serum albumin (HSA) and the serine protease domain (SPD) of CFI (CFI-HSA(SPD)-factor H-CCP2-4)
(g) FH domains 2-3 fused with human serum albumin (HSA) and the serine protease domain (SPD) of CFI (CFI-HSA(SPD)-factor H-CCP2-3).

Figure 6:
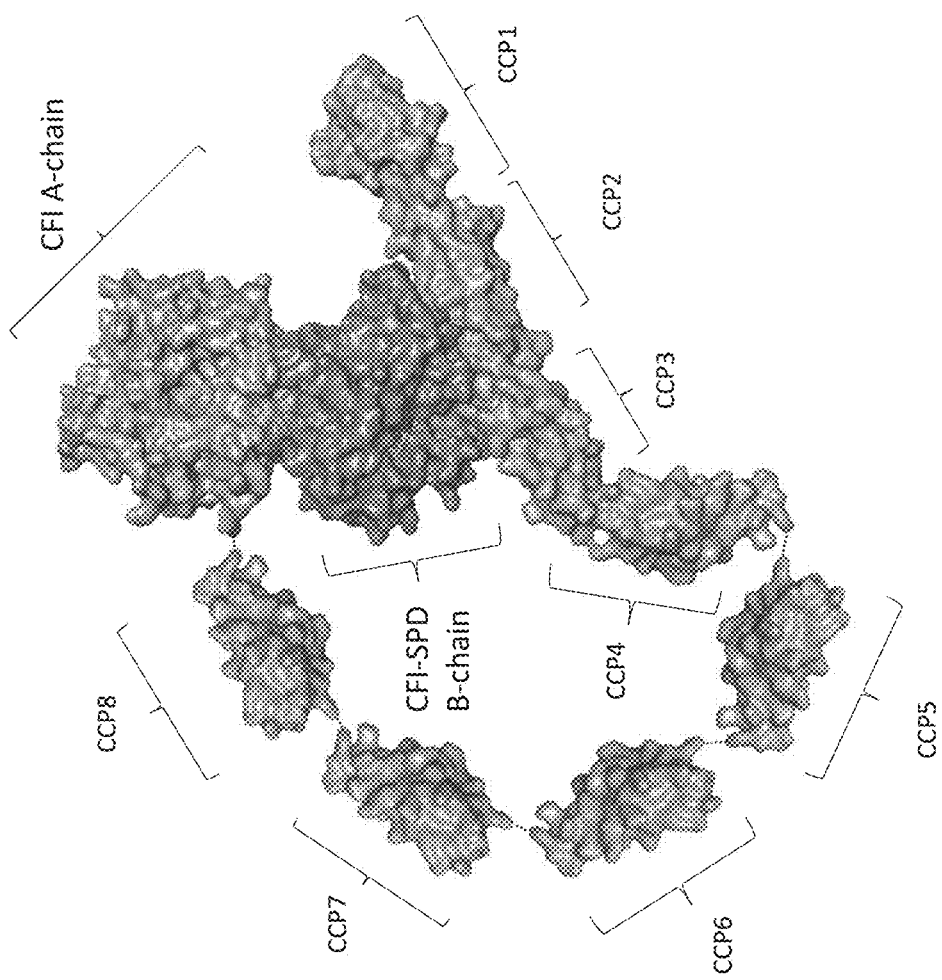
FIG. 6 depicts a model of an exemplary fusion construct comprising portions of Factor H and CFI, comprising domains 1-8 of FH fused with CFI, wherein the CFI comprises a wild type CFI.

FIG. 6 depicts a model of an exemplary fusion construct comprising FH and CFI, comprising CCP domains 1-8 of FH fused with CFI, wherein the FH portion of the fusion construct is a truncated mini FH, and wherein the CFI comprises a wild type CFI. The wild type CFI comprises each one of the SPD, the FIMAC domain, the SRCR domain, the LDLr1, and the LDLr2 domain. The exemplary fusion construct shown in FIG. 6 is also referred to herein as Factor H-CPPs1-8+CFI. The A-chain and B-chain are both included in the CFI. The FIMAC domain, the SRCR domain, and the LDLr1 and LDLr2 domains together are the A-chain, or heavy chain, while the SPD is the B-chain, or light chain. The FH comprises domains 1-4 and a linker comprising domains 5-8. In some embodiments, the amino acid residues of any one or more of domains of the FH and/or the CFI of the fusion construct may correspond to that of a wild type FH or a wild type CFI, respectively. In some embodiments, the amino acid residues of any one or more of domains of the FH and/or the CFI of the fusion construct may comprise one or more modifications with respect to the domains of a wild type FH or a wild type CFI, respectively.

Table 11a lists exemplary Factor H-containing fusion construct base molecules.

TABLE 11a

Factor H Fusion-Containing Construct Base Molecules

| Alteration | Base Molecule | Region/variant name |
|---|---|---|
| FH_CCP1-8 + GGGGGGGGGGGG (SEQ ID NO: 25) + ΔHSA | FH + wt hCFI | FH-CFI fusion (fusion #1) |

TABLE 11a-continued

Factor H Fusion-Containing Construct Base Molecules

| Alteration | Base Molecule | Region/variant name |
|---|---|---|
| FH_CCP1-4 + 19-20 + 5-8 + GGGGGGGGGGGG (SEQ ID NO: 25) + ΔHSA | | FH-CFI fusion (fusion #2) |
| Δ(K1-P305) (SEQ ID NO: 6) + FH_CCP1-4 | CFI-SPD + FH | HSA-SPD (ΔA-chain)-FH_CCP1-4 fusion |
| Δ(K1-P305) + GGSSGG (SEQ ID NO: 6) + FH_CCP2-4 | | HSA-SPD (ΔA-chain)-FH_CCP2-4 fusion |
| Δ(K1-P305) + GGSSGG (SEQ ID NO: 6) + FH_CCP2-3 | | HSA-SPD (ΔA-chain)-FH_CCP2-3 fusion |
| WT + GGSSGG (SEQ ID NO: 6) + CCP_1-4 | | CFI-HSA-FH_CCP1-4 fusion |
| WT + GGSSGG (SEQ ID NO: 6) + CCP_2-3 | | CFI-HSA-FH_CCP2-3 fusion |
| WT + GGSSGG (SEQ ID NO: 6) + CCP_2-4 | | CFI-HSA-FH_CCP2-4 fusion |
| FH_CCP1-4 + G(43) + wt hCFI | FH + wt hCFI | FH-CFI fusion (fusion #1) (100% Gly, 150Å) |
| FH_CCP1-4 + GGGGSS(7) (SEQ ID NO: 6) + wt hCFI | | FH-CFI fusion (fusion #1) (66% Gly, 150Å) |
| FH_CCP1-4 + GGSS(11) + wt hCFI | | FH-CFI fusion (fusion #1) (50% Gly, 150Å) |
| FH_CCP1-4 + G(53) + wt hCFI | | FH-CFI fusion (fusion #1) (100% Gly, 185Å) |
| FH_CCP1-4 + GGGGSS(9) + wt hCFI | | FH-CFI fusion (fusion #1) (66% Gly, 185Å) |
| FH_CCP1-4 + GGSS(13) + wt hCFI | | FH-CFI fusion (fusion #1) (50% Gly, 185Å) |
| FH_CCP2-4 + FH_CCP5-8 + GGGGGGGGGGGG (SEQ ID NO: 25) + ΔHSA | | FH-CFI fusion (fusion #1-derivatives) |
| FH_CCP1-3 + FH_CCP5-8 + GGGGGGGGGGGG (SEQ ID NO: 25) + ΔHSA | | FH-CFI fusion (fusion #1-derivatives) |
|

CFI. Accordingly, in some embodiments, a fusion construct comprising specific domains of CR1 fused to at least one CFI domain may allow for C3b and/or C4b cleavage independent of exogenous cofactor. An exogenous CR1 cofactor may be defined as any CR1 or portion thereof that is not fused to any CFI domain, and may be a wild type CR1, or may be CCP domains 1-3 or 15-17 of CR1. A wild type CR1 as used herein refers to any naturally occurring CR1 which is not a disease-causing CR1. In some embodiments, the CR1 is a human CR1.

In some embodiments, the second component of the fusion constructs of the disclosure is at least one CR1 domain, or part of a domain of CR1. In some embodiments, the at least one CR1 domain comprises CCP domains 15-17 of CR1. In some embodiments, the at least one CR1 domain comprises CCP domains 1-3 of CR1. In some embodiments, the fusion constructs of the disclosure comprising at least one CR1 domain also include fusion with albumin. In some embodiments, the fusion constructs of the disclosure comprising at least one CR1 domain also include fusion with albumin, and/or at least one domain of Factor H. In some embodiments, the at least one CR1 domain comprises CR1 CCP domain 15. In some embodiments, the at least one CR1 domain comprises CR1 CCP domain 16. In some embodiments, the at least one CR1 domain comprises CR1 CCP domain 17. In some embodiments, the at least one CR1 domain comprises CR1 CCP domains 15-16. In some embodiments, the at least one CR1 domain comprises CR1 CCP domains 16-17. In some embodiments, an exemplary fusion construct comprises a CFI having the modification N531G fused with CCP domains 15-17 of CR1. In some embodiments, the exemplary fusion construct comprises a CFI having the modification N531G fused with CCP domains 15-17 of CR1, and is further fused with albumin.

Table 11b lists exemplary CR1-containing fusion constructs and the corresponding sequence of an exemplary fusion construct comprising a wild type CFI and CR1 CCP domains 15-17.

TABLE 11b

Complement Factor 1 Fusion-Containing Constructs

| Fusion Construct | Terminal fused | Fragments or Base Molecules used | Sequence |
|---|---|---|---|
| HSA + CfI + GGSSGG (SEQ ID NO: 6) + CR1(ccp15-17) | C | GGSSGG (SEQ ID NO: 6) + CR1(ccp15-17) | METDTLLLWVLLLWVPGSTGDAHKSEV AHRFKDLGEENFKALVLIAFAQYLQQCPF EDHVKLVNEVTEFAKTCVADESAENCDK SLHTLFGDKLCTVATLRETYGEMADCCA KQEPERNECFLQHKDDNPNLPRLVRPEV DVMCTAFHDNEETFLKKYLYEIARRHPY FYAPELLFFAKRYKAAFTECCQAADKAA CLLPKLDELRDEGKASSAKQRLKCASLQ KFGERAFKAWAVARLSQRFPKAEFAEVS KLVTDLTKVHTECCHGDLLECADDRADL AKYICENQDSISSKLKECCEKPLLEKSHCI AEVENDEMPADLPSLAADFVESKDVCKN YAEAKDVFLGMFLYEYARRHPDYSVVLL LRLAKTYETTLEKCCAAADPHECYAKVF DEFKPLVEEPQNLIKQNCELFEQLGEYKF QNALLVRYTKKVPQVSTPTLVEVSRNLG KVGSKCCKHPEAKRMPCAEDYLSVVLN QLCVLHEKTPVSDRVTKCCTESLVNRRPC FSALEVDETYVPKEFNAETFTFHADICTLS EKERQIKKQTALVELVKHKPKATKEQLK AVMDDFAAFVEKCCKADDKETCFAEEG KKLVAASQAALGLGGSSGGKVTYTSQED LVEKKCLAKKYTHLSCDKVFCQPWQRCI EGTCVCKLPYQCPKNGTAVCATNRRSFP TYCQQKSLECLHPGTKFLNNGTCTAEGK FSVSLKHGNTDSEGIVEVKLVDQDKTMFI CKSSWSMREANVACLDLGFQQGADTQR RFKLSDLSINSTECLHVHCRGLETSLAECT FTKRRTMGYQDFADVVCYTQKADSPMD DFFQCVNGKYISQMKACDGINDCGDQSD ELCCKACQGKGFHCKSGVCIPSQYQCNG EVDCITGEDEVGCAGFASVTQEETEILTA DMDAERRRIKSLLPKLSCGVKNRMHIRR KRIVGGKRAQLGDLPWQVAIKDASGITC GGIYIGGCWILTAAHCLRASKTHRYQIWT TVVDWIHPDLKRIVIEYVDRIIFHENYNA GTYQNDIALIEMKKDGNKKDCELPRSIPA CVPWSPYLFQPNDTCIVSGWGREKDNER VFSLQWGEVKLISNCSKFYGNRFYEKEM ECAGTYDGSIDACKGDSGGPLVCMDANN VTYVWGVVSWGENCGKPEFPGVYTKVA NYFDWISYHVGRPFISQYNVGGSSGGGH CQAPDHFLFAKLKTQTNASDFPIGTSLKY ECRPEYYGRPFSITCLDNLVWSSPKDVCK RKSCKTPPDPVNGMVHVITDIQVGSRINY |

TABLE 11b-continued

Complement Factor 1 Fusion-Containing Constructs

| Fusion Construct | Terminal fused | Fragments or Base Molecules used | Sequence |
|---|---|---|---|
| | | | SCTTGHRLIGHSSAECILSGNAAHWSTKP PICQRIPCGLPPTIANGDFISTNRENFHYGS VVTYRCNPGSGGRKVFELVGEPSIYCTSN DDQVGIWSGPAPQCII (SEQ ID NO: 22) |
| CR1(ccp15) + fH(ccp2) + fH(ccp3) + fH(ccp4) | | fH and CR1 | |
| fH(ccp1) + CR1(ccp16) + fH(ccp3) + fH(ccp4) | | | |
| fH(ccp1) + fH(ccp2) + CR1(ccp17) + fH(ccp4) | | | |
| CR1(ccp15) + CR1(ccp16) + fH(ccp3) + fH(ccp4) | | | |
| fH(ccp1) + CR1(ccp16) + CR1(ccp17) + fH(ccp4) | | | |
| CR1(ccp15) + fH(ccp2) + CR1(ccp17) + fH(ccp4) | | | |
| CR1(ccp15) + CR1(ccp16) + CR1(ccp17) + fH(ccp4) | | | |
| CR1(ccp15-17) | | | |
| N531G-CR1(CCP15-17) | | | |

F. Combination Fusion Constructs

In some embodiments, provided herein are fusion constructs comprising at least one domain of complement factor I (CFI), a second component, and a third component. These exemplary fusion constructs may comprise a combination of components fused together, and each include at least one CFI domain. As noted above, some exemplary fusion constructs comprising a first component comprising CFI, a second component, and a third component may include a fusion construct comprising albumin, at least one CFI domain, and at least one domain of Factor H (FH).

Figure 7:
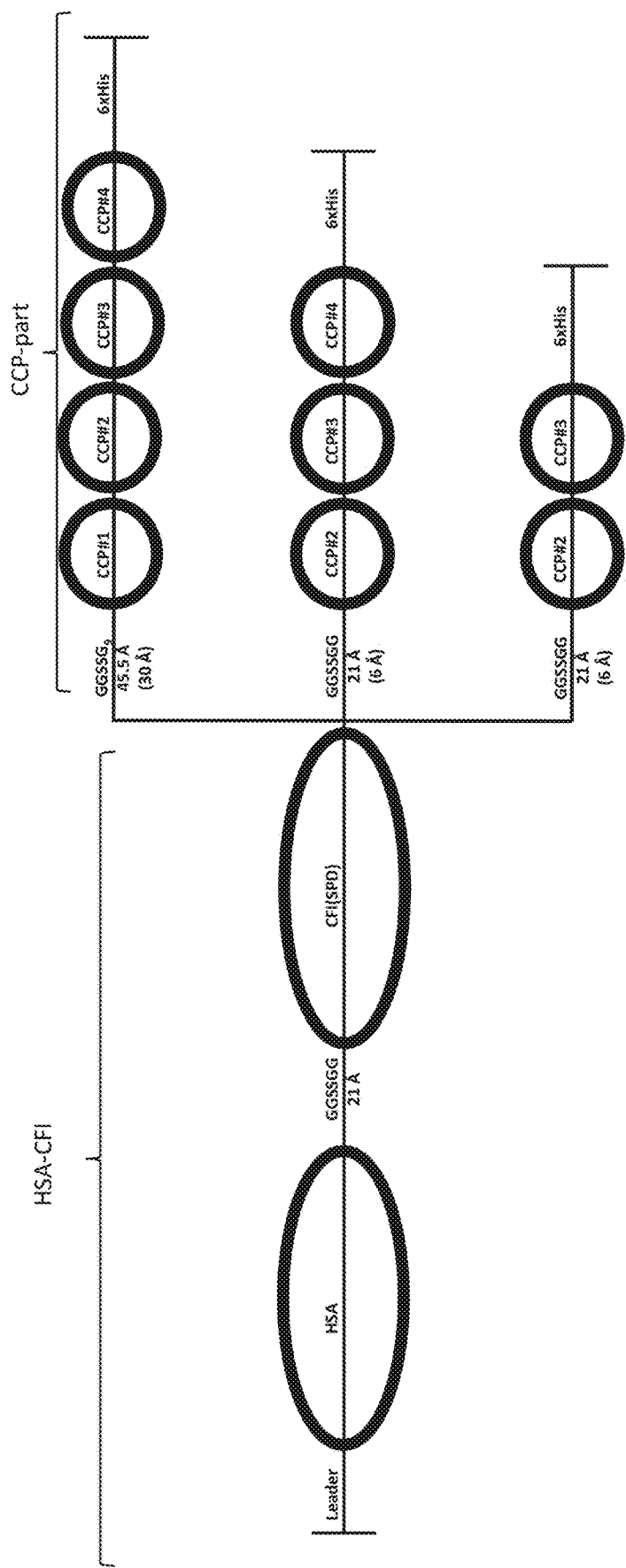
FIG. 7 depicts a schematic representation of three exemplary fusion constructs of the disclosure, each comprising HSA, at least one CFI domain, and various domains of Factor H, the part connected by optional/exemplary linkers.

FIG. 7 depicts a schematic representation of three exemplary fusion constructs comprising HSA, at least one CFI domain, and various domains of Factor H. Each of the exemplary fusion constructs shown may comprise a CFI-HSA portion comprising a leader sequence, HSA, a wild type CFI as described earlier herein, and varying domains of FH (referred to as the "CCP-part" in FIG. 7). As noted above, the CFI-HSA portion may be constructed as with a GGSSGG (SEQ ID NO: 6) linker fusing together the HSA and SPD of CFI. Exemplary fusion referred to herein as the CFI-HSA-FH_CCP1-4 fusion construct comprises a wild type CFI, and CCP domains of FH 1-4. CFI-HSA-FH_CCP1-4 also comprises a GGSSGG (SEQ ID NO: 6) linker, which is a combination of the GGSSGG-linker (SEQ ID NO: 6) and the Gly-only linker that connects together the CCP4 domain and the CCP19 domain in mini Factor H. Other exemplary fusion construct shown comprise CCP domains 2-4 of FH, and CCP domains 2-3 of FH. The lengths of the linkers used in the exemplary fusion constructs are shown, with conservative minimum lengths shown in parentheses. It should be understood that any other suitable flexible linkers may also be used.

Other exemplary fusion constructs provided herein comprise a wild type CFI or CFI variant, at least one FH domain, and at least one CR1 domain. In some embodiments, the fusion construct comprises wild type CFI or CFI variant, at least one FH domain, and at least one CR1 domain. In some embodiments, the fusion construct comprises human serum albumin, a wild type CFI or CFI variant, and at least one FH domain, and at least one CR1 domain. The fusion constructs comprising at least one FH domain and at least one CR1 domain can comprise an orientation including an FH domain fused to a CR1 domain, alternating FH and CR1 domains, one or more sequential FH domains fused to one or more sequential CR1 domains, one or more sequential CR1 domains fused to one more FH domains, or combinations thereof. In some embodiments, the fusion construct comprises a wild type CFI or CFI variant, hCR1; CCP15; CCP16; CCP17, and hFH; CCP1; CCP2; CCP3; CCP4. In some embodiments, the fusion construct comprises a wild type CFI or CFI variant and hCR1; CCP15; hFH; CCP2;

CCP3; CCP4. In some embodiments, the fusion construct comprises a wild type CFI or CFI variant and hFH; CCP1; hCR1; CCP16; hFH; CCP3; CCP4. In some embodiments, the fusion construct comprises a wild type CFI or CFI variant and hCR1; CCP15; CCP16; hFH; CCP3; CCP4. In some embodiments, the fusion construct comprises a wild type CFI or CFI variant and hFH; CCP1; hCR1; CCP16; CCP17; hFH; CCP4. In some embodiments, the fusion construct comprises a wild type CFI or CFI variant and hCR1; CCP15; CCP16; CCP17; hFH; CCP4. It is understood that any of the fusion constructs may further comprise one or more linkers as described herein. In some embodiments, the fusion construct comprises a wild type CFI or CFI variant, at least one FH domain, at least one CRI domain, and a linker region. It is understood that any of the fusion constructs may further comprise a human serum albumin. In some embodiments, the fusion construct comprises a human serum albumin, a wild type CFI or CFI variant, at least one FH domain, and at least one CRI domain.

In some embodiments, provided herein are fusion constructs comprising a first component comprising at least one CFI domain, a second component, and a third component, wherein the second component is at least one domain of FH, and the third component is any half-life extender. In some embodiments, the third component is a protein (e.g. serum albumin or Fc). In some embodiments, the third component is not a protein (e.g. PEG).

II. Generation of CFI Variants and CFI Fusion Constructs

Provided herein are methods and compositions for generating CFI variants and CFI fusion constructs. Accordingly provided are nucleic acids and vectors encoding any of the CFI variants or fusion constructs of the disclosure. Also provided are cells comprising one or more nucleic acids encoding a CFI or variant thereof, and fusion constructs of the disclosure.

Provided herein are nucleic acids encoding the CFI variants and fusion constructs described herein.

Provided herein are expression vectors encoding the CFI variants and fusion constructs described herein. Expression vectors can include transcription regulatory elements, such as enhancers or promoters, operably linked to the nucleic acid sequence encoding the CFI variant or fusion construct of the disclosure.

Cell lines can be developed to express production of the CFI and the variants and fusion constructs described herein. Cell lines for producing CFI, CFI can be accomplished using any host cell capable of expressing the CFI variants, and CFI fusions constructs described herein. Host cells can be mammalian cells, insect cells, fungal cells, plant cells, and/or bacterial cells. For expression of the CFI variants and fusion constructs, the host cell line can be transiently or stably transfected or transduced with expression vectors encoding the CFI, CFI variants, and CFI fusions. Vectors can be, for example, plasmids or viral vectors. In some embodiments, the host cell line is a mammalian cell line. In some embodiments, the host cell is a Chinese hamster ovary (CHO) cell.

CFI variants and fusion constructs described herein can be recombinantly expressed in mammalian cell lines known in the art for producing biologic products, e.g. Chinese hamster ovary (CHO) cells. Mammalian cells can be transfected or transduced with an expression vector encoding the CFI variants and fusion constructs described herein using any method known in the art.

Provided herein are methods of generating a CFI or a variant thereof in an activated state; the method comprising producing the CFI in a cell comprising one or more nucleic acid encoding the CFI or variant thereof, and an expression cassette for furin.

Provided herein are methods for production and purification of CFI variants and fusion constructs described herein. CFI variants and fusion constructs described herein may be purified from conditioned media by standard methods known in the art. In some embodiments CFI variants and fusion constructs may be purified by chromatography on affinity matrices. In some embodiments the affinity matrix is CaptureSelect™ human albumin affinity matrix. In some embodiments CFI variants and fusion constructs may be purified by chromatography on cation and/or anion exchange matrices and optionally size exclusion chromatography. CFI variants and fusion constructs may optimally be buffer exchanged into any suitable buffer known in the art. Purity can be assessed by any method known in the art including gel electrophoresis, orthogonal HPLC methods, staining and spectrophotometric techniques.

III. Uses of CFI Variants and CFI Fusion Constructs

The CFI variants and fusion constructs of the disclosure may be used for modulating the complement system.

As discussed herein, in some embodiments, a CFI variant or CFI fusion construct of the disclosure is capable of modulating the classical and lectin complement pathway.

As discussed herein, in some embodiments, a CFI variant or CFI fusion construct of the disclosure is capable of modulating the alternate complement pathway.

As discussed herein, in some embodiments, a CFI variant or CFI fusion construct of the disclosure is capable of decreasing the amplification of the complement system.

As discussed herein, in some embodiments, a CFI variant or CFI fusion construct of the disclosure is capable of increasing the cleavage of C3b.

As discussed herein, in some embodiments, a CFI variant or CFI fusion construct of the disclosure is capable of increasing the cleavage of C4b.

As discussed herein, in some embodiments, a CFI variant or CFI fusion construct of the disclosure is capable of increasing the generation of C4c.

As discussed herein, in some embodiments, a CFI variant or CFI fusion construct of the disclosure is capable of increasing the generation of iC3b.

As discussed herein, in some embodiments, a CFI variant or CFI fusion construct of the disclosure is capable of increasing the generation of C3dg from iC3b.

As discussed herein, in some embodiments, a CFI variant or CFI fusion construct of the disclosure is capable of increasing the generation of C3c from iC3b.

As discussed herein, in some embodiments, a CFI variant or CFI fusion construct of the disclosure is capable of reducing the level of C3b α-chain.

As discussed herein, in some embodiments, a CFI variant or CFI fusion construct of the disclosure is capable of increasing the hydrolysis of a peptide substrate.

As discussed herein, in some embodiments, a CFI variant or CFI fusion construct of the disclosure is capable of increasing the proteolysis of a macromolecular protein substrate.

As discussed herein, in some embodiments, a CFI variant or CFI fusion construct of the disclosure is capable of reducing in the level or function of membrane attack complex (MAC).

As discussed herein, in some embodiments, a CFI variant or CFI fusion construct of the disclosure is capable reducing observed hemolysis.

As discussed herein, in some embodiments, a CFI variant or CFI fusion construct of the disclosure is capable of increasing the cleavage of C3b in the absence of cofactor, e.g. in a cofactor independent manner.

As discussed herein, in some embodiments, a CFI variant or CFI fusion construct of the disclosure is capable of increasing the cleavage of C4b in the absence of cofactor, e.g. in a cofactor independent manner.

The CFI variants and fusion constructs of the disclosure may be used for therapeutics in a subject. As used herein, a subject includes any mammalian subject and includes primates, rodents, domestic animals, zoo animals, and pets. In some embodiments, the mammalian subject is a human subject. In some embodiments, the mammalian subject is a non-human primate.

A. CFI Variants and Fusion Constructs for Modulation of the Complement System

Provided herein is a method of modulating the complement system, comprising contacting a sample in vitro or a tissue in vivo with any one of the CFI variants or fusion constructs provided herein. In some embodiments, the sample is plasma.

B. CFI Variants and Fusion Constructs for Treatment of Non-Ocular Conditions

In some embodiments, the CFI variants or fusion constructs provided herein are useful for treating a non-ocular condition in a subject. In some embodiments, provided herein is a method of treating an ocular condition in a subject in need thereof, the method comprising administering to the subject a therapeutically effective amount of any one of the CFI variants or fusion constructs provided herein, or the pharmaceutical composition provided herein below.

In some embodiments, the non-ocular condition is characterized by a deficiency of CFI. In some embodiments, the non-ocular condition is characterized by dysregulation of the complement system.

In some embodiments, the non-ocular condition is a systemic acute indication. In some embodiments, the non-ocular condition is a systemic acute indication selected from the group consisting of: acute glomerulonephritis, acute renal injury, acute respiratory distress syndrome, bacterial meningitis, brain hemorrhage, burns, coronavirus infection, Epstein-Barr virus infection, hematopoietic stem cell transplantation, ischemia reperfusion injury, Lyme disease, myocardial infarction, organ transplantation, periodontitis, pneumonia, pre-eclampsia, schistosomiasis, sepsis, stroke, thromboembolism, and traumatic brain injury.

In some embodiments, the non-ocular condition is a systemic chronic indication. In some embodiments, the non-ocular condition is a systemic chronic indication selected from the group consisting of: Alzheimer's disease, anti-neutrophil cytoplasmic antibody (ANCA)-associated vasculitis, antiphospholipid syndrome, asthma, atherosclerosis, atypical hemolytic uremic syndrome (aHUS), autoimmune hemolytic anemia, bullous pemphigoid (BP), C3 glomerulopathy, chronic kidney failure, chronic obstructive pulmonary disease (COPD), Cold agglutinin disease (CAD), Crohn's disease, diabetic neuropathy, generalized myasthenia gravis (gMG), Granulomatosis with Polyangiitis (GPA), Guillain-Barré Syndrome (GBS), hereditary angioedema (HAE), hidradenitis suppurativa (HS), IgA nephropathy (IgAN), lupus nephritis (LN), membranous glomerulonephritis (MN), microscopic polyangiitis (MPA), motor neuron disease, multifocal motor neuropathy (MMN), multiple sclerosis (MS), non-insulin dependent diabetes, osteoarthritis, pancreatitis, Parkinson's disease, paroxysmal nocturnal hemoglobinuria (PNH), post-transplant lymphoproliferative disease, protein losing enteropathy, psoriasis, pyoderma gangrenosum, rheumatoid arthritis, schizophrenia (SZ), systemic lupus erythematosus (SLE), immune thrombocytopenia (ITP), and ulcerative colitis, Lampert-Eaton myasthenic syndrome (LEMS), CHAPLE syndrome (CD55 deficiency), thrombotic microangiography (TMA) and chronic inflammatory demyelinating polyneuropathy (CIDP), Huntington disease and ischemia reperfusion injuries.

In some embodiments, the CFI variants or fusion constructs provided herein have an improved characteristic as compared to a wild type CFI. In some embodiments, the improved characteristic is an increase in activity, wherein the increase in activity comprises an increase in the cleavage of C3b and/or C4b. The potency and specificity of the CFI variant provided herein can be tuned for particular therapeutic indications. In some embodiments, the CFI variants or fusion constructs provided herein are C3b degraders. In some embodiments, the C3b degraders are useful for the treatment of diseases. In some embodiments, the CFI variants provided herein are C4b degraders and are useful for the treatment of diseases. For example, the diseases that may be treated by use of the C4b degraders include, but are not limited to a non-ocular condition. In some embodiments, the non-ocular condition is a systemic chronic indication. In some embodiments, the non-ocular condition is a systemic chronic indication selected from the group consisting of: Alzheimer's disease, Amyotrophic lateral sclerosis (ALS), anti-neutrophil cytoplasmic antibody (ANCA)-associated vasculitis, antiphospholipid syndrome, asthma, atherosclerosis, atypical hemolytic uremic syndrome (aHUS), autoimmune hemolytic anemia, bullous pemphigoid (BP), C3 glomerulopathy, chronic kidney failure, chronic obstructive pulmonary disease (COPD), Cold agglutinin disease (CAD), Crohn's disease, diabetic neuropathy, generalized myasthenia gravis (gMG), Granulomatosis with Polyangiitis (GPA), Guillain-Barré Syndrome (GBS), hereditary angioedema (HAE), hidradenitis suppurativa (HS), IgA nephropathy, lupus nephritis (LN), membranous glomerulonephritis (MN), microscopic polyangiitis (MPA), motor neuron disease, multifocal motor neuropathy (MMN), multiple sclerosis (MS), non-insulin dependent diabetes, osteoarthritis, pancreatitis, Parkinson's disease, paroxysmal nocturnal hemoglobinuria (PNH), post-transplant lymphoproliferative disease, protein losing enteropathy, psoriasis, pyoderma gangrenosum, rheumatoid arthritis, schizophrenia (SZ), systemic lupus erythematosus (SLE), immune thrombocytopenia (ITP), warm Autoimmune hemolytic anemia (wAIHA), Immune-Complex Membranoproliferative Glomerulonephritis (IC-MPGN), and ulcerative colitis, Lampert-Eaton myasthenic syndrome (LEMS), CHAPLE syndrome (CD55 deficiency), thrombotic microangiography (TMA) and chronic inflammatory demyelinating polyneuropathy (CIDP), Huntington disease and ischemia reperfusion injuries.

In some embodiments, the non-ocular condition is non-oncological.

In some embodiments, the non-ocular condition is oncological. In some embodiments, the non-ocular condition is oncological, and is characterized by solid tumors, or by liquid tumors. In some embodiments, the non-ocular condition is characterized by solid tumors, and is selected from the group consisting of: colorectal tumors, hormone-refractory prostate cancer, melanoma, metastatic breast cancer, metastatic colorectal cancer, metastatic esophageal cancer, metastatic pancreas cancer, metastatic stomach cancer, nasopharyngeal carcinoma, non-small cell lung cancer, pancreas tumors, squamous cell carcinoma, and stomach tumors. In some embodiments, the non-ocular condition is characterized by liquid tumors, and is selected from the group consisting of: acute myelogenous leukemia, B-cell lymphoma, and Hodgkin's disease.

C. CFI Variants and Fusion Constructs for Treatment of Ocular Conditions

In some embodiments, the CFI variants or fusion constructs provided herein are useful for treating an ocular condition in a subject. In some embodiments, provided herein is a method of treating an ocular condition in a subject in need thereof, the method comprising administering to the subject a therapeutically effective amount of any of the CFI variants or fusion constructs provided herein, or the pharmaceutical composition provided herein below.

In some embodiments, the ocular condition is characterized by a deficiency of CFI. In some embodiments, the ocular condition is characterized by dysregulation of the complement system.

In some embodiments, the ocular condition is characterized by the presence of a dysfunctional CFI gene. In some embodiments, the ocular condition is characterized by dysregulation of the complement system and low CFI levels.

In some embodiments, the ocular condition selected from the group consisting of: diabetic macular edema (DME), diabetic retinopathy, dry age-related macular degeneration (AMD), glaucoma, keratoconjunctivitis, neuromyelitis optica spectrum disorder (NMOSD), open angle glaucoma, polypoidal choroidal vasculopathy, Stargardt Disease, uveitis, and vitreoretinopathy.

In some embodiments, wherein the ocular condition is non-oncological.

D. Combination Therapies

The administration of any one of the therapeutic CFI variants or fusion constructs provided herein may be a monotherapy, or may be in combination with any other known drugs or treatments. The other known drugs or treatments may be for conditions associated with dysregulation of the complement system, or may be associated with a CFI deficiency. In some embodiments, the conditions may be ocular. In some embodiments, the conditions may be non-ocular. In some embodiments, the therapeutic CFI variants or fusion constructs provided herein are co-administered with one or more C5 inhibitors. In some embodiments, the C5 inhibitor is eculizumab. In some embodiments, the C5 inhibitor is cemdisiran.

E. Administration

The CFI variants and fusion constructs described herein may be delivered as polypeptide-based therapies, or nucleic-acid based therapies.

Such treatment as contemplated herein includes both administration of a CFI variant of the disclosure or fusion construct of the disclosure, as well as administration of one or more nucleic acids encoding for a CFI variant of the disclosure or a fusion construct of the disclosure. Accordingly, provided herein are pharmaceutical compositions comprising the CFI variants of the disclosure, CFI fusion constructs of the disclosure, as well as pharmaceutical compositions comprising one or more nucleic acids encoding for CFI variants of the disclosure and encoding for fusion constructs of the disclosure.

Accordingly provided herein are nucleic acids encoding the CFI variants and fusions constructs of the disclosure and are delivered as a part of a nucleic acid-based gene therapy to a subject in need. In some embodiments, the nucleic acid encoding for a CFI variant or fusion construct of the disclosure is delivered as a part of a viral vector based gene therapy (e.g. lentiviral-based therapy, adenoviral-based therapy, adeno-associated viral-based therapy, and the like). In some embodiments, the nucleic acid encoding for a CFI variant or fusion construct of the disclosure is delivered as a naked nucleic acid. In some embodiments, the nucleic acid encoding for a CFI variant or fusion construct of the disclosure is delivered inside a liposome. In some embodiments, the nucleic acid encoding for a CFI variant or fusion construct of the disclosure is delivered as a part of a nanoparticle. In some embodiments, the nucleic acid encoding for a CFI variant or fusion construct of the disclosure is delivered as a part of a virus-like particle.

In some embodiments, the CFI variants and fusion constructs described herein may be delivered as polypeptide-based therapeutics.

The in vivo administration of the therapeutic CFI variants or fusion constructs described herein (protein or nucleic acid based therapeutics) may be carried out intravenously, intramuscularly, subcutaneously, topically, orally, transdermally, intraperitoneally, intraorbitally, intrathecally, intraventricularly, intranasally, transmucosally, through implantation, or through inhalation. Administration of the therapeutic fusion constructs may be performed with any suitable excipients, carriers, or other agents to provide suitable or improved tolerance, transfer, delivery, and the like.

In exemplary embodiments, administration of the therapeutic CFI variants or fusion constructs described herein is a subcutaneous administration. In some embodiments, the subcutaneous administration is a daily, every other day, twice weekly, or weekly administration.

In some embodiments, administration of the therapeutic CFI variants or fusion constructs described herein is an intravenous administration.

As generally contemplated herein, the CFI variants or fusion constructs described herein are delivered in an activated two chain form. However, in some instances, inactive CFI variants or fusion constructs can be delivered in an inactive single chain form. In some embodiments, what is delivered comprises both single chain inactive and two chain active forms.

F. Dosages

In some embodiments, any of the therapeutic CFI variants or fusion constructs described herein may be administered to a subject in need thereof in a dosage of about 0.1 mg/kg to about 10 mg/kg. In some embodiments, the dosage is about 1 mg/kg. In some embodiments, administration of the therapeutic CFI variants or fusion constructs described herein is a subcutaneous administration, at a dosage of about 0.1 mg/kg, about 0.5 mg/kg, about 1 mg/kg, about 1.5 mg/kg, about 2 mg/kg, about 2.5 mg/kg, about 3 mg/kg, about 3.5 mg/kg, about 4 mg/kg, about 4.5 mg/kg, about 5 mg/kg, about 5.5 mg/kg, about 6 mg/kg, about 6.5 mg/kg, about 7 mg/kg, about 7.5 mg/kg, about 8 mg/kg, about 8.5 mg/kg, about 9 mg/kg, about 9.5 mg/kg, or about 10 mg/kg. In some embodiments, administration of the therapeutic CFI variants or fusion constructs described herein is an intravenous administration, at a dosage of about 0.1 mg/kg, about 0.5 mg/kg, about 1 mg/kg, about 1.5 mg/kg, about 2 mg/kg, about 2.5 mg/kg, about 3 mg/kg, about 3.5 mg/kg, about 4 mg/kg, about 4.5 mg/kg, about 5 mg/kg, about 5.5 mg/kg, about 6 mg/kg, about 6.5 mg/kg, about 7 mg/kg, about 7.5 mg/kg, about 8 mg/kg, about 8.5 mg/kg, about 9 mg/kg, about 9.5 mg/kg, or about 10 mg/kg. In some embodiments, administration of the therapeutic CFI variants or fusion constructs described herein is daily administration, every other day administration, weekly administration, or twice weekly administration.

In some embodiments, the target level of the therapeutic fusion constructs in plasma may be about 0.1 µg/ml, about 0.5 µg/ml, about 1 µg/ml, about 1.5 µg/ml, about 2 µg/ml, about 2.5 µg/ml, about 3 µg/ml, about 3.5 µg/ml, about 4 µg/ml, about 4.5 µg/ml, 5 µg/ml, about 5.5 µg/ml, about 6 µg/ml, about 6.5 µg/ml, about 7 µg/ml, about 7.5 µg/ml, about 8 µg/ml, about 8.5 µg/ml, about 9 µg/ml, about 9.5 µg/ml, about 10 µg/ml, about 10.5 µg/ml, about 11 µg/ml, about 11.5 µg/ml, about 12 µg/ml, about 12.5 µg/ml, about 13 µg/ml, about 13.5 µg/ml, about 14 µg/ml, about 14.5 µg/ml, 15 µg/ml, about 15.5 µg/ml, about 16 µg/ml, about 16.5 µg/ml, about 17 µg/ml, about 17.5 µg/ml, about 18 µg/ml, about 18.5 µg/ml, about 19 µg/ml, about 19.5 µg/ml, about 20 µg/ml, about 20.5 µg/ml, about 21 µg/ml, about 21.5 µg/ml, about 22 µg/ml, about 22.5 µg/ml, about 23 µg/ml, about 23.5 µg/ml, about 24 µg/ml, about 24.5 µg/ml, 25 µg/ml, about 25.5 µg/ml, about 26 µg/ml, about 26.5 µg/ml, about 27 µg/ml, about 27.5 µg/ml, about 28 µg/ml, about 28.5 µg/ml, about 29 µg/ml, about 29.5 µg/ml, about 30 µg/ml. Exemplary fusion constructs that may be administered to a subject in need thereof to achieve a target level of about 20 µg/ml may include CFI-HSA, comprising a CFI corresponding to a wild type CFI.

G. Formulations

Pharmaceutical compositions containing a CFI variant or fusion constructs of the disclosure can be formulated in any conventional manner by mixing a selected amount of the polypeptide with one or more physiologically acceptable carriers or excipients, for use in the treatments provided herein. Selection of the carrier or excipient is within the skill of the administering profession and can depend upon a number of parameters. These include, for example, the mode of administration and disorder treated. The pharmaceutical compositions provided herein can be formulated for single dosage (direct) administration or for dilution or other modification. The concentrations of the compounds in the formulations are effective for delivery of an amount, upon administration, that is effective for the intended treatment. Typically, the compositions are formulated for single dosage administration, but not necessarily.

H. Pharmaceutical Compositions

The disclosure also provides pharmaceutical compositions comprising any one of the CFI variants or fusion constructs disclosed herein, and optionally a pharmaceutical acceptable excipient or carrier. In some embodiments, the pharmaceutical composition is sterile. The pharmaceutical compositions may be formulated to be compatible with their intended routes of administration. In some embodiments, the pharmaceutical compositions of the disclosure are suitable for administration to a human subject, or other non-human primate. In exemplary embodiments, the pharmaceutical composition is formulated for subcutaneous administration.

I. Kits and Articles of Manufacture for Therapeutic CFI Variants and Fusion Constructs The disclosure also provides a kit or article of manufacture comprising any one of the CFI variants or fusion constructs disclosed herein, or any pharmaceutical composition disclosed herein. In some embodiments, the kits may further include instructional materials for carrying out any of the methods disclosed herein. In some embodiments, the kits may further include sterile containers or vials for holding the fusion constructs and/or pharmaceutical compositions disclosed herein. In some embodiments, the kits may further include sterile delivery devices for administering the fusion constructs and/or pharmaceutical compositions disclosed herein. In some embodiments, an article of manufacture comprises any pharmaceutical composition of the disclosure.

EXAMPLES

Example 1: CFI-HSA Expression, Purification, Activation, and In Vitro Sialylation Overview For Example 1, reference to CFI-HSA refers to human serum albumin fused to the N-terminal end of wild type CFI (SEQ ID NO: 21).

A wild type CFI-HSA protein was expressed in Chinese hamster ovary (CHO) cells, purified with anti-albumin affinity purification, activated with furin, and purified by sizing columns. The activated CFI-HSA protein was subjected to in vitro sialylation to increase the total sialylation of CFI-HSA. Finally, the sialylated protein was purified using anti-albumin affinity purification and polished by size-exclusion column chromatography.

Expression

The CFI-HSA gene (SEQ ID NO: 21) was synthesized (ThermoFisher Scientific, Geneart, Regensburg, Germany), with the human serum albumin at the amino terminus of the CFI protein. The protein was made with the signal sequence of SEQ ID NO: 2, which was removed during expression. The amino terminal albumin tag was connected to the CFI gene through a linker (SEQ ID NO: 6). The gene of CFI-HSA was inserted into an expression vector (Lake Pharma, Hayward, CA) utilizing standard molecular biology techniques. The resulting plasmid DNA was transformed into E. coli. The transfected E. coli were grown in 200 ml of LB media for expression of plasmid DNA and harvested utilizing standard techniques. The plasmid DNA was run on an agarose gel for quality assessment and sequence confirmed before proceeding to transfection.

1.0 liter of suspension TunaCHO™ cells were seeded in a shake flask and were expanded using serum-free chemically defined medium. On the day of transfection, the expanded cells were seeded into a new flask with fresh medium. The plasmid DNA was transiently transfected into the CHO cells using Lipofectamine 2000 (ThermoFisher Scientific). The cells were maintained as a batch-fed culture until the end of the production run. The protein was expressed for 14 days at 37° C. at 125 RMP with 8% $CO_2$ concentration. Cells were centrifuged and supernatant was collected for purification of secreted CFI-HSA at the end of 14 days expression.

Purification

The supernatant with expressed CFI-HSA protein was passed through a 10 ml gravity flow column of CaptureSelect™ human albumin affinity matrix (ThermoFisher Scientific). Column-bound protein was washed with 10 column volume of 20 mM sodium phosphate buffer. Bound CFI-HSA protein was eluted in two steps: first, with 3 column volume of 20 mM Tris-HCl, pH 7.0 buffer with and 2 M MgCl2, and second, with 3 column volume of 20 mM citric acid, pH 3.0. Elution from both steps 1 and 2 was collected in 5 ml fractions. Each fraction of the step 2 elution was neutralized with 10% of neutralization buffer (1.5 M tris-HCL pH 7.4). All fractions were analyzed by reducing and non-reducing SD S-PAGE electrophoresis and bands were visualized by SimplyBlue™ SafeStain (ThermoFisher Scientific). CFI-HSA runs as a 130 kDa band on a non-reducing gel and as 102 kDa and 28 kDa bands on a reducing gel.

Fractions with maximum CFI-HSA concentration and purity were pooled for further processing.

Furin Activation

CFI-HSA is expressed as an inactive, single chain precursor protein, and is activated by furin, another serine protease. Furin is an endoprotease that cleaves CFI at its conserved RRKR sequence (also referred to as the furin recognition sequence), resulting in a heavy and light chain connected by a disulfide bond. The furin-processed, mature, two-chain protein is the activated form of the CFI protein.

Cleavage of CFI-HSA for producing the protein in its activated form was performed by incubation of 4 μg of recombinant furin per mg of purified CFI-HSA in Tris-NaCl (tris buffered saline), 2.5 mM $CaCl_2$ and 0.5% CHAPS at 30° C. for 18 hours. The CFI-HSA protein concentration was maintained at 1.4 mg/ml. This results in more than 90% activation of the protein. The activated protein was separated from inactivated CFI-HSA, and other proteins by size-exclusion chromatography. Size exclusion chromatography (SEC) was performed using a HiLoad 16/600 Superdex 200 column (GE Healthcare Life Sciences) and phosphate buffer saline (PBS, 137 mM NaCl, 2.7 mM KCl, 10 mM $Na_2HPO_4$, 2 mM $KH_2PO_4$, pH 7.4) as the mobile phase. Collected fractions were analyzed by CE-SDS (LabChip GXII, Perkin Elmer). Fractions containing the target protein were pooled and analyzed by SE-UPLC.

In Vitro sialylation

The activated CFI-HSA protein was subject to in vitro sialylation. Briefly, the sialylation was carried out in a two-step enzymatic reaction. First, a galactosylation reaction of CFI-HSA was performed in a 200 μl volume utilizing a 1:200 molar ratio of galactosyltransferase (GalT1) enzyme and CFI-HSA in 10 mM UDP-Galactose, 5 mM $MnCl_2$, and 100 mM MES, pH 6.5 buffer. Galactosylated CFI-HSA was purified from the reaction mixture by CaptureSelect™ Human Albumin affinity chromatography, as described earlier. Next, the sialylation reaction was performed in a 250 μl volume utilizing a 1:50 molar ratio of enzyme alpha 2,6-sialyl transferase and purified CFI-HSA in 80 μM Alkaline phospahatase, 6.1 mM CMP-NANA, 10 mM $ZnCl_2$ and 200 mM MES buffer, pH 6.5 at 37° C. for 1 hour. The sialylated CFI-HSA protein was purified from the reaction mixture by CaptureSelect™ Human Albumin affinity chromatography. The extent and characteristics of the sialic acid chain on CFI-HSA was determined by utilizing an Agilent/Prozyme Analytical service, GS-SAP method for total sialic acid quantitation (Agilent GS48), and mass spectrophotometric (MS) analysis (Lake Pharma analytical service), described in further detail below.

Briefly, total sialic acid quantitation was performed by mixing 20 μl of each sample with 10 μl of release reagent in a 96 well plate. The reaction mixture was incubated for 2 hours at 80° C. The samples were cooled to room temperature and 10 μl of labeling reagent was added to each sample for a further incubation of 3 hours at 50° C. The samples were again cooled down to room temperature and 160 μl of de-ionized (dI) water was added to bring the total volume to 200 μl. 10 μl of sample was injected in the Agilent UHPLC Poroshell C18 column to run at a flow rate of 0.4 ml/minute at 30° C. in 4% methanol, 8% acetonitrile in water (Line A1) and 100% ACN (Line B1). The peaks were recorded at 373/448 nm wavelength. A standard curve of total peak area versus picomoles (pmol) of sialic acid was generated by running 1-2000 pmol of NANA (N-acetylneuraminic acid, Neu5Ac) supplied with the kit on the same column Total sialic acid of each sample was quantitated by comparing the peak area of samples against the standard curve. The sialylation obtained is summarized in Table 1.1 below.

TABLE 1.1

Sialylation Assay Results

| Protein | Sialic Acid (Neu5Ac) pmol/ug protein |
|---|---|
| Recombinant CFI-HSA | 35 ± 0.7 |
| Recombinant CFI-HSA-In vitro sialylated | 69 ± 2.2 |
| Bovine Fetuin control | 222 ± 2.6 |

The mass spectrometric analysis was performed by a standard trypsin Q-TOF mass spectrometer. Briefly, all samples were treated, reduced and alkylated by DTT and iodoacetamide, followed by trypsin digestion. The digested samples were analyzed by Waters ACQUITY UPLC coupled to a Xevo G2-XS-QTOF mass spectrometer using a protein BEH C18 column. The performed analysis is summarized in Table 1.2 below.

TABLE 1.2

Peptide Analysis Results

| | Glycans | Recombinant CFI-HSA (%) | Recombinant CFI-HSA-In vitro sialylated (%) |
|---|---|---|---|
| Peptide Analysis | Man5 | 7.1 | 16.24 |
| | G0 | 2.39 | 0 |
| | G0F | 0.88 | 0 |
| | G1 | 6.07 | 0 |
| | G1F | 6.68 | 0.03 |
| | G2 | 13.62 | 2.37 |
| | G2F | 24.81 | 1.78 |
| | G2FSA | 13.38 | 19.44 |
| | G2FSA2 | 21.48 | 53.91 |

Polishing

Purified CFI-HSA protein was subjected to size-exclusion chromatography (SEC) using a HiLoad 16/600 Superdex 200 column (GE Healthcare Life Sciences) and phosphate buffer saline as the mobile phase. Collected fractions were analyzed by CE-SDS (LabChip GXII, Perkin Elmer). Fractions containing the target protein were pooled, and the concentration was brought to 5 mg/ml, and the samples were flash frozen for storage at −80° C.

Expression and Purification of CFI-HSA Variants

The DNA of CFI-HSA variants was generated either by synthesis or by site-directed mutagenesis utilizing standard techniques. The proteins were expressed in 250 ml of suspension in TunaCHO™ cells, as described herein with reference to wild type CFI-HSA protein, with the exception that the expression was done for 7 days instead of 14 days. After 7 days, the cells were centrifuged, and conditioned media was passed through a gravity flow column of CaptureSelect™ human albumin affinity matrix (ThermoFisher Scientific). Column-bound protein was washed with 10 column volume of 20 mM sodium phosphate buffer. Bound CFI-HSA protein was eluted with 3 column volume of 20 mM Tris-HCl, pH 7.0 buffer with and 2 M $MgCl_2$ in 5 ml fractions. CFI-HSA or its variants were buffer exchanged (either by dialysis or a spin concentrator) into 30 mM HEPES, 150 mM NaCl, 2.5 mM $CaCl_2$, pH 7.4. Recombinant human furin, at a molar ratio of 1:25 (furin:CFI-HSA), was added to CFI-HSA and the reaction mixture was incubated at 30° C. for 16 hours. Two micrograms of the activation mixture was run on a 9% SDS-PAGE gel to assess the activation efficiency. Generally, more than 80% activation was achieved.

Figure 17:
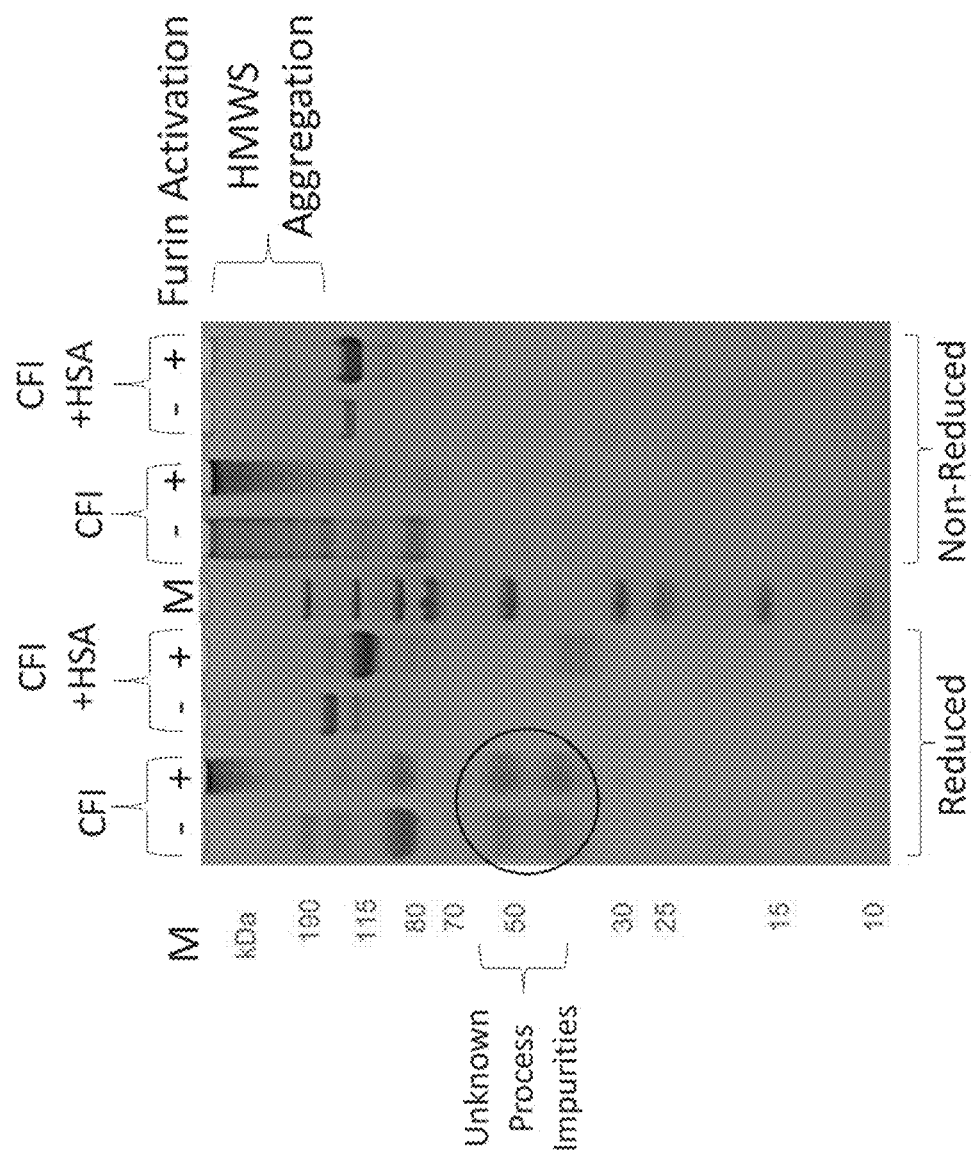
FIG. 17 is an image of a stained SDS-PAGE gel showing effects of N-terminal fusion of HSA to CFI on solubility, aggregation, and activation compared to wild-type CFI without a fusion tag.

N-terminal Albumin Fusion Provides Solubility and Facilitates Activation of CFI-HSA Activation was compared between CFI-HSA and wild-type CFI without an albumin, or other fusion tag (WT-CFI). A gene construct for WT-CFI was expressed essentially as described above for CFI-HSA. The recombinant WT-CFI protein showed moderate purity by reduced SDS-PAGE, however, significant High Molecular Weight Species (HMWS) and aggregates under reduced and non-reduced conditions were observed (FIG. 17). For CFI-HSA, which has the addition of an N-terminal HSA tag, transient expression using the TunaCHO™ cells followed by purification as described in above showed no HMWS or aggregates on reduced and non-reduced SD S-PAGE. As shown in FIG. 17, activation of the purified recombinant CFI with furin resulted in a further increase in aggregates and HMWS with almost complete polydispersity. Furthermore, essentially no activated CFI was observed by reducing SDS-PAGE. On the contrary, the addition of furin efficiently activated CFI-HSA almost completely under the same conditions and the CFI-HSA protein remained as a monomer under non-reduced conditions with no evidence of aggregates and HMWS (FIG. 17). When compared to CFI lacking any fusion tags, there is a significant and unexpected benefit of the N-terminal HSA tag for maintaining solubility, monodispersity and efficient furin activation.

Example 2: CFI-HSA Variants Characterization by Peptidolytic Activity Assay

For Example 2, reference to CFI-HSA refers to human serum albumin fused to the N-terminal end of wild type CFI (SEQ ID NO: 21).

The proteolytic activity of wild type CFI-HSA and CFI variant-HSA fusions (referred collectively herein as "CFI-HSA proteins") was tested by following the cleavage of chromogenic substrates by use of a chromophore. The S-2288 (Chromogenix) peptide substrate was selected for this assay as it is sensitive to a broad spectrum of serine proteases. The peptidolytic activity of the CFI-HSA proteins were measured by the rate of generation of p-nitroaniline (pNA) upon substrate cleavage, which occurred spectrophotometrically at 405 nm.

The CFI-HSA proteins were diluted to an initial concentration of 400 nM in 100 µl d of HBS/BSA (30 mM HEPES, 140 mM NaCl, 0.2% BSA, pH 7.4) in a non-coated 96-well microplate (Nunc). A working stock of 4 mM S-2288 was made in HBS/BSA in a separate tube. The microplate and diluted chromogenic substrate were pre-warmed to 37° C. for 5 minutes. The assay was initiated by the addition of 100 µl of pre-warmed S-2288 to the wells of the microplate containing the CFI-HSA proteins. This resulted in a final concentration of 200 nM of the CFI-HSA proteins, and 2 mM of S-2288 substrate in a 200 µl reaction volume. The rate of substrate cleavage was recorded every 30 seconds for 3 hours at 37° C. at 405 nm, using a microplate reader (Multiskan™ GO Microplate Spectrophotometer, Thermo Scientific). Peptide hydrolysis activity of wild type CFI-HSA was normalized as 100% in order to calculate the percentage of peptidolysis activity of the CFI-HSA variants. The results are summarized in Table 2.1 below.

TABLE 2.1

Peptide Hydrolysis Assay

| Domains | CFI Type | S-2288 Cleavage (% Activity) | % CV |
|---|---|---|---|
| Plasma derived CFI | CFI-PD | 132 | 12 |
| CFI-HSA Protein | wt | 100 | 15 |
| A:B chain interface | K14A | 75 | 15 |
| | Y20A | 22 | 11 |
| | Y20F | 52 | 43 |
| | D26A | 57 | 12 |
| | F29A | 36 | 20 |
| | R35A | 78 | 12 |
| | E38A | 54 | 18 |
| | M220A + K221Q | 60 | 38 |
| | L307G | 140 | 11 |
| LDLRA2 domain | S250A | 58 | 20 |
| | S250L | 5 | 30 |
| ΔA-chain (HSA-SPD) | Δ(K1-P305) | 73 | 16 |
| C-term extension | D425A | 85 | 11 |
| | D425K | 67 | 11 |
| | D425R | 58 | 11 |
| | ΔC-term (Δ558-PFISQYNV (SEQ ID NO: 14)-565) | 50 | 14 |
| | R557A | 69 | 14 |
| A:B chain Interface + C-term extension | E38A + D425R | 30 | 12 |
| | Y20F + D425R | 31 | 13 |
| | S250A + D425R | 33 | 14 |
| Activation loop | K326A-R327A | 34 | 17 |

TABLE 2.1-continued

| Domains | CFI Type | S-2288 Cleavage (% Activity) | % CV |
|---|---|---|---|
| Human Trypsin autolysis loop swap | 456-REKDNERVFS (SEQ ID NO: 9)-465 --> NTASSGADYPDE (SEQ ID NO: 10) | 1022 | 11 |
| Mouse autolysis loop | E457G | 397 | 62 |
| | E461Q | 144 | 26 |
| | R462K | 64 | 14 |
| | F464Y | 84 | 17 |
| | E457G + E461Q + R462K + F464Y | 753 | 11 |
| hTrypsin 200-loop swap | 514-MDANNVT (SEQ ID NO: 13)-520 --> NG | 8 | 41 |
| S1 entrance | E530D | 12 | 10 |
| | N531G | 851 | 133 |
| | N531A | 150 | 25 |
| | P535A | 127 | 20 |
| | N531G + P535A | 1531 | 12 |
| 99-loop | Y408F | 93 | 18 |
| | Y408L | 510 | 11 |
| 99-loop + S1 entrance | Y408L + N531G | 4755 | 12 |
| | Y408F + N531G | 1145 | 177 |
| 99-loop + S1 entrance + mCFI autolysis loop | Y408L + N531G + E457G + E461Q + R462K + F464Y | 11072 | 1735 |
| ΔA-chain + S1 entrance | Δ(K1-P305) + N531G | 664 | 112 |
| | Δ(K1-P305) + N531G + P535A | 799 | 122 |
| ΔA-chain + 99-loop + S1 entrance | Δ(K1-P305) + Y408L + N531G | 2571 | 402 |
| FH + wt hCFI | FH_CCP1-8 + GGGGGGGGGGGG (SEQ ID NO: 25) + ΔHSA | 0.7 | |
| FH + wt hCFI | FH_CCP1-4 + 19-20 + 5-8 + GGGGGGGGGGGG (SEQ ID NO: 25) + ΔHSA | 75 | 21 |
| Active site mutant | S195A | 18 | 6 |

Example 3: CFI-HSA Variants Characterization by a C3b Cleavage Assay

For Example 3, reference to CFI-HSA refers to human serum albumin fused to the N-terminal end of wild type CFI (SEQ ID NO: 21).

The C3b cleavage assay is a functional assay used to determine the ability of wild type CFI-HSA and CFI-HSA variants (referred collectively herein as "CFI-HSA proteins") to cleave its natural substrate, C3b. Briefly, the CFI-HSA proteins were incubated with C3b and a truncated Factor H (mini FH) at 37° C. for analysis of C3b cleavage. Mini FH has been previously shown to be functionally active and support the CFI-mediated C3b cleavage (*J Immunol.* 2013 Jul. 15;191(2):912-21). The cleavage of C3b into smaller fragments was then monitored over time by SDS-PAGE.

First, for each CFI-HSA variant, the master reaction mixture was set up at room temperature containing the final concentrations of 500 nM of mini FH and 5 nM of the CFI-HSA proteins in HBS buffer (30 mM HEPES, 140 mM NaCl pH 7.4). The master reaction mixtures were transferred to 37° C. and allowed to equilibrate for 5 minutes. The cleavage reaction was initiated by the addition of C3b to a final concentration of 0.5 μM. 20 μl samples from the master mixtures were withdrawn for each time point measured, and quenched by the addition of 5× SDS reducing sample buffer. Samples were run on a 9% SDS-PAGE gel and C3b cleavage was visualized by Coomassie staining The amount of C3b cleavage that occurred was quantitated by densitometry. The C3b cleavage activity of wild type CFI-HSA was normalized as 100% in order to calculate the percentage of C3b cleavage activity of the CFI-HSA variants. The results of the C3b cleavage assay are summarized in Table 3.1 below.

TABLE 3.1

| C3b Cleavage Assay | | | |
|---|---|---|---|
| Domain | Variants | % Activity | CV |
| Plasma derived CFI | CFI-PD | 99 | — |
| Human serum albumin with WT CFI | CFI-HSA | 100 | * |
| A:B Chain Interface | K14A | 93 | 5 |
| A:B Chain Interface | Y20A | 7 | — |
| A:B Chain Interface | Y20F | 80 | 12 |
| A:B Chain Interface | D26A | 94 | 6 |
| A:B Chain Interface | R35A | 47 | — |
| A:B Chain Interface | M220K + A221Q | 92 | 3 |
| SPD-(delta-A) | SPD-Δ(K1-P305) | 35 | 17 |
| LDLRA2 domain | S250A | 82 | 10 |
| LDLRA2 domain | S250L | -4 | — |
| Active site mutant | S195A | 0 | — |
| A:B Chain Interface | E38A | 79 | 9 |
| A:B Chain Interface | F29A | 16 | — |
| 200 loop | delta(200) | 11 | 2 |
| C-terminal extension/switch | delta(C-term) | 7 | 5 |
| C-terminal extension/switch | R557A | 21 | 7 |
| C-terminal extension/switch | D425A | 103 | 1 |
| C-terminal extension/switch | D425R | 104 | 3 |
| C-terminal extension/switch | D425K | 105 | 7 |
| Trypsin Autolysis loop swap | R456N + E457T + K458A + D459S + N460S + E461G + R462A + V463D + F464Y + S465P + Ins465aD-Ins465bE | 18 | 9 |
| Mouse CFI Autolysis loop swap | E457G-E461Q-F464Y | 106 | 4 |
| 99 loop | Y408L | 104 | 4 |
| Activation loop | K326A + R327A | 58 | 6 |
| 99 loop/S1 pocket | Y408L + N531G | 123 | 14 |
| S1 pocket entrance | N531G + P535A | 120 | 10 |
| C-terminal extension/switch | L307G | 91 | 10 |

Figure 8A:
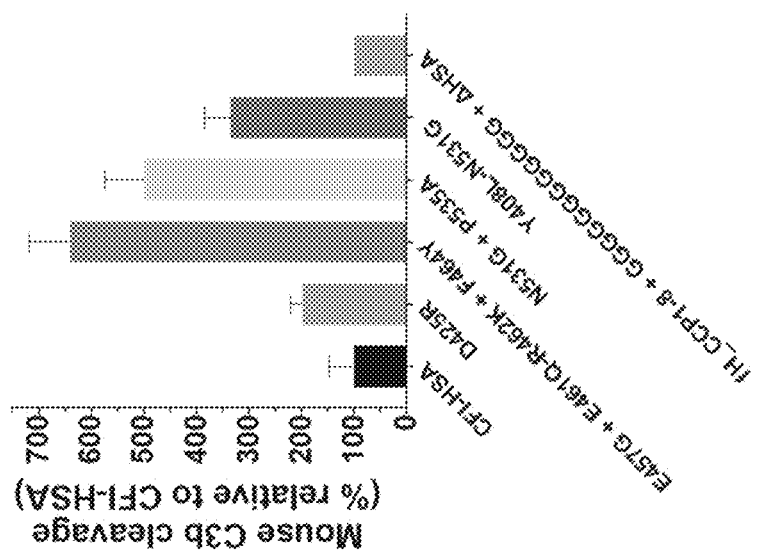
FIG. 8A and FIG. 8B are graphs depicting the relative percentage of human and mouse C3b cleavage, respectively, when various CFI variant fusion constructs (HSA and FH) were compared to CFI wild type fusion constructs.
Figure 8B:
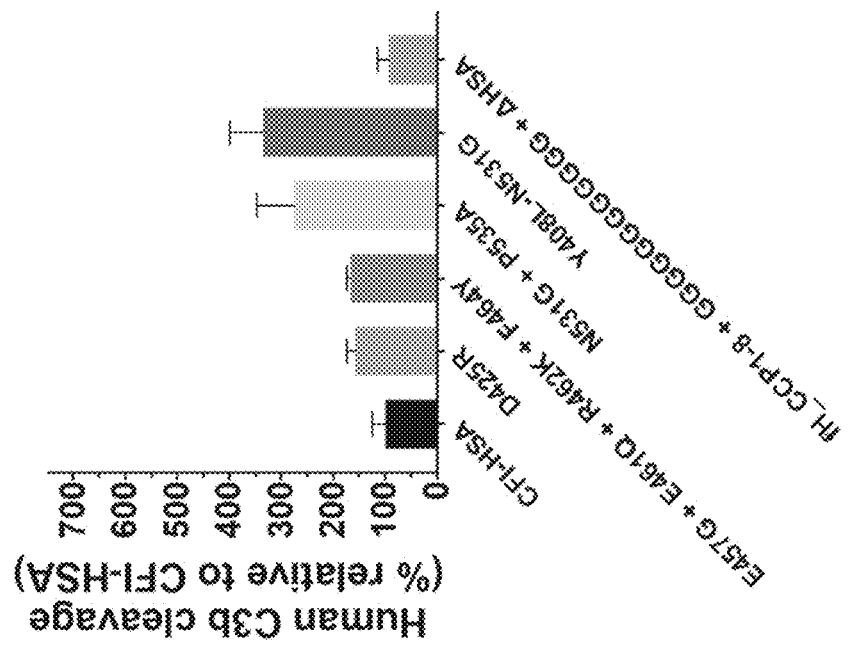

FIGS. 8A-8B are graphs depicting the relative percentage of human and mouse C3b cleavage, respectively, when various CFI variant fusion constructs were compared to CFI wild type fusion constructs. These results show that each variant tested had a higher percentage of C3b cleavage in comparison to a fusion construct comprising a wild type CFI, in both human and mouse.

To compare the rate of C3b cleavage by each CFI-HSA variant to that of the wild type CFI-HSA, a time course for C3b cleavage by the CFI-HSA proteins was performed in parallel. Disappearance of the C3(alpha)' band was observed as an indication of C3b cleavage. C3b includes two chains, (alpha)' and beta. When the disappearance of the C3(alpha)' band at a molecular weight of 114 kDa was observed, both SDS-PAGE and densitometry of the relevant stained band, corrected for the average background staining (lane intensity outside the band), were performed.

The apparent rate for loss of band intensity was estimated by fitting a simple exponential decay formula to the band intensity data as a function of time, thereby extracting an apparent rate constant (k) of C3b cleavage. The relative rate of C3b cleavage by the CFI-HSA variants was calculated by dividing with the corresponding WT rate: k(variant)/k(WT control). This procedure was performed on 3 independent SDS-PAGE experiments and the average of k(variant)/k(WT control) was calculated along with the accompanying standard deviation. These results are summarized in Table 3.2 below.

TABLE 3.2

| C3b Cleavage assay | | | |
|---|---|---|---|
| Domains | Variant name | kmut/kwt | % CV |
| CFI-HSA | WT | 1 | |
| A:B chain interface | L307G | 1 | 24 |
| C-term extension | D425A | 1 | 7 |
| | D425K | 1 | 37 |
| | D425R | 2 | 11 |
| | R557A | 0 | 57 |
| Interface + C-term extension | E38A + D425R | 1 | 8 |
| | Y20F + D425R | 1 | 14 |
| | S250A + D425R | 1 | 19 |
| Activation loop | K326A + R327A | 0 | 40 |
| human Trypsin autolysis loop swap | 456-REKDNERVFS (SEQ ID NO: 9)-465 --> NTASSGADYPDE (SEQ ID NO: 10) | 0 | |
| Mouse autolysis loop | E457G | 3 | 14 |
| | E461Q | 2 | 11 |
| mouse CFI autolysis loop swap | E457G + E461Q + R462K + F464Y | 2 | 4 |
| S1 entrance | N531G | 1 | 11 |
| | N531A | 1 | 46 |
| | P535A | 1 | 27 |
| | N531 + P535A | 3 | 26 |

TABLE 3.2-continued

C3b Cleavage assay

| Domains | Variant name | kmut/kwt | % CV |
|---|---|---|---|
| 99-loop | Y408L | 1 | 8 |
| 99-loop + S1 entrance | Y408L + N531G | 3 | 19 |

Figure 9:
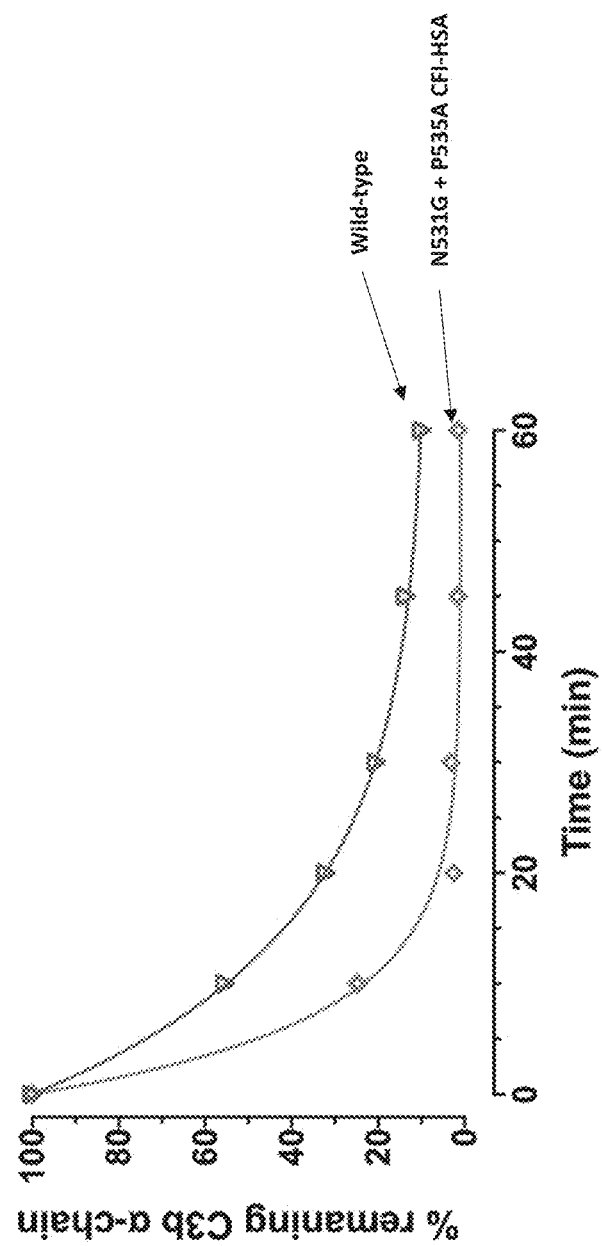
FIG. 9 is a graph depicting the activity of a fusion construct of the disclosure comprising a CFI variant (N531G+P535A) compared to the activity of a wild type CFI.

FIG. 9 is a graph depicting the activity of a fusion construct comprising a CFI variant comprising the substitutions N531G+P535A fused to HSA, as compared to the activity of a wild type CFI-HSA. The percentage of the C3b Δ-chain remaining after incubation over time was measured to evaluate activity of the tested CFI variant in comparison to wild type CFI. The tested CFI variant showed increased activity by about 2-fold to about 3-fold as compared to wild type CFI. Because even subtle differences in C3b cleavage can cause disease, such as atypical hemolytic uremic syndrome (aHUS), these results show that CFI-HSA variants can be useful for increasing activity of the complement system to counter C3-induced diseases.

Example 4: Quantitative Analysis of CFI-HSA C3b Cleavage Activity by Measurement of C3dg Formation by Time-Resolved Immuno-Fluorometric Assay (TRIFMA)

For Example 4, reference to CFI-HSA refers to human serum albumin fused to the N-terminal end of wild type CFI (SEQ ID NO: 21).

A C3dg assay was used to determine the cleavage of C3b caused by Complement Factor I (CFI). The formation of C3dg was used as a quantitative analysis of CFI-HSA C3b cleavage activity and was measured by a time-resolved immuno-fluorometric assay (TRIFMA). Briefly, the complement pathway in human serum was activated by using heat-aggregated IgG. The effect of plasma-derived CFI or CFI-HSA proteins, including CFI-HSA variants, on C3b cleavage was measured by capturing C3dg, utilizing a C3dg antibody on a microtiter plate. Bound C3dg was detected by a combination of a biotinylated C3dg antibody and Europium-labelled streptavidin, and measured by time-resolved fluorometry.

MaxiSorb microtiter plates (Nunc) were coated with 100 μl monoclonal IgM rat anti-human C3dg antibody at 2 μg/ml in 15 mM Na$_2$CO$_3$, 35 mM NaHCO$_3$, pH 9.6 coating buffer by overnight incubation at room temperature. The remaining protein binding sites were blocked by incubation with HSA at 1 mg/ml in TBS. Unbound HSA was washed with TBS-Tween.

Test samples were diluted in a 1 to 6 dilution of human serum to desired concentrations in a 100 μl volume with dilution buffer (0.14 M NaCl, 10 mM Tris, 14 mM sodium azide, with 0.05% (v/v) Tween 20 (TBS/Tween), 1 mg/ml HSA and 0.1 mg/ml of heat aggregated IgG. Four-fold, six point dilutions were made for each CFI-HSA variant to cover the variants concentration range from 3132 nM to 3 nM. The reaction mixture was incubated at 37° C. for 90 minutes and quenched by 10 mM EDTA. To capture the generated C3dg, 100 μl of each reaction mixture were added to the antibody-coated microtiter wells and incubated overnight at 4° C. To detect the bound C3dg, 100 μl of biotinylated rabbit anti-C3dg antibody (DAKO) was added at 0.5 μg/ml to the wells and incubated for 2 hours at room temperature. After washing with the Eu3+-streptavidin combination (Perkin Elmer), 25 μM EDTA was added to the wells and incubated for 1 hour at room temperature (1/1000). After washing, 200 μl enhancement buffer (Ampliqon) was added to each well. Plates were read using a DELFIA-reader Victor5+(Perkin Elmer) by time-resolved fluorometry. The results are summarized in Table 4.1 below.

TABLE 4.1

C3dg quantitation Assay (TRIFMA)

| Domain | Variants | EC$_{50}$ WT/ EC$_{50}$ Variant | % CV |
|---|---|---|---|
| Plasma derived CFI | CFI-PD | 0.9 | 15.0 |
| Human serum albumin with WT CFI | CFI-HSA | 1.0 | 0.0 |
| C-terminal extension/switch | D425A | 1.7 | 17.0 |
| C-terminal extension/switch | D425R | 4.2 | 5.0 |
| 99 loop/S1 pocket | Y408L + N531G | 0.6 | 79.0 |
| S1 pocket entrance | N531G + P535A | 26.2 | 68.0 |

Figure 10:
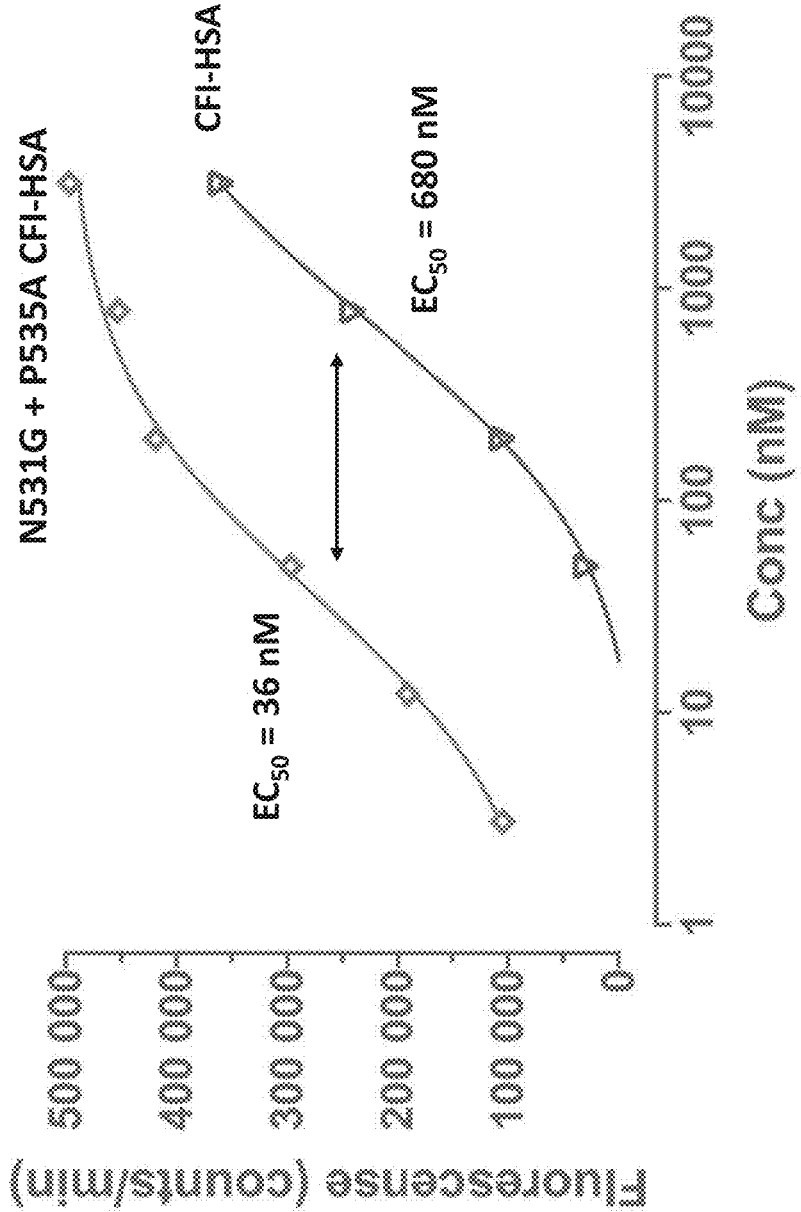
FIG. 10 is a graph depicting the half maximal effective concentration ($EC_{50}$) of a fusion construct of the disclosure comprising a CFI variant (N531G+P535A) as compared to a fusion construct comprising wild type CFI.

FIG. 10 is a graph depicting the half maximal effective concentration (EC$_{50}$) of a fusion construct comprising a CFI variant as compared to a fusion construct comprising wild type CFI. The tested CFI variant is a CFI variant comprising substitutions N531G+P535A, fused to HSA. The TRIFMA assay showed that the tested CFI variant showed approximately an 18-fold improvement in activity over the wild type.

These results showed that exemplary CFI-HSA variants had a higher percentage of C3b cleavage activity than wild type CFI-HSA, or plasma-derived CFI.

Example 5: Characterization of CFI-HSA Variants by Hemolysis Assay

For Example 5, reference to CFI-HSA refers to human serum albumin fused to the N-terminal end of wild type CFI (SEQ ID NO: 21).

A hemolysis assay is used for the measurement of hemolytic function of a compound that uses the complement pathway. Complement Factor I (CFI) mediates C3b cleavage with its cofactor Factor H (FH) within the alternate alternative pathway of the complement pathwaysystem. To test the hemolytic function of wild type CFI-HSA and CFI-HSA variants (referred collectively herein as "CFI-HSA proteins") in the alternate alternative pathway, C3-deficient human serum spiked with human C3 was incubated with CFI-HSA and rabbit Alsevers solution, and total hemolysis was measured spectrophotometrically. The hemolysis assay was performed on wild type CFI-HSA and plasma-derived CFI (CFI-PD) with or without FH in order to understand the effect of the cofactor FH on total hemolysis.

Briefly, 12 ml of rabbit red blood cells (RBC) was washed twice with GVB buffer (Gelatin Veronal buffer: Sigma, with 8 mM EGTA and 10 mM $MgCl_2$) and resuspended in 12 ml of ice cold GVB buffer. C3-deficient human serum was spiked with 1 μM of human C3, based on previous observations that 1 μM of C3 supports maximum hemolysis in this system. Three-fold eight-point serial dilutions of CFI-HSA in GVB buffer was done to achieve concentrations ranging from 260 μg/ml to 0.11 μg/ml in the reaction mixture. First, in a 96 well plate, 50 μl reaction mixture for each concentration point was prepared by adding 62.8% human serum, different concentrations of CFI-HSA with or without 200 μg/mL FH. The hemolysis reaction was started by adding 50 μl of rabbit RBC and incubated in a microtiter plate at 37° C. for 30 minutes. All assays were done in triplicates and all dilutions were done in GVB buffer. For a maximum hemolysis control, de-ionized water was added to the RBC, and 0.154 M NaCl was added to the RBC for a no hemolysis control. After incubation, the plate was centrifuged at 2000 rpm for 5 minutes and 90 μl of supernatant was transferred to another 96 well plate. The percent hemolysis was quantitated by measuring optical density (OD) of lysed RBC at 412 nm.

The absorbances at 412 nm were converted to a percentage of hemolysis, utilizing maximum hemolysis from the control as 100% and the buffer control 0%. The results of the hemolysis assay are summarized in Table 5.1 below.

TABLE 5.1

Hemolysis Assay Results

| | % Hemolysis | | | | | | | | | | | |
|---|---|---|---|---|---|---|---|---|---|---|---|---|
| CFI (nM) | CFI-HSA | | | CFI-HSA + 200 ug/ml CFH | | | CFI-PD | | | CFI-PD + 200 ug/ml CFH | | |
| 2000.0 | 68 | 78 | 72 | 22 | 23 | 24 | 60 | 62 | 62 | 5 | 5 | 5 |
| 666.7 | 77 | 78 | 80 | 53 | 51 | 53 | 75 | 81 | 84 | 51 | 48 | 46 |
| 222.2 | 85 | 88 | 92 | 69 | 68 | 67 | 98 | 100 | 93 | 74 | 72 | 72 |
| 74.1 | 98 | 94 | 100 | 81 | 82 | 82 | 98 | 105 | 110 | 87 | 83 | 82 |
| 24.7 | 99 | 109 | 104 | 87 | 88 | 90 | 86 | 108 | 107 | 82 | 85 | 80 |
| 8.2 | 99 | 100 | 98 | 89 | 79 | 81 | 105 | 103 | 108 | 90 | 87 | 89 |
| 2.7 | 99 | 93 | 93 | 77 | 78 | 84 | 91 | 92 | 100 | 89 | 91 | 82 |
| 0.9 | 84 | 79 | 84 | 78 | 74 | 71 | 97 | 98 | 95 | 81 | 79 | 80 |

Figure 11B:
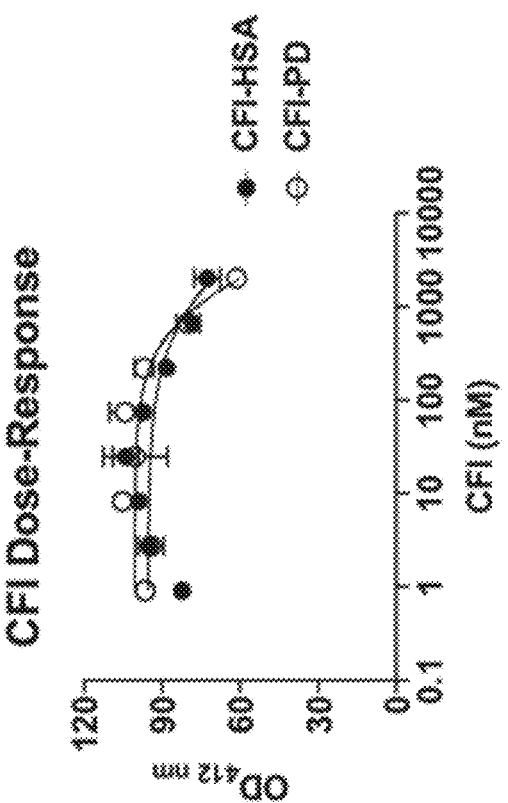
FIG. 11A and FIG. 11B depict dose response curves generated from a hemolysis assay for plasma-derived CFI (CFI-PD), and CFI-HSA wild type with and without its cofactor, Factor H, respectively.
Figure 11A:
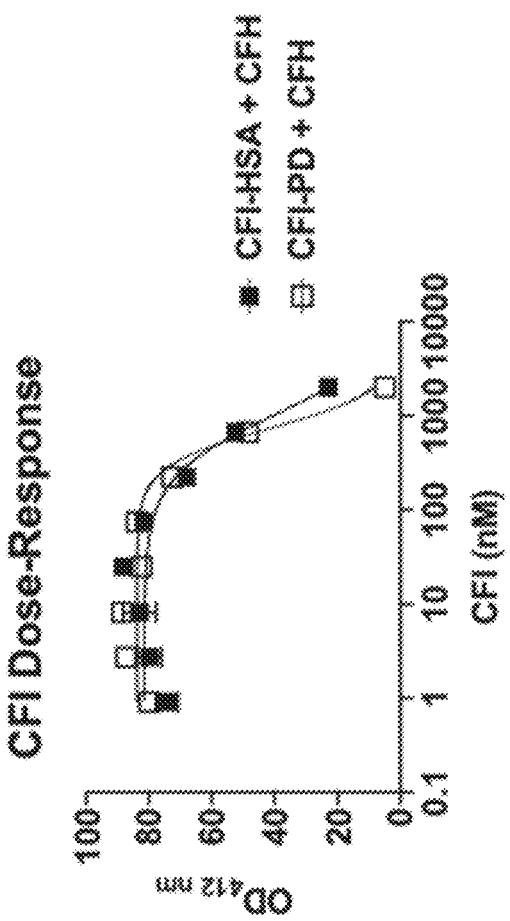

FIGS. 11A-11B depict dose response curves generated from the hemolysis assay for CFI with and without its cofactor Factor H, respectively. The dose response curves were generated by non-linear regression analysis and curve-fitting to a 4-parameter sigmoid curve in prism software. Table 5.2 below summarizes the results of the absorbances measured in the assay, showing 50% alternative pathway activity ($AP_{50}$) of wild type CFI-HSA with FH, and plasma derived CFI with FH.

Figure 11D:
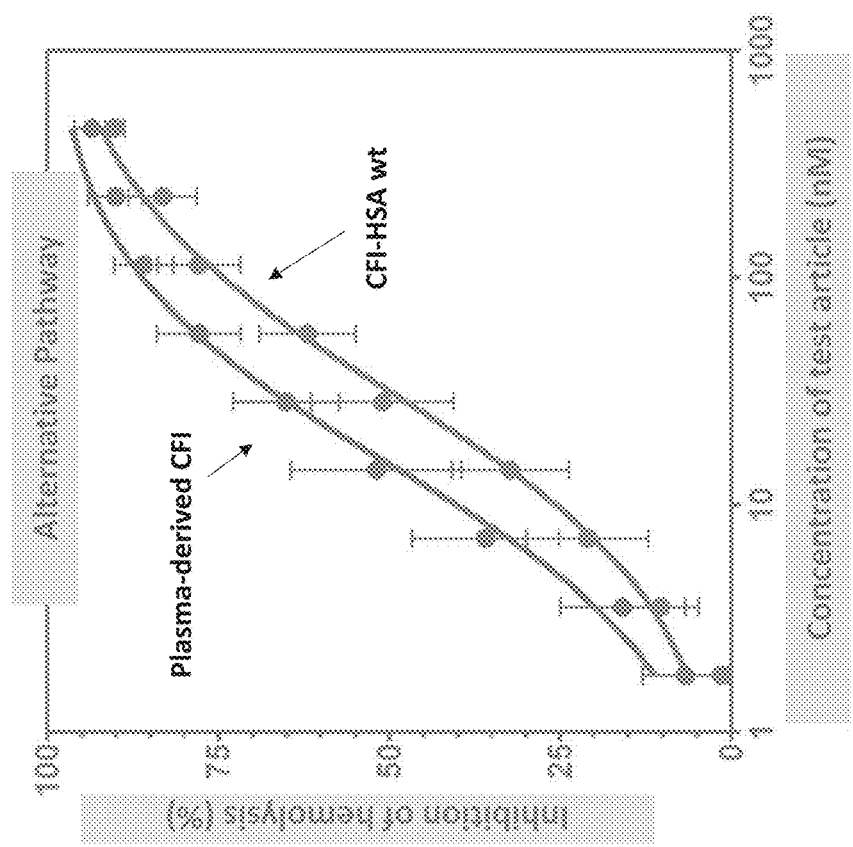
FIG. 11C and FIG. 11D depict dose response curves for percentage of hemolysis inhibition measured in the classical pathway and the alternative pathway, respectively, by plasma-derived CFI (CFI-PD), and CFI-HSA wild type.
Figure 11C:
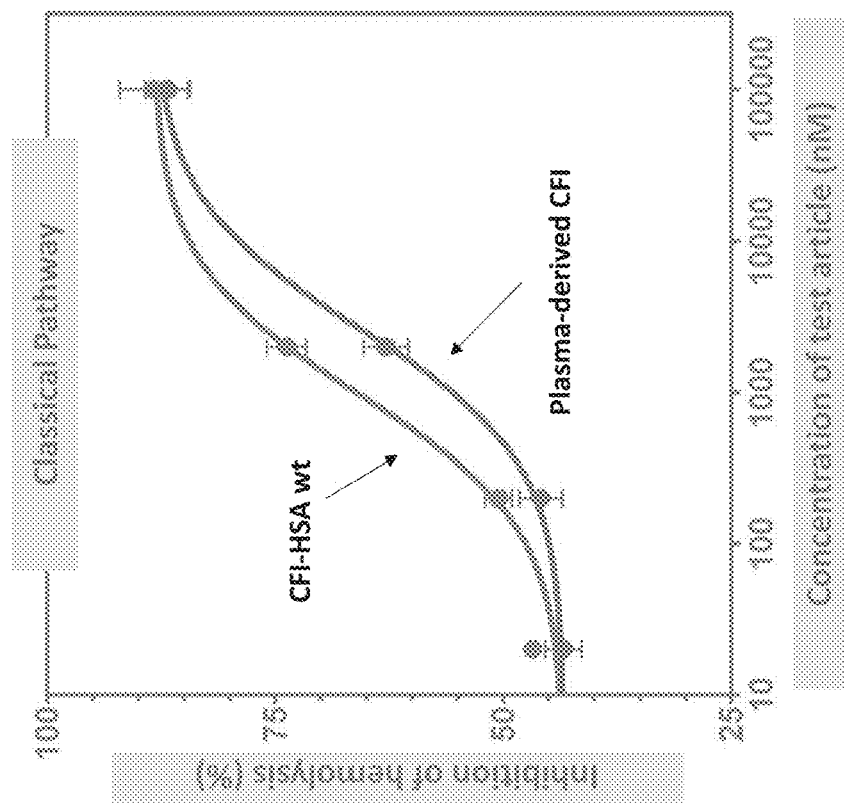

FIGS. 11C-11D depict dose response curves for percentage of hemolysis inhibition measured in the classical pathway and the alternative pathway, respectively, by plasma-derived CFI, and CFI-HSA wild type. These figures show that plasma-derived CFI and CFI-HSA wild type perform similarly in human serum.

TABLE 5.2

| Alternative Pathway Activity | |
|---|---|
| | $AP_{50}$ (nM) |
| CFI-HSA + FH | 990 ± 82 |
| CFI-PD + FH | 723 ± 84 |

These data showed that, at higher concentrations, both CFI-HSA and CFI-PD are active in the hemolysis assay. The inhibitory activity of CFI-HSA on the alternative pathway was similar to that of CFI-PD in the hemolysis assay. The hemolysis assay also showed that the inhibitory effect of CFI, both CFI-HSA and CFI-PD, on the alternative pathway increased significantly with cofactor FH.

The capacity to inhibit classical pathway hemolysis by CFI variants was measured. Sheep red blood cells were activated by anti-SRBC antibodies (Amboceptor, Testline, UK). The SRBCs were suspended in gelatin veronal buffer (GVB). In the assay plates, a dilution series of the CFI variants were added followed by the activated SRBC and Factor B and I depleted serum at ~1% (v/v). The activated SRBC were incubated with test articles for 30 mins. The cells were pelleted and the supernatant transferred to a separate plate for absorbance readings at 412 nM. Percentage lysis was calculated as follows: 100* (Absorbance test sample)/(Absorbance no CFI (0% inhibition)). Data was plotted and analyzed using four parameter non-linear regression (GraphPad Software, USA). $IC_{50}$ values were calculated for data from individual plates and averages were performed on log $IC_{50}$ values and transformed to concentration (nM) as summarized in Table 5.3.

The capacity to inhibit alternative pathway hemolysis by CFI cariants was measured. Sheep red blood cells were activated by anti-SRBC antibodies (Amboceptor, Testline, UK). The SRBCs were suspended in 8% (v/v) of normal human serum depleted of Factors B and H to which was added eculizumab to deposit C3b. The activated SRBC with deposited C3b were incubated with full-length Factor H (Complement Technologies, USA) and the test articles. After a 10 min incubation Factors B and D (Complement Technologies, USA) were added and incubated for a further 10 min. Finally, guinea pig serum (Sigma-Aldrich, UK) was added and incubated for 20 min. The cells were pelleted and the supernatant transferred to a separate plate for absorbance readings at 412 nM. Percentage lysis was calculated as follows: 100* (Absorbance test sample)/(Absorbance no CFI (0% inhibition)). Data was plotted and analyzed using four parameter non-linear regression (GraphPad Software, USA). IC50 values were calculated for data from individual plates and averages were performed on log IC50 values and transformed to concentration (nM) as summarized in Table 5.3.

TABLE 5.3

$IC_{50}$ Values for a Panel of Variants in the Classical and Alternate Pathway

| Variant | CP $IC_{50}$ (nM) | AP $IC_{50}$ (nM) |
|---|---|---|
| Plasma-derived CFI | 135 | 6.05 |
| CFI-HSA | 87.5 | 8.90 |
| E457G; N531G | 58.0 | 2.44 |
| E457G + CR1(CCP15-17) | 84.0 | 17.2 |
| E457G; N531G + CR1(CCP15-17) | 121 | 14.8 |
| N422K; E457G; N531G | 10.1 | 1.91 |
| E457G + CR1(CCP1-3) | 122 | 86.0 |
| E457G; E461Q; R462K; F464Y; N531G + CR1(CCP15-17) | 44.7 | 12.8 |
| E416A; N531G | 97.5 | 2.99 |
| E416A; D425R; E457G; N531G | 28.3 | 1.80 |
| E457G; E461Q; R462K; F464Y; E530Y; N531G | 13.8 | 1.66 |
| T377G; E457G; E461Q | 57.1 | 1.77 |
| N531G; P535A; R557A | 45.2 | 16.3 |
| E457G; E461Q; N531G; Δ(558-PFISQYNV (SEQ ID NO: 14)-565) | 217 | 26.8 |

Example 6: Pharmacokinetic Modeling to Determine Dosing in Humans Based on Non-Human Primate Data For Example 6, reference to CFI-HSA refers to human serum albumin fused to the N-terminal end of wild type CFI (SEQ ID NO: 21).

Figure 12A:
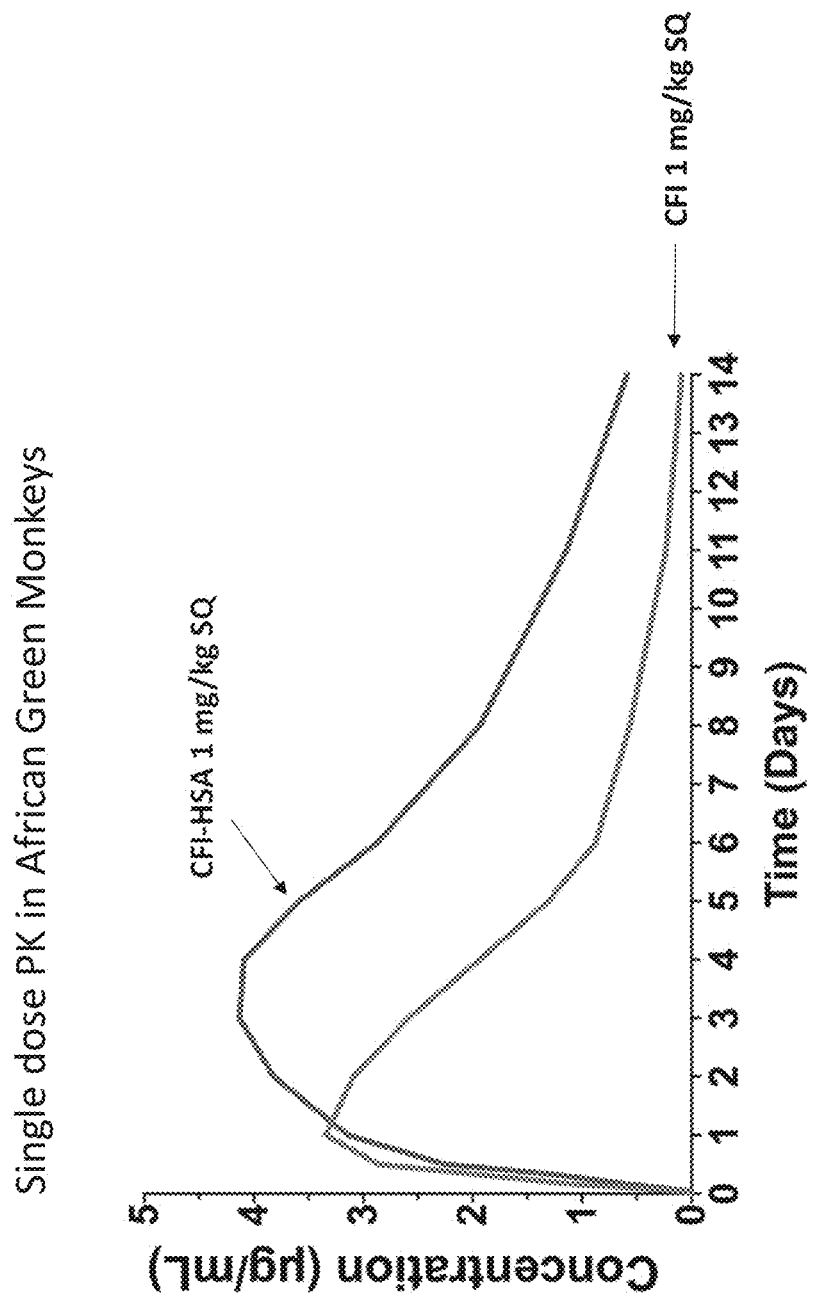
FIG. 12A and FIG. 12B are graphs depicting the measured concentrations of a wild type CFI-HSA fusion construct as compared to free plasma purified CFI, after a single subcutaneous administration to monkeys at a dose of 1 mg/kg.

A Complement Factor I (CFI) fusion construct and a free wild type CFI were tested for concentration levels in plasma after a single subcutaneous dose in African green monkeys. The fusion construct comprised a human serum albumin (HSA) and a wild type CFI (CFI-HSA). FIG. 12A is a graph depicting the measured concentrations of the CFI-HSA fusion construct as compared to the free CFI, after subcutaneous administration to the monkeys at a dose of 1 mg/kg. The CFI-HSA fusion construct showed that it could achieve a target level of about 20 µg/ml. A measurable concentration of the CFI-HSA fusion construct persisted for up to 14 days, and the target concentrate of about 20 µg/ml was measured for about 7 days. These data support a weekly subcutaneous administration of a CFI-HSA fusion construct for therapeutic uses. The data using non-human primates was used for modeling plasma concentrations in humans, shown in Table 6.1 below. These data support that weekly subcutaneous administration can be used for therapeutic purposes in humans.

Figure 12B:
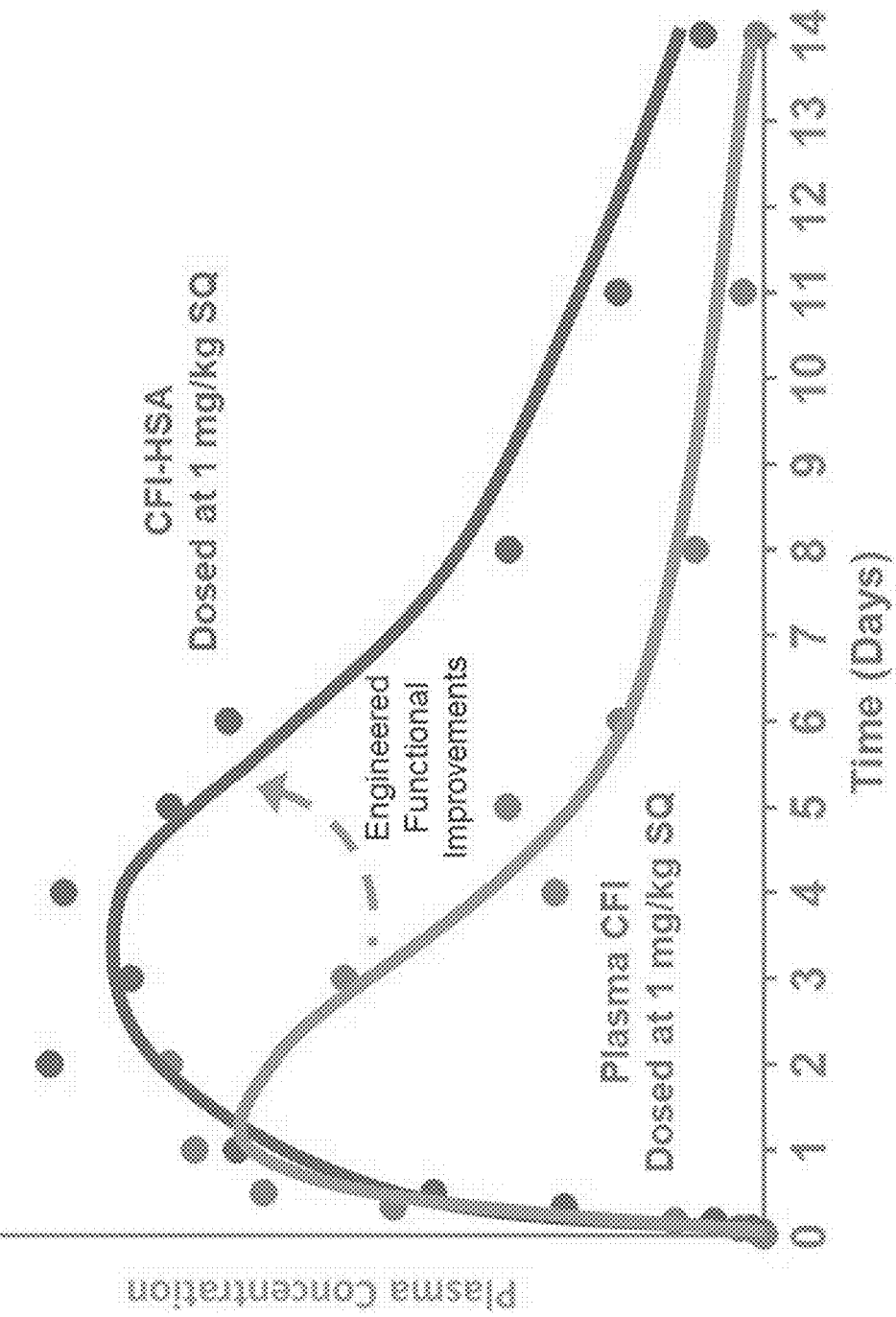

FIG. 12B depicts the graph shown in FIG. 12A with the individual data points shown along the curves for additional clarity.

TABLE 6.1

Modeled Plasma Concentrations of CFI-HSA Fusion Construct in Humans Based on Non-Human Primate Data

| Dosing frequency | Average (µg/ml) | Peak (µg/ml) | Trough (µg/ml) |
|---|---|---|---|
| Daily | 135 | 142 | 128 |
| Every second day | 68 | 75 | 61 |
| Twice weekly | 45 | 52 | 38 |
| Weekly | 19 | 27 | 13 |

Example 7: CFI-HSA and CFI Variants Characterization by C3b and C4b Cleavage Assays C3b Cleavage Reactions For Example 7, reference to CFI-HSA refers to human serum albumin fused to the N-terminal end of wild type CFI (SEQ ID NO: 21).

First, for each CFI-HSA variant, the master reaction mixture was set up at room temperature containing the final concentrations of 500 nM of mini FH and 500 nM of C3b in HBS buffer (30 mM HEPES, 140 mM NaCl pH 7.4). The master reaction mixtures were transferred to 37° C. and allowed to equilibrate for 5 minutes. The cleavage reaction was initiated by the addition of CFI-HSA protein to a final concentration of 5 nM. A sample volume corresponding to 0.6 ug of C3b was withdrawn from the master mixtures for each time point measured and quenched by the addition of 5× SDS reducing sample buffer. Samples were run on a 9 or 10% SDS-PAGE gel and C3b cleavage was visualized by Coomassie staining The amount of C3b cleavage that occurred was quantitated by densitometry. The C3b cleavage activity of wild type CFI-HSA was normalized as 100% in order to calculate the percentage of C3b cleavage activity of the CFI-HSA variants.

Another example of the cleavage reactions was performed as follows. C3b cleavage reactions were performed using 1 nM CFI (variant or wild type), 500 nM cofactor mini FH, and 500 nM soluble human C3b incubated for 10 minutes at 37° C. in HEPES buffered saline (HBS). The reaction was quenched by the addition of 1 M NaCl in HBS. The reactions were further diluted to a final concentration of 5 nM C3b in buffer (HBS, 0.5M NaCl, 0.05% Tween 20) before proceeding with an iC3b ELISA. The C3b cleavage activity was determined from the amount of iC3b generated in the cleavage reaction. The amount of iC3b formed was assayed using the MicroVue iC3b A006 ELISA kit (Quidel). The ELISA assay consists of a microplate coated with an iC3b specific monoclonal antibody for capture of formed iC3b during the reactions and detection of bound iC3b using an HRP-conjugated anti-iC3b antibody and a chromogenic substrate. The absorbance recorded is a relative measure of the iC3b product generated in the cleavage reactions. The fold difference of C3b cleavage activity of CFI variants relative to a reference molecule, CFI-HSA wild type, was calculated by dividing the background-corrected absorbance from CFI-HSA variants by the background-corrected absorbance for CFI-HSA wild type. Table 7.1 summarizes these results, presenting the fold difference of the median value for each CFI variant relative to the median value of the reference molecule. The fold differences were also calculated from SDS-PAGE gels. Samples from a C3b cleavage time course were run on a 9 or 10% SDS-PAGE gel and C3b cleavage was visualized by Coomassie staining The amount of C3b cleavage that occurred was quantitated by densitometry and the data plotted and an apparent rate constant (k) for loss of band intensity determined by fit to an exponential decay. The fold difference of C3b cleavage activity of CFI variants relative to a reference molecule, the CFI-HSA wild type, was calculated by dividing the k-value from the CFI-HSA variants by the k-value for CFI-HSA wild type.

C3b cleavage by CFI variants was further characterized by determining the EC50 for the C3b cleavage. Briefly, C3b cleavage reactions were performed using 25 nM mini FH, 75 nM soluble human C3b and a dilution series of the CFI variants. Reaction mixtures at each of the concentrations of the CFI variants were incubated for 5 min at 37° C. in HBS. The reaction was quenched by the addition of 1 M NaCl in HBS. The reactions were further diluted to a final concentration of 5 nM C3b in buffer (HBS, 0.5M NaCl, 0,05% Tween 20) before proceeding with an iC3b ELISA. The amount of iC3b generated in the reaction was determined using the MicroVue iC3b A006 ELISA kit (Quidel). The ELISA assay consists of a microplate coated with an iC3b specific monoclonal antibody for capture of formed iC3b during the reactions and detection of bound iC3b using an HRP-conjugated anti-iC3b antibody and a chromogenic substrate. The absorbance recorded is a relative measure of the iC3b product generated in the cleavage reactions. The EC50 values were calculated using a four-parameter non-linear regression fit without constraints in GraphPad Prism. Table 7.2 below summarizes the results of the iC3b ELISA titration analyses. EC50 values above 500 nM were set to be 500 nM. The cleavage reactions were also performed in the absence of mini FH where noted and analyzed in the same fashion as those containing mini FH.

C4b Cleavage Reactions

CFI regulates the classical complement pathway by proteolytic inactivation of the C4b protein. CR1, a C3b/C4b receptor, and C4 binding protein (C4BP) act as cofactors for the CFI-catalyzed cleavage reaction of C4b. The C4b cleavage assay is a functional assay to determine the ability of CFI and variants thereof for C4b cleavage activity in the presence of either the CR1 or C4BP cofactors. Complement factor protein C2, which binds specifically to C4b and not to the CFI-cleaved product iC4b, was used for C4b capturing. The CFI-catalyzed cleavage of C4b was measured by measuring the decrease in the concentration of C4b bound to C2 protein, immobilized on an ELISA plate. The captured C4b protein was detected by Anti-C4c polyclonal rabbit Ab (DAKO, #A0065) in an ELISA assay. C4b cleavage activity by CFI-HSA was normalized as 100% to calculate the percentage of C4b cleavage activity of CFI variants.

For each CFI-HSA variant, the master reaction mixture was set up at room temperature containing the final concentrations of 250 nM cofactor (CR1 domains 1-3) and 250 nM human C4b in HBS buffer (30 mM HEPES, 140 mM NaCl pH 7.4). The master reaction mixtures were transferred to 37° C. and allowed to equilibrate for 5 minutes. The cleavage reaction was initiated by the addition of CFI-HSA protein to a final concentration of 250 nM. A sample volume corresponding to 0.6 ug of C3b was withdrawn from the master mixtures for each time point measured and quenched by the addition of 5× SDS reducing sample buffer followed by incubation at 95° C. for 5 minutes. Samples were run on a 9 or 10% SDS-PAGE gel and C4b cleavage was visualized by Coomassie staining The amount of C4b cleavage that occurred was quantitated by densitometry. The C4b cleavage activity of wild type CFI-HSA was normalized as 100% in order to calculate the percentage of C4b cleavage activity of the CFI-HSA variants.

Another example of the C4b cleavage activity assay was performed as follows, to determine the C4b cleavage activity of CFI variants relative to a reference molecule, CFI-HSA wild type. The cleavage reaction was performed with 250 nM of the CFI variants in the presence of 250 nM of cofactor (CR1 domains 1-3) and 250 nM human C4b, which was incubated for 30 minutes at 37° C. The reaction mixture was diluted 20-fold before addition to a blocked ELISA plate coated with a mouse monoclonal anti-C4c antibody. The absorbance recorded from the ELISA plate is a relative measure of the C4c product generated in the cleavage reactions and therefore a measure of C4b cleavage activity. The fold difference of C4b cleavage activity of CFI variants relative to a reference molecule, CFI-HSA wild type, was calculated by dividing the background-corrected absorbance from CFI-HSA variants by the background-corrected absorbance for CFI-HSA wild type. Table 7.1 below summarizes the fold differences of the C4b cleavage activity assay of CFI variants relative to the CFI-HSA reference molecule, as measured by C4c ELISA screen with CR1.

The $EC_{50}$ of the C4b cleavage by CFI variants was measured. The assay was performed using 250 nM cofactor (CR1 domains 1-3), 250 nM human C4b and a dilution series of the CFI variants. The reaction mixtures were incubated for 30 minutes at 37° C. and then the reaction mixture was diluted 20-fold before beginning the ELISA. The amount of generated C4c was measured by ELISA using a mouse monoclonal antibody specific towards C4c. The absorbance recorded from the ELISA plate is a relative measure of the C4c product generated in the cleavage reactions and therefore a measure of C4b cleavage activity. The EC50 values were calculated using a four-parameter non-linear regression fit without constraints in GraphPad Prism. EC50 values above 1000 nM were set to be 1000 nM The cleavage reactions were also performed in the absence of CR1 where noted and analyzed in the same fashion as those containing CR1. Tables 7.2 summarizes the results of the C4c ELISA titration with the CR1 cofactor.

CFI Variant Activity in the Absence of Cofactor

C4b cleavage reactions were carried out as described above in the absence of cofactor for a panel of CFI variants (Table 7.3). The results show that CFI variants with a C-terminal fusion protein that include a human CR1 domain maintained their ability to cleave C4b in the absence of cofactor in the reaction mixture. In contrast, the CFI variants lacking a CR1 C-terminal fusion did not maintain their ability to cleave C4b. These results suggest that CFI variants with a C-terminal CR1 fusion can be CR1 cofactor independent.

TABLE 7.3

CFI Variant Cleavage of C4b in the Absence of Cofactor

| CFI Variant | C-Terminal Fusion | C4c No Cofactor $EC_{50}$ (nM) |
|---|---|---|
| Wild Type | | >2000 |
| Wild Type | hCR1; CCP15; CCP16; CCP17 | 63.5 |
| E457G; N531G; | | >1000 |
| N531G | hCR1; CCP15; CCP16; CCP17 | 76.2 |
| P535G | hCR1; CCP15; CCP16; CCP17 | 160.5 |
| E457G; P535G | hCR1; CCP15; CCP16; CCP17 | 35.9 |
| Y408L; N531G | hCR1; CCP15; CCP16; CCP17 | 57.1 |
| E457G; N531G | hCR1; CCP15; CCP16; CCP17 | 27.2 |
| Y408L; E457G; N531G | hCR1; CCP15; CCP16; CCP17 | 155.7 |
| Y408L; N531G; P535G | hCR1; CCP15; CCP16; CCP17 | 50.1 |
| E457G; N531G; P535G | hCR1; CCP15; CCP16; CCP17 | 44.8 |
| Y408L; E457G; N531G; P535G | hCR1; CCP15; CCP16; CCP17 | 97.7 |
| N531G; P535A | hCR1; CCP15; CCP16; CCP17 | 50.3 |
| E416A; N531G | | >2000 |
| E416A; D425R; E457G; N531G | | >2000 |
| E457G; E461Q; N531G | hCR1; CCP15; CCP16; CCP17 | 77.6 |
| Y408L; E457G; E461Q; R462K; N531G | hCR1; CCP15; CCP16; CCP17 | 106.4 |
| Y408L; E457G; R462K; F464Y; N531G | hCR1; CCP15; CCP16; CCP17 | 104.3 |
| T377G; E457G; E461Q | | >2000 |
| E457G; E461Q; N531G; Δ(558-PFISQYNV (SEQ ID NO: 14)-565) | | 718.8 |

C3b cleavage reactions were carried out as described above in the absence of cofactor for a panel of CFI variants (Table 7.4). The results show that CFI variants with a C-terminal fusion protein that include a human CR1 domain maintained their ability to cleave C3b in the absence of cofactor in the reaction mixture. In contrast, the CFI variants lacking a CR1 C-terminal fusion did not maintain their ability to cleave C3b. These results suggest that CFI variants with a C-terminal CR1 fusion can be CR1 cofactor independent.

TABLE 7.4

CFI Variant Cleavage of C3b in the Absence of Cofactor

| CFI Variant | C-Terminal Fusion | C3c No Cofactor $EC_{50}$ (nM) |
|---|---|---|
| Wild Type | | >2000 |
| Wild Type | hCR1; CCP15; | 33.7 |

TABLE 7.4-continued

CFI Variant Cleavage of C3b in the Absence of Cofactor

| CFI Variant | C-Terminal Fusion | C3c No Cofactor EC$_{50}$ (nM) |
|---|---|---|
| | CCP16; CCP17 | |
| E457G; N531G; | | >2000 |
| E457G; N531G | hCR1; CCP15; CCP16; CCP17 | 23.4 |
| E416A; N531G | | >2000 |
| E416A; D425R; E457G; N531G | | >2000 |
| T377G; E457G; E461Q | | >1000 |
| E457G; E461Q; N531G; Δ(558-PFISQYNV (SEQ ID NO: 14)-565) | | >1000 |

Single Point Screening of CFI Variants for C4b and C3b Cleavage

The specificity for C4b cleavage versus C3b cleavage and C3b cleavage versus C4b cleavage was calculated in two different ways. For the single point assays listed in Table 7.1, the baseline-subtracted median values used to calculate the fold difference values were used. Values below 0.01 were adjusted to 0.01. Each single median value for C4b and C3b was converted to a percent maximum using the following formula: 100%*(variant value/max value among all variants). Specificity for C4b was calculated as the ratio of the percent maximum C4b divided by percent maximum C3b. Specificity for C3b was calculated as the ratio of the percent maximum C3b divided by percent maximum C4b.

TABLE 7.1

Variant Screening for C4b and C3b Cleavage

| Variant Description | C4b Screen Ref Fold | iC3b Screen Ref Fold | Specificity C4b | Specificity C3b |
|---|---|---|---|---|
| Wild Type | 1.00 | 1.00 | 0.45 | 2.20 |
| K14A | 0.30 | 0.73 | 0.19 | 5.38 |
| Y20A | 0.14 | 0.05 | 1.23 | 0.81 |
| Y20F | 0.27 | 0.67 | 0.18 | 5.56 |
| D26A | | 0.34 | | |
| F29A | 0.17 | 0.05 | 1.66 | 0.60 |
| R35A | 0.06 | 0.12 | 0.30 | 3.30 |
| E38A | 0.09 | 0.43 | 0.09 | 10.74 |
| M220A-K221Q | 1.85 | 0.49 | 1.72 | 0.58 |
| S507A | 0.13 | 0.04 | 1.28 | 0.78 |
| S250A | 0.07 | 0.38 | 0.09 | 10.57 |
| S250L | | 0.09 | | |
| Δ(K1-P305) | 0.06 | 0.04 | 0.81 | 1.24 |
| D425A | 2.71 | 1.07 | 1.15 | 0.87 |
| D425K | 0.42 | 1.34 | 0.14 | 6.96 |
| D425R | 0.69 | 1.46 | 0.22 | 4.64 |
| 514-MDANNVT (SEQ ID NO: 13)-520 --> NG | 0.12 | 0.04 | 1.25 | 0.80 |
| ΔC-term (Δ558-PFISQYNV (SEQ ID NO: 14)-565) | 0.11 | 0.03 | 1.14 | 0.88 |
| R557A | 1.74 | 0.04 | 17.61 | 0.06 |
| K326A-R327A | 0.20 | 0.37 | 0.24 | 4.12 |

TABLE 7.1-continued

Variant Screening for C4b and C3b Cleavage

| Variant Description | C4b Screen Ref Fold | iC3b Screen Ref Fold | Specificity C4b | Specificity C3b |
|---|---|---|---|---|
| Y408L-N531G | 5.29 | 1.09 | 2.21 | 0.45 |
| L307G | 2.85 | 0.79 | 1.65 | 0.61 |
| fH_CCP1-8; GGGGGGGGGGGG (SEQ ID NO: 25); ΔHSA | 0.48 | 0.40 | 0.55 | 1.83 |
| fH_CCP1-4; 19-20; 5-8; GGGGGGGGGGGG (SEQ ID NO: 25); ΔHSA | | 0.10 | | |
| N531G; P535A | 5.60 | 1.53 | 1.66 | 0.60 |
| Y408L | 1.46 | 1.40 | 0.48 | 2.10 |
| 456-REKDNERVFS (SEQ ID NO: 9)-465 → NTASSGADYPDE (SEQ ID NO: 10) | 0.08 | 0.03 | 0.82 | 1.22 |
| E457G; E461Q-R462K; F464Y | 5.50 | 0.69 | 3.63 | 0.28 |
| E38A; D425R | 0.96 | 0.83 | 0.53 | 1.89 |
| Y20F; D425R | 0.42 | 1.01 | 0.19 | 5.31 |
| S250A; D425R | 0.14 | 1.01 | 0.06 | 15.89 |
| Δ(K1-P305); GGSSGG (SEQ ID NO: 6); fH_CCP1-4 | 0.15 | 0.04 | 1.49 | 0.67 |
| Δ(K1-P305); GGSSGG (SEQ ID NO: 6); fH_CCP2-4 | 0.06 | 0.03 | 0.81 | 1.24 |
| Δ(K1-P305); GGSSGG (SEQ ID NO: 6); fH_CCP2-3 | 0.05 | 0.01 | 0.81 | 1.24 |
| N531G | 6.26 | 2.10 | 1.35 | 0.74 |
| N531A | 0.31 | 1.21 | 0.12 | 8.65 |
| P535A | 1.86 | 1.01 | 0.84 | 1.19 |
| Y408F | 1.88 | 0.61 | 1.41 | 0.71 |
| Y408F; N531G | 5.78 | 1.24 | 2.13 | 0.47 |
| Y408L; N531G; E457G; E461Q; R462K; F464Y | 5.37 | 0.46 | 5.28 | 0.19 |
| E530D | 0.24 | 0.25 | 0.43 | 2.30 |
| E457G | 5.37 | 1.58 | 1.54 | 0.65 |
| E461Q | 5.47 | 1.94 | 1.28 | 0.78 |
| R462K | 0.27 | 0.24 | 0.51 | 1.94 |
| F464Y | 0.55 | 0.27 | 0.91 | 1.10 |
| I317D-R318D-R319D-K320D-R321K | | 0.03 | | |
| Δ(K1-P305); N531G | 0.02 | 0.03 | 0.81 | 1.24 |
| Δ(K1-P305); Y408L; N531G | 0.14 | 0.05 | 1.34 | 0.75 |
| Δ(K1-P305); N531G; P535A | 0.15 | 0.05 | 1.47 | 0.68 |
| WT; GGSSGG (SEQ ID NO: 6); CCP_1-4 | 0.21 | 0.02 | 2.17 | 0.46 |
| WT; GGSSGG (SEQ ID NO: 6); CCP_2-4 | 0.38 | 0.00 | 3.89 | 0.26 |
| P535G | 0.30 | 0.19 | 0.71 | 1.41 |

TABLE 7.1-continued

Variant Screening for C4b and C3b Cleavage

| Variant Description | C4b Screen Ref Fold | iC3b Screen Ref Fold | Specificity C4b | Specificity C3b |
|---|---|---|---|---|
| Y408L; N531G; E457G | 6.16 | 0.63 | 4.47 | 0.22 |
| Y408L; N531G; E457G; E461Q | 4.63 | 0.39 | 5.42 | 0.18 |
| Δ(K1-P305); Y408L; N531G; E457G; E461Q; R462K; F464Y | 0.01 | 0.03 | 0.81 | 1.24 |
| Y408L; N531G; P535A | 5

TABLE 7.1-continued

Variant Screening for C4b and C3b Cleavage

| Variant Description | C4b Screen Ref Fold | iC3b Screen Ref Fold | Specificity C4b | Specificity C3b |
|---|---|---|---|---|
| K504H | 3.84 | 0.54 | 3.21 | 0.31 |
| A361G | 0.84 | 0.64 | 0.59 | 1.69 |
| T495F; Y496L; D497E; S499G; I500K | -0.04 | 0.00 | 0.81 | 1.24 |
| T495F; Y496L; D497E; S499G; I500K; G533A; K534Q; P535K; E536N; F537K | -0.02 | 0.02 | 0.81 | 1.24 |
| F537K | 0.30 | 1.28 | 0.11 | 9.47 |
| F537R | 0.16 | 1.08 | 0.07 | 14.96 |
| Q467K | 3.04 | 0.95 | 1.45 | 0.69 |
| Q467R | 0.48 | 0.59 | 0.37 | 2.73 |
| Q467K; F537K | 0.85 | 1.31 | 0.30 | 3.37 |
| E530G | -0.02 | 0.12 | 0.30 | 3.28 |
| E530G; N531G | 0.04 | 0.54 | 0.07 | 15.01 |
| E530F | 0.08 | 0.98 | 0.04 | 25.50 |
| E530Y | 0.33 | 1.16 | 0.13 | 7.64 |
| E530D; F537K | 0.92 | 0.98 | 0.43 | 2.34 |
| R557K | 3.09 | 0.28 | 5.03 | 0.20 |
| P558L | 0.89 | 0.99 | 0.41 | 2.45 |
| E457G; E461Q | 5.84 | 1.44 | 1.84 | 0.54 |
| WT; GGSSGG (SEQ ID NO: 6); CCP_1-4; GGSS(6) + G; compstatin | 0.25 | 0.11 | 1.03 | 0.97 |
| WT; GGSSGG (SEQ ID NO: 6); CCP_1-5; GGSS(3) + GGG; compstatin | 0.25 | 0.03 | 2.53 | 0.40 |
| WT; GGSSGG (SEQ ID NO: 6); CR1(ccp15-17); GGSSGG (SEQ ID NO: 6); fH(ccp1-4) | 2.96 | 0.08 | 16.42 | 0.06 |
| WT; GGSSGG (SEQ ID NO: 6); CR1(ccp15-17) | 5.25 | 0.04 | 53.59 | 0.02 |
| R462A | 0.31 | 0.11 | 1.25 | 0.80 |
| R462D | -0.05 | 0.00 | 0.81 | 1.24 |
| E457G; E461G | 4.31 | 1.28 | 1.53 | 0.65 |
| N531G; E457G; E461Q | 6.42 | 0.95 | 3.07 | 0.33 |
| W381K | 0.00 | 0.02 | 0.81 | 1.24 |
| N404G | 0.31 | 0.68 | 0.21 | 4.79 |
| D506A | 0.02 | 0.00 | 0.81 | 1.24 |
| D506V | 0.06 | 0.00 | 0.81 | 1.24 |
| D506E | 0.01 | 0.00 | 0.81 | 1.24 |
| D506G | 0.09 | 0.00 | 0.93 | 1.08 |
| I322V | 0.38 | 0.39 | 0.45 | 2.24 |
| I322V; V323I | 0.31 | 0.39 | 0.37 | 2.72 |
| R327P | 1.67 | 0.67 | 1.13 | 0.88 |

TABLE 7.1-continued

Variant Screening for C4b and C3b Cleavage

| Variant Description | C4b Screen Ref Fold | iC3b Screen Ref Fold | Specificity C4b | Specificity C3b |
|---|---|---|---|---|
| I322V; V323I; R327P | 0.38 | 0.36 | 0.47 | 2.11 |
| V323A | 0.01 | 0.05 | 0.79 | 1.26 |
| A328C; W468C | -0.06 | 0.00 | 0.81 | 1.24 |
| A328C; W468C; K326Y; R327N | 0.15 | 0.01 | 1.48 | 0.67 |
| Y408

TABLE 7.1-continued

Variant Screening for C4b and C3b Cleavage

| Variant Description | C4b Screen Ref Fold | iC3b Screen Ref Fold | Specificity C4b | Specificity C3b |
|---|---|---|---|---|
| N52Q; N85Q; N159Q | 0.24 | 1.93 | 0.06 | 17.56 |
| N446Q; N476Q; N518Q | | 0.06 | | |
| E457A | 4.68 | 1.43 | 1.49 | 0.67 |
| E457D | 4.70 | 1.21 | 1.77 | 0.57 |
| E457F | 0.01 | 0.05 | 0.70 | 1.43 |
| E457H | 0.31 | 0.26 | 0.54 | 1.84 |
| E457I | 1.75 | 0.99 | 0.80 | 1.25 |
| E457K | 4.58 | 1.37 | 1.52 | 0.66 |
| E457L | 0.14 | 0.21 | 0.30 | 3.29 |
| E457M | 1.60 | 1.05 | 0.69 | 1.45 |
| E457N | 4.31 | 0.90 | 2.19 | 0.46 |
| E457P | 0.01 | 0.07 | 0.53 | 1.87 |
| E457Q | 1.80 | 1.00 | 0.82 | 1.21 |
| E457R | 4.60 | 1.42 | 1.48 | 0.68 |
| E457S | 0.81 | 1.07 | 0.35 | 2.90 |
| E457T | 1.34 | 1.50 | 0.41 | 2.47 |
| E457W | 0.09 | 0.15 | 0.29 | 3.51 |
| E457Y | 0.12 | 0.03 | 1.18 | 0.84 |
| E457V | 0.99 | 0.80 | 0.56 | 1.79 |
| Y408E | | 0.23 | | |
| K14A; Y20F D26A; R35A; E38A | 0.15 | 0.11 | 0.60 | 1.65 |
| K14A; Y20F; D26A; R35A; E38A; L304G; P305G; K306G; L307G; S308G | 4.19 | 0.04 | 42.78 | 0.

TABLE 7.1-continued

Variant Screening for C4b and C3b Cleavage

| Variant Description | C4b Screen Ref Fold | iC3b Screen Ref Fold | Specificity C4b | Specificity C3b |
|---|---|---|---|---|
| E461P | -0.01 | 0.02 | 0.81 | 1.24 |
| E461S | 1.32 | 0.95 | 0.63 | 1.58 |
| E461T | 3.24 | 1.53 | 0.96 | 1.04 |
| E461W | 0.80 | 0.67 | 0.55 | 1.82 |
| E461Y | 2.38 | 0.99 | 1.09 | 0.92 |
| E461V | 4.79 | 2.03 | 1.07 | 0.93 |
| R456A | 0.29 | 0.20 | 0.64 | 1.56 |
| I317D-R318D-R319D-K320D-R321K; Y408L; N531G; E457G; E461Q; R462K; F464Y | -0.02 | 0.01 | 0.81 | 1.24 |
| K312A | 0.09 | 0.84 | 0.05 | 21.17 |
| R314A | 1.83 | 0.85 | 0.98 | 1.02 |
| K312

TABLE 7.1-continued

Variant Screening for C4b and C3b Cleavage

| Variant Description | C4b Screen Ref Fold | iC3b Screen Ref Fold | Specificity C4b | Specificity C3b |
|---|---|---|---|---|
| A405S | 2.12 | 0.94 | 1.03 | 0.97 |
| G406R | 1.31 | 1.31 | 0.46 | 2.20 |
| Q409D | 0.09 | 0.14 | 0.30 | 3.37 |
| A405S; G406R; Y408L; Q409D | -0.08 | 0.13 | 0.29 | 3.50 |
| A405S; G406A; Y408L; Q409D | 0.11 | 0.06 | 0.88 | 1.14 |
| Q TABLE 7.1-continued Variant Screening for C4b and C3b Cleavage

| Variant Description | C4b Screen Ref Fold | iC3b Screen Ref Fold | Specificity C4b | Specificity C3b |
|---|---|---|---|---|
| G406F | 0.72 | 0.73 | 0.45 | 2.22 |
| G406H | 1.17 | 0.60 | 0.89 | 1.13 |
| G406I | 0.97 | 0.40 | 1.11 | 0.90 |
| G406K | 0.77 | 1.28 | 0.28 | 3.63 |
| G406L | 0.92 | 0.82 | 0.51 | 1.96 |
| G406M | 1.17 | 0.60 | 0.89 | 1.12 |
| G406N | 0.94 | 0.59 | 0.72 | 1.38 |
| G406P | 0.49 | 0.47 | 0.47 | 2.12 |
| G406Q | 0.91 | 0.68 | 0.61 | 1.65 |
| G406S | 1.83 | 0.40 | 2.06 | 0.49 |
| G406T | 1.09 | 0.52 | 0.96 | 1.04 |
| G406V | 1.09 | 0.44 | 1.13 | 0.88 |
| G406W | 1.57 | 0.38 | 1.87 | 0.53 |
| G406Y | 0.43 | 0.39 | 0.50 | 2.02 |
| G406D; Y408L | 0.15 | −0.02 | 1.49 | 0.67 |
| G406D; N531G | 6.15 | 0.83 | 3.37 | 0.30 |
| G406D; P535A | 0.95 | 0.13 | 3.31 | 0.30 |
| G406D; Y408L; N531G) | 5.16 | 0.93 | 2.52 | 0.40 |
| G406D; Y408L; P535A) | 0.38 | 0.23 | 0.75 | 1.33 |
| G406D; N531G; P535A | 5.98 | 0.88 | 3.10 | 0.32 |
| G406D; Y408L; N531G; P535A | 5.44 | 0.96 | 2.59 | 0.39 |
| K340G | 0.15 | −0.01 | 1.49 | 0.67 |
| I345G | 0.16 | −0.01 | 1.59 | 0.63 |
| K340G; I345G | 0.14 | 0.00 | 1.39 | 0.72 |
| Y372G | 0.08 | 0.00 | 0.83 | 1.20 |
| P384A | 0.29 | 0.03 | 3.00 | 0.33 |
| P384G | 0.10 | 0.01 | 1.04 | 0.97 |
| W381G | 0.32 | 0.00 | 3.23 | 0.31 |
| V390G | 0.50 | 0.35 | 0.65 | 1.53 |
| W381G; V390G | 0.04 | −0.01 | 0.81 | 1.24 |
| W381G; P384A; V390G | 0.26 | −0.01 | 2.61 | 0.38 |
| W381G; P384G; V390G | 0.12 | −0.02 | 1.23 | 0.81 |
| N404G | 0.53 | 0.94 | 0.26 | 3.89 |
| Q409G | 0.36 | 0.33 | 0.50 | 2.02 |
| K418G | 0.69 | 0.39 | 0.80 | 1.25 |
| D425G | 2.18 | 0.70 | 1.41 | 0.71 |
| K418G; D425G | 0.84 | 0.19 | 2.05 | 0.49 |

TABLE 7.1-continued

Variant Screening for C4b and C3b Cleavage

| Variant Description | C4b Screen Ref Fold | iC3b Screen Ref Fold | Specificity C4b | Specificity C3b |
|---|---|---|---|---|
| S465G | 1.32 | 0.34 | 1.76 | 0.57 |
| WT; GGSSGG (SEQ ID NO: 6); CR1(ccp15); fH(ccp2); fH(ccp3); fH(ccp4) | 1.44 | −0.01 | 14.70 | 0.07 |
| WT; GGSSGG (SEQ ID NO: 6); fH(ccp1); CR1(ccp16); fH(ccp3); fH(ccp4) | 0.59 | 0.00 | 6.02 | 0.17 |
| WT; GGSSGG (SEQ ID NO: 6); CR1(ccp15); CR1(ccp16); fH(ccp3); fH(ccp4) | 0.25 | −0.01 | 2.51 | 0.40 |
| WT; GGSSGG (SEQ ID NO: 6); fH(ccp1); CR1(ccp16); CR1(ccp17); fH(ccp4) | 0.42 | 0.00 | 4.26 | 0.23 |
| WT; GGSSGG (SEQ ID NO: 6); CR1(ccp15); CR1(ccp16); CR1(ccp17); fH(ccp4) | 2.57 | 0.01 | 26.26 | 0.04 |
| G344R | 0.74 | 0.56 | 0.61 | 1.65 |
| G344K | 0.36 | 0.16 | 0.99 | 1.01 |
| G344Y | 1.93 | 0.43 | 2.05 | 0.49 |
| T346R | 0.54 | 0.95 | 0.26 | 3.88 |
| T346K | 0.57 | 0.96 | 0.27 | 3.70 |
| T346H | 1.81 | 0.67 | 1.22 | 0.82 |
| K504E | 0.24 | 0.12 | 0.89 | 1.12 |
| K504D | 0.15 | 0.17 | 0.39 | 2.53 |
| E530R | 0.76 | 0.80 | 0.43 | 2.32 |
| E530K | 0.19 | 0.96 | 0.09 | 11.08 |
| T346R; K504E; E530R | | 0.51 | | |
| T346K; K504D; E530K | −0.02 | 0.40 | 0.09 | 11.02 |
| G344R; Y408L; N531G | 3.03 | 0.98 | 1.40 | 0.71 |
| G344K; Y408L; N531G | 1.20 | 0.93 | 0.59 | 1.69 |
| T346R; Y408L; N531G | 3.42 | 0.93 | 1.66 | 0.60 |
| T346K; Y408L; N531G | 4.81 | 1.10 | 1.98 | 0.50 |
| K504D; Y408L; N531G | 3.45 | 0.07 | 23.29 | 0.04 |
| K504E; Y408L; N531G | 3.27 | 0.15 | 10.21 | 0.10 |
| Y408L; E530R; N531G | 4.67 | 1.09 | 1.95 | 0.51 |
| Y408L; E530K; N531G | 4.89 | 1.12 | 1.98 | 0.50 |
| T346R; Y408L; K504E; E530R; N531G | 0.10 | 0.67 | 0.07 | 14.47 |
| T346K; Y408L; K504D; E530K; N531G | 0.04 | 0.29 | 0.12 | 8.12 |
| Y408L; S507A; N531G | 0.12 | −0.01 | 1.26 | 0.79 |
| Y408L; N531G; E457G; E461Q; R462K; F464Y; S507A | 0.04 | −0.01 | 0.81 | 1.24 |
| E457G; S507A | 0.01 | −0.01 | 0.81 | 1.24 |

TABLE 7.1-continued

Variant Screening for C4b and C3b Cleavage

| Variant Description | C4b Screen Ref Fold | iC3b Screen Ref Fold | Specificity C4b | Specificity C3b |
|---|---|---|---|---|
| N531G; P535A; S507A | 0.26 | −0.02 | 2.62 | 0.38 |
| S507A; GGSSGG (SEQ ID NO: 6); CCP_1-4 | 0.43 | 0.00 | 4.36 | 0.23 |
| Y408L; S507A; N531G; GGSSGG (SEQ ID NO: 6); CCP_1-4 | 0.10 | 0.01 | 1.00 | 1.00 |
| E457G; S507A; GGSSGG (SEQ ID NO: 6); CCP_1-4 | 0.12 | 0.01 | 1.20 | 0.84 |
| N531G; P535A; S507A; GGSSGG (SEQ ID NO: 6); CCP_1-4 | 0.20 | −0.02 | 1.99 | 0.50 |
| WT; GGSSGGSSGG (SEQ ID NO: 26); CCP_1-4 | 0.80 | 0.01 | 8.19 | 0.12 |
| WT; GGSSGGSSGG (SEQ ID NO: 26); CCP_2-4 | 1.32 | −0.01 | 13.46 | 0.07 |
| WT; GGSSGGSSGG (SEQ ID NO: 26); CR1(ccp15); fH(ccp2); fH(ccp3); fH(ccp4) | 1.59 | 0.00 | 16.20 | 0.06 |
| WT; GGSSGGSSGG (SEQ ID NO: 26); fH(ccp1); CR1(ccp16); fH(ccp3); fH(ccp4) | 0.73 | 0.01 | 7.41 | 0.13 |
| WT; GGSSGGSSGG (SEQ ID NO: 26); CR1(ccp15); CR1(ccp16); fH(ccp3); fH(ccp4) | 0.65 | −0.01 | 6.65 | 0.15 |
| WT; GGSSGGSSGG (SEQ ID NO: 26); fH(ccp1); CR1(ccp16); CR1(ccp17); fH(ccp4) | 4.76 | 0.08 | 28.80 | 0.03 |
| WT; GGSSGGSSGG (SEQ ID NO: 26); CR1(ccp15); CR1(ccp16); CR1(ccp17); fH(ccp4) | 2.90 | 0.01 | 29.57 | 0.03 |
| WT; GGSSGGSSGG (SEQ ID NO: 26); CR1(ccp15-17) | 3.54 | −0.05 | 36.13 | 0.03 |
| Y408L; N531G; GGSSGGSSGG (SEQ ID NO: 26); CCP_1-4 | 2.83 | 0.06 | 22.67 | 0.04 |
| Y408L; N531G; E457G; GGSSGGSSGG (SEQ ID NO: 26); CCP_1-4 | 3.61 | 0.09 | 18.49 | 0.05 |
| Y408L; N531G; E457G; E461Q; R462K; F464Y; GGSSGGSSGG (SEQ ID NO: 26); CCP_1-4 | 1.76 | 0.09 | 8.59 | 0.12 |
| F208Y | 0.60 | 1.50 | 0.18 | 5.48 |
| F246Y | 0.48 | 1.56 | 0.14 | 7.09 |
| F480Y | 1.84 | 1.14 | 0.73 | 1.36 |
| F537Y | 1.64 | 1.03 | 0.72 | 1.38 |
| F208Y; F246Y; F480Y; F537Y | 0.42 | 1.45 | 0.13 | 7.60 |
| H362T; V463S; R456I; D459W; S343R | 0.26 | 0.00 | 2.69 | 0.37 |
| H362T; V463S; R456I; D459W; S343K | 0.04 | −0.02 | 0.81 | 1.24 |
| H362T; V463S; R456F; D459W; S343R | 0.30 | −0.01 | 3.08 | 0.32 |
| H362T; V463S; R456I; S343R | 0.13 | −0.02 | 1.33 | 0.75 |

TABLE 7.1-continued

Variant Screening for C4b and C3b Cleavage

| Variant Description | C4b Screen Ref Fold | iC3b Screen Ref Fold | Specificity C4b | Specificity C3b |
|---|---|---|---|---|
| H362T; R456I; D459W; S343R | 0.13 | −0.04 | 1.33 | 0.75 |
| H362T; R456I; S343R | 0.08 | −0.01 | 0.84 | 1.19 |
| H362T; R456I; S343K | 0.18 | 0.00 | 1.88 | 0.53 |
| K14A; D425R; Y408L-N531G | 3.94 | 1.78 | 1.00 | 1.00 |
| Y408L; E457G; S507A; N531G | 0.12 | −0.01 | 1.23 | 0.81 |
| E457G; N531G | 6.50 | 0.88 | 3.35 | 0

TABLE 7.1-continued

Variant Screening for C4b and C3b Cleavage

| Variant Description | C4b Screen Ref Fold | iC3b Screen Ref Fold | Specificity C4b | Specificity C3b |
|---|---|---|---|---|
| Y408L; F464Y | 0.67 | 0.55 | 0.56 | 1.80 |
| N531G; E461Q | 6.13 | 1.45 | 1.92 | 0.52 |
| N531G; R462K | 6.13 | 1.17 | 2.39 | 0.42 |
| N531G; F464Y | 6.48 | 1.47 | 2.01 | 0.50 |
| E457G; R462K | 4.33 | 1.11 | 1.77 | 0.56 |
| E457G; F464Y | 5.55 | 1.31 | 1.92 | 0.52 |
| E461Q; R462K | 4.69 | 1.23 | 1.73 | 0.58 |
| E461Q; F464Y | 6.36 | 1.11 | 2.61 | 0.38

TABLE 7.1-continued

Variant Screening for C4b and C3b Cleavage

| Variant Description | C4b Screen Ref Fold | iC3b Screen Ref Fold | Specificity C4b | Specificity C3b |
|---|---|---|---|---|
| K534R | 1.81 | 1.44 | 0.57 | 1.75 |
| K534H | 1.90 | 1.79 | 0.48 | 2.07 |
| K534D | 2.29 | 0.72 | 1.45 | 0.69 |
| K534E | 0.82 | 1.19 | 0.31 | 3.21 |
| K534S | 2.65 | 0.92 | 1.31 | 0.76 |
| K534T | 1.44 | 0.77 | 0.85 | 1.18 |
| K534N | 3.36 | 0.88 | 1.74 | 0.58 |
| K534G | 0.17 | 0.13 | 0.59 | 1.69 |
| K534P | 0.11 | 0.00 | 1.13 | 0.88 |
| K534A | 1.14 | 1.31 | 0.40 | 2.51 |
| K534I | 3.03 | 0.83 | 1.66 | 0.60 |
| K534L | 3.12 | 0.87 | 1.64 | 0.61 |
| K534M | 3.89 | 0.95 | 1.86 | 0.54 |
| K534F | 0.97 | 0.91 | 0.48 | 2.08 |
| K534W | 2.19 | 0.81 | 1.23 | 0.81 |
| K534Y | 1.39 | 1.42 | 0.45 | 2.24 |
| K534V | 1.96 | 1.49 | 0.60 | 1.67 |
| D425H | 1.79 | 1.75 | 0.47 | 2.15 |
| D425E | 1.75 | 1.52 | 0.52 | 1.91 |
| D425S | 1.13 | 2.21 | 0.23 | 4.30 |
| D425T | 2.05 | 2.16 | 0.43 | 2.31 |
| D425N | 1.54 | 1.66 | 0.42 | 2.37 |
| D425Q | 1.83 | 1.87 | 0.45 | 2.25 |
| D425P | 0.29 | 0.72 | 0.19 | 5.37 |
| D425I | 1.38 | 1.86 | 0.34 | 2.96 |
| D425L | 1.46 | 0.94 | 0.71 | 1.42 |
| D425M | 2.18 | 0.91 | 1.09 | 0.92 |
| D425F | 1.60 | 1.91 | 0.38 | 2.63 |
| D425W | 0.89 | 1.59 | 0.25 | 3.93 |
| D425Y | 2.87 | 1.15 | 1.13 | 0.88 |
| D425V | 2.51 | 0.98 | 1.17 | 0.86 |
| L307A | 4.05 | 0.73 | 2.51 | 0.40 |
| L307S | 2.94 | 1.54 | 0.87 | 1.15 |
| T407G | 0.11 | 0.59 | 0.08 | 12.14 |
| T407G; Y408L | 0.09 | 0.34 | 0.12 | 8.23 |
| T407G; E457G | 0.42 | 0.89 | 0.22 | 4.60 |
| T407G; N531G | 0.83 | 0.85 | 0.45 | 2.25 |
| T407G; Y408L; N531G | 0.46 | 1.43 | 0.14 | 6.91 |

TABLE 7.1-continued

Variant Screening for C4b and C3b Cleavage

| Variant Description | C4b Screen Ref Fold | iC3b Screen Ref Fold | Specificity C4b | Specificity C3b |
|---|---|---|---|---|
| T407G; Y408L; E457G | 0.12 | 0.74 | 0.07 | 14.09 |
| T407G; Y408L; E457G; N531G | 0.67 | 0.56 | 0.55 | 1.83 |
| F464L | 0.15 | 0.00 | 1.53 | 0.65 |
| F464I | 0.09 | 0.01 | 0.94 | 1.07 |
| F464A | -0.01 | 0.02 | 0.81 | 1.24 |
| F464

TABLE 7.1-continued

Variant Screening for C4b and C3b Cleavage

| Variant Description | C4b Screen Ref Fold | iC3b Screen Ref Fold | Specificity C4b | Specificity C3b |
|---|---|---|---|---|
| N531G; K534Q | 5.23 | 1.39 | 1.71 | 0.58 |
| P535G; K534Q | 0.35 | 0.24 | 0.66 | 1.52 |
| Y

TABLE 7.1-continued

Variant Screening for C4b and C3b Cleavage

| Variant Description | C4b Screen Ref Fold | iC3b Screen Ref Fold | Specificity C4b | Specificity C3b |
|---|---|---|---|---|
| Y553F; P558S; F559L | 0.60 | 0.50 | 0.55 | 1.83 |
| S552G | 1.08 | 0.58 | 0.85 | 1.18 |
| Y553H | 4.13 | 0.52 | 3.62 | 0.28 |
| V565I | 1.11 | 1.25 | 0.41 | 2.47 |
| S552G; Y553H | 2.53 | 0.26 | 4.38 | 0

TABLE 7.1-continued

Variant Screening for C4b and C3b Cleavage

| Variant Description | C4b Screen Ref Fold | iC3b Screen Ref Fold | Specificity C4b | Specificity C3b |
|---|---|---|---|---|
| N531G; WT; GGSSGG (SEQ ID NO: 6); CR1(ccp15-17) | 5.30 | 0.05 | 47.15 | 0.02 |
| P535G; WT; GGSSGG (SEQ ID NO: 6); CR1(ccp15-17) | 2.73 | 0.00 | 27.82 | 0.04 |
| Y408L; P535G; WT; GGSSGG (SEQ ID NO: 6); CR1(ccp15-17) | 3.01 | 0.03 | 30.75 | 0.03 |
| E457G; P535G; WT; GGSSGG (SEQ ID NO: 6); CR1(ccp15-17) | 3.89 | 0.07 | 25.17 | 0.04 |
| N531G; P535G; WT; GGSSGG (SEQ ID NO: 6); CR1(ccp15-17) | 3.06 | 0.06 | 22.50 | 0.04 |
| Y408L; E457G; WT; GGSSGG (SEQ ID NO: 6); CR1(ccp15-17) | 3.18 | 0.12 | 11.76 | 0.09 |
| Y408L; N531G; WT; GGSSGG (SEQ ID NO: 6); CR1(ccp15-17) | 4.17 | 0.22 | 8.65 | 0.12 |
| E457G; N531G; WT; GGSSGG (SEQ ID NO: 6); CR1(ccp15-17) | 4.95 | 0.15 | 14.57 | 0.07 |
| Y408L; E457G; N531G; WT; GGSSGG (SEQ ID NO: 6); CR1(ccp15-17) | 3.65 | 0.10 | 16.91 | 0.06 |
| Y408L; E457G; P535G; WT; GGSSGG (SEQ ID NO: 6); CR1(ccp15-17) | 1.99 | 0.23 | 3.98 | 0.25 |
| Y408L; N531G; P535G; WT; GGSSGG (SEQ ID NO: 6); CR1(ccp15-17) | 3.60 | 0.05 | 35.43 | 0.03 |
| E457G; N531G; P535G; WT; GGSSGG (SEQ ID NO: 6); CR1(ccp15-17) | 5.82 | 0.03 | 59.44 | 0.02 |
| Y408L; E457G; N531G; P535G; WT; GGSSGG (SEQ ID NO: 6); CR1(ccp15-17) | 3.14 | 0.05 | 29.43 | 0.03 |
| Y408L; N422K | 0.60 | 1.27 | 0.22 | 4.64 |
| E457G; N422K | 5.49 | 1.51 | 1.65 | 0.60 |
| N531G; N422K | 4.68 | 2.43 | 0.88 | 1.14 |
| P535G; N422K | 0.09 | 0.52 | 0.08 | 12.53 |
| Y408L; P535G; N422K | 0.17 | 1.03 | 0.07 | 13.35 |
| E457G; P535G; N422K | 1.87 | 1.43 | 0.59 | 1.68 |
| N531G; P535G; N422K | 2.85 | 1.96 | 0.66 | 1.51 |
| Y408L; E457G; N422K | 3.10 | 1.87 | 0.75 | 1.33 |
| Y408L; N531G; N422K | 3.78 | 1.94 | 0.89 | 1.13 |
| E457G; N531G; N422K | 4.37 | 1.46 | 1.36 | 0.73 |
| Y408L; E457G; N531G; N422K | 3.66 | 0.95 | 1.76 | 0.57 |
| Y408L; E457G; P535G; N422K | 1.07 | 1.39 | 0.35 | 2.84 |
| E457G; N531G; P535G; N422K | 4.46 | 1.87 | 1.09 | 0.92 |
| Y408L; E457G; N531G; P535G; N422K | 3.64 | 1.77 | 0.94 | 1.07 |

TABLE 7.1-continued

Variant Screening for C4b and C3b Cleavage

| Variant Description | C4b Screen Ref Fold | iC3b Screen Ref Fold | Specificity C4b | Specificity C3b |
|---|---|---|---|---|
| E457G; GGSSGG (SEQ ID NO: 6); CR1(ccp1-3) | 1.73 | -0.04 | 17.64 | 0.06 |
| E457G; E461Q; R462K; F464Y; N531G; GGSSGG (SEQ ID NO: 6); CR1(ccp15-17) | 5.42 | -0.01 | 55.37 | 0.02 |
| N531G; P535A; GGSSGG (SEQ ID NO: 6); CR1(ccp15-17) | 3.53 | 0.14 | 11.10 | 0.09 |
| S507A; GGSSGG (SEQ ID NO: 6); CR1(ccp15-17) | -0.01 | -0.01 | 0.81 | 1.24 |
| S507A; GGSSGG (SEQ ID NO: 6); CR1(ccp1-3) | 0.12 | 0.02 | 1.27 | 0.79 |
| Y408L; E416A | 0.41 | 1.21 | 0.15 | 6.46 |
| E457G; E416A | 4.63 | 1.41 | 1.49 | 0.67 |
| N531G; E416A | 4.82 | 1.11 | 1.98 | 0.50 |
| P535G; E416A | 0.13 | 0.53 | 0.11 | 9.07 |
| Y408L; D425R; E416A | 0.43 | 2.26 | 0.09 | 11.60 |
| E457G; D425R; E416A | 4.35 | 2.48 | 0.80 | 1.25 |
| N531G; D425R; E416A | 2.64 | 3.03 | 0.40 | 2.52 |
| Y408L; E457G; E416A | 2.11 | 2.51 | 0.38 | 2.62 |
| Y408L; N531G; E416A | 2.54 | 2.07 | 0.56 | 1.79 |
| E457G; N531G; E416A | 5.02 | 2.66 | 0.86 | 1.16 |
| Y408L; E457G; N531G; E416A | 4.66 | 2.15 | 0.99 | 1.01 |
| Y408L; E457G; D425R; E416A | 2.03 | 3.02 | 0.31 | 3.28 |
| Y408L; N531G; D425R; E416A | 1.41 | 2.15 | 0.30 | 3.35 |
| E457G; N531G; D425R; E416A | 4.54 | 2.12 | 0.97 | 1.03 |
| D425R; Y408L; N531G; E457G; E461Q; R462K; F464Y; E416A | 3.88 | 1.63 | 1.08 | 0.93 |
| E457G; N531G; E461Q; R462K; F464Y; E416A | 4.38 | 2.21 | 0.90 | 1.11 |
| Y408L; E530Y | 0.33 | 1.93 | 0.08 | 13.07 |
| E457G; E530Y | 2.48 | 2.03 | 0.56 | 1.80 |
| N531G; E530Y | 3.41 | 2.48 | 0.63 | 1.60 |
| P535G; E530Y | 0.11 | 0.22 | 0.22 | 4.64 |
| Y408L; D425R; E530Y | 1.05 | 1.95 | 0.25 | 4.07 |
| E457G; D425R; E530Y | 4.29 | 1.73 | 1.13 | 0.89 |
| N531G; D425R; E530Y | 2.71 | 2.05 | 0.60 | 1.66 |
| Y408L; E457G; E530Y | 2.00 | 1.12 | 0.81 | 1.23 |
| Y408L; N531G; E530Y | 2.25 | 2.11 | 0.48 | 2.06 |
| E457G; N531G; E530Y | 4.22 | 1.67 | 1.15 | 0.87 |
| Y408L; E457G; N531G; E530Y | 4.16 | 2.07 | 0.91 | 1.10 |
| Y408L; E457G; D425R; E530Y | 1.68 | 1.74 | 0.44 | 2.27 |

TABLE 7.1-continued

Variant Screening for C4b and C3b Cleavage

| Variant Description | C4b Screen Ref Fold | iC3b Screen Ref Fold | Specificity C4b | Specificity C3b |
|---|---|---|---|---|
| Y408L; N531G; D425R; E530Y | 2.99 | 2.08 | 0.65 | 1.53 |
| E457G; N531G; D425R; E530Y | 5.37 | 0.78 | 3.15 | 0.32 |
| Y408L; E457G; N531G; D425R; E530Y | 4.10 | 1.08 | 1.72 | 0.58 |
| D425R; Y408L; N531G; E457G; E461Q; R462K; F464Y; E530Y | 4.98 | 1.57 | 1.44 | 0.69 |
| E457G; N531G; E461Q; R462K; F464Y; E530Y | 5.70 | 1.83 | 1.41 | 0.71 |
| E457G; N531G; E461Q; R462K; F464Y; E530Y; GGSSGG (SEQ ID NO: 6); CR1(ccp15-17) | 2.87 | 0.01 | 29.32 | 0.03 |
| E457G; E461Q; N531G; GGSSGG (SEQ ID NO: 6); CR1 (ccp15-17) | 4.82 | 0.12 | 17.93 | 0.06 |
| Y408L; E457G; E461Q; R462K; N531G; GGSSGG (SEQ ID NO: 6); CR1 (ccp15-17) | 1.84 | 0.18 | 4.69 | 0.21 |
| Y408L; E457G; R462K; F464Y; N531G; GGSSGG (SEQ ID NO: 6); CR1 (ccp15-17) | 2.74 | 0.02 | 27.96 | 0.04 |
| E457G; N531G; E461Q; R462K; F464Y; GGSSGG (SEQ ID NO: 6); CR1 (ccp15-17) | 4.36 | 0.10 | 19.23 | 0.05 |
| E457G; N531G; E461Q; R462K; F464Y; GGSSGG (SEQ ID NO: 6); CR1 (ccp1-3) | 0.46 | 0.14 | 1.52 | 0.66 |
| E457G; E461Q; F464Y; N531G; GGSSGG (SEQ ID NO: 6); CR1 (ccp15-17) | 4.44 | 0.13 | 16.15 | 0.06 |
| R365A | 0.56 | 0.50 | 0.51 | 1.97 |
| R365V | 1.25 | 0.43 | 1.32 | 0.76 |
| R365I | 1.16 | 0.30 | 1.78 | 0.56 |
| R365L | 0.60 | 0.16 | 1.75 | 0.57 |
| R365M | 0.13 | 0.43 | 0.14 | 7.28 |
| R365F | 0.23 | 0.64 | 0.16 | 6.22 |
| R365Y | 0.63 | 0.74 | 0.39 | 2.58 |
| R365W | 0.24 | 0.89 | 0.12 | 8.15 |
| R365G | 0.35 | 0.16 | 1.03 | 0.97 |
| R365P | 0.18 | 0.07 | 1.23 | 0.81 |
| R365S | 0.18 | 0.60 | 0.13 | 7.56 |
| R365T | 0.96 | 0.56 | 0.78 | 1.29 |
| R365N | 0.10 | 0.04 | 1.01 | 0.99 |
| R365Q | 0.18 | 0.64 | 0.13 | 7.73 |
| R365H | 0.31 | 0.43 | 0.33 | 3.01 |
| R365K | 0.39 | 1.01 | 0.18 | 5.62 |
| R365D | 0.02 | 0.03 | 0.81 | 1.24 |
| R365E | −0.06 | 0.02 | 0.81 | 1.24 |

TABLE 7.1-continued

Variant Screening for C4b and C3b Cleavage

| Variant Description | C4b Screen Ref Fold | iC3b Screen Ref Fold | Specificity C4b | Specificity C3b |
|---|---|---|---|---|
| A366G | 0.74 | 1.46 | 0.23 | 4.36 |
| K368G | 0.24 | 0.16 | 0.69 | 1.45 |
| K368E | 0.06 | 0.20 | 0.18 | 5.56 |
| K424A | 0.26 | 0.87 | 0.13 | 7.44 |
| K424V | 0.29 | 0.89 | 0.15 | 6.65 |
| K424I | 0.28 | 1.48 | 0.08 | 11.78 |
| K424L | 0.28 | 0.91 | 0.14 | 7.11 |
| K424M | 0.33 | 0.95 | 0.16 | 6.38 |
| K424F | 0.35 | 1.04 | 0.15 | 6.53 |
| K424Y | 0.42 | 0.95 | 0.20 | 4.94 |
| K424W | 0.25 | 1.52 | 0.07 | 13.41 |
| K424G | 0.32 | 1.44 | 0.10 | 9.78 |
| K424P | 0.33 | 1.05 | 0.14 | 7.03 |
| K424S | −0.10 | 0.29 | 0.12 | 8.05 |
| K424T | 0.03 | 0.13 | 0.28 | 3.58 |
| K424N | 0.50 | 1.48 | 0.15 | 6.50 |
| K424Q | 0.47 | 1.27 | 0.17 | 5.97 |
| K424R | 0.32 | 0.97 | 0.15 | 6.55 |
| K424H | 0.53 | 1.46 | 0.16 | 6.11 |
| K424D | 0.27 | 1.15 | 0.11 | 9.25 |
| K424E | 0.23 | 1.08 | 0.10 | 10.24 |
| K423G | 0.15 | 0.69 | 0.10 | 9.86 |
| K423A | 0.11 | 0.23 | 0.22 | 4.46 |
| K423E | 0.32 | 0.61 | 0.24 | 4.25 |
| K423D | 0.31 | 0.33 | 0.42 | 2.40 |
| D549A | 1.04 | 0.66 | 0.71 | 1.41 |
| D549V | 0.07 | 0.46 | 0.08 | 12.73 |
| D549

TABLE 7.1-continued

Variant Screening for C4b and C3b Cleavage

| Variant Description | C4b Screen Ref Fold | iC3b Screen Ref Fold | Specificity C4b | Specificity C3b |
|---|---|---|---|---|
| D549R | 0.52 | 0.27 | 0.88 | 1.13 |
| D549H | 0.92 | 0.73 | 0.57 | 1.75 |
| D549K | 1.00 | 0.18 | 2.55 | 0.39 |
| Y553A | 0.52 | 1.10 | 0.22 | 4.64 |
| Y553V | 0.37 | 1.10 | 0.15 | 6.59 |
| Y553I | 0.51 | 1.06 | 0.22 | 4.52 |
| Y553L | 0.67 | 0.93 | 0.33 | 3.02 |
| Y553S | 0.76 | 0.93 | 0.37 | 2.69 |
| Y553N | 0.60 | 0.63 | 0.43 | 2.31 |
| Y553Q | 0.77 | 1.09 | 0.32 | 3.13 |
| Y553R | 0.78 | 1.38 | 0.26 | 3.87 |
| Y553H | 1.56 | 1.11 | 0.64 | 1.57 |
| Y553K | 1.49 | 1.12 | 0.60 | 1.65 |
| Y553E | 0.51 | 0.38 | 0.61 | 1.65 |
| R557V | 2.23 | 0.21 | 4.85 | 0.21 |
| R557I | 3.27 | 0.16 | 9.22 | 0.11 |
| R557L | 2.27 | 0.15 | 6.83 | 0.15 |
| R557M | 2.48 | 0.16 | 6.85 | 0.15 |
| R557F | 2.13 | 0.12 | 8.36 | 0.12 |
| R557Y | 3.23 | 0.21 | 6.88 | 0.15 |
| R557W | 2.36 | 0.12 | 8.94 | 0.11 |
| R557S | 1.11 | 0.10 | 4.92 | 0.20 |
| R557T | 1.63 | 0.09 | 8.71 | 0.11 |
| R557N | 1.87 | 0.05 | 18.04 | 0.06 |
| R557Q | 2.12 | 0.08 | 11.49 | 0.09 |
| R557G | 1.61 | 0.04 | 16.44 | 0.06 |
| R557P | 3.00 | 0.04 | 30.58 | 0.03 |
| R557H | 2.44 | 0.11 | 10.50 | 0.10 |
| R557D | 0.50 | -0.01 | 5.10 | 0.20 |
| R557E | 1.15 | -0.02 | 11.69 | 0.09 |
| T377G; N531G | 4.53 | 2.34 | 0.88 | 1.14 |
| T377G; E457G | 4.38 | 2.31 | 0.86 | 1.16 |
| T377G; E461Q | 3.17 | 2.82 | 0.51 | 1.95 |
| T377G; E457G; E461Q | 3.75 | 2.27 | 0.75 | 1.33 |
| T377G; E457G; E461Q; N531G | 4.73 | 1.57 | 1.37 | 0.73 |
| Y408L; N531G; R557A | 3.77 | 0.77 | 2.23 | 0.45 |
| N531G; P535A; R557A | 3.98 | 0.57 | 3.17 | 0.32 |
| E457G; E461Q; R557A | 4.50 | 1.29 | 1.58 | 0.63 |

TABLE 7.1-continued

Variant Screening for C4b and C3b Cleavage

| Variant Description | C4b Screen Ref Fold | iC3b Screen Ref Fold | Specificity C4b | Specificity C3b |
|---|---|---|---|---|
| N531G; E457G; E461Q; R557A | 4.46 | 0.93 | 2.18 | 0.46 |
| Y408L; E457G; E461Q; R462K; N531G; R557A | 3.22 | 1.29 | 1.13 | 0.88 |
| N531G; P535A; R557K | 4.13 | 1.65 | 1.14 | 0.88 |
| E457G; E461Q; R557K | 4.28 | 1.81 | 1.08 | 0.93 |
| N531G; E457G; E461Q; R557K | 4.69 | 1.81 | 1.18 | 0.85 |
| Y408L; E457G; E461Q; R462K; N531G; R557K | 4.01 | 1.14 | 1.60 | 0.63 |
| Y408L; N531G; ΔC-term (Δ558-PFISQYNV (SEQ ID NO: 14)-565) | 1.85 | 0.30 | 2.77 | 0.36 |
| N531G; P535A; ΔC-term (Δ558-PFISQYNV (SEQ ID NO: 14)-565) | 0.96 | 0.24 | 1.83 | 0.55 |
| N531G; E457G; E461Q; ΔC-term (Δ558-PFISQYNV (SEQ ID NO: 14)-565) | 3.57 | 0.50 | 3.25 | 0.31 |
| Y408L; E457G; E461Q; R462K; N531G; ΔC-term (Δ558-PFISQYNV (SEQ ID NO: 14)-565) | 1.67 | 0.24 | 3.17 | 0.32 |
| ΔC-term (Δ557-RPFISQYNV (SEQ ID NO: 27)-565) | 0.15 | -0.02 | 1.58 | 0.63 |
| Q69G | 0.14 | 1.17 | 0.06 | 18.01 |
| L73G | 0.17 | 0.30 | 0.26 | 3.79 |
| L76G | 0.07 | 0.50 | 0.07 | 13.76 |
| H362G | 0.03 | -0.02 | 0.81 | 1.24 |
| H370G | 0.13 | 0.52 | 0.11 | 8.78 |
| F399G | 0.05 | 0.65 | 0.06 | 18.15 |
| E401G | 0.82 | 2.10 | 0.18 | 5.63 |
| A405G | 1.06 | 1.74 | 0.28 | 3.62 |
| R456G | 0.04 | 0.03 | 0.81 | 1.24 |
| D459G | 1.07 | 1.93 | 0.25 | 3.95 |
| R484G | 0.64 | 0.77 | 0.38 | 2.62 |
| D501G | -0.01 | -0.04 | 0.81 | 1.24 |
| A502G | 0.06 | 0.09 | 0.42 | 2.40 |
| V526G | 0.03 | -0.01 | 0.81 | 1.24 |
| S527G | 0.09 | 0.16 | 0.26 | 3.81 |
| W528G | 0.01 | -0.05 | 0.81 | 1.24 |
| F537G | 0.03 | 0.37 | 0.10 | 10.14 |
| P538G | 0.07 | -0.01 | 0.81 | 1.24 |
| V540G | 0.01 | 0.03 | 0.81 | 1.24 |
| Y553G | 0.48 | 0.88 | 0.25 | 4.02 |
| A342G | 0.91 | 1.23 | 0.33 | 2.99 |
| R371G | 0.15 | 0.17 | 0.40 | 2.50 |

TABLE 7.1-continued

Variant Screening for C4b and C3b Cleavage

| Variant Description | C4b Screen Ref Fold | iC3b Screen Ref Fold | Specificity C4b | Specificity C3b |
|---|---|---|---|---|
| R327G | 0.26 | 0.50 | 0.23 | 4.28 |
| S343G | 0.92 | 1.32 | 0.32 | 3.17 |
| Q373G | 0.00 | 0.02 | 0.81 | 1.24 |
| W375G | 0.08 | -0.03 | 0.81 | 1.24 |
| I382G | 0.33 | -0.03 | 3.33 | 0.30 |
| H383G | -0.02 | 0.02 | 0.81 | 1.24 |
| L386G | 0.07 | 0.54 | 0.07 | 15.07 |
| K387G | 0.37 | 0.23 | 0.74 | 1.35 |
| R388G | 0.18 | 0.22 | 0.37 | 2.69 |
| I389G | 0.00 | -0.03 | 0.81 | 1.24 |
| I391G | 0.03 | 0.01 | 0.81 | 1.24 |
| E392G | 1.30 | 1.66 | 0.36 | 2.80 |
| Y393G | -0.01 | 0.71 | 0.05 | 19.75 |
| K419G | 0.21 | 0.78 | 0.12 | 8.20 |
| D420G | 2.71 | 2.53 | 0.49 | 2.06 |
| N422G | 0.88 | 1.34 | 0.30 | 3.34 |
| N460G | 1.69 | 1.61 | 0.48 | 2.09 |
| R462G | 0.25 | 0.00 | 2.58 | 0.39 |
| V463G | 0.08 | 0.09 | 0.41 | 2.46 |
| WT mouse CFI; His tag | -0.08 | 0.03 | 0.81 | 1.24 |
| Y408F; E457G; E461Q; N531G | 4.63 | 1.42 | 1.48 | 0.68 |
| Y408F; E457G; E461Q; R462K; F464Y; N531G | 4.57 | 1.87 | 1.11 | 0.90 |
| Y408F; E457G; E461Q; R462K; N531G | 4.58 | 1.90 | 1.09 | 0.91 |
| Y408F; E457G; E461Q; F464Y; N531G | 4.43 | 1.81 | 1.11 | 0.90 |
| E457G; E461Q; R462K; F464Y; N531G; R557K | 4.47 | 1.49 | 1.36 | 0.74 |
| E457G; E461Q; F464Y; N531G; R557K | 4.54 | 2.17 | 0.95 | 1.05 |
| E530F; P558S | 0.34 | 1.40 | 0.11 | 9.10 |
| E530Y; P558S | 0.43 | 1.62 | 0.12 | 8.38 |
| E457G; E461Q; E530F; N531G; P558S | 4.57 | 1.37 | 1.52 | 0.66 |
| E457G; E461Q; R462K; F464Y; E530F; N531G; P558S | 4.65 | 2.22 | 0.95 | 1.05 |
| Y408L; E457G; E461Q; R462K; E530F; N531G; P558S | 3.96 | 1.81 | 0.99 | 1.01 |
| E457G; E461Q; F464Y; E530F; N531G; P558S | 4.21 | 2.01 | 0.95 | 1.05 |

TABLE 7.1-continued

Variant Screening for C4b and C3b Cleavage

| Variant Description | C4b Screen Ref Fold | iC3b Screen Ref Fold | Specificity C4b | Specificity C3b |
|---|---|---|---|---|
| E457G; E461Q; E530Y; N531G; P558S | 4.04 | 1.25 | 1.47 | 0.68 |
| E457G; E461Q; R462K; F464Y; E530Y; N531G; P558S | 4.51 | 2.69 | 0.76 | 1.31 |
| Y408L; E457G; E461Q; R462K; E530Y; N531G; P558S | 4.18 | 2.06 | 0.92 | 1.08 |
| Y408F; E457G; E461Q; R462K; E530Y; N531G; P558S | 4.41 | 2.21 | 0.91 | 1.10 |
| E457G; E461Q; F464Y; E530Y; N531G; P558S | 4.03 | 2.44 | 0.75 | 1.33 |
| E457G; E461Q; K504H; N531G | 3.91 | 1.20 | 1.48 | 0.68 |
| E457G; E461Q; R462K; F464Y; K504H; N531G | 4.01 | 2.00 | 0.91 | 1.10 |
| Y408L; E457G; E461Q; R462K; K504H; N531G | 3.83 | 0.84 | 2.09 | 0.48 |
| E457G; E461Q; F464Y; K504H; N531G | 1.78 | 0.49 | 1.64 | 0.61 |
| E416A; E457G; E461Q; N531G | 4.01 | 1.69 | 1.08 | 0.93 |
| Y408L; E416A; E457G; E461Q; R462K; N531G | 4.04 | 1.63 | 1.13 | 0.89 |
| Y408F; E416A; E457G; E461Q; R462K; N531G | 4.51 | 1.99 | 1.03 | 0.97 |
| E416A; E457G; E461Q; F464Y; N531G | 4.74 | 1.79 | 1.20 | 0.83 |
| T377G; E457G; E461Q; R462K; F464Y; N531G | 4.50 | 2.05 | 1.00 | 1.00 |
| T377G; Y408L; E457G; E461Q; R462K; N531G | 3.44 | 1.06 | 1.47 | 0.68 |
| T377G; E457G; E461Q; F464Y; N531G | 4.08 | 2.12 | 0.88 | 1.14 |
| T377G; E416A; K504H | 3.37 | 0.77 | 1.99 | 0.50 |
| E416A; K504H | 0.63 | 0.59 | 0.48 | 2.07 |
| T377G; K504H | 3.01 | 0.95 | 1.44 | 0.70 |
| N422K; E457G; E461Q; N531G | 3.52 | 2.02 | 0.79 | 1.26 |
| N422K; E457G; E461Q; Q467K; N531G | 3.85 | 2.84 | 0.62 | 1.62 |
| E416A; N422K; E457G; E461Q; Q467K; N531G | 3.84 | 3.05 | 0.57 | 1.75 |
| K504R; E530F; D425K; P558S | 0.05 | 2.91 | 0.01 | 80.68 |
| K504R; E530F; D425R; P558S | 0.09 | 3.00 | 0.01 | 71.41 |
| K504R; E530F; D425R; P558G | 0

TABLE 7.1-continued

| Variant Screening for C4b and C3b Cleavage | | | | |
|---|---|---|---|---|
| Variant Description | C4b Screen Ref Fold | iC3b Screen Ref Fold | Specificity C4b | Specificity C3b |
| D425R; E457G; E461Q; N531G | 4.25 | 1.90 | 1.02 | 0.98 |
| D425K; E457G; E461Q; N531G | 4.26 | 2.07 | 0.94 | 1.07 |
| P558S; E457G; E461Q; N531G | 4.21 | 1.89 | 1.01 | 0.99 |
| P558G; E457G; E461Q; N531G | 3.97 | 1.87 | 0.97 | 1.03 |
| K504R; E530F; E457G; E461Q; N531G | 3.91 | 1.80 | 0.99 | 1.01 |
| K504R; D425R; E457G; E461Q; N531G | 4.19 | 1.59 | 1.20 | 0.84 |
| K504R; P558S; E457G; E461Q; N531G | 4.03 | 2.12 | 0.87 | 1.15 |
| E530F; P558S; E457G; E461Q; N531G | 4.37 | 1.50 | 1.32 | 0.76 |
| D425R; P558S; E457G; E461Q; N531G | 4.41 | 1.29 | 1.55 | 0.64 |
| D425R; E530F; E457G; E461Q; N531G | 4.48 | 0.99 | 2.05 | 0.49 |
| D425K; E530F; E457G; E461Q; N531G | 4.40 | 1.08 | 1.85 | 0.54 |
| D425R; E530F; P558G; E457G; E461Q; N531G | 4.13 | 0.87 | 2.17 | 0.46 |
| K504R; E530F; P558G; E457G; E461Q; N531G | 3.96 | 1.77 | 1.02 | 0.98 |
| K504R; D425R; P558G; E457G; E461Q; N531G | 4.14 | 1.58 | 1.19 | 0.84 |
| K504R; D425R; E530F; E457G; E461Q; N531G | 4.20 | 1.18 | 1.62 | 0.62 |
| R557A; N531M | 2.91 | 0.09 | 14.00 | 0.07 |
| R557K; N531M | 2.93 | 0.41 | 3.26 | 0.31 |
| R557A; N531M; Y403F; K504Y | 3.28 | 0.03 | 33.46 | 0.03 |
| R557A; N531D; Y403F; K504Y | 3.81 | 0.11 | 15.38 | 0.07 |
| R557A; N531M; Y403F; K504Y; E457G; E461Q | 3.97 | 0.21 | 8.42 | 0.12 |
| R557A; N531G; Y403F; K504Y; E457G; E461Q | 4.28 | 0.36 | 5.40 | 0.19 |
| R557A; N531D; Y403F; K504Y; E457G; E461Q | 3.51 | 0.42 | 3.85 | 0.26 |
| R557A; N531M; Y403F; K504Y; E457G; E461L | 3.18 | 0.46 | 3.15 | 0.32 |
| R557A; N531M; Y403F; K504Y; E457G; E461T | 3.31 | 0.40 | 3.72 | 0.27 |
| R557A; N531M; Y403F; K504Y; E457G; E461V | 3.17 | 0.46 | 3.14 | 0.32 |
| R557A; N531M; Y403F; K504Y; E457N; E461Q | 3.18 | 0.36 | 3.96 | 0.25 |
| R557A; N531M; Y403F; K504Y; E457N; E461L | 2.29 | 0.28 | 3.72 | 0.27 |

TABLE 7.1-continued

Variant Screening for C4b and C3b Cleavage

| Variant Description | C4b Screen Ref Fold | iC3b Screen Ref Fold | Specificity C4b | Specificity C3b |
|---|---|---|---|---|
| R557A; N531M; Y403F; K504Y; E457N; E461T | 3.13 | 0.24 | 5.81 | 0.17 |
| R557A; N531M; Y403F; K504Y; E457N; E461V | 3.20 | 0.36 | 4.00 | 0.25 |
| N531M; Y403F; K504Y; E457G; E461Q | 3.46 | 0.70 | 2.24 | 0.45 |
| N422K; E461Q | 2.54 | 2.67 | 0.43 | 2.31 |
| T377G; N422K | 2.25 | 2.55 | 0.40 | 2.49 |
| N531G; E457G; T377G | 4.33 | 1.54 | 1.28 | 0.78 |
| N531G; E461Q; N422K | 4.01 | 1.81 | 1.01 | 0.99 |
| N531G; E461Q; T377G | 4.10 | 2.28 | 0.82 | 1.22 |
| N531G; N422K; T377G | 3.88 | 2.74 | 0.64 | 1.55 |
| E457G; E461Q; N422K | 3.61 | 2.37 | 0.69 | 1.44 |
| E457G; N422K; T377G | 4.25 | 2.99 | 0.65 | 1.55 |
| E461Q; N422K; T377G | 3.96 | 2.75 | 0.65 | 1.53 |
| N531G; E457G; N422K; T377G | 4.39 | 1.28 | 1.56 | 0.64 |
| N531G; E461Q; N422K; T377G | 4.24 | 1.70 | 1.13 | 0.88 |
| E457G; E461Q; N422K; T377G | 4.28 | 1.74 | 1.12 | 0.90 |
| T377G; N422K; E457G; E461Q; N531G | 3.92 | 0.78 | 2.29 | 0.44 |
| D425K; Y408M | 0.19 | 1.88 | 0.05 | 22.13 |
| D425K; E530F | 0.08 | 2.17 | 0.02 | 60.33 |
| D425K; F537K | 0.22 | 2.11 | 0.05 | 21.12 |
| D425K; K504R | 0.12 | 2.05 | 0.03 | 38.57 |
| D425K; P558S | 0.77 | 2.11 | 0.17 | 5.99 |
| Y408M; E530F | 0.11 | 0.95 | 0.05 | 19.11 |
| Y408M; K504R | 0.09 | 0.83 | 0.05 | 20.92 |
| Y408M; P558S | 0.06 | 1.13 | 0.03 | 31.43 |
| E530F; F537K | 0.00 | 0.03 | 0.81 | 1.24 |
| E530F; K504R | 0.05 | 1.14 | 0.03 | 31.51 |
| E530F; P558S | 0.16 | 1.38 | 0.05 | 19.07 |
| F537K; K504R | 0.11 | 1.06 | 0.05 | 21.82 |
| F537K; P558S | 0.38 | 1.18 | 0.15 | 6.85 |
| K504R; P558S | 0.17 | 1.19 | 0.07 | 15.19 |
| D425K; Y408M; F537K | 0.09 | 1.52 | 0.03 | 38.72 |
| D425K; Y408M; K504R | 0.10 | 1.57 | 0.03 | 34.64 |
| D425K; Y408M; E530F; F537K | 0.03 | 0.07 | 0.55 | 1.82 |
| D425K; Y408M; E530F; P558S | 0.07 | 1.53 | 0.02 | 42.32 |
| D425K; E530F; F537K; K504R | 0.02 | 0.13 | 0.27 | 3.65 |

TABLE 7.1-continued

Variant Screening for C4b and C3b Cleavage

| Variant Description | C4b Screen Ref Fold | iC3b Screen Ref Fold | Specificity C4b | Specificity C3b |
|---|---|---|---|---|
| Y408M; E530F; F537K; K504R | 0.05 | 0.01 | 0.81 | 1.24 |
| Y408M; F537K; K504R; P558S | 0.07 | 1.26 | 0.03 | 35.04 |
| D425K; Y408M; E530F; F537K; K504R | 0.15 | 0.02 | 1.57 | 0.64 |
| D425K; Y408M; E530F; F537K; P558S | 0.07 | 0.04 | 0.81 | 1.24 |
| D425K; Y408M; E530F; K504R; P558S | 0.49 | 1.84 | 0.12 | 8.19 |
| D425K; Y408M; F537K; K504R; P558S | 0.08 | 1.49 | 0.03 | 39.78 |
| D425K; E530F; F537K; K504R; P558S | 0.16 | 0.09 | 0.84 | 1.19 |
| D425K; Y408M; E530F; F537K; K504R; P558S | 0.11 | 0.01 | 1.12 | 0.89 |
| D425K; E457G; E461Q; K504R; N531G | 3.53 | 2.46 | 0.65 | 1.53 |
| D425K; E457G; E461Q; N531G; P558S | 3.25 | 1.98 | 0.75 | 1.34 |
| T377G; Y408M; N422K; E457G; E461

TABLE 7.1-continued

Variant Screening for C4b and C3b Cleavage

| Variant Description | C4b Screen Ref Fold | iC3b Screen Ref Fold | Specificity C4b | Specificity C3b |
|---|---|---|---|---|
| D425K | 2.86 | 0.11 | 11.98 | 0.08 |
| Y403F; D425K; E457G; N531G | 3.85 | 0.22 | 7.94 | 0.13 |
| G406A; D425K; E457G; E461Q; N531G | 3.17 | 0.18 | 7.95 | 0.13 |
| Y403F; G406A; D425K; E457G; E461Q; N531G | 4.12 | 0.14 | 13.69 | 0.07 |
| Y403F; D425K; E457G; E461Q; K504Y; N531G | 3.11 | 0.03 | 31.76 | 0.03 |
| Y403F; G406A; D425K; E457G; E461Q; K504Y; N531G | 3.16 | 0.02 | 32.27 | 0.03 |
| D425K; E457G; E461Q; N531G | 3.28 | 0.09 | 16.68 | 0.06 |
| D425K; E457G; E461Q; N531G; R557A | 2.80 | 0.08 | 16.15 | 0.06 |
| R557A | 1.72 | −0.01 | 17.54 | 0.06 |
| Δ(V565) | 1.57 | 0.54 | 1.32 | 0.76 |
| F559Y | 0.66 | 1.23 | 0.25 | 4.08 |
| Δ(S308) | 0.21 | −0.01 | 2.10 | 0.48 |

For the assays where EC50 values were determined, the specificity was calculated by normalizing to CFI-HSA. For C4b cleavage the max value was set at 1000 nM and all values above that were set to 1000 nM. For C3b cleavage the max value was set at 500 nM and all values above that were set to 500 nM. Specificity for C4b was calculated as follows: (C4b EC50 CFI-HSA/C4b EC50 variant)/(C3b EC50 CFI-HSA/C3b EC50 variant). Specificity for C3b was calculated as follows: (C3b EC50 CFI-HSA/C3b EC50 variant)/(C4b EC50 CFI-HSA/C4b EC50 variant). Results are reported in Table 7.2.

TABLE 7.2

$EC_{50}$ Values for Variants in C4b and C3b Cleavage Assays

| Variant Description | C4c $EC_{50}$ (nM) | iC3b $EC_{50}$ (nM) | Fold Change Specificity C4b | Fold Change Specificity C3b | Fold Change Activity C4b | Fold Change Activity C3b |
|---|---|---|---|---|---|---|
| Wild Type | 299.2 | 28.4 | 1 | 1 | 1.0 | 1.0 |
| K14A | 400.9 | | | | 0.7 | |
| R557A | 326.6 | 500 | 16.1 | 0.1 | 0.9 | 0.1 |
| Y408L-N531G | 70.5 | 10.6 | 1.6 | 0.6 | 4.2 | 2.7 |
| L307G | 316.2 | 39.2 | 1.3 | 0.8 | 0.9 | 0.7 |
| fH_CCP1-8; GGGGGGGGGGGG (SEQ ID NO: 25); ΔHSA | 294.7 | 15.6 | 0.6 | 1.8 | 1.0 | 1.8 |
| N531G; P535A | 53.4 | 7.9 | 1.6 | 0.6 | 5.6 | 3.6 |
| Y408L | 1000 | 21.3 | 0.2 | 4.5 | 0.3 | 1.3 |
| E457G; E461Q-R462K; F464Y | 65.2 | | | | 4.6 | |
| N531G | 58.4 | 8.3 | 1.5 | 0.7 | 5.1 | 3.4 |
| N531A | 277.9 | 24.3 | 0.9 | 1.1 | 1.1 | 1.2 |
| Y408F | 224.7 | 19.2 | 0.9 | 1.1 | 1.3 | 1.5 |

TABLE 7.2-continued

EC$_{50}$ Values for Variants in C4b and C3b Cleavage Assays

| Variant Description | C4c EC$_{50}$ (nM) | iC3b EC$_{50}$ (nM) | Fold Change Specificity C4b | Fold Change Specificity C3b | Fold Change Activity C4b | Fold Change Activity C3b |
|---|---|---|---|---|---|---|
| Y408F; N531G | 75.7 | | | | 4.0 | |
| Y408L; N531G; E457G; E461Q; R462K; F464Y | 82.1 | | | | 3.6 | |
| E457G | 137.9 | 11.1 | 0.8 | 1.2 | 2.2 | 2.6 |
| E461Q | 120.8 | 12 | 1 | 1 | 2.5 | 2.4 |
| F464Y | 346.6 | 55.4 | 1.7 | 0.6 | 0.9 | 0.5 |
| Y408L; N531G; E457G | 94.4 | | | | 3.2 | |
| Y408L; N531G; E457G; E461Q | 84.8 | | | | 3.5 | |
| Y408L; N531G; P535A | 117.8 | | | | 2.5 | |
| Y408P | 338.3 | | | | 0.9 | |
| Y408N | 710 | 64.2 | 1 | 1.1 | 0.4 | 0.4 |
| Y408H | 1000 | 43.3 | 0.5 | 2.2 | 0.3 | 0.7 |
| K534Q | 595 | 21.7 | 0.4 | 2.6 | 0.5 | 1.3 |
| E530D-N531G; G533A-K534Q-P535K-E536N | 469.9 | | | | 0.6 | |
| R321A | 897.4 | | | | 0.3 | |
| WT mouse CFI | 54 | 500 | 97.6 | 0 | 5.5 | 0.1 |
| N422K | 358.9 | 10.9 | 0.3 | 3.1 | 0.8 | 2.6 |
| A502S; K504Q; F537K | 810 | 31.2 | 0.4 | 2.5 | 0.4 | 0.9 |
| A502S | 640 | 26.7 | 0.4 | 2.3 | 0.5 | 1.1 |
| K504R | 439.1 | 33.7 | 0.8 | 1.2 | 0.7 | 0.8 |
| K504A | 1000 | 51.9 | 0.5 | 1.8 | 0.3 | 0.5 |
| K504L | 1000 | 144.2 | 1.5 | 0.7 | 0.3 | 0.2 |
| K504H | 229.1 | 53.6 | 2.5 | 0.4 | 1.3 | 0.5 |
| F537K | 890 | 40.2 | 0.5 | 2.1 | 0.3 | 0.7 |
| F537R | 645 | 29.1 | 0.5 | 2.1 | 0.5 | 1.0 |
| Q467K | 246 | 18.7 | 0.8 | 1.3 | 1.2 | 1.5 |
| Q467R | 398.9 | 27.1 | 0.7 | 1.4 | 0.8 | 1.0 |
| Q467K; F537K | 615 | 12.7 | 0.2 | 4.6 | 0.5 | 2.2 |
| E530G; N531G | 1000 | 31.3 | 0.3 | 3 | 0.3 | 0.9 |
| E530F | 1000 | 21.8 | 0.2 | 4.3 | 0.3 | 1.3 |
| E530Y | 381.3 | 16.1 | 0.4 | 2.2 | 0.8 | 1.8 |
| E530D; F537K | 372.9 | 15.6 | 0.4 | 2.3 | 0.8 | 1.8 |
| R557K | 266.1 | 99.9 | 4 | 0.3 | 1.1 | 0.3 |
| P558L | 471.7 | 12.4 | 0.3 | 3.6 | 0.6 | 2.3 |
| E457G; E461Q | 53.1 | 5.5 | 1.1 | 0.9 | 5.6 | 5.2 |

TABLE 7.2-continued

EC$_{50}$ Values for Variants in C4b and C3b Cleavage Assays

| Variant Description | C4c EC$_{50}$ (nM) | iC3b EC$_{50}$ (nM) | Fold Change Specificity C4b | Fold Change Specificity C3b | Fold Change Activity C4b | Fold Change Activity C3b |
|---|---|---|---|---|---|---|
| WT;GGSSGG (SEQ ID NO: 6); CR1(ccp15-17); GGSSGG (SEQ ID NO: 6); fH(ccp1-4) | 60.3 | | | | 5.0 | |
| WT; GGSSGG (SEQ ID NO: 6); CR1(ccp15-17) | 53.1 | 31.9 | 6.3 | 0.2 | 5.6 | 0.9 |
| E457G; E461G | 221.8 | 22.2 | 1.1 | 0.9 | 1.3 | 1.3 |
| N531G; E457G; E461Q | 29.3 | 5.6 | 2 | 0.5 | 10.2 | 5.1 |
| D506G | 1000 | 500 | 5.3 | 0.2 | 0.3 | 0.1 |
| Y408L; N531G; E461Q | 51.5 | 5.8 | | | | |
| D425R; Y408L; N531G; E457G; E461Q; R462K; F464Y | 26.1 | 4.9 | 2 | 0.5 | 11.5 | 5.8 |
| Y20F; E38A; 5250A; D425A; Y408L; N531G; E457G; E461Q; R462K; F464Y | 106.4 | | | | 2.8 | |
| Y408L; N531G; E457G; E461Q; R462K | 60 | | | | 5.0 | |
| Y408L; N531G; E457G; E461Q; F464Y | 79.9 | | | | 3.7 | |
| Y408L; N531G; E457G; R462K; F464Y | 45.8 | | | | 6.5 | |
| Y408L; N531G; E461Q; R462K; F464Y | 82.7 | | | | 3.6 | |
| Y408L; E457G; E461Q; R462K; F464Y | 163 | | | | 1.8 | |
| E457G; N531G; E461Q; R462K; F464Y | 37.9 | | | | 7.9 | |
| Y408L; E457G; E461Q; R462K | 90.2 | | | | 3.3 | |
| N531G; E457G; E461Q; F464Y | 44.1 | | | | 6.8 | |
| E416A | 425.1 | 12.8 | 0.3 | 3.2 | 0.7 | 2.2 |
| N476Q | 1000 | 15.7 | 0.2 | 6.1 | 0.3 | 1.8 |
| N518Q | 509.8 | 20.2 | 0.4 | 2.4 | 0.6 | 1.4 |
| E457A | 113 | 16.9 | 1.6 | 0.6 | 2.6 | 1.7 |
| E457D | 162.2 | 12.3 | 0.8 | 1.3 | 1.8 | 2.3 |
| E457F | 1000 | 96.8 | 1 | 1 | 0.3 | 0.3 |
| E457H | 886.3 | 78.7 | 0.9 | 1.1 | 0.3 | 0.4 |
| E4571 | 256 | 20.5 | 0.8 | 1.2 | 1.2 | 1.4 |
| E457K | 135.2 | 9.5 | 0.7 | 1.4 | 2.2 | 3.0 |
| E457L | 1000 | 51.4 | 0.5 | 1.8 | 0.3 | 0.6 |
| E457M | 482 | 25.4 | 0.6 | 1.8 | 0.6 | 1.1 |

TABLE 7.2-continued

EC$_{50}$ Values for Variants in C4b and C3b Cleavage Assays

| Variant Description | C4c EC$_{50}$ (nM) | iC3b EC$_{50}$ (nM) | Fold Change Specificity C4b | Fold Change Specificity C3b | Fold Change Activity C4b | Fold Change Activity C3b |
|---|---|---|---|---|---|---|
| E457N | 215.4 | 16.3 | 0.8 | 1.3 | 1.4 | 1.7 |
| E457P | 1000 | | | | 0.3 | |
| E457Q | 395.1 | 19.8 | 0.5 | 1.9 | 0.8 | 1.4 |
| E457R | 182.4 | 10.5 | 0.6 | 1.6 | 1.6 | 2.7 |
| E457S | 428.1 | 21.3 | 0.5 | 1.9 | 0.7 | 1.3 |
| E457T | 1000 | 10.4 | 0.1 | 9.1 | 0.3 | 2.7 |
| E457W | 1000 | 109.8 | 1.2 | 0.9 | 0.3 | 0.3 |
| E457Y | 1000 | 90.6 | 1 | 1 | 0.3 | 0.3 |
| E457V | 567.3 | 40.6 | 0.8 | 1.3 | 0.5 | 0.7 |
| K14A; Y20F; D26A; R35A; E38A; L304G; P305G; K306G; L307G; S308G | 1000 | | | | 0.3 | |
| Y408M | 930 | 29.1 | 0.3 | 3 | 0.3 | 1.0 |
| Y408Q | 530 | 49.1 | 1 | 1 | 0.6 | 0.6 |
| D341A | 1000 | 57.2 | 0.6 | 1.7 | 0.3 | 0.5 |
| E461H | 133.5 | 11.7 | 0.9 | 1.1 | 2.2 | 2.4 |
| E461I | 100.1 | 9.8 | 1 | 1 | 3.0 | 2.9 |
| E461L | 87.5 | 7.3 | 0.9 | 1.1 | 3.4 | 3.9 |
| E461M | 148.3 | 6.9 | 0.5 | 2 | 2.0 | 4.1 |
| E461T | 125 | | | | 2.4 | |
| E461V | 64.4 | 8.9 | 1.5 | 0.7 | 4.6 | 3.2 |
| Y563H | 855 | 24.6 | 0.3 | 3.3 | 0.3 | 1.2 |
| N531D | 77.2 | | | | 3.9 | |
| N531F | 183.2 | | | | 1.6 | |
| N531K | 222.7 | 13 | 0.6 | 1.6 | 1.3 | 2.2 |
| N531L | 219 | 17.6 | 0.8 | 1.2 | 1.4 | 1.6 |
| N531M | 99.8 | 21.2 | 2.2 | 0.4 | 3.0 | 1.3 |
| N531Q | 309.7 | | | | 1.0 | |
| N531S | 175.6 | | | | 1.7 | |
| Y403F | 337.8 | 47.8 | 1.5 | 0.7 | 0.9 | 0.6 |
| A405S | 352.6 | 23.9 | 0.7 | 1.4 | 0.8 | 1.2 |
| G406R | 474.4 | 19 | 0.4 | 2.4 | 0.6 | 1.5 |
| G406A | 175.8 | 42.6 | 2.6 | 0.4 | 1.7 | 0.7 |
| T377G | 147.2 | 16.4 | 1.2 | 0.9 | 2.0 | 1.7 |
| R456N | 920 | 60.5 | 0.7 | 1.4 | 0.3 | 0.5 |
| K504D | 1000 | 53.1 | 0.6 | 1.8 | 0.3 | 0.5 |
| K504F | 1000 | 77.5 | 0.8 | 1.2 | 0.3 | 0.4 |

TABLE 7.2-continued

EC$_{50}$ Values for Variants in C4b and C3b Cleavage Assays

| Variant Description | C4c EC$_{50}$ (nM) | iC3b EC$_{50}$ (nM) | Fold Change Specificity C4b | Fold Change Specificity C3b | Fold Change Activity C4b | Fold Change Activity C3b |
|---|---|---|---|---|---|---|
| K504I | 1000 | 175.6 | 1.8 | 0.5 | 0.3 | 0.2 |
| K504M | 1000 | 43.8 | 0.5 | 2.2 | 0.3 | 0.6 |
| K504N | 1000 | 76.8 | 0.8 | 1.2 | 0.3 | 0.4 |
| K504S | 1000 | 43.7 | 0.5 | 2.2 | 0.3 | 0.6 |
| K504T | 1000 | 43.5 | 0.5 | 2.2 | 0.3 | 0.7 |
| K504V | 1000 | 104.1 | 1.1 | 0.9 | 0.3 | 0.3 |
| K504W | 1000 | 48.7 | 0.5 | 2 | 0.3 | 0.6 |
| K504Y | 195.5 | 51.6 | 2.8 | 0.4 | 1.5 | 0.6 |
| G406D | 1000 | 150.7 | 1.6 | 0.6 | 0.3 | 0.2 |
| G406E | 1000 | 116 | 1.2 | 0.8 | 0.3 | 0.2 |
| G406F | 1000 | 37.2 | 0.4 | 2.5 | 0.3 | 0.8 |
| G406H | 197.3 | 20.4 | 1.1 | 0.9 | 1.5 | 1.4 |
| G406I | 1000 | 54.4 | 0.6 | 1.7 | 0.3 | 0.5 |
| G406K | 182.8 | | | | 1.6 | |
| G406L | 386.4 | 31.9 | 0.9 | 1.1 | 0.8 | 0.9 |
| G406M | 1000 | 40.5 | 0.4 | 2.3 | 0.3 | 0.7 |
| G406N | 1000 | 35.2 | 0.4 | 2.7 | 0.3 | 0.8 |
| G406P | 1000 | 35.9 | 0.4 | 2.6 | 0.3 | 0.8 |
| G406Q | 1000 | 30.7 | 0.3 | 3.1 | 0.3 | 0.9 |
| G406S | 314.8 | 32.6 | 1.1 | 0.9 | 1.0 | 0.9 |
| G406T | 1000 | 52.4 | 0.6 | 1.8 | 0.3 | 0.5 |
| G406V | 1000 | 43.1 | 0.5 | 2.2 | 0.3 | 0.7 |
| G406W | 1000 | 65.5 | 0.7 | 1.4 | 0.3 | 0.4 |
| G406Y | 1000 | 14.9 | 0.2 | 6.4 | 0.3 | 1.9 |
| G406D; Y408L | 1000 | 78.2 | 0.8 | 1.2 | 0.3 | 0.4 |
| G406D; N531G | 124.2 | | | | 2.4 | |
| G406D; Y408L; N531G) | 178 | | | | 1.7 | |
| G406D; N531G; P535A | 128.8 | | | | 2.3 | |
| G406D; Y408L; N531G; P535A | 101.7 | | | | 2.9 | |
| P384A | 1000 | | | | 0.3 | |
| W381G | 1000 | 500 | 5.3 | 0.2 | 0.3 | 0.1 |
| N404G | 310 | | | | 1.0 | |
| D425G | 1000 | 13.5 | 0.1 | 7.1 | 0.3 | 2.1 |
| K418G; D425G | 865 | 28.5 | 0.3 | 2.9 | 0.3 | 1

TABLE 7.2-continued

EC$_{50}$ Values for Variants in C4b and C3b Cleavage Assays

| Variant Description | C4c EC$_{50}$ (nM) | iC3b EC$_{50}$ (nM) | Fold Change Specificity C4b | Fold Change Specificity C3b | Fold Change Activity C4b | Fold Change Activity C3b |
|---|---|---|---|---|---|---|
| T346K; Y408L; N531G | 209.3 | | | | 1.4 | |
| K504D; Y408L; N531G | 242.2 | 20.9 | 0.9 | 1.1 | 1.2 | 1.4 |
| K504E; Y408L; N531G | 120.2 | 19.4 | 1

TABLE 7.2-continued

EC$_{50}$ Values for Variants in C4b and C3b Cleavage Assays

| Variant Description | C4c EC$_{50}$ (nM) | iC3b EC$_{50}$ (nM) | Fold Change Specificity C4b | Fold Change Specificity C3b | Fold Change Activity C4b | Fold Change Activity C3b |
|---|---|---|---|---|---|---|
| E457G; R462K; F464Y | 84.6 | | | | 3.5 | |
| E461Q; R462K; F464Y | 158.8 | | | | 1.9 | |
| Y408L; N531G | 71.9 | | | | 4.2 | |
| N531G; E461Q | 24.2 | 5.4 | 2.3 | 0.4 | 12.4 | 5.3 |
| N531G; R462K | 51.2 | | | | 5.8 | |
| N531G; F464Y | 63.5 | | | | 4.7 | |
| E457G; R462K | 52.7 | | | | 5.7 | |
| E457G; F464Y | 82.3 | | | | 3.6 | |
| E461Q; R462K | 95.9 | | | | 3.1 | |
| E461Q; F464Y | 123 | | | | 2.4 | |
| R462K; F464Y | 1000 | 106.3 | 1.1 | 0.9 | 0.3 | 0.3 |
| K534H | 104.2 | 15.7 | 1.6 | 0.6 | 2.9 | 1.8 |
| K534N | 299.9 | | | | 1.0 | |
| K534M | 153.5 | | | | 1.9 | |
| D425H | 123 | 10.7 | 0.9 | 1.1 | 2.4 | 2.7 |
| D425T | 226.6 | 11.5 | 0.5 | 1.9 | 1.3 | 2.5 |
| D425P | 640 | 13.6 | 0.2 | 4.5 | 0.5 | 2.1 |
| D4251 | 111.8 | 13 | 1.2 | 0.8 | 2.7 | 2.2 |
| D425W | 87.6 | 14.2 | 1.7 | 0.6 | 3.4 | 2.0 |
| D425Y | 112.1 | 14.3 | 1.3 | 0.7 | 2.7 | 2.0 |
| L307A | 93.4 | 17.1 | 1.9 | 0.5 | 3.2 | 1.7 |
| L307S | 54.1 | 18.4 | 3.6 | 0.3 | 5.5 | 1.5 |
| T407G | 329 | | | | 0.9 | |
| T407G; Y408L | 435 | | | | 0.7 | |
| T407G; E457G | 545 | | | | 0.5 | |
| T407G; N531G | 620 | | | | 0.5 | |
| T407G; Y408L; E457G | 300 | | | | | 1.0 |
| F464L | 1000 | | | | 0.3 | |
| F4641 | 1000 | | | | 0.3 | |
| F464A | 1000 | | | | 0.3 | |
| F464P | 1000 | 500 | 5.3 | 0.2 | 0.3 | 0.1 |
| F464G | 1000 | | | | 0.3 | |
| P558A | 213.2 | 20.8 | 1 | 1 | 1.4 | 1.4 |
| G556A | 1000 | 76 | 0.8 | 1.2 | 0.3 | 0.4 |
| G556S | 179.9 | 29.7 | 1.7 | 0.6 | 1.7 | 1.0 |
| Y408L; P535G | 1000 | 50.9 | 0.5 | 1.9 | 0.3 | 0.6 |

TABLE 7.2-continued $EC_{50}$ Values for Variants in C4b and C3b Cleavage Assays

| Variant Description | C4c $EC_{50}$ (nM) | iC3b $EC_{50}$ (nM) | Fold Change Specificity C4b | Fold Change Specificity C3b | Fold Change Activity C4b | Fold Change Activity C3b |
|---|---|---|---|---|---|---|
| E457G; P535G | 157.9 | 13.8 | 0.9 | 1.1 | 1.9 | 2.1 |
| N531G; P535G | 126.1 | | | | 2.4 | |
| Y408L; E457G; P535G | 205 | 11.7 | 0.6 | 1.7 | 1.5 | 2.4 |
| E457G; N531G; P535G | 54 | | | | 5.5 | |
| Y408L; E457G; N531G; P535G | 50.5 | | | | 5.9 | |
| E457G; D425K | 43.3 | 4.1 | 1 | 1 | 6.9 | 6.9 |
| N531G; D425K | 51.9 | 5.2 | 1.1 | 0.9 | 5.8 | 5.5 |
| P535G; D425K | 865 | 19.4 | 0.2 | 4.2 | 0.3 | 1.5 |
| Y408L; P535G D425K | 1000 | 19.7 | 0.2 | 4.8 | 0.3 | 1.4 |
| E457G; P535G; D425K | 90 | 6 | 0.7 | 1.4 | 3.3 | 4.7 |
| N531G; P535G; D425K | 78.9 | | | | 3.8 | |
| Y408L; E457G; D425K | 102.5 | | | | 2.9 | |
| Y408L; N531G; D425K | 50.1 | | | | 6.0 | |
| E457G; N531G; D425K | 12.7 | 4.4 | 3.7 | 0.3 | 23.6 | 6.5 |
| Y408L; E457G; N531G; D425K | 13.5 | 4.7 | 3.6 | 0.3 | 22.2 | 6.0 |
| Y408L; E457G; P535G; D425K | 46.5 | 5.2 | 1.2 | 0.8 | 6.4 | 5.5 |
| Y408L; N531G; P535G; D425K | 65.4 | | | | 4.6 | |
| E457G; N531G; P535G; D425K | 39.4 | | | | 7.6 | |
| Y408L; E457G; N531G; P535G; D425K | 32.2 | | | | 9.3 | |
| E457G; K534Q | 55.2 | | | | 5.4 | |
| N531G; K534Q | 43.5 | | | | 6.9 | |
| E457G; P535G; K534Q | 154.3 | | | | 1.9 | |
| N531G; P535G; K534Q | 117.8 | | | | 2.5 | |
| Y408L; E457G; K534Q | 83.8 | | | | 3.6 | |
| Y408L; N531G; K534Q | 64.3 | | | | 4.7 | |
| E457G; N531G; K534Q | 16.9 | 7.1 | 4.4 | 0.2 | 17.7 | 4.0 |
| Y408L; E457G; N531G; K534Q | 26.4 | | | | 11.3 | |
| E457G; N531G; P535G; K534Q | 48.3 | 8.2 | 1.8 | 0.6 | 6.2 | 3.5 |
| Y408L; E457G; N531G; P535G; K534Q | 21.1 | | | | 14.2 | |
| E457G; P558S | 65.9 | | | | 4.5 | |
| N531G; P558S | 63.2 | | | | 4.7 | |
| E457G; P535G; P558S | 185.6 | | | | 1.6 | |

TABLE 7.2-continued

EC$_{50}$ Values for Variants in C4b and C3b Cleavage Assays

| Variant Description | C4c EC$_{50}$ (nM) | iC3b EC$_{50}$ (nM) | Fold Change Specificity C4b | Fold Change Specificity C3b | Fold Change Activity C4b | Fold Change Activity C3b |
|---|---|---|---|---|---|---|
| N531G; P535G; P558S | 135.9 | | | | 2.2 | |
| Y408L; E457G; P558S | 67.3 | | | | 4.4 | |
| Y408L; N531G; P558S | 77.5 | | | | 3.9 | |
| E457G; N531G; P558S | 17.5 | 6.7 |

TABLE 7.2-continued

EC$_{50}$ Values for Variants in C4b and C3b Cleavage Assays

| Variant Description | C4c EC$_{50}$ (nM) | iC3b EC$_{50}$ (nM) | Fold Change Specificity C4b | Fold Change Specificity C3b | Fold Change Activity C4b | Fold Change Activity C3b |
|---|---|---|---|---|---|---|
| E457G; N531G; P535G; WT; GGSSGG (SEQ ID NO: 6); CR1(ccp15-17) | 44.4 | 14.3 | 3.4 | 0.3 | 6.7 | 2.0 |
| E457G; N422K | 32.6 | 5.2 | 1.7 | 0.6 | 9.2 | 5.5 |
| N531G; N422K | 42.6 | 5.2 | 1.3 | 0.8 | 7.0 | 5.5 |
| Y408L; E457G; N422K | 43.6 | | | | 6.9 | |
| Y408L; N531G; N422K | 83.7 | | | | 3.6 | |
| E457G; N531G; N422K | 7 | 4.7 | 7 | 0.1 | 42.7 | 6.0 |
| Y408L; E457G; N531G; N422K | 48.4 | | | | 6.2 | |
| E457G; N531G; P535G; N422K | 51.6 | | | | 5.8 | |
| Y408L; E457G; N531G; P535G; N422K | 59.7 | | | | 5.0 | |
| N531G; P535A; GGSSGG (SEQ ID NO: 6); CR1(ccp15-17) | 60.1 | 20.4 | 3.6 | 0.3 | 5.0 | 1.4 |
| Y408L; E416A | 1000 | 20.8 | 0.2 | 4.6 | 0.3 | 1.4 |
| E457G; E416A | 94.9 | 7.1 | 0.8 | 1.3 | 3.2 | 4.0 |
| N531G; E416A | 11.9 | 6.9 | 6.1 | 0.2 | 25.1 | 4.1 |
| P535G; E416A | 1000 | 41.6 | 0.4 | 2.3 | 0.3 | 0.7 |
| Y408L; D425R; E416A | 221 | | | | 1.4 | |
| E457G; D425R; E416A | 59.3 | 3.1 | 0.5 | 1.8 | 5.0 | 9.2 |
| N531G; D425R; E416A | 81.4 | | | | 3.7 | |
| Y408L; E457G; E416A | 170.4 | | | | 1.8 | |
| E457G; N531G; E416A | 5.4 | | | | 55.4 | |
| Y408L; E457G; N531G; E416A | 34.8 | | | | 8.6 | |
| Y408L; E457G; D425R; E416A | 181.3 | | | | 1.7 | |
| Y408L; N531G; D425R; E416A | 60.6 | | | | 4.9 | |
| E457G; N531G; D425R; E416A | 4.1 | 3.1 | 8.1 | 0.1 | 73.0 | 9.2 |
| E457G; N531G; E461Q; R462K; F464Y; E416A | 7.5 | 5.2 | 7.3 | 0.1 | 39.9 | 5.5 |
| Y408L; E530Y | 1000 | | | | 0.3 | |
| E457G; E530Y | 332.5 | | | | 0.9 | |
| N531G; E530Y | 38.2 | | | | 7.8 | |
| Y408L; D425R; E530Y | 900 | | | | 0.3 | |
| E457G; D425R; E530Y | 234.1 | 3.6 | 0.2 | 6.1 | 1.3 | 7.9 |
| N531G; D425R; E530Y | 162.3 | | | | 1.8 | |

TABLE 7.2-continued

EC$_{50}$ Values for Variants in C4b and C3b Cleavage Assays

| Variant Description | C4c EC$_{50}$ (nM) | iC3b EC$_{50}$ (nM) | Fold Change Specificity C4b | Fold Change Specificity C3b | Fold Change Activity C4b | Fold Change Activity C3b |
|---|---|---|---|---|---|---|
| Y408L; E457G; E530Y | 26.5 | | | | 11.3 | |
| Y408L; N531G; E530Y | 54 | | | | 5.5 | |
| E457G; N531G; E530Y | 13 | 5 | 4.1 | 0.2 | 23.0 | 5.7 |
| Y408L; E457G; N531G; E530Y | 35.4 | | | | 8.5 | |
| Y408L; N531G; D425R; E530Y | 41.2 | | | | 7.3 | |
| E457G; N531G; D425R; E530Y | 16.4 | 4.4 | 2.8 | 0.4 | 18.2 | 6.5 |
| Y408L; E457G; N531G; D425R; E530Y | 92.9 | | | | 3.2 | |
| D425R; Y408L; N531G; E457G; E461Q; R462K; F464Y; E530Y | 12.3 | 4.3 | 3.6 | 0.3 | 24.3 | 6.6 |
| E457G; N531G; E461Q; R462K; F464Y; E530Y | 7.8 | 3.5 | 4.8 | 0.2 | 38.4 | 8.1 |
| E457G; N531G; E461Q; R462K; F464Y; E530Y; GGSSGG (SEQ ID NO: 6); CR1(ccp15-17) | 86.7 | | | | 3.5 | |
| E457G; E461Q; N531G; GGSSGG (SEQ ID NO: 6); CR1 (ccp15-17) | 50.3 | 33 | 6.9 | 0.1 | 5.9 | 0.9 |
| Y408L; E457G; E461Q; R462K; N531G; GGSSGG (SEQ ID NO: 6); CR1 (ccp15-17) | 91 | | | | 3.3 | |
| Y408L; E457G; R462K; F464Y; N531G; GGSSGG (SEQ ID NO: 6); CR1 (ccp15-17) | 76.4 | | | | 3.9 | |
| E457G; N531G; E461Q; R462K; F464Y; GGSSGG (SEQ ID NO: 6); CR1 (ccp15-17) | 43.1 | 32.7 | 8 | 0.1 | 6.9 | 0.9 |
| E457G; N531G; E461Q; R462K; F464Y; GGSSGG (SEQ ID NO: 6); CR1 (ccp1-3) | 1000 | | | | 0.3 | |
| E457G; E461Q; F464Y; N531G; GGSSGG (SEQ ID NO: 6); CR1 (ccp15-17) | 38.4 | | | | 7.8 | |
| R365A | 1000 | 64.3 | 0.7 | 1.5 | 0.3 | 0.4 |
| D549A | 1000 | 32.2 | 0.3 | 2.9 | 0.3 | 0.9 |
| D549N | 168.3 | 21.9 | 1.4 | 0.7 | 1.8 | 1.3 |
| D549P | 1000 | 41.7 | 0.4 | 2.3 | 0.3 | 0.7 |
| Y553H | 166.5 | | | | 1.8 | |
| Y553K | 197.8 | | | | 1.5 | |
| R557V | 138.5 | 164.9 | 12.5 | 0.1 | 2.2 | 0.2 |

TABLE 7.2-continued

EC$_{50}$ Values for Variants in C4b and C3b Cleavage Assays

| Variant Description | C4c EC$_{50}$ (nM) | iC3b EC$_{50}$ (nM) | Fold Change Specificity C4b | Fold Change Specificity C3b | Fold Change Activity C4b | Fold Change Activity C3b |
|---|---|---|---|---|---|---|
| R557I | 117.2 | 127.6 | 11.5 | 0.1 | 2.6 | 0.2 |
| R557L | 177.4 | 112.9 | 6.7 | 0.1 | 1.7 | 0.3 |
| R557M | 82 | 164.1 | 21.1 | 0 | 3.6 | 0.2 |
| R557F | 145.4 | 168.5 | 12.2 | 0.1 | 2.1 | 0.2 |
| R557Y | 145.2 | 115.7 | 8.4 | 0.1 | 2.1 | 0.2 |
| R557W | 164.9 | 197.7 | 12.6 | 0.1 | 1.8 | 0.1 |
| R557S | 246.6 | 208 | 8.9 | 0.1 | 1.2 | 0.1 |
| R557T | 324.5 | 216.6 | 7 | 0.1 | 0.9 | 0.1 |
| R557N | 154.5 | 359.6 | 24.5 | 0 | 1.9 | 0.1 |
| R557Q | 120.4 | 285.5 | 25 | 0 | 2.5 | 0.1 |
| R557G | 143.1 | 500 | 36.8 | 0 | 2.1 | 0.1 |
| R557P | 96.3 | 288.1 | 31.5 | 0 | 3.1 | 0.1 |
| R557H | 98.8 | 198 | 21.1 | 0 | 3.0 | 0.1 |
| R557D | 147.9 | 500 | 35.6 | 0 | 2.0 | 0.1 |
| R557E | 151.2 | 500 | 34.8 | 0 | 2.0 | 0.1 |
| T377G; N531G | 19.2 | 6.6 | 3.6 | 0.3 | 15.6 | 4.3 |
| T377G; E457G | 20.7 | 5.9 | 3 | 0.3 | 14.5 | 4.8 |
| T377G; E461Q | 28.4 | 6.5 | 2.4 | 0.4 | 10.5 | 4.4 |
| T377G; E457G; E461Q | 14.9 | 4.5 | 3.2 | 0.3 | 20.1 | 6.3 |
| T377G; E457G; E461Q; N531G | 10.9 | 4.3 | 4.1 | 0.2 | 27.4 | 6.6 |
| Y408L; N531G; R557A | 54.5 | 51.6 | 10 | 0.1 | 5.5 | 0.6 |
| N531G; P535A; R557A | 28.2 | 47.5 | 17.7 | 0.1 | 10.6 | 0.6 |
| E457G; E461Q; R557A | 61.8 | 36.6 | 6.2 | 0.2 | 4.8 | 0.8 |
| N531G; E457G; E461Q; R557A | 25 | 19.1 | 8.1 | 0.1 | 12.0 | 1.5 |
| Y408L; E457G; E461Q; R462K; N531G; R557A | 27.4 | 24.2 | 9.3 | 0.1 | 10.9 | 1.2 |
| N531G; P535A; R557K | 52.2 | 17 | 3.4 | 0.3 | 5.7 | 1.7 |
| E457G; E461Q; R557K | 52.6 | 10.8 | 2.2 | 0.5 | 5.7 | 2.6 |
| N531G; E457G; E461Q; R557K | 23.2 | 8.3 | 3.8 | 0.3 | 12.9 | 3.4 |
| Y408L; E457G; E461Q; R462K; N531G; R557K | 17.3 | 24.6 | 15 | 0.1 | 17.3 | 1.2 |
| Y408L; N531G; ΔC-term (Δ558-PPISQYNV (SEQ ID NO: 14)-565) | 172.7 | 109.9 | 6.7 | 0.1 | 1.7 | 0.3 |
| N531G; E457G; E461Q; ΔC-term (Δ558-PPISQYNV (SEQ ID NO: 14)-565) | 51.1 | 97.1 | 20 | 0 | 5.9 | 0.3 |

TABLE 7.2-continued

EC$_{50}$ Values for Variants in C4b and C3b Cleavage Assays

| Variant Description | C4c EC$_{50}$ (nM) | iC3b EC$_{50}$ (nM) | Fold Change Specificity C4b | Fold Change Specificity C3b | Fold Change Activity C4b | Fold Change Activity C3b |
|---|---|---|---|---|---|---|
| Y408L; E457G; E461Q; R462K; N531G; ΔC-term (Δ558-PFISQYNV (SEQ ID NO: 14)-565) | 110.8 | 130.8 | 12.4 | 0.1 | 2.7 | 0.2 |
| ΔC-term (Δ557-RPFISQYNV (SEQ ID NO: 27)-565) | 825 | 500 | 6.4 | 0.2 | 0.4 | 0.1 |
|

TABLE 7.2-continued

EC$_{50}$ Values for Variants in C4b and C3b Cleavage Assays

| Variant Description | C4c EC$_{50}$ (nM) | iC3b EC$_{50}$ (nM) | Fold Change Specificity C4b | Fold Change Specificity C3b | Fold Change Activity C4b | Fold Change Activity C3b |
|---|---|---|---|---|---|---|
| E530Y; N531G; P558S | | | | | | |
| E457G; E461Q; K504H; N531G | 39 | | | | 7.7 | |
| E457G; E461Q; R462K; F464Y; K504H; N531G | 51.7 | | | | 5.8 | |
| Y408L; E457G; E461Q; R462K; K504H; N531G | 27.5 | | | | 10.9 | |
| E457G; E461Q; F464Y; K504H; N531G | 1000 | 22.7 | 0.2 | 4.2 | 0.3 | 1.3 |
| E416A; E457G; E461Q; N531G | 26.1 | 4.2 | 1.7 | 0.6 | 11.5 | 6.8 |
| Y408L; E416A; E457G; E461Q; R462K; N531G | 17.8 | | | | 16.8 | |
| Y408F; E416A; E457G; E461Q; R462K; N531G | 11.5 | | | | 26.0 | |
| E416A; E457G; E461Q; F464Y; N531G | 12 | | | | 24.9 | |
| T377G; E457G; E461Q; R462K; F464Y; N531G | 3.5 | 4.2 | 12.5 | 0.1 | 85.5 | 6.8 |
| T377G; Y408L; E457G; E461Q; R462K; N531G | 6.3 | 6.6 | 11 | 0.1 | 47.5 | 4.3 |
| T377G; E457G; E461Q; F464Y; N531G | 23.3 | 3.4 | 1.6 | 0.6 | 12.8 | 8.4 |
| T377G; E416A; K504H | 47.8 | 12 | 2.6 | 0.4 | 6.3 | 2.4 |
| E416A; K504H | 168.1 | 20.8 | 1.3 | 0.8 | 1.8 | 1.4 |
| T377G; K504H | 50.1 | 15.7 | 3.3 | 0.3 | 6.0 | 1.8 |
| N422K; E457G; E461Q; Q467K; N531G | 5 | 2.5 | 5.2 | 0.2 | 59.8 | 11.4 |
| E416A; N422K; E457G; E461Q; Q467K; N531G | 4.4 | 1.7 | 4.1 | 0.2 | 68.0 | 16.7 |
| K504R; E530F; D425K; P558S | 1000 | 5.7 | 0.1 | 16.6 | 0.3 | 5.0 |
| K504R; E530F; D425R; P558S | 1000 | 5.2 | 0.1 | 18.4 | 0.3 | 5.5 |
| K504R; E530F; D425R; P558G | 1000 | 6.2 | 0.1 | 15.2 | 0.3 | 4.6 |
| K504R; E530F; D425K; P558G | 1000 | 5.2 | 0.1 | 18.2 | 0.3 | 5.5 |
| K504R; E530F; D425K; P558S; E457G; E461Q; N531G | 6.9 | 2.4 | 3.7 | 0.3 | 43.4 | 11.8 |
| K504R; E457G; E461Q; N531G | 8.2 | 3 | 3.8 | 0.3 | 36.5 | 9.5 |
| E530F; E457G; E461Q; N531G | 9.1 | 2.9 | 3.3 | 0.3 | 32.9 | 9.8 |
| D425R; E457G; E461Q; N531G | 4 | 2.2 | 6 | 0.2 | 74.8 | 12.9 |

TABLE 7.2-continued

EC$_{50}$ Values for Variants in C4b and C3b Cleavage Assays

| Variant Description | C4c EC$_{50}$ (nM) | iC3b EC$_{50}$ (nM) | Fold Change Specificity C4b | Fold Change Specificity C3b | Fold Change Activity C4b | Fold Change Activity C3b |
|---|---|---|---|---|---|---|
| D425K; E457G; E461Q; N531G | 6 | 2.5 | 4.5 | 0.2 | 49.9 | 11.4 |
| P558S; E457G; E461Q; N531G | 7.2 | 4.3 | 6.2 | 0.2 | 41.6 | 6.6 |
| P558G; E457G; E461Q; N531G | 7.1 | 5 | 7.4 | 0.1 | 42.1 | 5.7 |
| K504R; E530F; E457G; E461Q; N531G | 16.2 | 4.6 | 3 | 0.3 | 18.5 | 6.2 |
| K504R; D425R; E457G; E461Q; N531G | 8.4 | 4.2 | 5.2 | 0.2 | 35.6 | 6.8 |
| K504R; P558S; E457G; E461Q; N531G | 9 | 5.5 | 6.5 | 0.2 | 33.2 | 5.2 |
| E530F; P558S; E457G; E461Q; N531G | 9.1 | 4.8 | 5.6 | 0.2 | 32.9 | 5.9 |
| D425R; P558S; E457G; E461Q; N531G | 4.6 | 4 | 9.1 | 0.1 | 65.0 | 7.1 |
| D425R; E530F; E457G; E461Q; N531G | 6.2 | 3.2 | 5.5 | 0.2 | 48.3 | 8.9 |
| D425K; E530F; E457G; E461Q; N531G | 6.4 | 3.4 | 5.7 | 0.2 | 46.8 | 8.4 |
| D425R; E530F; P558G; E457G; E461Q; N531G | 5 | | | | 59.8 | |
| K504R; E530F; P558G; E457G; E461Q; N531G | 8.2 | | | | 36.5 | |
| K504R; D425R; P558G; E457G; E461Q; N531G | 4.8 | | | | 62.3 | |
| K504R; D425R; E530F; E457G; E461Q; N531G | 7.4 | | | | 40.4 | |
| R557A; N531M | 78.7 | 288.5 | 38.6 | 0 | 3.8 | 0.1 |
| R557K; N531M | 124.3 | | | | 2.4 | |
| R557A; N531M; Y403F; K504Y | 76.3 | 334.4 | 46.2 | 0 | 3.9 | 0.1 |
| R557A; N531D; Y403F; K504Y | 38.6 | 155.5 | 42.5 | 0 | 7.8 | 0.2 |
| R557A; N531M; Y403F; K504Y; E457G; E461Q | 26.3 | 79.4 | 31.8 | 0 | 11.4 | 0.4 |
| R557A; N531G; Y403F; K504Y; E457G; E461Q | 22.4 | 38.2 | 18 | 0.1 | 13.4 | 0.7 |
| N422K; E461Q | 51.1 | 4.1 | 0.9 | 1.2 | 5.9 | 6.9 |
| T377G; N422K | 37.4 | 4.1 | 1.2 | 0.9 | 8.0 | 6.9 |
| N531G; E457G; T377G | 2.9 | 4.5 | 16.2 | 0.1 | 103.2 | 6.3 |
| N531G; E461Q; N422K | 7.2 | 3.7 | 5.5 | 0.2 | 41.6 | 7.7 |
| N531G; E461Q; T377G | 5 | 4.9 | 10.2 | 0.1 | 59.8 | 5.8 |
| N531G; N422K; T377G | 6.8 | 3.3 | 5.1 | 0.2 | 44.0 | 8.6 |
| E457G; E461Q; N422K | 17.2 | 3.5 | 2.1 | 0.5 | 17.4 | 8.1 |

TABLE 7.2-continued

EC$_{50}$ Values for Variants in C4b and C3b Cleavage Assays

| Variant Description | C4c EC$_{50}$ (nM) | iC3b EC$_{50}$ (nM) | Fold Change Specificity C4b | Fold Change Specificity C3b | Fold Change Activity C4b | Fold Change Activity C3b |
|---|---|---|---|---|---|---|
| E457G; N422K; T377G | 7.5 | 3.5 | 4.9 | 0.2 | 39.9 | 8.1 |
| E461Q; N422K; T377G | 7.9 | 3.6 | 4.9 | 0.2 | 37.9 | 7.9 |
| N531G; E457G; N422K; T377G | 4.2 | 3.2 | 8.2 | 0.1 | 71.2 | 8.9 |
| N531G; E461Q; N422K; T377G | 5 | 2.4 | 5.1 | 0.2 | 59.8 | 11.8 |
| E457G; E461Q; N422K; T377G | 5 | 2.2 | 4.7 | 0.2 | 59.8 | 12.9 |
| T377G; N422K; E457G; E461Q; N531G | 3.5 | 3.7 | 11.3 | 0.1 | 85.5 | 7.7 |
| D425K; Y408M | 1000 | 9.4 | 0.1 | 10.1 | 0.3 | 3.0 |
| D425K; E530F | 1000 | 5.8 | 0.1 | 16.4 | 0.3 | 4.9 |
| D425K; P558S | 152.9 | 7 | 0.5 | 2.1 | 2.0 | 4.1 |
| D425K; Y408M; F537K | 1000 | 10.8 | 0.1 | 8.8 | 0.3 | 2.6 |
| D425K; Y408M; K504R | 1000 | 14.6 | 0.2 | 6.5 | 0.3 | 1.9 |

Example 8: Tunability and Selection of CFI Variants for C3b, C4b, or both C3b and C4b For Example 8, reference to CFI-HSA refers to human serum albumin fused to the N-terminal end of wild type CFI (SEQ ID NO: 21).

Figure 13:
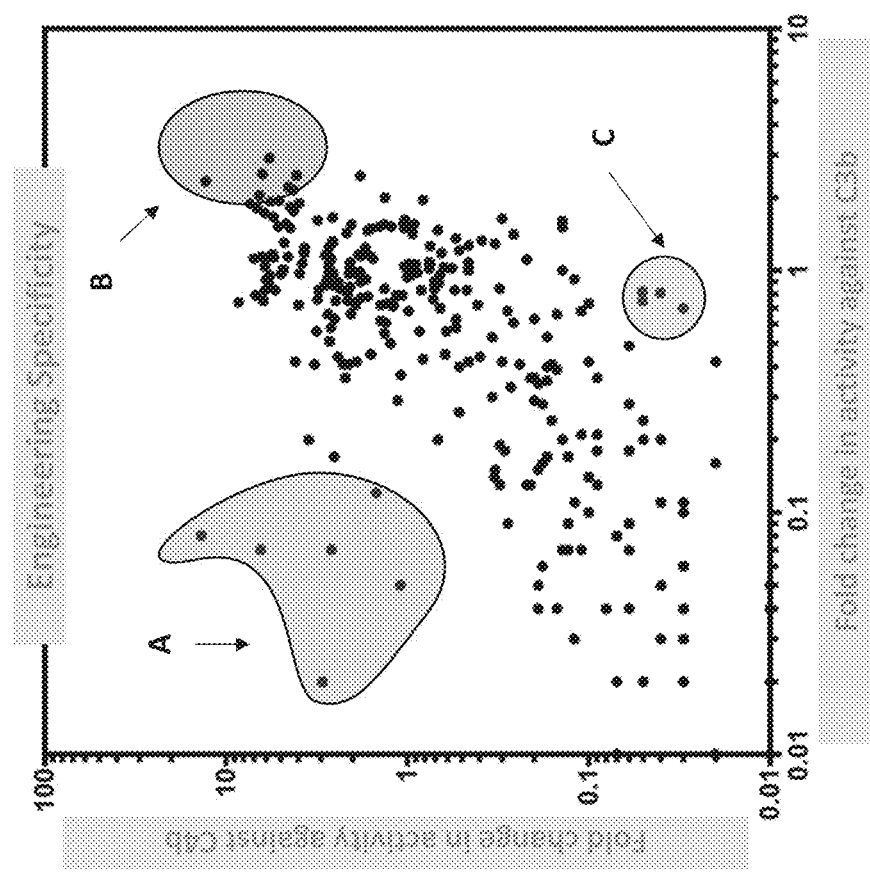
FIG. 13 depicts a scatter plot showing fold change in activity against C4b, fold change in activity against C3b, and engineering specificity, showing that the various CFI variants can be tunable and selected for C3b, C4b, or both. A: specificity for C4b; B: specificity for both; and C: specificity for C3b

FIG. 13 depicts a scatter plot showing fold change in activity against C4b, fold change in activity against C3b, and engineering specificity, showing that the various CFI variants can be tunable and selected for C3b, C4b, or both. Each dot in the dot plot represents a different CFI variant. Those that are clustered in region A are classical and lectin pathway specific regulators, and have at least 10 times specificity for C4b over C3b. Those that are clustered in region B are clustered in region C are central pathway regulators, and have increased activity on both C3b and C4b, as compared to a CFI that is wild typealternative pathway specific regulators, and have at least 10 times specificity for C3b over C4b. Those that are clustered in region C are alternative pathway specific regulators, and have at least 10 times specificity for C3b over C4b central pathway regulators, and have increased activity on both C3b and C4b, as compared to a CFI that is wild type.

Figure 14B:
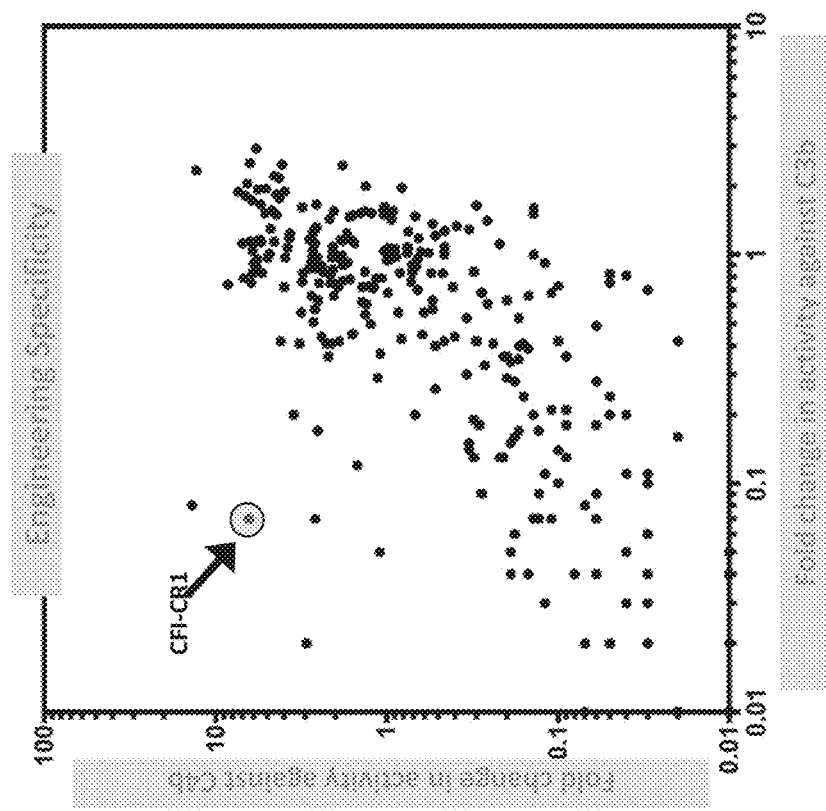
FIG. 14B depicts a dot plot showing the fold change in activity against C4b, fold change in activity against C3b, and engineering specificity, of CFI variants as was previously shown in FIG. 13, with the dot representing the CFI-CR1 fusion of FIG. 14A pointed out by an arrow.
Figure 14A:
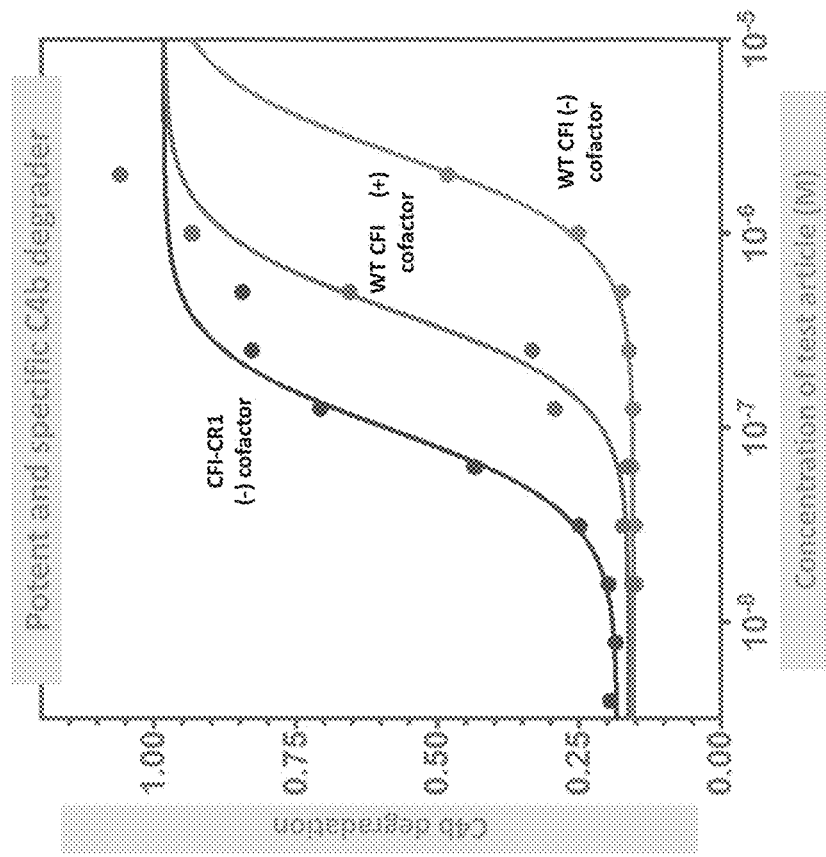
FIG. 14A depicts a dose response curve showing the effect of the presence of CR1 on C4b degradation. The CR1 is either supplied as an exogenous co-factor in the presence of a CFI variant of the disclosure, or is fused to a CFI variant of the disclosure.

FIG. 14A depicts a dose response curve showing the C4b degradation and the potency and specificity of a CFI variant that is characterized as a C4b degrader. The C4b degrader is a CFI fusion of CFI wild type and CCP domains 15-17 of CR1, linked by a flexible linker (GGSSGG) (SEQ ID NO: 6), and is also further fused with albumin. The CFI-CR1 fusion was tested without exogenous CR1 cofactor, and the wild type CFI was tested with and without exogenous CR1 cofactor.

FIG. 14B depicts a dot plot showing the fold change in activity against C4b, fold change in activity against C3b, and engineering specificity, of the CFI variant shown previously in FIG. 13. The dot that represents the CFI-CR1 fusion of FIG. 14A is pointed out by an arrow. Together, FIGS. 14A-14B demonstrate the engineered C4b potency and specificity of the CFI-CR1 fusion protein.

Figures 14C, 14D:
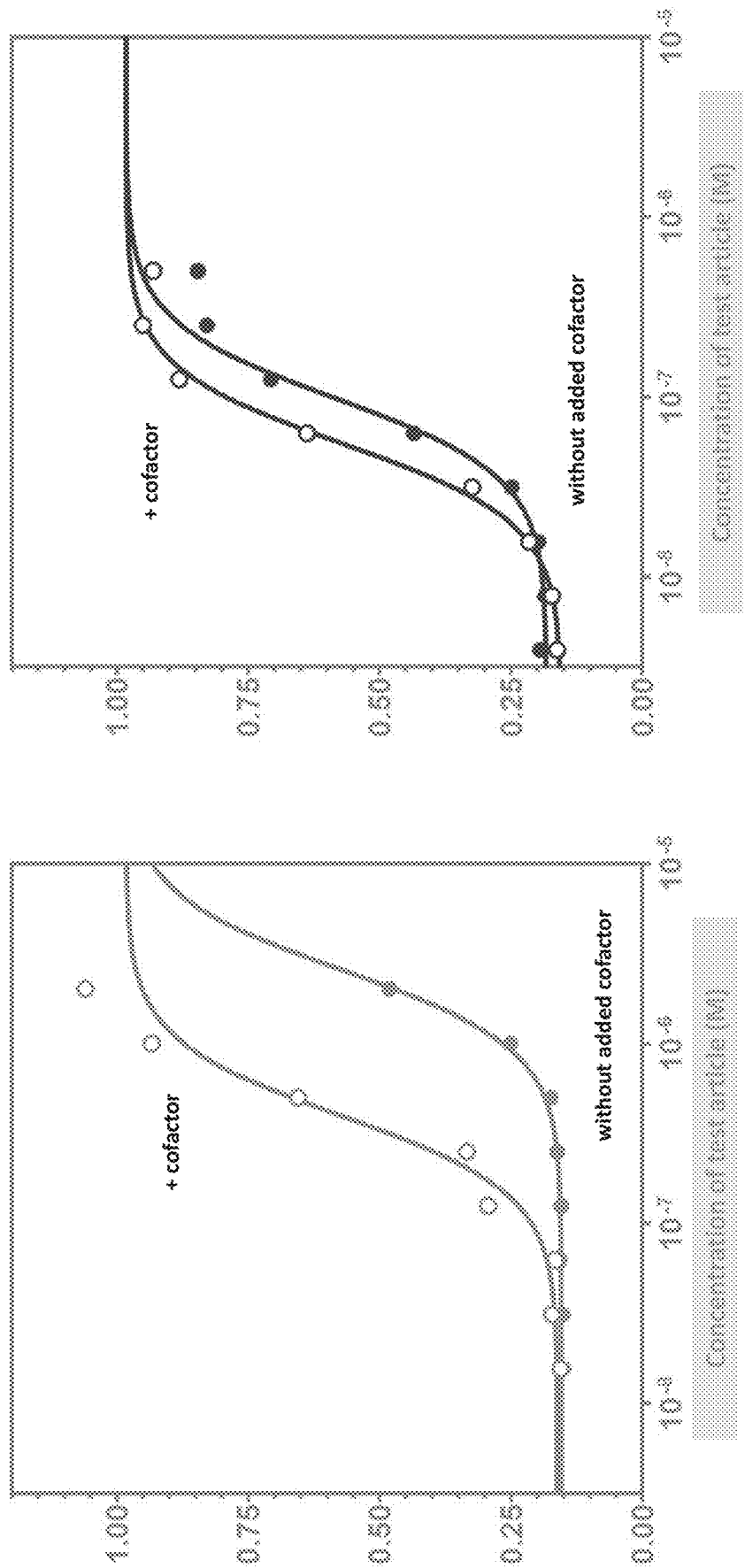
FIG. 14C depicts a dose response curve showing the classical pathway activity of a CFI variant of the disclosure, in the presence and absence of an exogenous CR1 cofactor. Both exogenous CR1 and fused CR1 boost classical pathway activity.
FIG. 14D depicts a dose response showing the classical pathway activity of a CFI variant of the disclosure that is fused to a CR1 in the presence and absence of an exogenous CR1 cofactor.

FIGS. 14C-14D depict dose response curves showing the activity of a CFI variant that relies on exogenous CR1 cofactor to boost classical pathway activity, as compared to a CFI variant that is active even in the absence of exogenous CR1 cofactor, respectively. These figures depict the concentration of the test article (M) and show classical pathway activity as measured by C4b degradation. The CFI variant of FIG. 14C is T495F+Y496L+D497E+S499G+I500K+G533A+K534Q+P535K+E536N+F537K, and the CFI variant of FIG. 14D is a CFI-CR1 fusion of CFI wild type and CCP domains 15-17 of CR1, linked by a flexible linker (GGSSGG) (SEQ ID NO: 6). These figures show that C4b degraders can be engineered with increased potency and exogenous CR1 cofactor independence. These figures also show that, when fused with CFI, CR1 can act similarly to exogenous CR1 cofactor.

Figure 14F:
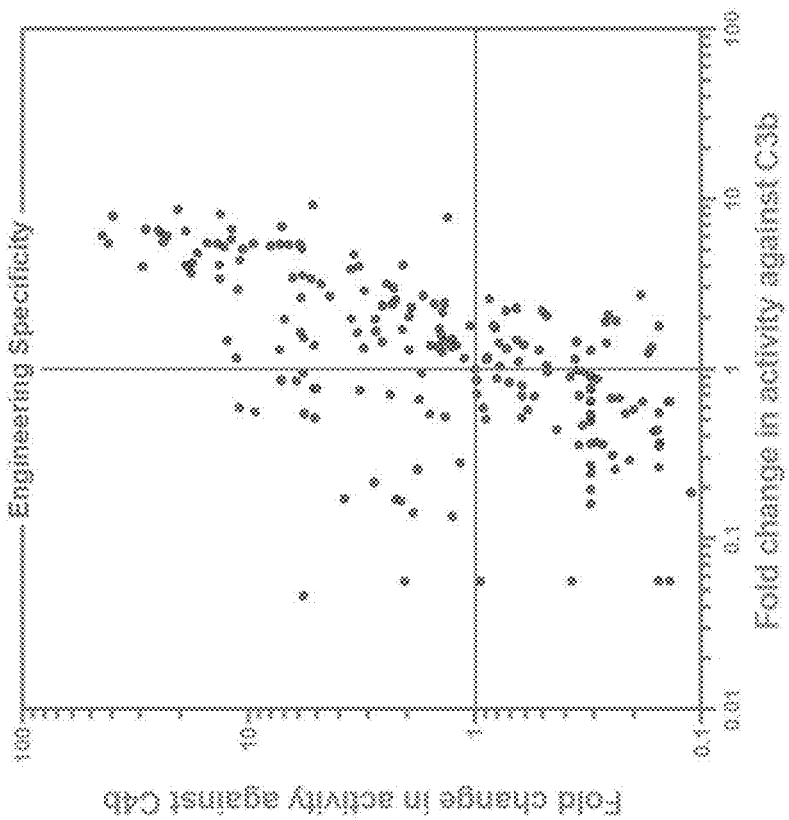
FIG. 14E and FIG. 14F depict scatter plots of the fold change in activity against C4b and C3b of various CFI variants provided herein, demonstrating further tunability of the tested CFI variants.
Figure 14E:
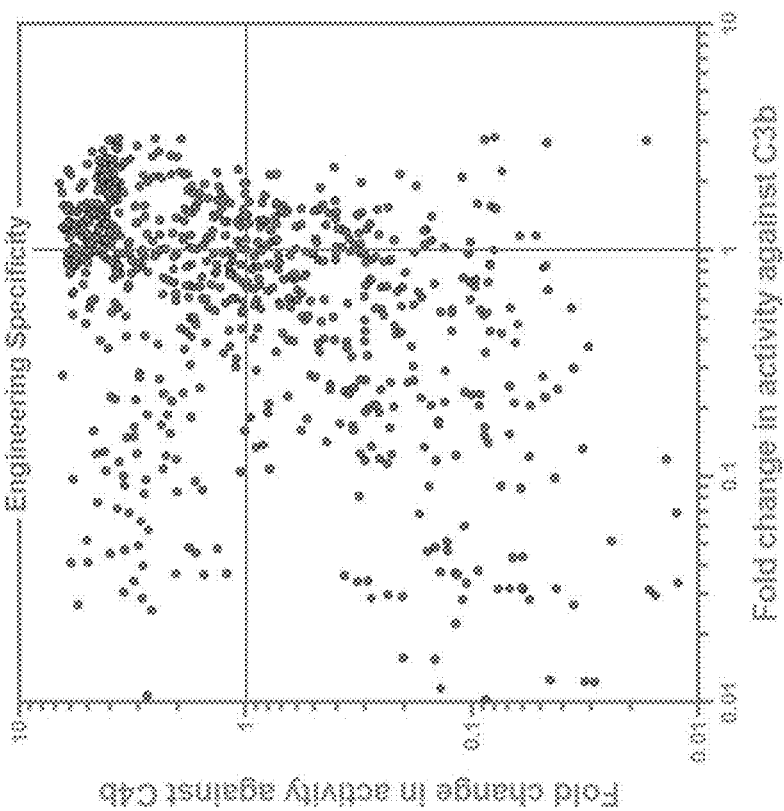

FIGS. 14E-14F depict scatter plots of the fold change in activity against C4b and C3b of various CFI variants provided herein, demonstrating further tunability of the tested CFI variants. FIG. 14E depicts the results of a screening assay performed of the CFI variants, measuring a fold change relative to CFI-HSA, showing the fold change in activity against C4b and the fold change in activity against C3b. FIG. 14F depicts the EC50 values from the data of 14E.

Example 9: CFI-HSA Activity Compared to Plasma-Derived CFI Measured by In Vitro Cleavage of C3b and C4b and Hemolytic Assays For Example 9, reference to CFI-HSA refers to human serum albumin fused to the N-terminal end of wild type CFI (SEQ ID NO: 21).

Various hemolytic assays were performed to assess the activity of CFI-HSA, CFI variants as compared to plasma-derived CFI. Hemolysis mediated through the classical pathway (CP) and alternative pathway (AP) was assessed.

Briefly, the summary of the assays performed and the focus of the assays are presented in Table 9.1 below.

TABLE 9.1

| Assay | RBC | Serum | Additives | Assay Focus |
|---|---|---|---|---|
| AP + C3b | Sheep | ΔFHΔFB | FH (fixed), FD (fixed), CFI (titration) | Hemolysis of C3b-loaded erythrocytes; amplification loop active |
| AP + CP | Sheep | ΔCFI | CFI (titration) | Hemolysis through AP and CP |
| CP | Sheep | ΔBΔCFI | CFI (titration) | Hemolysis through CP; AP limited by lack of amplification loop |

Figure 15A:
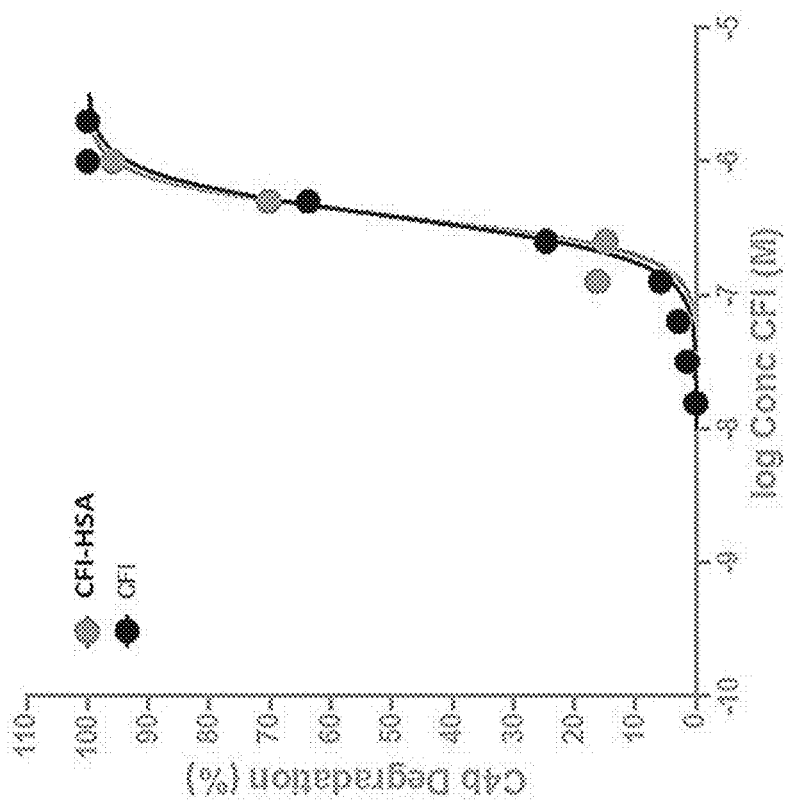
FIG. 15A and FIG. 15B depict graphs of C3b degradation and C4b degradation, respectively, by CFI-HSA and plasma-derived CFI.
Figure 15B:
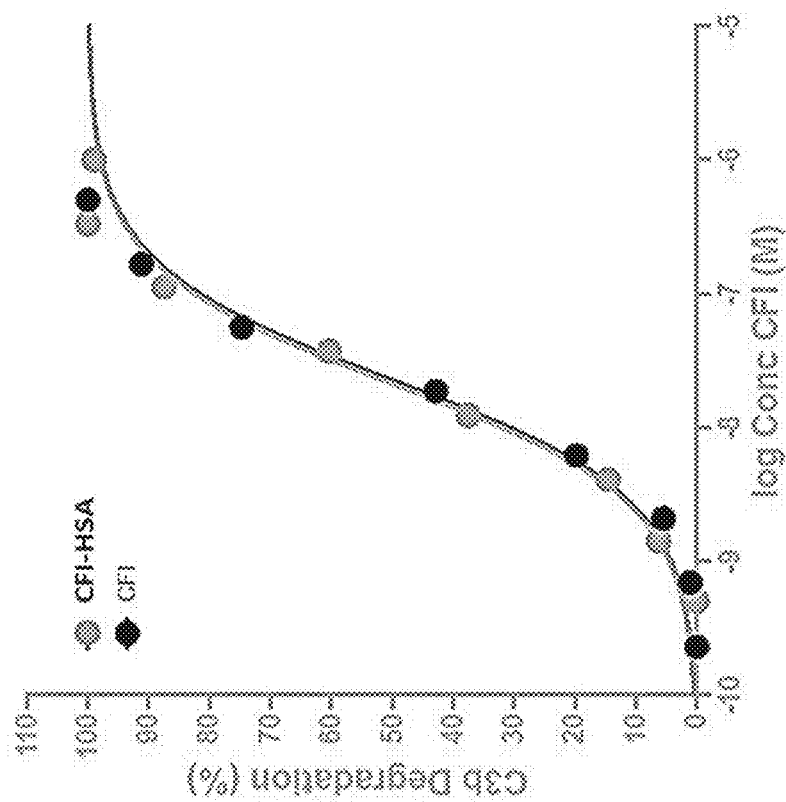

FIGS. 15A-15B depict graphs of C3b degradation and C4b degradation, respectively, by CFI-HSA and plasma-derived CFI. CFI-HSA was able to cleave both C3b and C4b in buffer with $EC_{50}$ values of 25.5 nM (95% CI: 21.9-29.6 nM) and 365 nM (95% CI: 297-448 nM), respectively. These data are summarized in Table 9.2 below. The plots shown in FIGS. 15A-15B are normalized, and the data is derived from the analysis of non-normalized data. These results demonstrate that the cleavage activity by CFI-HSA is not significantly different from physiological (plasma-derived) CFI, indicating the recombinant CFI-HSA can perform as well as plasma-derived CFI and potentially act as a replacement or supplement for CFI activity in physiological conditions.

TABLE 9.2

| Protein | C3b cleavage EC50, nM | 95% CI, nM | C4b cleavage EC50, nM | 95% CI, nM |
|---|---|---|---|---|
| CFI | 25.3 | 18.2-35.1 | 385 | 326-455 |
| CFI-HSA | 25.5 | 21.9-29.6 | 365 | 297-448 |

Figure 15D:
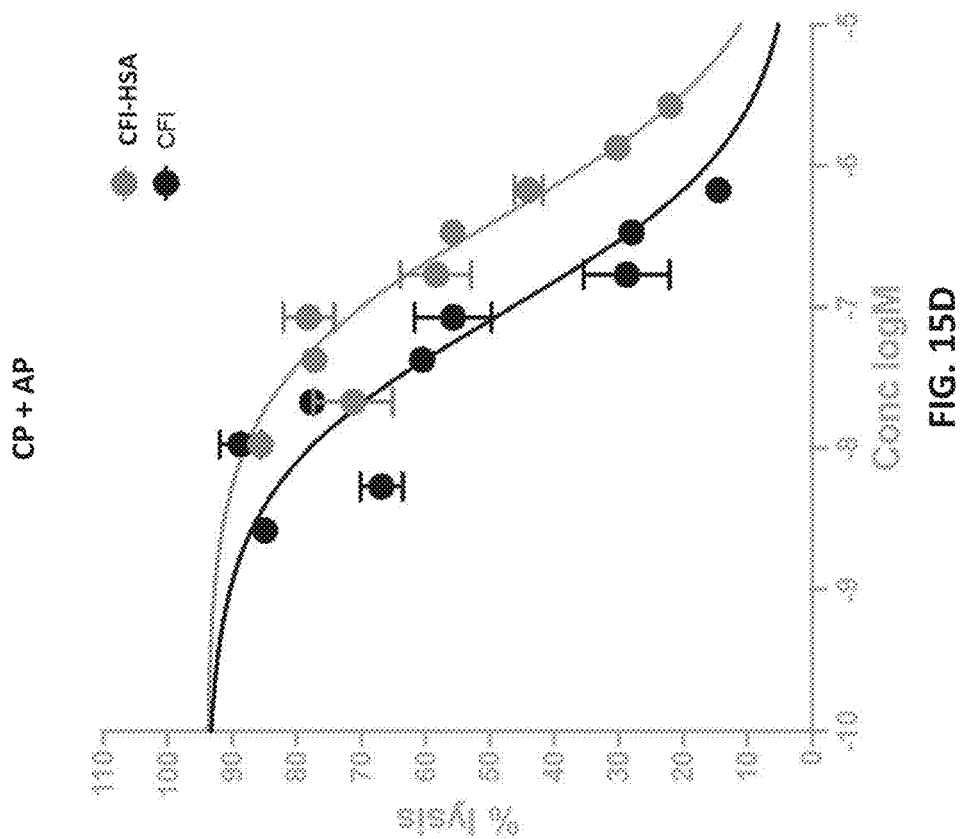
FIG. 15C and FIG. 15D depict graphs of hemolytic assays of CFI-HSA and plasma-derived CFI. Wherein AP represents an alternative pathway focused assay and CP+AP represents an alternative and classical pathway focused assay.
Figure 15C:
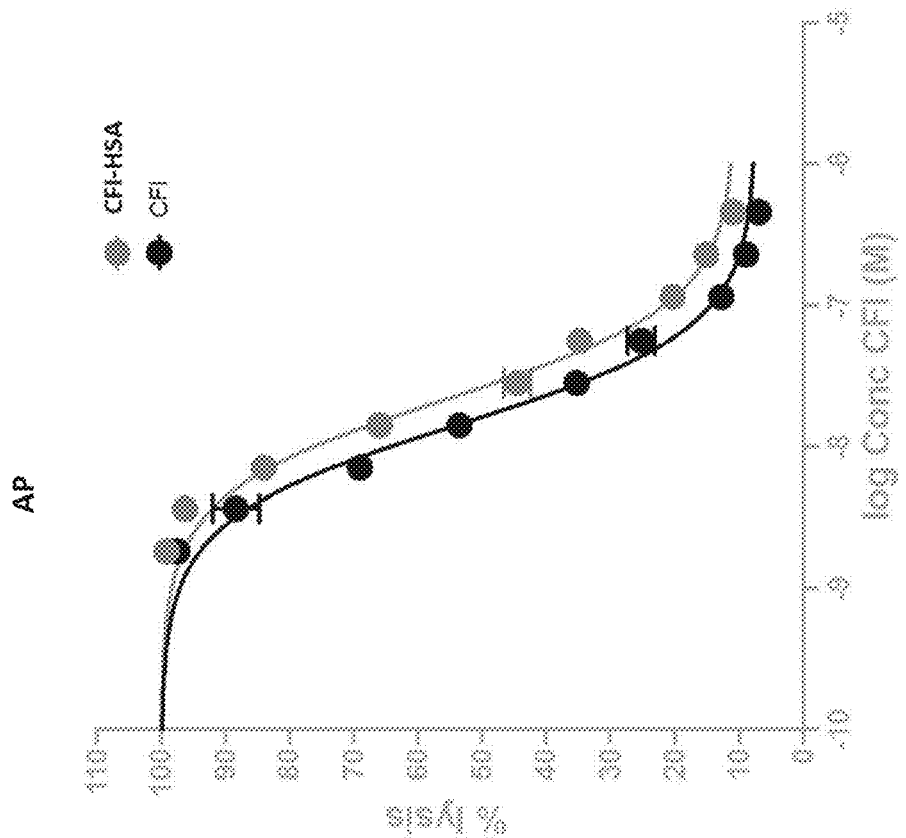

FIGS. 15C-15D depict graphs of hemolytic assays in AP+C3b and mixed AP+CP, respectively, by CFI-HSA and plasma-derived CFI. CFI-HSA was able to fully inhibit complement-mediated lysis in a C3b degradation human serum hemolytic assay with an IC50 value of 26.4 nM (95% CI: 15.5-44.7 nM) and was equipotent with physiological (plasma-derived) CFI. In addition, CFI-HSA was able to fully inhibit complement-mediated lysis in a CFI-depleted human serum hemolytic assay with an IC50 value of 426 nM (95% CI: 162-1120 nM) and was equipotent with physiological CFI. These data are summarized in Table 9.3 below. These results again demonstrate that the activity of CFI-HSA is not significantly differently from the activity of physiological (plasma-derived CFI).

TABLE 9.3

| Protein | C3b-enriched AP hemolytic assay IC50, nM | 95% CI, nM | CFI-depleted CP + AP hemolyitc assay IC50, nM | 95% CI, nM |
|---|---|---|---|---|
| CFI | 12.9 | 7.8-21.1 | 116 | 37.8-356 |
| CFI-HSA | 26.4 | 15.5-44.7 | 426 | 162-1120 |

Generally, the above results demonstrate that, along with the advantages of the half-life extension and higher production of the recombinantly-produced CFI-HSA, the CFI-HSA performs as well as plasma-derived CFI. An illustrative application for the CFI-HSA can therefore be use in an enzyme replacement therapy for endogenous CFI in complement-related disorders.

Figure 15F:
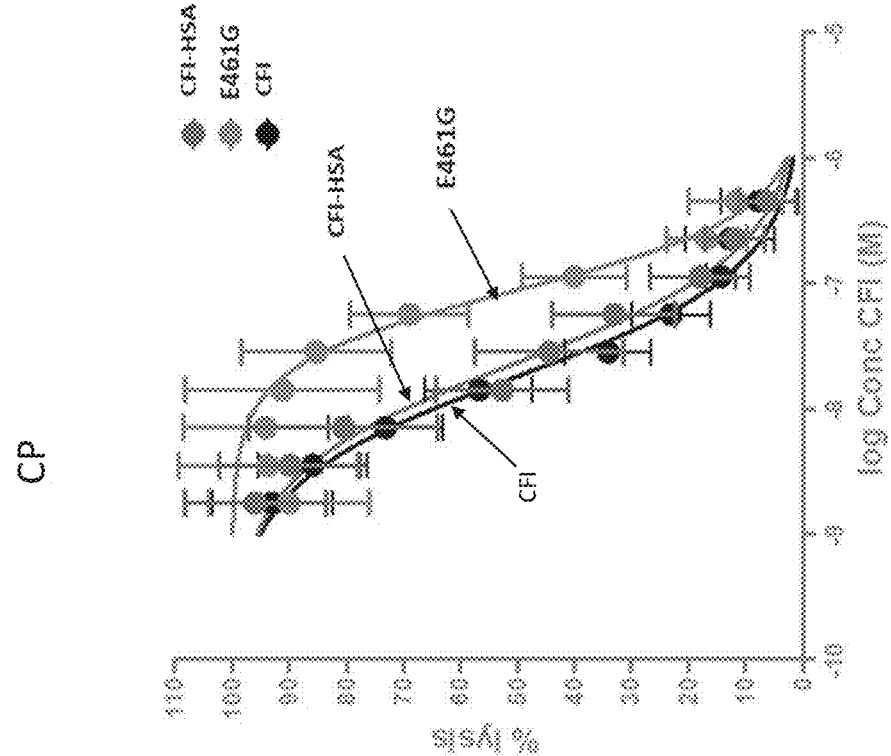
FIG. 15E and FIG. 15F depict the results of hemolytic assays using the E461G variant, CFI-HSA, and plasma-derived CFI. Wherein CP represents a classical pathway focused assay and CP+AP represents an alternative and classical pathway focused assay.
Figure 15E:
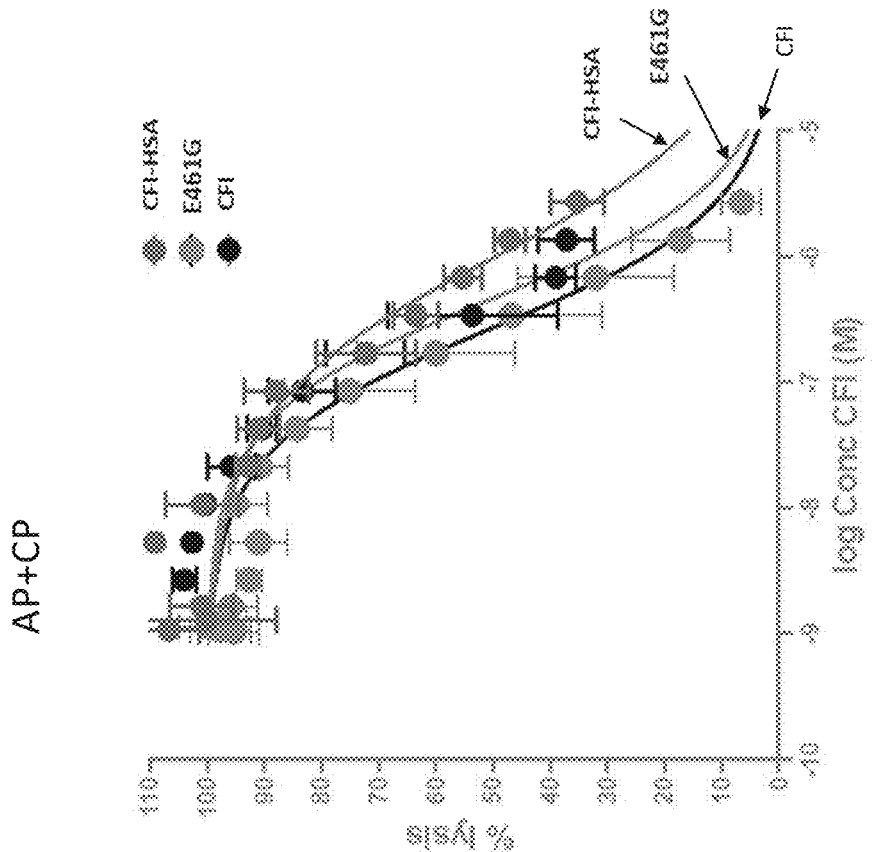

Further, the CFI variant E461G tested relative to CFI-HSA. FIGS. 15E-15F depict the results of the AP+CP assay and the CP assay, respectively, using the E461G variant, CFI-HSA, and plasma-derived CFI. These results demonstrate that E461G has engineered C3b potency and specificity.

Example 10: Prediction of Human Exposure Pharmacokinetic Profiles with Multiple Subcutaneous Dosing of CFI-HSA For Example 10, reference to CFI-HSA refers to human serum albumin fused to the N-terminal end of wild type CFI (SEQ ID NO: 21).

Figure 16A:
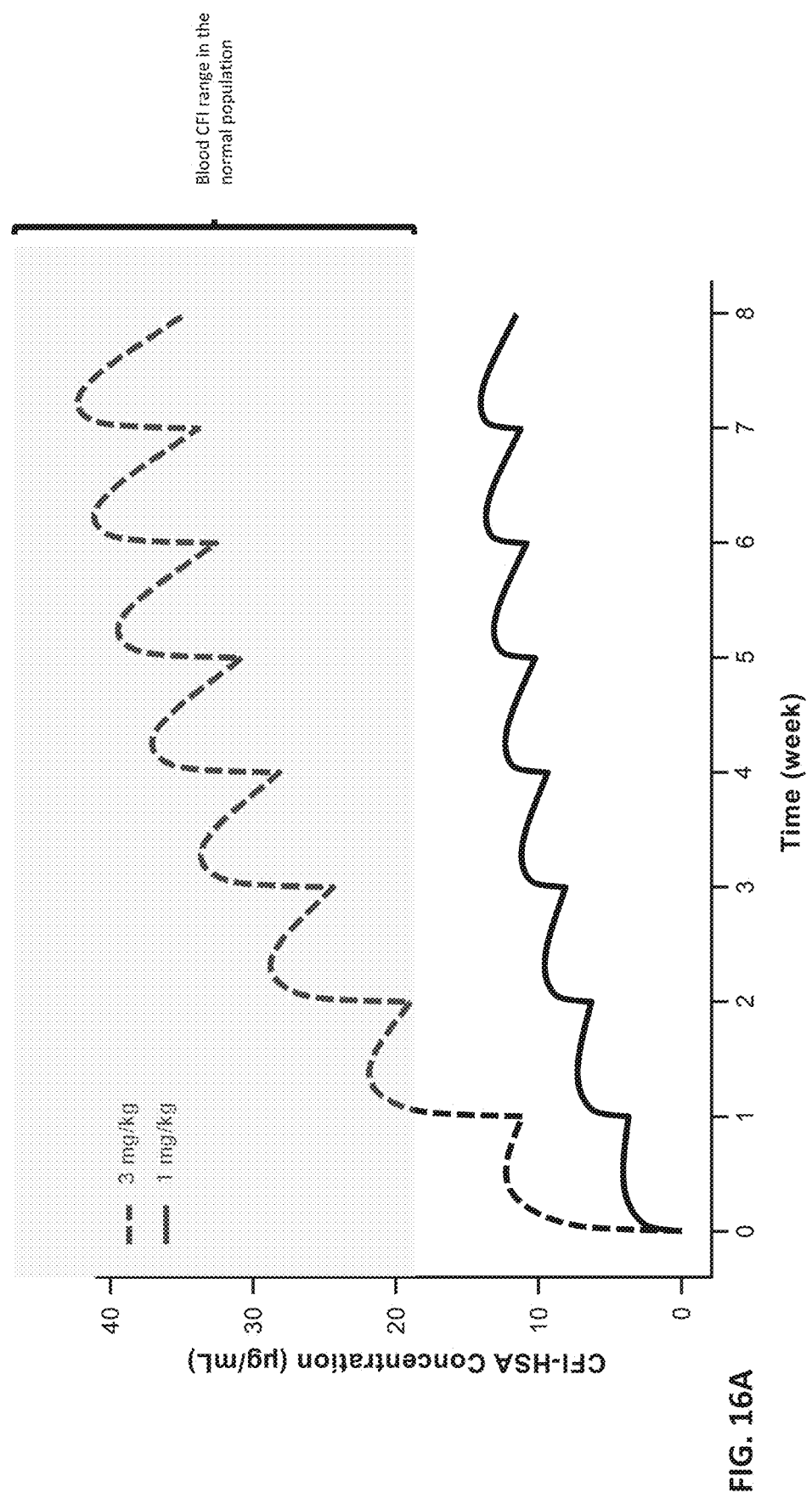
FIG. 16A depicts a graph of a prediction of human exposure pharmacokinetic (PK) profile after multiple subcutaneous dosing of CFI-HSA.
Figure 16C:
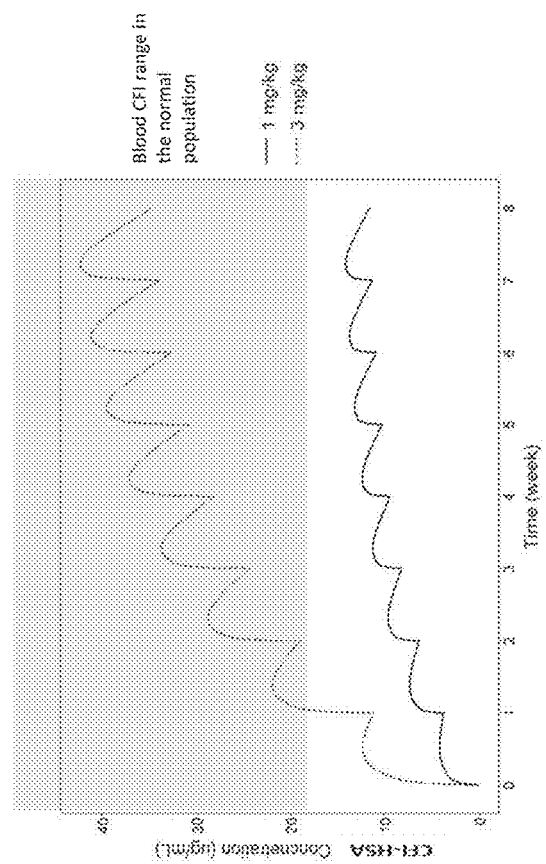
FIG. 16B and FIG. 16C depict the predicted concentration of CFI-HSA over time, for a single dose (FIG. 16B) or multiple dosing (FIG. 16C), as compared with the predicted pharmacokinetic profiles of FIG. 16A.
Figure 16B:
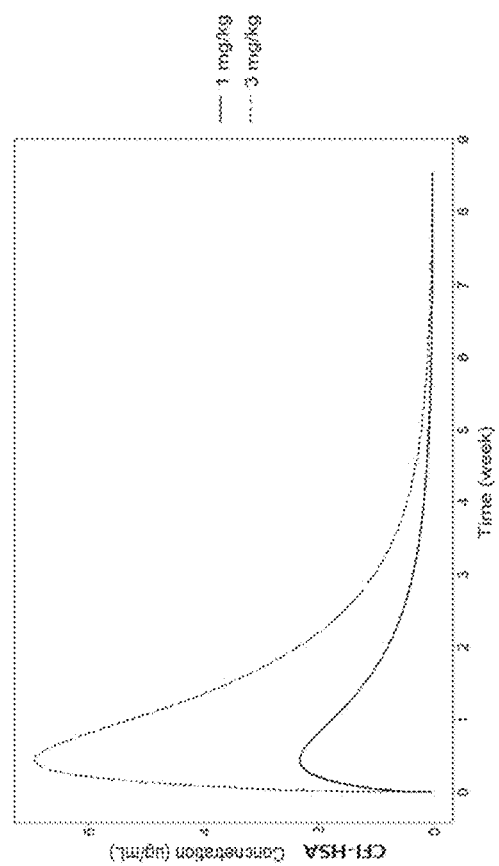

FIG. 16A depicts a graph of a prediction of human exposure pharmacokinetic (PK) profile after multiple subcutaneous dosing of CFI-HSA. The multiple dosing is once weekly, over a period of eight weeks. These results demonstrate that the blood CFI range is in the range of the normal population beginning at around weeks 3-4 when using a dose of 3 mg/kg. Human allometric scaling was based on rat and cynomolgus monkey population PK Model/Exponents 0.37 for Clearance and 0.88 for Volume of Distribution FIGS. 16B-16C depict the concentration of CFI-HSA over time (FIG. 16B) compared with the predicted pharmacokinetic profiles described above (FIG. 16C). These results demonstrate that after multiple, weekly dosing of CFI-HSA, the blood CFI range in the pharmacokinetic profile can increase, while the CFI-HSA concentration follows the curve as shown in FIG. 16B.

Example 11: CFI-HSA Half-Life in Vitreous Humor of Non-Human Primates

For Example 11, reference to CFI-HSA refers to human serum albumin fused to the N-terminal end of wild type CFI (SEQ ID NO: 21).

Pharmacokinetics of CFI-HSA Following Intravitreal Injection

The ocular pharmacokinetics of the N-terminal albumin fusion of wild-type CFI-HSA were examined after intravitreal dosing to six African Green Monkeys (AGMs). The six animals were divided into two groups treated at 2 dose levels: one group received a single intravitreal injection of 500 µg of CFI-HSA (right eye, OD, N=3) and the other group received a single intravitreal injection of 250 µg of CFI-HSA (right eye, OD, N=3). The left eye (OS) of all six animals was injected with an equivalent volume of 100 µL of sterile PBS for injection as a vehicle control. Non-terminal, vitreous humor samples (100 µL) were taken on days 1, 7, 14, 21 and 28 post dosing. Vitreous humor CFI-HSA drug concentrations were determined using a quantitative electrochemiluminescence (ECL) antigen assay optimized for measuring CFI-HSA in vitreous humor of AGMs. The assay employs coating of anti-CFI antibody (clone OX21, LS Bio, Seattle WA) at 2 µg/ml on the Meso Scale Discovery (MSD, Rockville, MA) assay plate to capture the CFI-HSA levels. Detection of the captured CFI-HSA is performed with a goat polyclonal anti-HSA antibody (Abcam, Cambridge, MA) at 0.5 µg/ml conjugated with SULFO-TAG which emits light [electrochemiluminescence (ECL)] on application of an electric potential. The ECL relative light units (RLU) is measured on a MESO® SECTOR S 600 Reader and the unknown CFI-HSA concentrations in vitreous humor are interpolated from a standard curve ranging from 0.05 µg/ml to 40 µg/ml Factor I-HSA. Data are provided in Table 11.1.

TABLE 11.1

CFI-HSA levels at day 1, 7, 14, 21 and 28 after intravitreal dosing

| Dose level | No of animals | timepoints | Levels of Factor I-HSA +/− SD (µg/ml) |
|---|---|---|---|
| 5.01 mg/ml | 3 | baseline | BLQ |
|  |  | Day 1 | 66.4 +/− 18.9 |
|  |  | Day 7 | 34.7 +/− 5.5 |
|  |  | Day 14 | 9.0 +/− 6.4 |
|  |  | Day 21 | 2.0 +/− 1.3 |
|  |  | Day 28 | 0.9 +/− 0.6 |
| 2.50 mg/ml | 3 | baseline | BLQ |
|  |  | Day 1 | 46.9 +/− 11.1 |
|  |  | Day 7 | 12.5 +/− 5.0 |
|  |  | Day 14 | 2.8 +/− 3.0 |
|  |  | Day 21 | 0.2 +/− 0.1 |
|  |  | Day 28 | 0.6 |

*BLQ: measurement below the limit of quantification of the assay

Non-compartmental analysis yielded apparent ocular terminal half-lives of 3.6 and 4.1 days for the 250 and 500 µg dose levels, respectively.

TABLE 11.2

Estimated PK parameters for CFI-HSA in vitreous humor of African Green Monkeys

| Parameters | 500 µg | 250 µg |
|---|---|---|
| Terminal half-life (days) | 4.1 | 3.7 |
| $T_{max}$ (days) | 1.0 | 1.0 |
| $C_{max}$ (µg/ml) | 66.4 | 46.9 |
| MRT (days) | 6.0 | 4.4 |
| AUC 0-inf (µg/ml × days) | 543.2 | 271.5 |
| AUC 0-t (µg/ml × days) | 537.8 | 268.5 |

Figure 18:
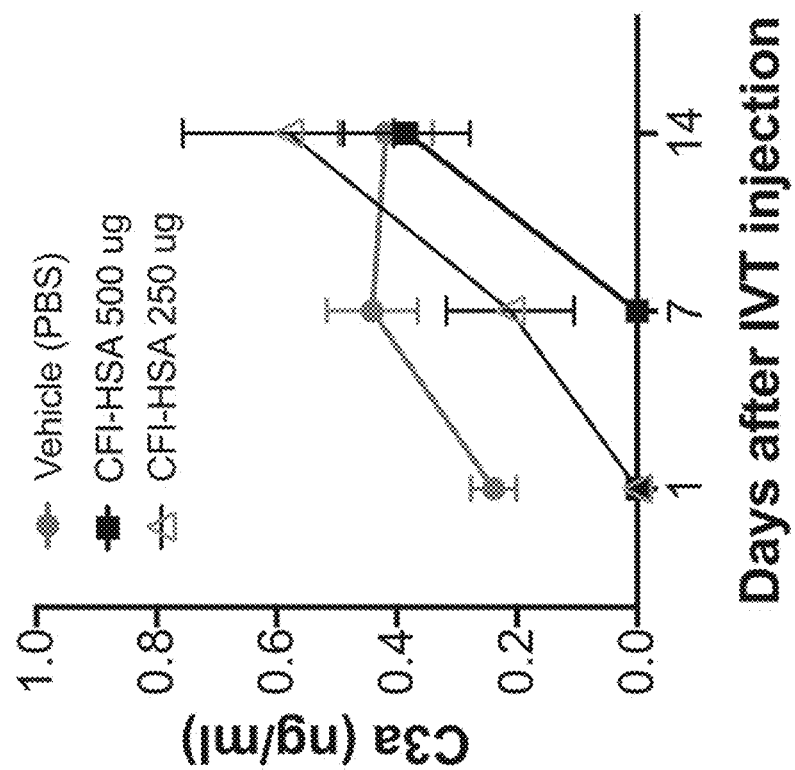
FIG. 18 depicts a plot showing the amount of C3a detected in samples from the vitreous humor following intravitreal injection (IVT) of CFI-HSA at a dose of 250 μg or 500 μg in an african green monkey primate model.

Complement Component 3a (C3a) levels in vitreous humor were determined by ELISA using the Quidel kit for C3a ELISA (FIG. 18). CFI-HSA fusion protein reduces ocular C3a levels in a dose-dependent manner up to 7 days after intraocular injection. The increase in C3b degradation by CFI-HSA reduces the complex formation between C3b and Bb which leads to a reduction of C3 cleavage into C3a and C3b via the amplification loop of the alternative pathway.

Example 12: CFI-HSA and Plasma CFI Pharmacokinetics in Mouse Plasma

For Example 12, reference to CFI-HSA refers to human serum albumin fused to the N-terminal end of wild type CFI (SEQ ID NO: 21).

The pharmacokinetics of the N-terminal albumin fusion of wild-type CFI (CFI-HSA) was examined after intravenous and subcutaneous administration to CD-1 mice. Employing a sparse sampling design with up to two samples per mouse and three mice sampled at each timepoint, CD-1 mice were divided into four groups and treated with a single dose of either the plasma purified wild type CFI, or the recombinant wild-type CFI-HSA.

To compare the circulating half-life in plasma and bioavailability of the plasma-derived CFI and CFI-HSA, animals were dosed with either plasma-derived CFI or CFI-HSA both intravenously and subcutaneously. Plasma-derived CFI was administered at 1.3 mg/kg intravenously (group 1) and 6.5 mg/kg subcutaneously (group 2). CFI-HSA was administered at 3 mg/kg intravenously (group 3) and subcutaneously (group 4). An additional 3 animals received a single dose of an equivalent volume of PBS delivered subcutaneously as a vehicle control (group 5; not shown). Blood (~30-50 µL) was collected in EDTA at various time points from 5 minutes to 144 hours post dosing and plasma separated by centrifugation.

CFI-HSA and plasma CFI concentrations were determined with a quantitative electrochemiluminescence (ECL) antigen assay for CFI-HSA and plasma CFI in CD-1 mouse EDTA plasma. For the CFI assay, the mouse monoclonal anti-Factor I antibody (MAB12907, Abnova, Taipei City, Taiwan) is coated at 2 µg/ml on the Meso Scale Discovery (MSD, Rockville, MA) assay plate to capture the plasma CFI. Detection of the captured CFI is performed with a mouse monoclonal anti-CFI antibody (clone 3R/8, CABT-47940MH, Creative diagnostic, Shirley NY) at 0.5 µg/ml conjugated with SULFO-TAG which emits light [electrochemiluminescence (ECL)] on application of an electric potential. For the CFI-HSA assay, the mouse monoclonal anti-CFI antibody (clone 3R/8, CABT-47940MH) is coated at 1 µg/ml on the Meso Scale Discovery (MSD, Rockville, MA) assay plate to capture the CFI-HSA. Detection of the captured CFI-HSA is performed with a rabbit polyclonal anti-HSA antibody (ab24207, Abcam, Cambridge, MA) at 2 µg/ml conjugated with SULFO-TAG which emits light [electrochemiluminescence (ECL)] on application of an electric potential. The ECL relative light units (RLU) is measured on a MESO® SECTOR S 600 Reader and unknown plasma CFI and CFI-HSA concentrations are interpolated from the standard curves. Pharmacokinetic parameters were derived from the analysis of plasma CFI and CFI-HSA concentrations and provided in Table 12.1.

TABLE 12.1

Pharmacokinetics of plasma CFI and CFI-HSA as assessed by measurement of CFI antigen in plasma from CD-1 mice after single bolus IV and SC administration.

|  | Dose (mg/kg) | α-phase half-life (hours) | β-phase half-life (hours) | Clearance (mL/hour) | MRT (hours) | Vdss (mL/kg) | Cmax (µg/mL) | AUC 0-/dose (µg/mL × hr)/(µg/kg) | AUC 0-t/dose (µg/mL × hr)/µg/kg | Bio-availability (%) |
|---|---|---|---|---|---|---|---|---|---|---|
| Group 1 Factor I (IV) | 1.3 | 4.1 ± 1.2 | 13.1 ± 1.5 | 0.009 ± 0.001 | 15.0 ± 1.6 | 0.131 ± 0.007 | 20.2 ± 2.7 | 114.4 ± 11.3 | 114.3 ± 11.3 | — |
| Group 2 Factor I (SC) | 6.5 | — | 13.3 ± 0.8 | 0.017 ± 0.002 | 21.6 ± 2.7 | 0.353 ± 0.041 | 13.2 ± 1.7 | 61.3 ± 6.2 | 61.3 ± 6.2 | 53.6 |

TABLE 12.1-continued

Pharmacokinetics of plasma CFI and CFI-HSA as assessed by measurement of CFI antigen in plasma from CD-1 mice after single bolus IV and SC administration.

| | Dose (mg/kg) | α-phase half-life (hours) | β-phase half-life (hours) | Clearance (mL/hour) | MRT (hours) | Vdss (mL/kg) | Cmax (µg/mL) | AUC 0-/dose (µg/mL × hr)/µg/kg) | AUC 0-t/dose (µg/mL × hr)/µg/kg | Bio-availability (%) |
|---|---|---|---|---|---|---|---|---|---|---|
| Group 3 Factor I-HSA (IV) | 3.0 | 6.3 ± 1.0 | 21.8 ± 2.4 | 0.005 ± 0.001 | 16.7 ± 0.9 | 0.082 ± 0.009 | 74.7 ± 5.5 | 205.4 ± 20.3 | 203.8 ± 19.9 | — |
| Group 4 Factor I-HSA (SC) | 3.0 | — | 21.9 ± 0.7 | 0.01 ± 0 | 31.7 ± 2.4 | 0.327 ± 0.038 | 9.8 ± 1.5 | 97.2 ± 3.8 | 95.2 ± 3.8 | 46.7 |

Figure 19:
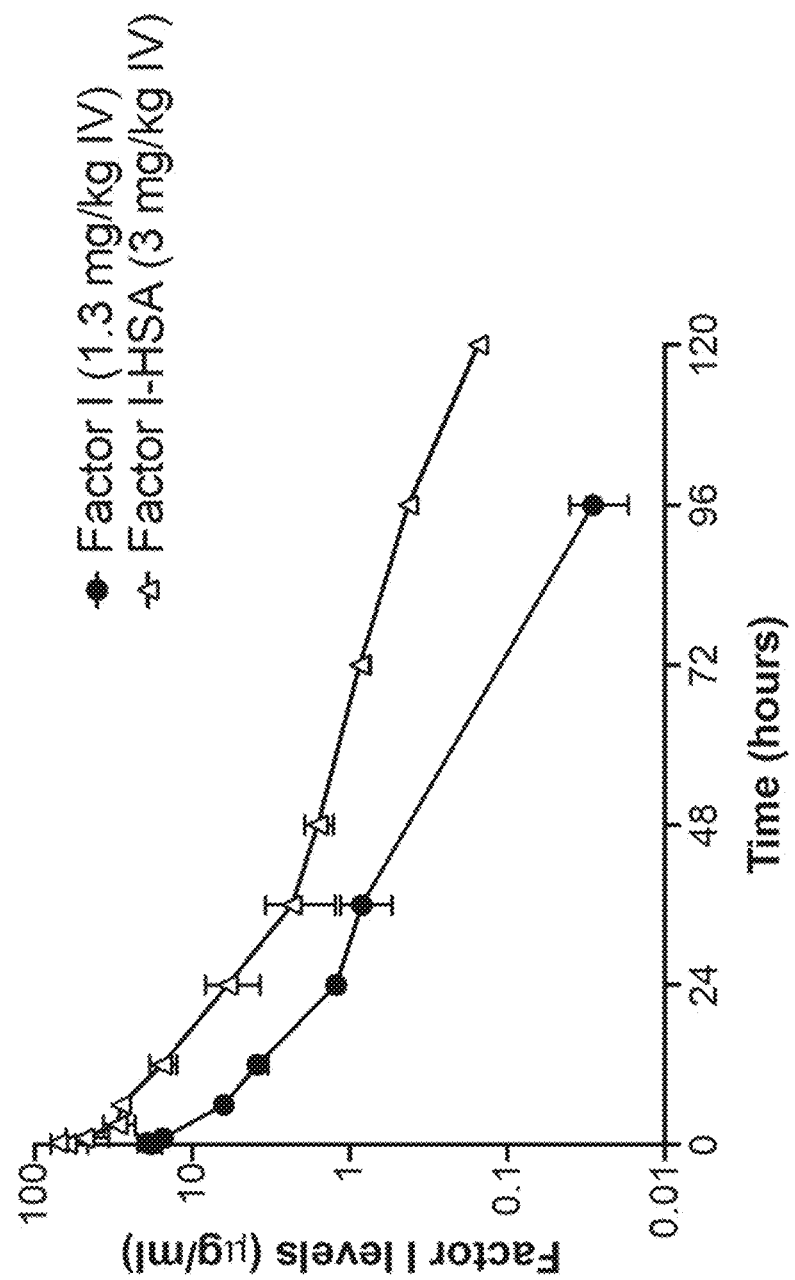
FIG. 19 depicts a plot of Factor I levels detected in plasma at the indicated time points following intravenous injection of CFI-HSA (Factor I-HSA) at 3 mg/kg or CFI (Factor I) at 1.3 mg/kg in CD1 mice.
Figure 20:
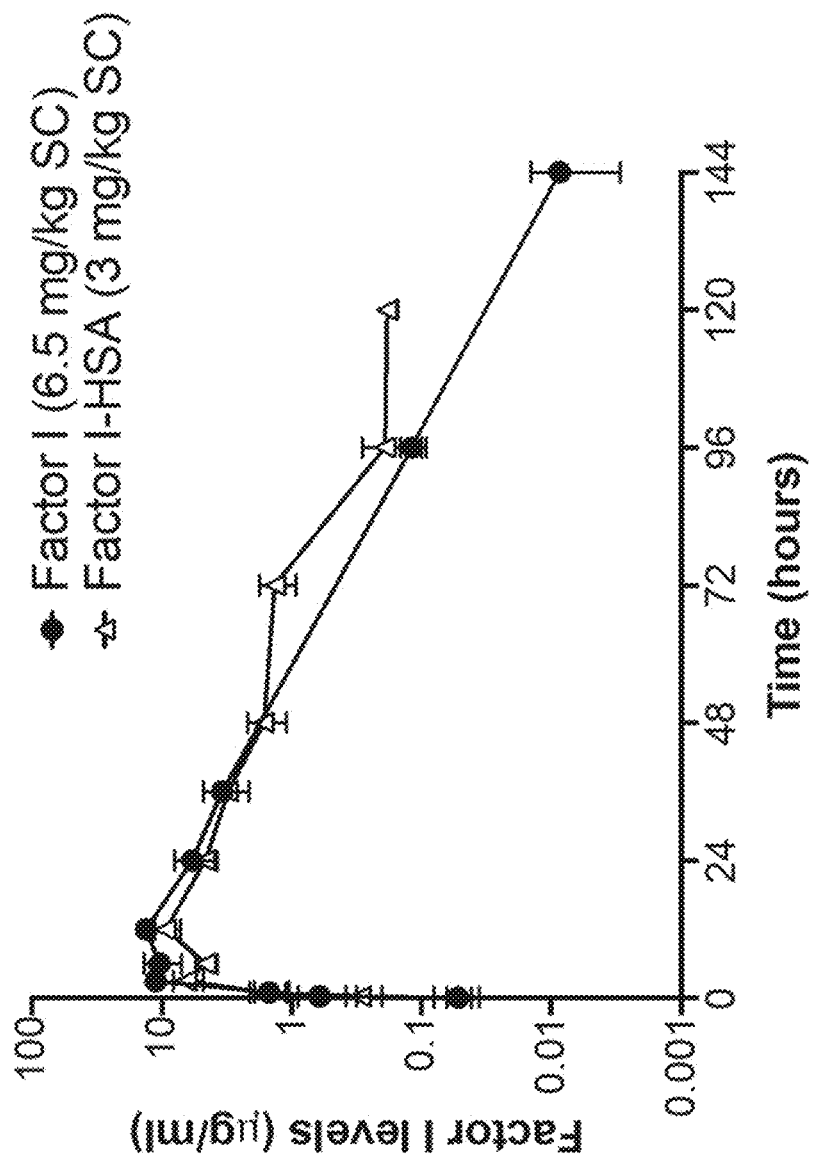
FIG. 20 depicts a plot of Factor I levels detected in plasma at the indicated time points following subcutaneous injection of CFI-HSA (Factor I-HSA) at 3 mg/kg or CFI (Factor I) at 6.5 mg/kg in CD1 mice.

The circulation half-life following intravenous infusion of CFI-HSA was longer (~22 hours) than the non-fusion version plasma CFI protein (~13 hours), indicating that fusion of HSA to the CFI protein increases the half-life of compared to unfused CFI. Importantly, the bioavailability of CFI (53.6%) was similar to the CFI-HSA (46.7%), indicating that fusion of HSA to the CFI protein did not adversely affect bioavailability of CFI after subcutaneous dosing (Table 12.1). Fusing HSA to CFI protein increases half-life by ~2-fold compared to the non-fusion version CFI protein after intravenous (FIG. 19) or subcutaneous dosing (FIG. 20). Similar exposure is achieved with a 2-fold lower dose of fusion protein CFI-HSA compared to CFI after subcutaneous injection (FIG. 20).

Example 13: CFI-HSA Bioactivity Following Intravenous Administration in Rodent Models of Complement Activation For Example 13, reference to CFI-HSA refers to human serum albumin fused to the N-terminal end of wild type CFI (SEQ ID NO: 21).

A rat model of peripheral nerve injury was developed to study complement involvement in Wallerian degeneration due to mechanical damage of the myelinated sciatic nerve. Male CD Sprague Dawley rats (Charles River Laboratories) weighing between 300 and 350 g at enrollment were anesthetized with a mixture of 2 to 2.5% isoflurane USP (Abbot Laboratories, Montreal, Canada) in oxygen, and placed on a heating pad to maintain body temperature. Both legs underwent a sterile surgery to expose the sciatic nerve. One leg underwent a sciatic nerve injury (SNI) by clamping the sciatic nerve three times for 10 seconds using Dumont #7 forceps. The contralateral leg received no clamp injury and served as an internal control for each subject.

Immediately following induction of SNI, animals received an intravenous injection of CFI-HSA (Y408L; N531G variant) 4 mg/kg (n=10), CFI-HSA (Y408L; N531G variant) 1.25 mg/kg (n=10), or control article (1× PBS; n=10) at a dose volume of 4 mL/kg. A subcutaneous injection of slow-release buprenorphine (0.01 mg/kg) was also administered for pain management. 4 or 24 hours after SNI, 5 animals from each treatment group were sacrificed by exsanguination.

At sacrifice, a 1 cm (0.5 cm proximal and distal to the site of injury) piece of nerve was collected from the injured (ipsilateral) and sham legs, snap frozen, and stored at −80° C. until processed for mass spectrometry analysis (Phenoswitch Bioscience, Canada). K2-EDTA plasma samples were collected prior to SNI (baseline) as well as 1, 4, and 24 hours (where applicable) after SNI for evaluation of complement component fragments by mass spectrometry (MS). Cytokine and chemokine levels (Rat 27 plex Multiplex Immunoassay analyzed with a BioPlex 200 Cytokine Array, Assay Kit Millipore MILLIPLEX, performed by Eve Technologies, Calgary, Canada) were assessed in K2-EDTA plasma collected at baseline (vehicle only), 4, and 24 hours (where applicable) after SNI. At sacrifice, whole blood and serum were collected for clinical pathology evaluation [complete blood counts (CBC) and serum chemistry; Biovet Inc., Canada].

Mass Spectrometry Analysis of In Vivo Samples

Samples were denatured and precipitated, with a wash and buffer exchange before N-terminal labeling via reductive amine dimethylation. Samples were then digested with trypsin (or a mix of trypsin and chymotrypsin) before analysis via LC-MS/MS using SWATH. SWATH data was integrated on an ion library produced for each species and sample type. Top 10 peptides per protein contained in the ion library were integrated, and a peptide centric analysis was carried out for specific quantification of C3, C5, C4 and CFB N-terminal labeled peptides.

Figure 21B:
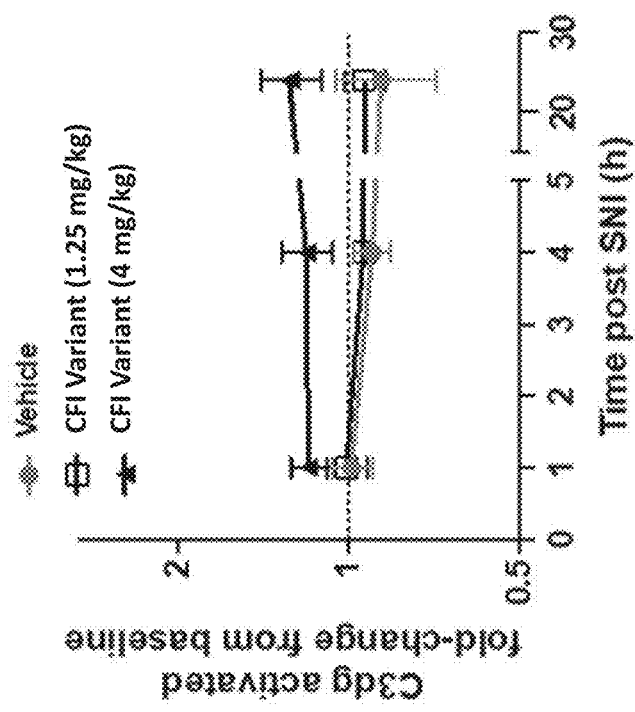
FIG. 21A and FIG. 21B depict charts and plots showing the level of CFI cleavage products (C3dg) detected by mass spectrometry resulting from CFI-HSA (hCFI; Y408L; N531G variant) catalytic activity on C3b in the nerve tissue (membrane-bound fragments) (FIG. 21A) and in circulation (soluble fragments in plasma) (FIG. 21B) in rat model of sciatic nerve injury.
Figure 21A:
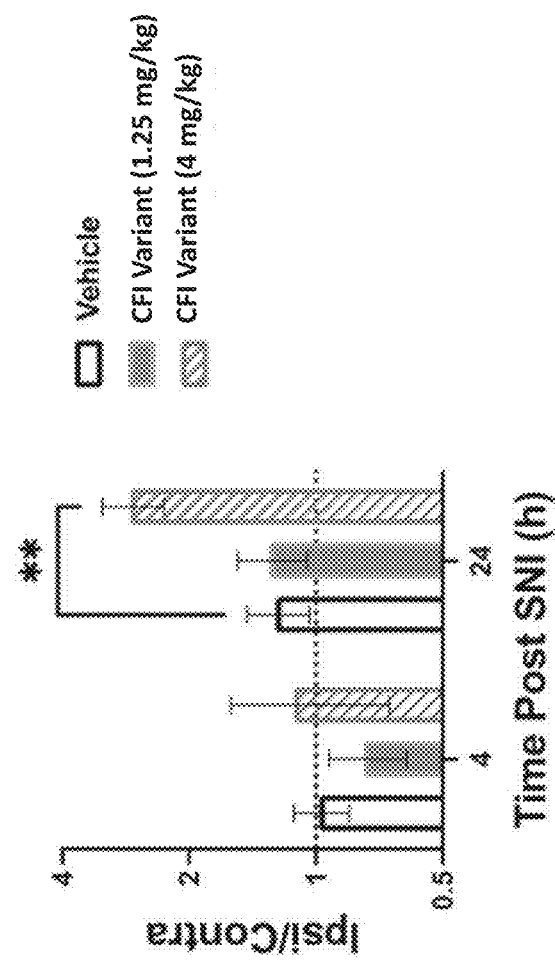

Cleavage products resulting from CFI-HSA (Y408L; N531G variant) catalytic activity on C3b were monitored in the nerve tissue (membrane-bound fragments) (FIG. 21A) and circulation (soluble fragments in plasma) (FIG. 21B) by mass spectrometry. CFI-HSA (Y408L; N531G variant) cleavage activity results in 2 major cleavage fragments detected by mass spectrometry: C3dg and C3f. Cleavage of surface-bound C3b by CFI will result in a surface-bound C3dg fragment and a soluble C3f fragment. Both fragments are soluble when formed from soluble C3b. Therefore, the detection of C3dg in plasma may be attributed to cleavage of soluble C3b while detection of C3dg in tissue may result from cleavage of membrane-bound C3b. N-terminal labelled C3dg (E[2Me]DVPAADLSDQVPDTDSETR) (SEQ ID NO: 24) is the product of CFI cleavage of iC3b. The activity of CFI variants was determined as the percent of C3dg peptides with N-terminal labeling (termed "activated C3dg") multiplied by the total signal size of C3dg (EDVPAADLSDQVPDTDSETR) (SEQ ID NO: 24). A dose-dependent increase in activated C3dg fragments was significantly more prominent in injured nerve tissue compared to plasma, suggesting that CFI-HSA (Y408L; N531G variant) may be more active in the surface-bound configuration than in circulation. This effect was not detected at early timepoints (4 hours) but observed 24 hours after injury indicating that either tissue C3b formation is delayed, CFI-HSA (Y408L; N531G variant) exhibits slow cleavage activity in vivo, or the effect observed is a consequence of CFI-HSA (Y408L; N531G variant) activity.

Overall, mass spectrometry results confirmed that mechanical nerve injury can trigger complement response at the site of nerve tissue. In addition, CFI-HSA (Y408L; N531G variant) showed greater cleavage activity on surface bound C3b than circulating C3b when compared to vehicle, suggesting CFI-HSA (Y408L; N531G variant) may perform better on surface-bound C3 where CR1 and C4bp cofactor are present.

Example 14: In Vivo Activity of CFI Variants in Peripheral Nerve Injury Rat Model For Example 14, reference to CFI-HSA refers to human serum albumin fused to the N-terminal end of wild type CFI (SEQ ID NO: 21).

The efficacy of a panel of CFI variants on complement activation in a sciatic nerve (SN) injury (SNI) rat model was determined Immediately following induction of SNI, animals received an IV injection with a CFI variant (n=6 for each variant) from a panel of CFI variants (Table 14.1), or a control article (1X PBS; n=6) at a dose volume of 5 mL/kg. 24 hours after SNI, all animals were sacrificed by exsanguination. Cytokine and chemokine levels (Rat 27 plex Multiplex Immunoassay analyzed with a BioPlex 200 Cytokine Array, Assay Kit Millipore MILLIPLEX, performed by Eve Technologies, Calgary, Canada) were assessed in K2-EDTA plasma collected at 4 and 24 hours after SNI. At sacrifice, serum was collected for serum chemistry [Biovet Inc., Canada].

Figure 22:
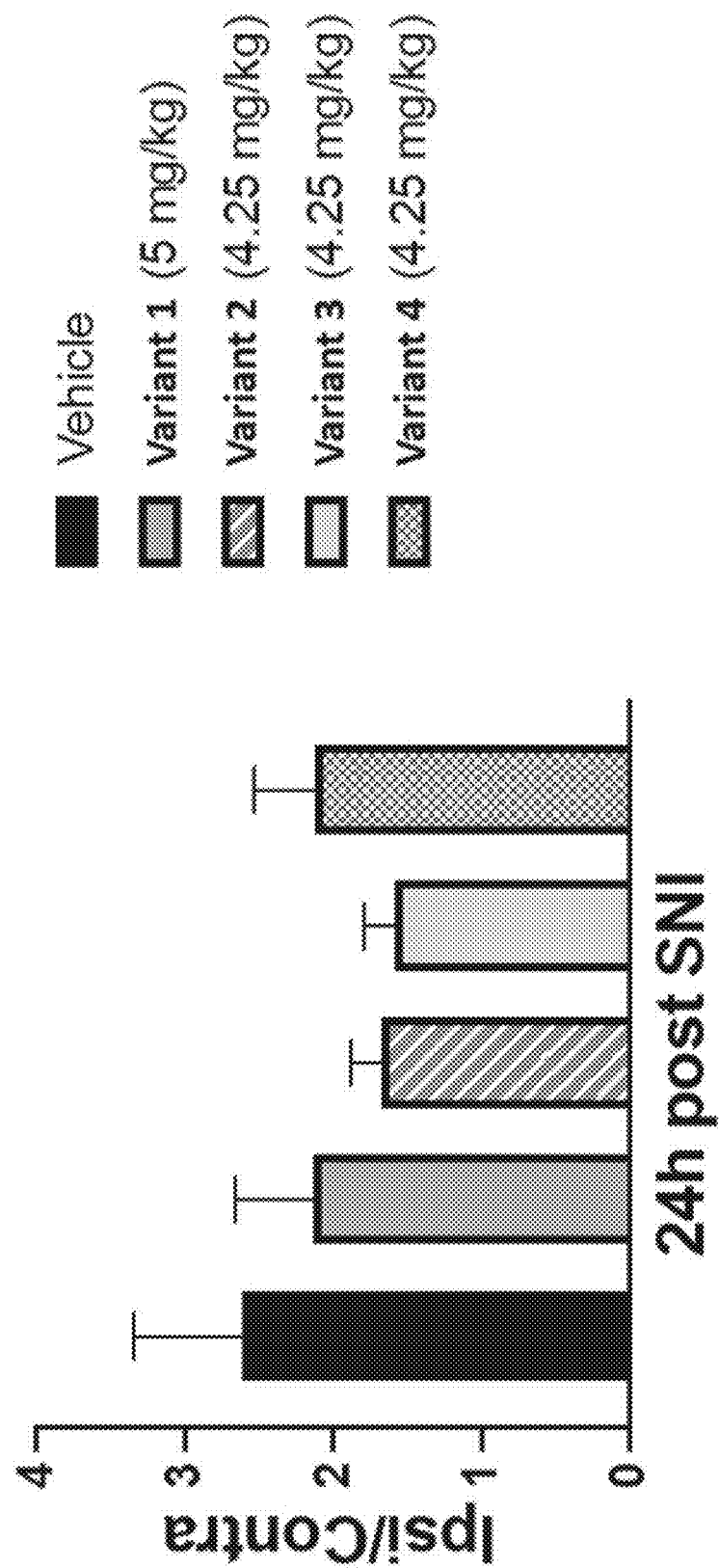
FIG. 22 depicts a chart showing levels of CFI cleavage products (C3dg) detected in nerve tissue 24-hours following injury and administration of CFI variants in a rat model of sciatic nerve injury.
Figure 23A:
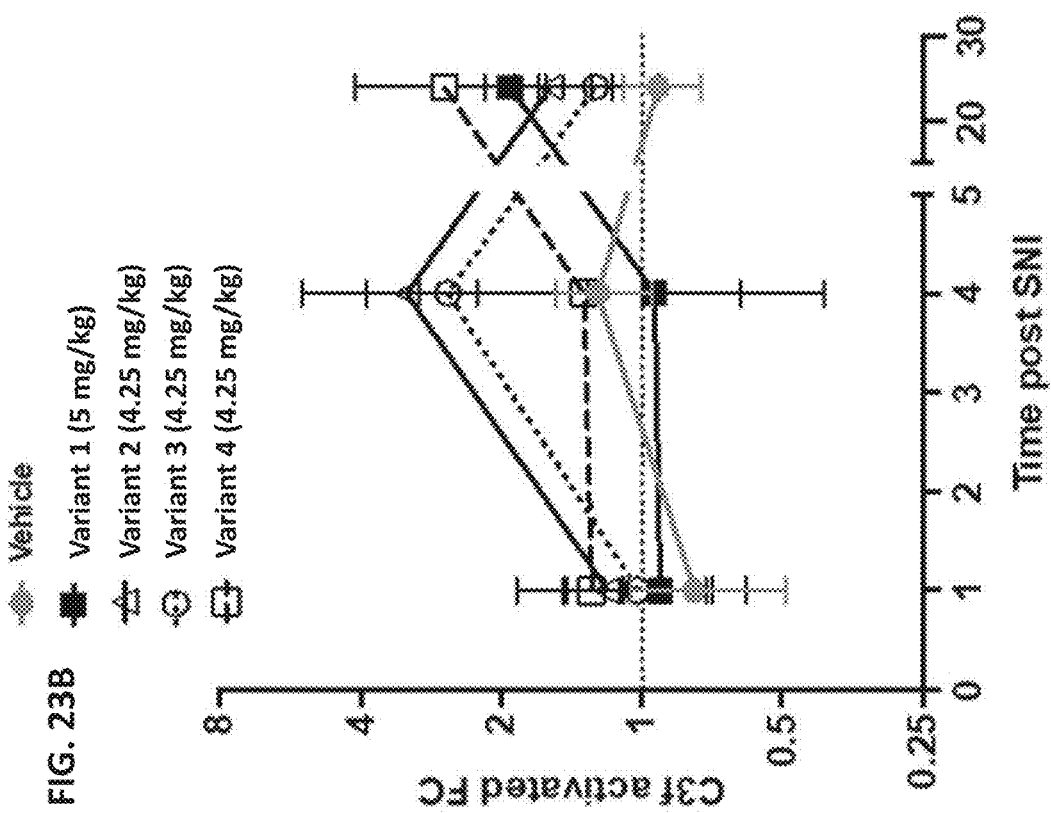
FIG. 23A and FIG. 23B depict plots showing the levels of CFI cleavage products detected by mass spectrometry in plasma of animals treated with CFI variants following sciatic nerve injury. CFI cleavage products detected included C3dg (FIG. 23A) and C3f levels (FIG. 23B).
Figure 23B:
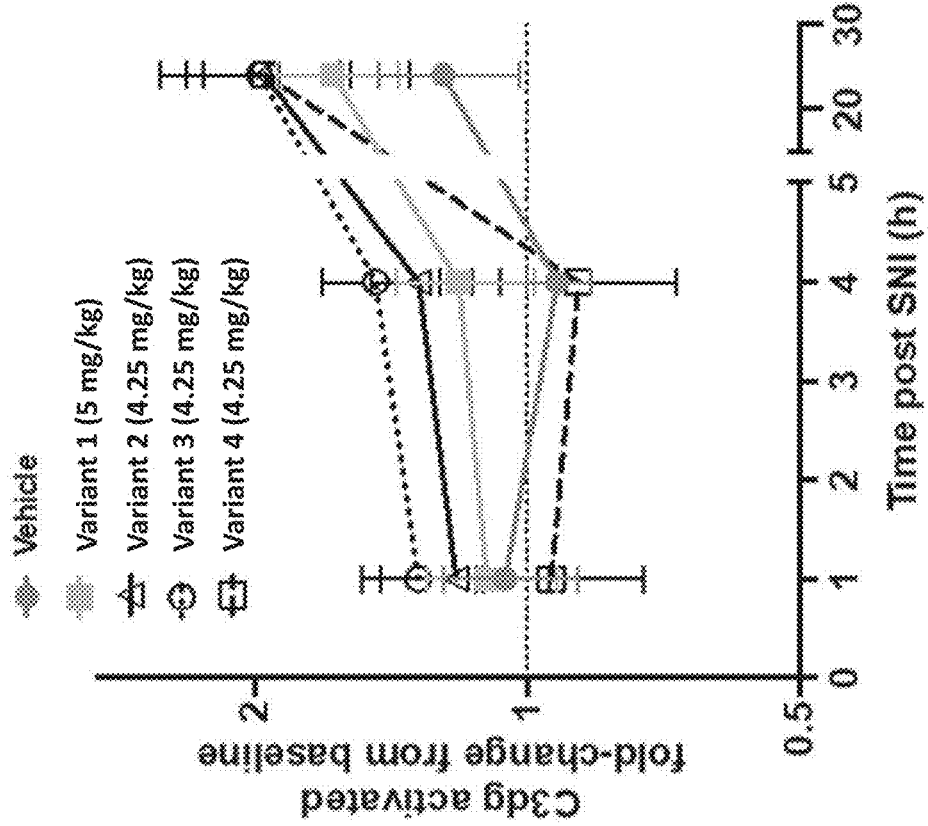

A 2.5-fold increase in nerve C3dg levels 24-hours after injury were observed in vehicle-treated animals and no effect of CFI variant treatment was detected (FIG. 22). No significant increase in C3dg and C3f levels were detected in plasma of vehicle-treated animals (FIG. 23A and FIG. 23B). However, 4 hours after Variant 2 and Variant 3 treatment, a trend toward an increase in plasma C3f levels was observed (FIG. 23B) followed by an increase in plasma C3dg levels at 24 hours (FIG. 23A). Variant 4 showed a delayed activity, with C3f and C3dg levels peaking in plasma at 24 hours. The higher levels of plasma C3dg after 4 hours of Variant 1 treatment indicate that the cofactor fusion outperformed Variant 4 for soluble C3b cleavage at earlier time-points but this effect was not sustained at 24 hours (FIG. 23A).

To compare the in vitro activity of CFI variants with the wild-type CFI, the iC3b $EC_{50}$ (Table 14.2, column A) and the $IC_{50}$ in classical pathway hemolysis (Table 14.2, column B) of wild-type CFI was divided by the iC3b $EC_{50}$ and $IC_{50}$ of each variant. To compare the in vivo increase in plasma C3f with in vitro data, total N-terminal labelled C3f at each time-point was divided by the baseline N-terminal labelled circulating C3f signal in plasma for each animal to provide an estimate of CFI-mediated cleavage of fluid-phase and surface-bound C3b (Table 14.2, column C and D). Plasma-derived CFI was selected as the closest approximation to activity of endogenous rodent CFI. The results of these data transformations are summarized in the table below.

TABLE 14.2

| Variant | A<br>Fold-<br>decrease<br>EC50<br>(iC3b)<br>vs. CFI WT | B<br>Fold-<br>decrease<br>IC50 (CP<br>hemolysis) vs.<br>CFI WT | C<br>Mean<br>circulating<br>C3f N-<br>terminal<br>labelled fold-<br>change (4 h post SNI) | D<br>Mean<br>circulating<br>C3f N-<br>terminal<br>labelled fold-<br>change (24 h post SNI) |
|---|---|---|---|---|
| Variant 2 | 8.03 | 4.82 | 3.18 | 1.57 |
| Variant 4 | 3.67 | 1.39 | 1.33 | 2.64 |
| Variant 3 | 3.86 | 2.33 | 2.60 | 1.26 |
| Variant 1 | 0.79 | 0.63 | 0.94 | 1.92 |

TABLE 14.1

| Identifier | CFI Variant | Dose (mg/kg) | Dose Volume (mL/kg) |
|---|---|---|---|
| Variant 1 | CFI-HSA (hCR1; CCP15; CCP16; CCP17 C-terminal fusion) | 5 | 5 |
| Variant 2 | CFI-HSA (E416A; D425R; E457G; N531G variant) | 4.25 | 5 |
| Variant 3 | CFI-HSA (E457G; N531G variant) | 4.25 | 5 |
| Variant 4 | CFI-HSA (E416A; N531G variant) | 4.25 | 5 |

The activity of CFI variants was monitored by detecting CFI cleavage products (C3dg and C3f) using mass spectrometry. N-terminal labelled C3f (S[2Me]EETK[2Me]QNEGF) (SEQ ID NO: 28) is the product of CFI cleavage of C3b and N-terminal labelled C3dg (E[2Me]DVPAADLSDQVPDTDSETR) (SEQ ID NO: 24) is the product of CFI cleavage of iC3b. Total activated C3f was determined as the percent of C3f peptides with N-terminal labeling (S[2Me]EETK[2Me]QNEGF) (SEQ ID NO: 28) multiplied by the total peptide signal size of C3f (SEETKQNEGF) (SEQ ID NO: 28).

The resulting fold-changes from both the CP hemolysis assay and the iC3b ELISA assay measures yielded similar rankings to circulating C3f levels at 4 hours. By 24 hours after injury the relative improvements in C3 cleavage activity between variants was less discernable. In this setting, Variant 2 and Variant 3 markedly outperformed the other CFI variants 4 hours after SNI while Variant 4 outperformed all variants at 24 hours. Overall, these data suggest that the addition of D425R and E416A substitutions into Variant 3 do not dramatically improve in vivo C3b cleavage. However, the addition of E457G and D425R into Variant 4 would result in a faster in vivo cleavage activity that may not be sustained over time. Further work is needed to confirm the accuracy of CP Hemolysis to predict circulating CFI activity in rodents, but the trend suggests this assay may provide a close estimate to acute circulating cleavage activity in rats.

Figure 24:
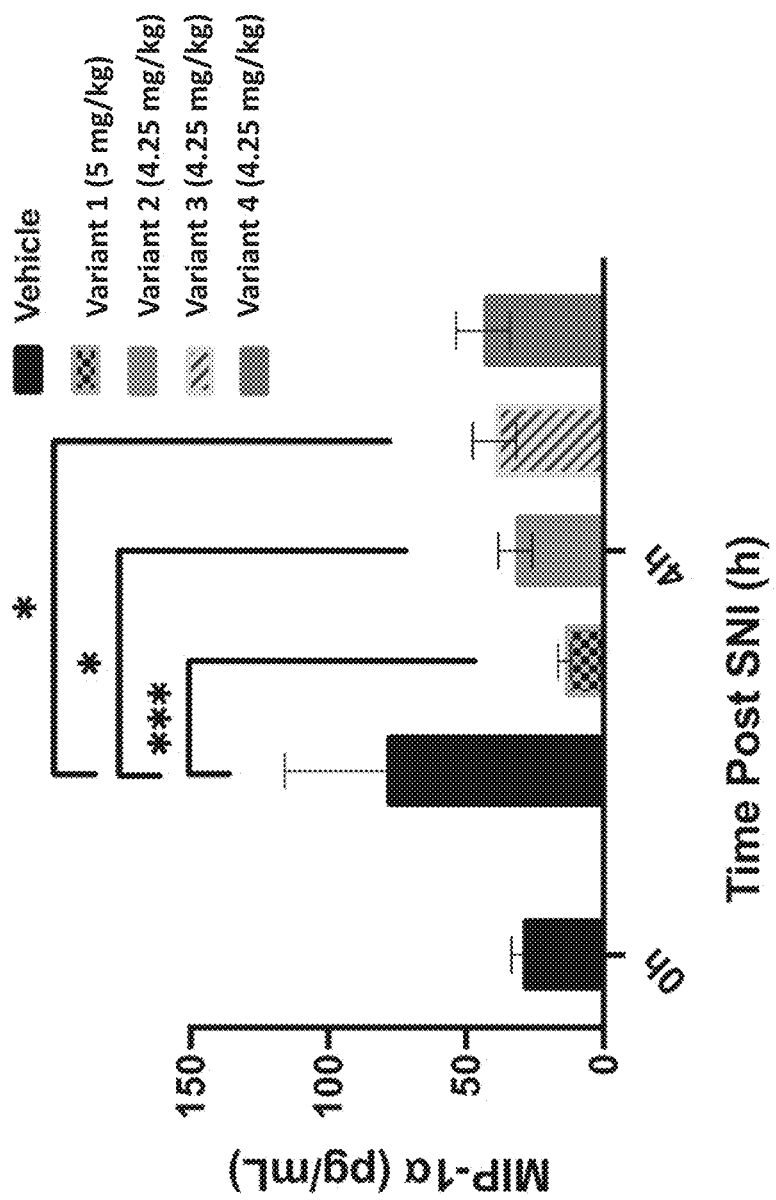
FIG. 24 depicts a chart showing circulating macrophage inflammatory protein-1 alpha (MIP-1α) following sciatic nerve injury after intravenous injection with a CFI variant in a rat model of sciatic nerve injury.

Untreated, rats undergoing surgery and nerve pinch demonstrated strong increases in circulating macrophage inflammatory protein-1 alpha (MIP-1α) compared to historical baseline (FIG. 24). MIP-1α has been shown to contribute to the pathogenesis of neuropathic pain in a similar sciatic nerve injury model in mice.1 Acute increases were reduced with administration of all CFI variants, but most markedly with the cofactor fusion Variant 1.

Example 15: In Vivo Activity of CFI Variants in Cecal Ligation and Puncture Model CFI variant effect on limiting complement activation in a model of cecal ligation and puncture (CLP)-induced sepsis in rats was assessed. For Example 15, reference to CFI-HSA refers to human serum albumin fused to the N-terminal end of wild type CFI (SEQ ID NO: 21).

A rat model of non-aseptic sepsis was used to study complement involvement following a cecal ligation and puncture (CLP) surgery. This surgery provides three facets of complement activation and inflammation (mechanical damage, bacterial exposure, and ischemic injury) that make it particularly relevant as a screening tool for other indications. Male CD Sprague Dawley rats (Charles River Laboratories) weighing between 300 and 350 g at enrollment were anesthetized with a mixture of 2 to 2.5% isoflurane USP (Abbot Laboratories, Montreal, Canada) in oxygen, and placed on a heating pad to maintain body temperature. Sepsis was induced by a CLP surgical procedure. A midline incision was made in the abdominal wall, the cecum exteriorized, and ligated with a nylon suture (4-0) proximal to the ileo-cecal valve, then perforated using a 16-gauge needle passed through the distal portion of the cecum resulting in a small amount of cecum contents entering the abdominal cavity. The abdominal wall and skin were then sutured.

Immediately following the CLP procedure, animals received an intravenous injection of Variant 1 [CFI-HSA (E457G; N531G variant)] 4.25 mg/kg (n=6), Variant 2 [CFI-HSA (E457G; N531G variant with C-term CCP15; CCP16; CCP17 fusion)] 5 mg/kg (n=6), Variant 3 [CFI-HSA (E457G; E461Q; N531G; Δ(558-PFISQYNV (SEQ ID NO: 14)-565) variant)] 4.25 mg/kg (n=6), or control article (1× PBS; n=6) at a dose volume of 5 mL/kg. No sham arm was performed. 16 hours after CLP surgery all animals were sacrificed by exsanguination. K2-EDTA plasma samples were collected the day prior to enrolment (baseline), 3, and 16 hours after CLP for evaluation of complement component fragments by mass spectrometry (MS) and cytokine/chemokine levels (Rat 27 plex Multiplex Immunoassay analyzed with a BioPlex 200 Cytokine Array, Assay Kit Millipore MILLIPLEX, performed by Eve Technologies, Calgary, Canada). Whole blood and serum were collected for clinical pathology evaluation [complete blood counts (CBC) and serum chemistry; Biovet Inc., Canada] at baseline and 16 hours.

Figures 25A, 25B:
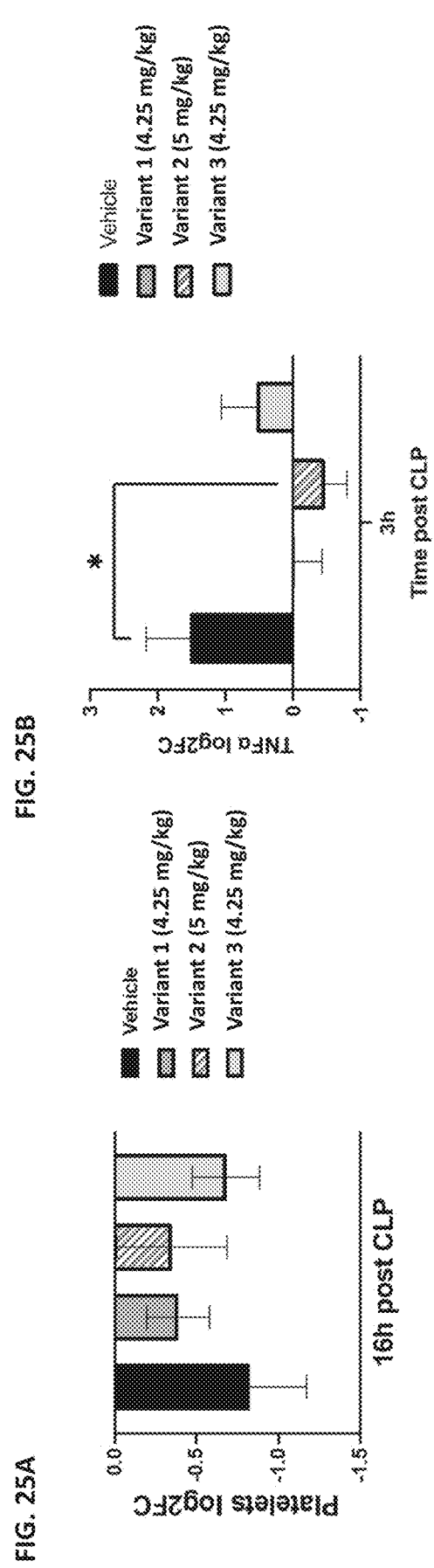
FIG. 25A and FIG. 25B depict charts showing change in the number of platelets at 16 hours (FIG. 25A) and the levels of tumor necrosis factor alpha (TNFα) at 3 hours (FIG. 25B) following cecal ligation and puncture (CLP) surgery and intravenous administration of CFI variants in a rat CLP model.

The thrombocytopenia was observed for vehicle-treated animals 16 hours post-injury. A trend towards protection against thrombocytopenia was observed in Variant 1 and Variant 2 treated animals (FIG. 25A). This protection was less prominent in Variant 3 treated animals, suggesting that deletion of the C-terminal portion of CFI may not improve catalytic activity. This in vivo observation is consistent with the lower cleavage activity of Variant 3 observed in vitro on C4c and iC3b compared to Variant 1 and Variant 2. Variant 1 and Variant 2 showed a similar effect on thrombocytopenia, suggesting that adding a CR1 cofactor fusion to Variant 1 may not improve in vivo activity.

The sepsis inflammatory cytokine tumor necrosis factor alpha (TNFα) is released rapidly following the CLP surgery (FIG. 25B). In untreated animals, TNFα increased ~2.9-fold within 3-hours from surgery. In contrast, treatment with Variant 2 significantly reduced these effects with an average decline in circulating TNFα levels compared to baseline. A similar protective trend was observed in animals receiving Variant 1. Variant 3 treated rats still demonstrated increases in circulating TNFα (mean fold-change of ~1.5), albeit to a lesser extent than untreated animals Example 16: In vivo Activity of CFI Variants in Acute Respiratory Distress Syndrome Evaluation of the therapeutic effects of CFI variants in an LPS-induced acute respiratory distress syndrome (ARDS) mouse model. For Example 16, reference to CFI-HSA refers to human serum albumin fused to the N-terminal end of wild type CFI (SEQ ID NO: 21).

Purpose: The purpose of this study was to assess the efficacy of Variant 1 [CFI-HSA (E457G; E461Q)] and Variant 2 [CFI-HSA (E457G; E461Q; N531G)] to limit complement mediated acute pulmonary inflammation in a mouse model of ARDS induced by a single administration of lipopolysaccharide (LPS).

A mouse model of aseptic ARDS was used to study complement involvement following an intratracheal instillation (IT) of LPS. Male C57BL/6 mice (Charles River Laboratories) weighing 20 to 25 g at enrolment were anesthetized under isoflurane and intratracheally instilled with 50 µg LPS (1 mg/mL LPS isolated from E. coli 0111:B4 in 0.9% saline solution, Sigma).

Three hours following the CLP procedure, animals received an intravenous injection of 5 mg/kg Variant 1 (n=8), 5 mg/kg Variant 2 (n=8) or control article (1× PBS; n=10) at a dosing volume of 5 mL/kg. To evaluate the potential impacts of repeat daily dosing, 27 hours post-LPS IT, Variant 2 treated animals received a second 5 mg/kg dose. A sham arm was subjected to a 50 µL intratracheal instillation of 0.9% saline solution (n=5) without any IV treatment. Variant 1 treated animals were sacrificed 24 hours post-LPS IT while Variant 2 treated animals were sacrificed 48 hours post-LPS IT.

K₂-EDTA plasma, lung tissue, and bronchoalveolar lavage fluid (BALF) samples were collected at sacrifice for evaluation of complement component fragments by mass spectrometry (MS). BALF was harvested in three 300 µL perfusions of the right lung with cold PBS 1× containing Protease Inhibitor 1× (SigmaFAST®). Cytokine and chemokine levels (Mouse 31 plex Multiplex Immunoassay analyzed with a BioPlex 200 Cytokine Array, Assay Kit Millipore MILLIPLEX, performed by Eve Technologies, Calgary, Canada) were assessed in K₂-EDTA plasma, BALF, and lung tissue (homogenized in PBS 1×+0.1% Triton X-100 with protease cocktail inhibitors) collected at sacrifice. At sacrifice, whole blood and serum were collected for clinical pathology evaluation [complete blood counts (CBC) and serum chemistry; Biovet Inc., Canada]. A cell count differential was performed on BALF samples to assess leukocyte recruitment to the lung.

Figure 26A:
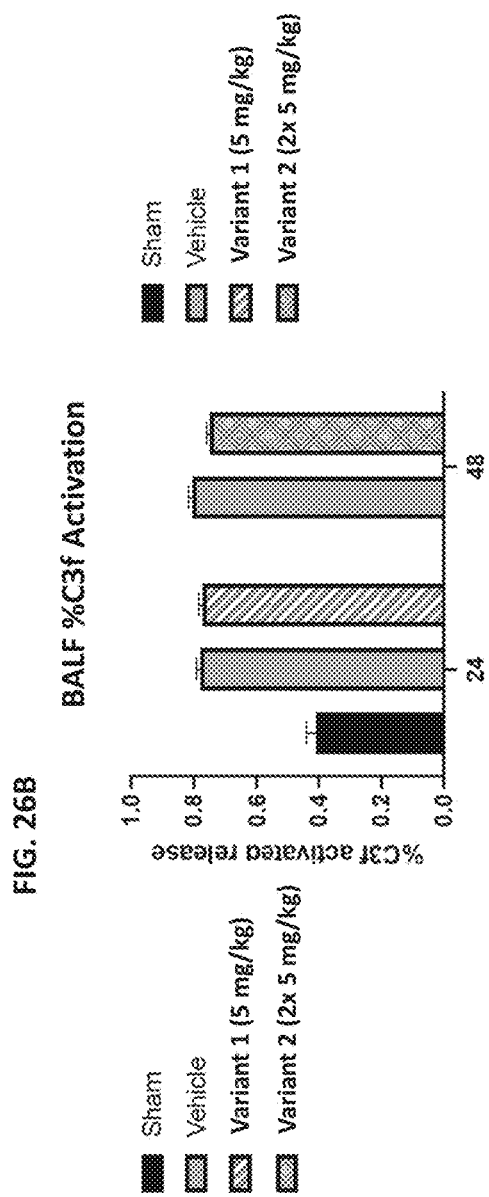
FIG. 26A, FIG. 26B, and FIG. 26C depict charts showing % C3f activation; in lung (FIG. 26A), in bronchoalveolar lavage fluid (BALF) (FIG. 26B), and in plasma (FIG. 26C) collected from animals at 24 hours and 48 hours following an intratracheal instillation (IT) of LPS and intravenous administration of CFI variants in a mouse model of acute respiratory distress syndrome (ARDS).
Figure 26B:
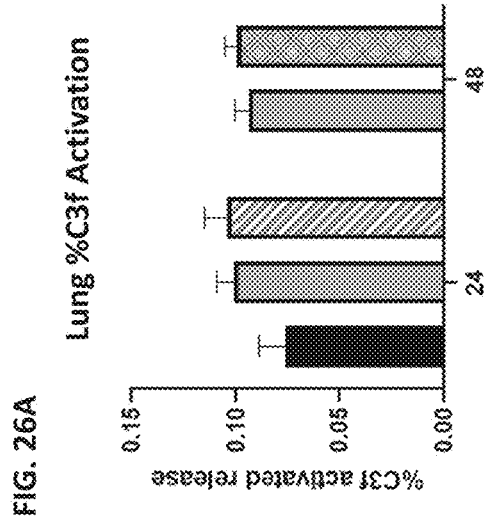
Figure 26C:
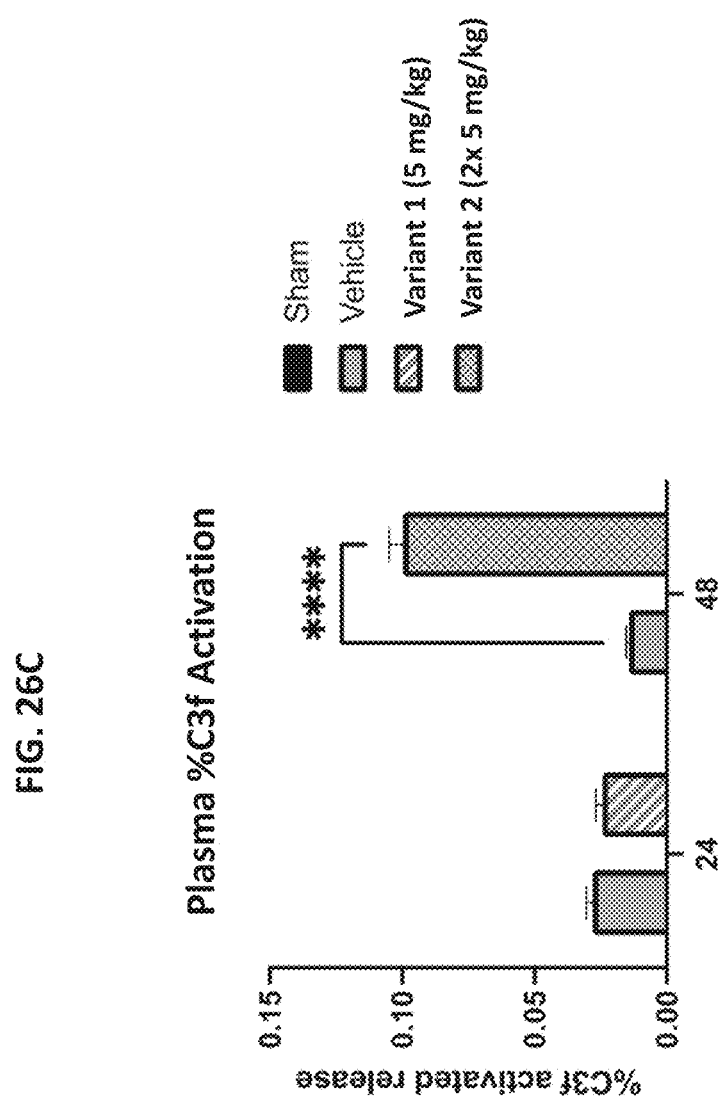

LPS is a known alternative complement pathway inducing agent. We assessed CFI activity on circulating C3b cleavage products using mass spectrometry. Percent activated C3f was determined as the percent of the C3f peptide with N-terminal labeling (S[2Me]EETK[2Me]QNEGF) (SEQ ID NO: 28) multiplied by the total peptide signal size of C3f (SEETKQNEGF) (SEQ ID NO: 28). In the BALF, increased cleavage release of C3f was observed at 24 hours in all LPS-treated animals and sustained up to 48 hours (FIG. 26B). A similar trend and time course was observed in the lung regardless of CFI variant treatment (FIG. 26A). At 24 and 48 hours after LPS administration, no cleavage activity (C3f being released) of Variant 1 and Variant 2 was detected in the bronchoalveolar fluid nor the lung tissue. However, we cannot exclude the possibility that C3f fragments could have been detected at earlier timepoints after LPS administration. In contrast, 48 hours after LPS administration, a significant increase in circulating C3f was detected in animals receiving two doses of Variant 2, suggesting accumulation of the 5 mg/kg dose enhanced C3b cleavage in circulation.

The invention claimed is:

1. A fusion construct comprising a first component and a second component, wherein the first component comprises a wild type complement factor I (CFI), wherein the second component comprises a half-life extender, wherein the second component is fused to the N-terminal end of the first component, and wherein the fusion construct has a cleavage activity for C3b and/or C4b that is substantially equivalent to a plasma-derived CFI.

2. The fusion construct of claim 1, wherein the first component comprises an amino acid sequence set forth in SEQ ID NO: 5.

3. The fusion construct of claim 2, wherein the second component is albumin.

4. The fusion construct of claim 3, wherein the second component is human serum albumin.

5. The fusion construct of claim 4, wherein the second component comprises a human serum albumin comprising an amino acid sequence set forth in SEQ ID NO: 7.

6. The fusion construct of claim 1, comprising an amino acid sequence set forth in SEQ ID NO: 21, or an amino acid sequence comprising at least 80% identity thereto.

7. The fusion construct of claim 1, consisting of an amino acid sequence set forth in SEQ ID NO: 21.

8. A pharmaceutical composition comprising the fusion construct of claim 1.

9. The fusion construct of claim 1, wherein the second component is fused to the N-terminal end of the first component by a linker.

10. The fusion construct of claim 2, further comprising the amino acid sequence of SEQ ID NO: 7, wherein the fusion construct comprises a structural arrangement from N-terminus to C-terminus (SEQ ID NO: 7)-(optional linker)-(SEQ ID NO: 5).

11. The fusion construct of claim 10, wherein the fusion construct comprises a structural arrangement from N-terminus to C-terminus (SEQ ID NO: 7)-(linker)-(SEQ ID NO: 5).

12. The fusion construct of claim 10, wherein the fusion construct comprises a structural arrangement from N-terminus to C-terminus (SEQ ID NO: 7)-(SEQ ID NO: 6)-(SEQ ID NO: 5).

13. The fusion construct of claim 1, wherein the half-life extender is a modified albumin or albumin derivative.

14. The fusion construct of claim 1, wherein the half-life extender is a wild type albumin.

15. The fusion construct of claim 1, wherein the half-life extender is a human serum albumin or a variant thereof.

16. The fusion construct of claim 1, wherein the fusion construct has a cleavage activity for C3b that is substantially equivalent to a plasma-derived CFI.

17. The fusion construct of claim 1, wherein the fusion construct has a cleavage activity for C4b that is substantially equivalent to a plasma-derived CFI.

18. The fusion construct of claim 1, wherein the fusion construct has a cleavage activity for C4b and C3b that is substantially equivalent to a plasma-derived CFI.

19. The fusion construct of claim 1, wherein the half-life extender comprises peptide repeats.

20. The fusion construct of claim 1, wherein the half-life extender is selected from albumin, PEG, a non-biodegradable polymer, a biodegradable polymer, and Fc.

* * * * *

```
                        SEQUENCE LISTING

<160> NUMBER OF SEQ ID NOS: 28

<210> SEQ ID NO 1
<211> LENGTH: 583
<212> TYPE: PRT
<213> ORGANISM: Homo Sapiens

<400> SEQUENCE: 1

Met Lys Leu Leu His Val Phe Leu Leu Phe Leu Cys Phe His Leu Arg
1               5                   10                  15

Phe Cys Lys Val Thr Tyr Thr Ser Gln Glu Asp Leu Val Glu Lys Lys
            20                  25                  30

Cys Leu Ala Lys Lys Tyr Thr His Leu Ser Cys Asp Lys Val Phe Cys
        35                  40                  45

Gln Pro Trp Gln Arg Cys Ile Glu Gly Thr Cys Val Cys Lys Leu Pro
    50                  55                  60

Tyr Gln Cys Pro Lys Asn Gly Thr Ala Val Cys Ala Thr Asn Arg Arg
65                  70                  75                  80

Ser Phe Pro Thr Tyr Cys Gln Gln Lys Ser Leu Glu Cys Leu His Pro
                85                  90                  95

Gly Thr Lys Phe Leu Asn Asn Gly Thr Cys Thr Ala Glu Gly Lys Phe
            100                 105                 110

Ser Val Ser Leu Lys His Gly Asn Thr Asp Ser Glu Gly Ile Val Glu
        115                 120                 125

Val Lys Leu Val Asp Gln Asp Lys Thr Met Phe Ile Cys Lys Ser Ser
    130                 135                 140

Trp Ser Met Arg Glu Ala Asn Val Ala Cys Leu Asp Leu Gly Phe Gln
145                 150                 155                 160

Gln Gly Ala Asp Thr Gln Arg Arg Phe Lys Leu Ser Asp Leu Ser Ile
                165                 170                 175

Asn Ser Thr Glu Cys Leu His Val His Cys Arg Gly Leu Glu Thr Ser
            180                 185                 190

Leu Ala Glu Cys Thr Phe Thr Lys Arg Arg Thr Met Gly Tyr Gln Asp
        195                 200                 205

Phe Ala Asp Val Val Cys Tyr Thr Gln Lys Ala Asp Ser Pro Met Asp
    210                 215                 220

Asp Phe Phe Gln Cys Val Asn Gly Lys Tyr Ile Ser Gln Met Lys Ala
225                 230                 235                 240

Cys Asp Gly Ile Asn Asp Cys Gly Asp Gln Ser Asp Glu Leu Cys Cys
                245                 250                 255

Lys Ala Cys Gln Gly Lys Gly Phe His Cys Lys Ser Gly Val Cys Ile
            260                 265                 270

Pro Ser Gln Tyr Gln Cys Asn Gly Glu Val Asp Cys Ile Thr Gly Glu
        275                 280                 285

Asp Glu Val Gly Cys Ala Gly Phe Ala Ser Val Thr Gln Glu Glu Thr
    290                 295                 300

Glu Ile Leu Thr Ala Asp Met Asp Ala Glu Arg Arg Arg Ile Lys Ser
305                 310                 315                 320

Leu Leu Pro Lys Leu Ser Cys Gly Val Lys Asn Arg Met His Ile Arg
                325                 330                 335
```

```
Arg Lys Arg Ile Val Gly Gly Lys Arg Ala Gln Leu Gly Asp Leu Pro
            340                 345                 350

Trp Gln Val Ala Ile Lys Asp Ala Ser Gly Ile Thr Cys Gly Gly Ile
        355                 360                 365

Tyr Ile Gly Gly Cys Trp Ile Leu Thr Ala Ala His Cys Leu Arg Ala
    370                 375                 380

Ser Lys Thr His Arg Tyr Gln Ile Trp Thr Thr Val Val Asp Trp Ile
385                 390                 395                 400

His Pro Asp Leu Lys Arg Ile Val Ile Glu Tyr Val Asp Arg Ile Ile
                405                 410                 415

Phe His Glu Asn Tyr Asn Ala Gly Thr Tyr Gln Asn Asp Ile Ala Leu
            420                 425                 430

Ile Glu Met Lys Lys Asp Gly Asn Lys Lys Asp Cys Glu Leu Pro Arg
        435                 440                 445

Ser Ile Pro Ala Cys Val Pro Trp Ser Pro Tyr Leu Phe Gln Pro Asn
    450                 455                 460

Asp Thr Cys Ile Val Ser Gly Trp Gly Arg Glu Lys Asp Asn Glu Arg
465                 470                 475                 480

Val Phe Ser Leu Gln Trp Gly Glu Val Lys Leu Ile Ser Asn Cys Ser
                485                 490                 495

Lys Phe Tyr Gly Asn Arg Phe Tyr Glu Lys Glu Met Glu Cys Ala Gly
            500                 505                 510

Thr Tyr Asp Gly Ser Ile Asp Ala Cys Lys Gly Asp Ser Gly Gly Pro
        515                 520                 525

Leu Val Cys Met Asp Ala Asn Asn Val Thr Tyr Val Trp Gly Val Val
    530                 535                 540

Ser Trp Gly Glu Asn Cys Gly Lys Pro Glu Phe Pro Gly Val Tyr Thr
545                 550                 555                 560

Lys Val Ala Asn Tyr Phe Asp Trp Ile Ser Tyr His Val Gly Arg Pro
                565                 570                 575

Phe Ile Ser Gln Tyr Asn Val
            580

<210> SEQ ID NO 2
<211> LENGTH: 20
<212> TYPE: PRT
<213> ORGANISM: Homo Sapiens

<400> SEQUENCE: 2

Met Glu Thr Asp Thr Leu Leu Leu Trp Val Leu Leu Leu Trp Val Pro
1               5                   10                  15

Gly Ser Thr Gly
            20

<210> SEQ ID NO 3
<211> LENGTH: 18
<212> TYPE: PRT
<213> ORGANISM: Homo Sapiens

<400> SEQUENCE: 3

Met Lys Leu Leu His Val Phe Leu Leu Phe Leu Cys Phe His Leu Arg
1               5                   10                  15

Phe Cys

<210> SEQ ID NO 4
<211> LENGTH: 1231
```

<212> TYPE: PRT
<213> ORGANISM: Homo Sapiens

<400> SEQUENCE: 4

Met Arg Leu Leu Ala Lys Ile Ile Cys Leu Met Leu Trp Ala Ile Cys
1               5                   10                  15

Val Ala Glu Asp Cys Asn Glu Leu Pro Pro Arg Arg Asn Thr Glu Ile
                20                  25                  30

Leu Thr Gly Ser Trp Ser Asp Gln Thr Tyr Pro Glu Gly Thr Gln Ala
            35                  40                  45

Ile Tyr Lys Cys Arg Pro Gly Tyr Arg Ser Leu Gly Asn Val Ile Met
        50                  55                  60

Val Cys Arg Lys Gly Glu Trp Val Ala Leu Asn Pro Leu Arg Lys Cys
65                  70                  75                  80

Gln Lys Arg Pro Cys Gly His Pro Gly Asp Thr Pro Phe Gly Thr Phe
                85                  90                  95

Thr Leu Thr Gly Gly Asn Val Phe Glu Tyr Gly Val Lys Ala Val Tyr
            100                 105                 110

Thr Cys Asn Glu Gly Tyr Gln Leu Leu Gly Glu Ile Asn Tyr Arg Glu
        115                 120                 125

Cys Asp Thr Asp Gly Trp Thr Asn Asp Ile Pro Ile Cys Glu Val Val
130                 135                 140

Lys Cys Leu Pro Val Thr Ala Pro Glu Asn Gly Lys Ile Val Ser Ser
145                 150                 155                 160

Ala Met Glu Pro Asp Arg Glu Tyr His Phe Gly Gln Ala Val Arg Phe
                165                 170                 175

Val Cys Asn Ser Gly Tyr Lys Ile Glu Gly Asp Glu Glu Met His Cys
            180                 185                 190

Ser Asp Asp Gly Phe Trp Ser Lys Glu Lys Pro Lys Cys Val Glu Ile
        195                 200                 205

Ser Cys Lys Ser Pro Asp Val Ile Asn Gly Ser Pro Ile Ser Gln Lys
210                 215                 220

Ile Ile Tyr Lys Glu Asn Glu Arg Phe Gln Tyr Lys Cys Asn Met Gly
225                 230                 235                 240

Tyr Glu Tyr Ser Glu Arg Gly Asp Ala Val Cys Thr Glu Ser Gly Trp
                245                 250                 255

Arg Pro Leu Pro Ser Cys Glu Glu Lys Ser Cys Asp Asn Pro Tyr Ile
            260                 265                 270

Pro Asn Gly Asp Tyr Ser Pro Leu Arg Ile Lys His Arg Thr Gly Asp
        275                 280                 285

Glu Ile Thr Tyr Gln Cys Arg Asn Gly Phe Tyr Pro Ala Thr Arg Gly
290                 295                 300

Asn Thr Ala Lys Cys Thr Ser Thr Gly Trp Ile Pro Ala Pro Arg Cys
305                 310                 315                 320

Thr Leu Lys Pro Cys Asp Tyr Pro Asp Ile Lys His Gly Gly Leu Tyr
                325                 330                 335

His Glu Asn Met Arg Arg Pro Tyr Phe Pro Val Ala Val Gly Lys Tyr
            340                 345                 350

Tyr Ser Tyr Tyr Cys Asp Glu His Phe Glu Thr Pro Ser Gly Ser Tyr
        355                 360                 365

Trp Asp His Ile His Cys Thr Gln Asp Gly Trp Ser Pro Ala Val Pro
370                 375                 380

Cys Leu Arg Lys Cys Tyr Phe Pro Tyr Leu Glu Asn Gly Tyr Asn Gln
385                 390                 395                 400

```
Asn Tyr Gly Arg Lys Phe Val Gln Gly Lys Ser Ile Asp Val Ala Cys
            405                 410                 415

His Pro Gly Tyr Ala Leu Pro Lys Ala Gln Thr Val Thr Cys Met
        420                 425                 430

Glu Asn Gly Trp Ser Pro Thr Pro Arg Cys Ile Arg Val Lys Thr Cys
        435                 440                 445

Ser Lys Ser Ser Ile Asp Ile Glu Asn Gly Phe Ile Ser Glu Ser Gln
    450                 455                 460

Tyr Thr Tyr Ala Leu Lys Glu Lys Ala Lys Tyr Gln Cys Lys Leu Gly
465                 470                 475                 480

Tyr Val Thr Ala Asp Gly Glu Thr Ser Gly Ser Ile Thr Cys Gly Lys
                485                 490                 495

Asp Gly Trp Ser Ala Gln Pro Thr Cys Ile Lys Ser Cys Asp Ile Pro
            500                 505                 510

Val Phe Met Asn Ala Arg Thr Lys Asn Asp Phe Thr Trp Phe Lys Leu
        515                 520                 525

Asn Asp Thr Leu Asp Tyr Glu Cys His Asp Gly Tyr Glu Ser Asn Thr
    530                 535                 540

Gly Ser Thr Thr Gly Ser Ile Val Cys Gly Tyr Asn Gly Trp Ser Asp
545                 550                 555                 560

Leu Pro Ile Cys Tyr Glu Arg Glu Cys Glu Leu Pro Lys Ile Asp Val
                565                 570                 575

His Leu Val Pro Asp Arg Lys Lys Asp Gln Tyr Lys Val Gly Glu Val
            580                 585                 590

Leu Lys Phe Ser Cys Lys Pro Gly Phe Thr Ile Val Gly Pro Asn Ser
        595                 600                 605

Val Gln Cys Tyr His Phe Gly Leu Ser Pro Asp Leu Pro Ile Cys Lys
    610                 615                 620

Glu Gln Val Gln Ser Cys Gly Pro Pro Glu Leu Leu Asn Gly Asn
625                 630                 635                 640

Val Lys Glu Lys Thr Lys Glu Glu Tyr Gly His Ser Glu Val Val Glu
                645                 650                 655

Tyr Tyr Cys Asn Pro Arg Phe Leu Met Lys Gly Pro Asn Lys Ile Gln
            660                 665                 670

Cys Val Asp Gly Glu Trp Thr Thr Leu Pro Val Cys Ile Val Glu Glu
        675                 680                 685

Ser Thr Cys Gly Asp Ile Pro Glu Leu Glu His Gly Trp Ala Gln Leu
    690                 695                 700

Ser Ser Pro Pro Tyr Tyr Tyr Gly Asp Ser Val Glu Phe Asn Cys Ser
705                 710                 715                 720

Glu Ser Phe Thr Met Ile Gly His Arg Ser Ile Thr Cys Ile His Gly
                725                 730                 735

Val Trp Thr Gln Leu Pro Gln Cys Val Ala Ile Asp Lys Leu Lys Lys
            740                 745                 750

Cys Lys Ser Ser Asn Leu Ile Ile Leu Glu Glu His Leu Lys Asn Lys
        755                 760                 765

Lys Glu Phe Asp His Asn Ser Asn Ile Arg Tyr Arg Cys Arg Gly Lys
    770                 775                 780

Glu Gly Trp Ile His Thr Val Cys Ile Asn Gly Arg Trp Asp Pro Glu
785                 790                 795                 800

Val Asn Cys Ser Met Ala Gln Ile Gln Leu Cys Pro Pro Pro Gln
                805                 810                 815
```

```
Ile Pro Asn Ser His Asn Met Thr Thr Thr Leu Asn Tyr Arg Asp Gly
            820                 825                 830

Glu Lys Val Ser Val Leu Cys Gln Glu Asn Tyr Leu Ile Gln Glu Gly
            835                 840                 845

Glu Glu Ile Thr Cys Lys Asp Gly Arg Trp Gln Ser Ile Pro Leu Cys
850                 855                 860

Val Glu Lys Ile Pro Cys Ser Gln Pro Pro Gln Ile Glu His Gly Thr
865                 870                 875                 880

Ile Asn Ser Ser Arg Ser Ser Gln Glu Ser Tyr Ala His Gly Thr Lys
            885                 890                 895

Leu Ser Tyr Thr Cys Glu Gly Gly Phe Arg Ile Ser Glu Glu Asn Glu
            900                 905                 910

Thr Thr Cys Tyr Met Gly Lys Trp Ser Ser Pro Pro Gln Cys Glu Gly
            915                 920                 925

Leu Pro Cys Lys Ser Pro Pro Glu Ile Ser His Gly Val Val Ala His
            930                 935                 940

Met Ser Asp Ser Tyr Gln Tyr Gly Glu Glu Val Thr Tyr Lys Cys Phe
945                 950                 955                 960

Glu Gly Phe Gly Ile Asp Gly Pro Ala Ile Ala Lys Cys Leu Gly Glu
                965                 970                 975

Lys Trp Ser His Pro Pro Ser Cys Ile Lys Thr Asp Cys Leu Ser Leu
            980                 985                 990

Pro Ser Phe Glu Asn Ala Ile Pro  Met Gly Glu Lys Lys  Asp Val Tyr
            995                 1000                1005

Lys Ala Gly Glu Gln Val Thr  Tyr Thr Cys Ala Thr  Tyr Tyr Lys
     1010                1015                1020

Met Asp Gly Ala Ser Asn Val  Thr Cys Ile Asn Ser  Arg Trp Thr
     1025                1030                1035

Gly Arg Pro Thr Cys Arg Asp  Thr Ser Cys Val Asn  Pro Pro Thr
     1040                1045                1050

Val Gln Asn Ala Tyr Ile Val  Ser Arg Gln Met Ser  Lys Tyr Pro
     1055                1060                1065

Ser Gly Glu Arg Val Arg Tyr  Gln Cys Arg Ser Pro  Tyr Glu Met
     1070                1075                1080

Phe Gly Asp Glu Glu Val Met  Cys Leu Asn Gly Asn  Trp Thr Glu
     1085                1090                1095

Pro Pro Gln Cys Lys Asp Ser  Thr Gly Lys Cys Gly  Pro Pro Pro
     1100                1105                1110

Pro Ile Asp Asn Gly Asp Ile  Thr Ser Phe Pro Leu  Ser Val Tyr
     1115                1120                1125

Ala Pro Ala Ser Ser Val Glu  Tyr Gln Cys Gln Asn  Leu Tyr Gln
     1130                1135                1140

Leu Glu Gly Asn Lys Arg Ile  Thr Cys Arg Asn Gly  Gln Trp Ser
     1145                1150                1155

Glu Pro Pro Lys Cys Leu His  Pro Cys Val Ile Ser  Arg Glu Ile
     1160                1165                1170

Met Glu Asn Tyr Asn Ile Ala  Leu Arg Trp Thr Ala  Lys Gln Lys
     1175                1180                1185

Leu Tyr Ser Arg Thr Gly Glu  Ser Val Glu Phe Val  Cys Lys Arg
     1190                1195                1200

Gly Tyr Arg Leu Ser Ser Arg  Ser His Thr Leu Arg  Thr Thr Cys
     1205                1210                1215

Trp Asp Gly Lys Leu Glu Tyr  Pro Thr Cys Ala Lys  Arg
```

<210> SEQ ID NO 5
<211> LENGTH: 565
<212> TYPE: PRT
<213> ORGANISM: Homo Sapiens

<400> SEQUENCE: 5

Lys Val Thr Tyr Thr Ser Gln Glu Asp Leu Val Glu Lys Lys Cys Leu
1               5                   10                  15

Ala Lys Lys Tyr Thr His Leu Ser Cys Asp Lys Val Phe Cys Gln Pro
            20                  25                  30

Trp Gln Arg Cys Ile Glu Gly Thr Cys Val Cys Lys Leu Pro Tyr Gln
        35                  40                  45

Cys Pro Lys Asn Gly Thr Ala Val Cys Ala Thr Asn Arg Arg Ser Phe
    50                  55                  60

Pro Thr Tyr Cys Gln Gln Lys Ser Leu Glu Cys Leu His Pro Gly Thr
65                  70                  75                  80

Lys Phe Leu Asn Asn Gly Thr Cys Thr Ala Glu Gly Lys Phe Ser Val
                85                  90                  95

Ser Leu Lys His Gly Asn Thr Asp Ser Glu Gly Ile Val Glu Val Lys
            100                 105                 110

Leu Val Asp Gln Asp Lys Thr Met Phe Ile Cys Lys Ser Ser Trp Ser
        115                 120                 125

Met Arg Glu Ala Asn Val Ala Cys Leu Asp Leu Gly Phe Gln Gln Gly
    130                 135                 140

Ala Asp Thr Gln Arg Arg Phe Lys Leu Ser Asp Leu Ser Ile Asn Ser
145                 150                 155                 160

Thr Glu Cys Leu His Val His Cys Arg Gly Leu Glu Thr Ser Leu Ala
                165                 170                 175

Glu Cys Thr Phe Thr Lys Arg Arg Thr Met Gly Tyr Gln Asp Phe Ala
            180                 185                 190

Asp Val Val Cys Tyr Thr Gln Lys Ala Asp Ser Pro Met Asp Asp Phe
        195                 200                 205

Phe Gln Cys Val Asn Gly Lys Tyr Ile Ser Gln Met Lys Ala Cys Asp
    210                 215                 220

Gly Ile Asn Asp Cys Gly Asp Gln Ser Asp Glu Leu Cys Cys Lys Ala
225                 230                 235                 240

Cys Gln Gly Lys Gly Phe His Cys Lys Ser Gly Val Cys Ile Pro Ser
                245                 250                 255

Gln Tyr Gln Cys Asn Gly Glu Val Asp Cys Ile Thr Gly Glu Asp Glu
            260                 265                 270

Val Gly Cys Ala Gly Phe Ala Ser Val Thr Gln Glu Glu Thr Glu Ile
        275                 280                 285

Leu Thr Ala Asp Met Asp Ala Glu Arg Arg Ile Lys Ser Leu Leu
    290                 295                 300

Pro Lys Leu Ser Cys Gly Val Lys Asn Arg Met His Ile Arg Arg Lys
305                 310                 315                 320

Arg Ile Val Gly Gly Lys Arg Ala Gln Leu Gly Asp Leu Pro Trp Gln
                325                 330                 335

Val Ala Ile Lys Asp Ala Ser Gly Ile Thr Cys Gly Gly Ile Tyr Ile
            340                 345                 350

Gly Gly Cys Trp Ile Leu Thr Ala Ala His Cys Leu Arg Ala Ser Lys
        355                 360                 365

```
Thr His Arg Tyr Gln Ile Trp Thr Val Val Asp Trp Ile His Pro
    370                 375                 380
Asp Leu Lys Arg Ile Val Ile Glu Tyr Val Asp Arg Ile Ile Phe His
385                 390                 395                 400
Glu Asn Tyr Asn Ala Gly Thr Tyr Gln Asn Asp Ile Ala Leu Ile Glu
                405                 410                 415
Met Lys Lys Asp Gly Asn Lys Asp Cys Glu Leu Pro Arg Ser Ile
                420                 425                 430
Pro Ala Cys Val Pro Trp Ser Pro Tyr Leu Phe Gln Pro Asn Asp Thr
                435                 440                 445
Cys Ile Val Ser Gly Trp Gly Arg Glu Lys Asp Asn Glu Arg Val Phe
    450                 455                 460
Ser Leu Gln Trp Gly Glu Val Lys Leu Ile Ser Asn Cys Ser Lys Phe
465                 470                 475                 480
Tyr Gly Asn Arg Phe Tyr Glu Lys Glu Met Glu Cys Ala Gly Thr Tyr
                485                 490                 495
Asp Gly Ser Ile Asp Ala Cys Lys Gly Asp Ser Gly Gly Pro Leu Val
                500                 505                 510
Cys Met Asp Ala Asn Asn Val Thr Tyr Val Trp Gly Val Val Ser Trp
    515                 520                 525
Gly Glu Asn Cys Gly Lys Pro Glu Phe Pro Gly Val Tyr Thr Lys Val
    530                 535                 540
Ala Asn Tyr Phe Asp Trp Ile Ser Tyr His Val Gly Arg Pro Phe Ile
545                 550                 555                 560
Ser Gln Tyr Asn Val
                565
```

<210> SEQ ID NO 6
<211> LENGTH: 6
<212> TYPE: PRT
<213> ORGANISM: Artificial Sequence
<220> FEATURE:
<223> OTHER INFORMATION: Linker sequence

<400> SEQUENCE: 6

```
Gly Gly Ser Ser Gly Gly
1               5
```

<210> SEQ ID NO 7
<211> LENGTH: 585
<212> TYPE: PRT
<213> ORGANISM: Homo Sapiens

<400> SEQUENCE: 7

```
Asp Ala His Lys Ser Glu Val Ala His Arg Phe Lys Asp Leu Gly Glu
1               5                   10                  15
Glu Asn Phe Lys Ala Leu Val Leu Ile Ala Phe Ala Gln Tyr Leu Gln
                20                  25                  30
Gln Cys Pro Phe Glu Asp His Val Lys Leu Val Asn Glu Val Thr Glu
                35                  40                  45
Phe Ala Lys Thr Cys Val Ala Asp Glu Ser Ala Glu Asn Cys Asp Lys
    50                  55                  60
Ser Leu His Thr Leu Phe Gly Asp Lys Leu Cys Thr Val Ala Thr Leu
65                  70                  75                  80
Arg Glu Thr Tyr Gly Glu Met Ala Asp Cys Cys Ala Lys Gln Glu Pro
                85                  90                  95
Glu Arg Asn Glu Cys Phe Leu Gln His Lys Asp Asp Asn Pro Asn Leu
```

-continued

```
                100               105                110
Pro Arg Leu Val Arg Pro Glu Val Asp Val Met Cys Thr Ala Phe His
            115                120                125
Asp Asn Glu Glu Thr Phe Leu Lys Lys Tyr Leu Tyr Glu Ile Ala Arg
        130                135                140
Arg His Pro Tyr Phe Tyr Ala Pro Glu Leu Leu Phe Phe Ala Lys Arg
145                150                155                160
Tyr Lys Ala Ala Phe Thr Glu Cys Cys Gln Ala Ala Asp Lys Ala Ala
                165                170                175
Cys Leu Leu Pro Lys Leu Asp Glu Leu Arg Asp Glu Gly Lys Ala Ser
            180                185                190
Ser Ala Lys Gln Arg Leu Lys Cys Ala Ser Leu Gln Lys Phe Gly Glu
        195                200                205
Arg Ala Phe Lys Ala Trp Ala Val Ala Arg Leu Ser Gln Arg Phe Pro
    210                215                220
Lys Ala Glu Phe Ala Glu Val Ser Lys Leu Val Thr Asp Leu Thr Lys
225                230                235                240
Val His Thr Glu Cys Cys His Gly Asp Leu Leu Glu Cys Ala Asp Asp
                245                250                255
Arg Ala Asp Leu Ala Lys Tyr Ile Cys Glu Asn Gln Asp Ser Ile Ser
            260                265                270
Ser Lys Leu Lys Glu Cys Cys Glu Lys Pro Leu Leu Glu Lys Ser His
        275                280                285
Cys Ile Ala Glu Val Glu Asn Asp Glu Met Pro Ala Asp Leu Pro Ser
    290                295                300
Leu Ala Ala Asp Phe Val Glu Ser Lys Asp Val Cys Lys Asn Tyr Ala
305                310                315                320
Glu Ala Lys Asp Val Phe Leu Gly Met Phe Leu Tyr Glu Tyr Ala Arg
                325                330                335
Arg His Pro Asp Tyr Ser Val Val Leu Leu Leu Arg Leu Ala Lys Thr
            340                345                350
Tyr Glu Thr Thr Leu Glu Lys Cys Cys Ala Ala Ala Asp Pro His Glu
        355                360                365
Cys Tyr Ala Lys Val Phe Asp Glu Phe Lys Pro Leu Val Glu Glu Pro
    370                375                380
Gln Asn Leu Ile Lys Gln Asn Cys Glu Leu Phe Glu Gln Leu Gly Glu
385                390                395                400
Tyr Lys Phe Gln Asn Ala Leu Leu Val Arg Tyr Thr Lys Lys Val Pro
                405                410                415
Gln Val Ser Thr Pro Thr Leu Val Glu Val Ser Arg Asn Leu Gly Lys
            420                425                430
Val Gly Ser Lys Cys Cys Lys His Pro Glu Ala Lys Arg Met Pro Cys
        435                440                445
Ala Glu Asp Tyr Leu Ser Val Val Leu Asn Gln Leu Cys Val Leu His
    450                455                460
Glu Lys Thr Pro Val Ser Asp Arg Val Thr Lys Cys Cys Thr Glu Ser
465                470                475                480
Leu Val Asn Arg Arg Pro Cys Phe Ser Ala Leu Glu Val Asp Glu Thr
                485                490                495
Tyr Val Pro Lys Glu Phe Asn Ala Glu Thr Phe Thr Phe His Ala Asp
            500                505                510
Ile Cys Thr Leu Ser Glu Lys Glu Arg Gln Ile Lys Lys Gln Thr Ala
        515                520                525
```

```
Leu Val Glu Leu Val Lys His Lys Pro Lys Ala Thr Lys Glu Gln Leu
            530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585

<210> SEQ ID NO 8
<211> LENGTH: 415
<212> TYPE: PRT
<213> ORGANISM: Homo Sapiens

<400> SEQUENCE: 8

Met Arg Leu Leu Ala Lys Ile Ile Cys Leu Met Leu Trp Ala Ile Cys
1               5                   10                  15

Val Ala Glu Asp Cys Asn Glu Leu Pro Pro Arg Arg Asn Thr Glu Ile
            20                  25                  30

Leu Thr Gly Ser Trp Ser Asp Gln Thr Tyr Pro Glu Gly Thr Gln Ala
        35                  40                  45

Ile Tyr Lys Cys Arg Pro Gly Tyr Arg Ser Leu Gly Asn Ile Ile Met
    50                  55                  60

Val Cys Arg Lys Gly Glu Trp Val Ala Leu Asn Pro Leu Arg Lys Cys
65                  70                  75                  80

Gln Lys Arg Pro Cys Gly His Pro Gly Asp Thr Pro Phe Gly Thr Phe
                85                  90                  95

Thr Leu Thr Gly Gly Asn Val Phe Glu Tyr Gly Val Lys Ala Val Tyr
            100                 105                 110

Thr Cys Asn Glu Gly Tyr Gln Leu Leu Gly Glu Ile Asn Tyr Arg Glu
        115                 120                 125

Cys Asp Thr Asp Gly Trp Thr Asn Asp Ile Pro Ile Cys Glu Val Val
    130                 135                 140

Lys Cys Leu Pro Val Thr Ala Pro Glu Asn Gly Lys Ile Val Ser Ser
145                 150                 155                 160

Ala Met Glu Pro Asp Arg Glu Tyr His Phe Gly Gln Ala Val Arg Phe
                165                 170                 175

Val Cys Asn Ser Gly Tyr Lys Ile Glu Gly Asp Glu Glu Met His Cys
            180                 185                 190

Ser Asp Asp Gly Phe Trp Ser Lys Glu Lys Pro Lys Cys Val Glu Ile
        195                 200                 205

Ser Cys Lys Ser Pro Asp Val Ile Asn Gly Ser Pro Ile Ser Gln Lys
    210                 215                 220

Ile Ile Tyr Lys Glu Asn Glu Arg Phe Gln Tyr Lys Cys Asn Met Gly
225                 230                 235                 240

Tyr Glu Tyr Ser Glu Arg Gly Asp Ala Val Cys Thr Glu Ser Gly Trp
                245                 250                 255

Arg Pro Leu Pro Ser Cys Glu Glu Ala Gly Gly Gly Gly Gly Gly Gly
            260                 265                 270

Gly Gly Gly Gly Gly Lys Cys Gly Pro Pro Pro Ile Asp Asn
        275                 280                 285       Asn

Gly Asp Ile Thr Ser Phe Pro Leu Ser Val Tyr Ala Pro Ala Ser Ser
    290                 295                 300

Val Glu Tyr Gln Cys Gln Asn Leu Tyr Gln Leu Glu Gly Asn Lys Arg
```

```
305                 310                 315                 320
Ile Thr Cys Arg Asn Gly Gln Trp Ser Glu Pro Pro Lys Cys Leu His
                325                 330                 335

Pro Cys Val Ile Ser Arg Glu Ile Met Glu Asn Tyr Asn Ile Ala Leu
                340                 345                 350

Arg Trp Thr Ala Lys Gln Lys Leu Tyr Ser Arg Thr Gly Glu Ser Val
                355                 360                 365

Glu Phe Val Cys Lys Arg Gly Tyr Arg Leu Ser Ser Arg Ser His Thr
            370                 375                 380

Leu Arg Thr Thr Cys Trp Asp Gly Lys Leu Glu Tyr Pro Thr Cys Ala
385                 390                 395                 400

Lys Arg Glu Asn Leu Tyr Phe Gln Gly His His His His His His
                405                 410                 415

<210> SEQ ID NO 9
<211> LENGTH: 10
<212> TYPE: PRT
<213> ORGANISM: Homo Sapiens

<400> SEQUENCE: 9

Arg Glu Lys Asp Asn Glu Arg Val Phe Ser
1               5                   10

<210> SEQ ID NO 10
<211> LENGTH: 12
<212> TYPE: PRT
<213> ORGANISM: Homo Sapiens

<400> SEQUENCE: 10

Asn Thr Ala Ser Ser Gly Ala Asp Tyr Pro Asp Glu
1               5                   10

<210> SEQ ID NO 11
<211> LENGTH: 10
<212> TYPE: PRT
<213> ORGANISM: Homo Sapiens

<400> SEQUENCE: 11

Arg Gly Lys Asp Asn Gln Lys Val Tyr Ser
1               5                   10

<210> SEQ ID NO 12
<211> LENGTH: 260
<212> TYPE: PRT
<213> ORGANISM: Homo Sapiens

<400> SEQUENCE: 12

Lys Leu Ser Cys Gly Val Lys Asn Arg Met His Ile Arg Arg Lys Arg
1               5                   10                  15

Ile Val Gly Gly Lys Arg Ala Gln Leu Gly Asp Leu Pro Trp Gln Val
                20                  25                  30

Ala Ile Lys Asp Ala Ser Gly Ile Thr Cys Gly Gly Ile Tyr Ile Gly
                35                  40                  45

Gly Cys Trp Ile Leu Thr Ala Ala His Cys Leu Arg Ala Ser Lys Thr
            50                  55                  60

His Arg Tyr Gln Ile Trp Thr Thr Val Val Asp Trp Ile His Pro Asp
65                  70                  75                  80

Leu Lys Arg Ile Val Ile Glu Tyr Val Asp Arg Ile Ile Phe His Glu
                85                  90                  95
```

```
Asn Tyr Asn Ala Gly Thr Tyr Gln Asn Asp Ile Ala Leu Ile Glu Met
            100                 105                 110
Lys Lys Asp Gly Asn Lys Lys Asp Cys Glu Leu Pro Arg Ser Ile Pro
        115                 120                 125
Ala Cys Val Pro Trp Ser Pro Tyr Leu Phe Gln Pro Asn Asp Thr Cys
    130                 135                 140
Ile Val Ser Gly Trp Gly Arg Glu Lys Asp Asn Glu Arg Val Phe Ser
145                 150                 155                 160
Leu Gln Trp Gly Glu Val Lys Leu Ile Ser Asn Cys Ser Lys Phe Tyr
                165                 170                 175
Gly Asn Arg Phe Tyr Glu Lys Glu Met Glu Cys Ala Gly Thr Tyr Asp
            180                 185                 190
Gly Ser Ile Asp Ala Cys Lys Gly Asp Ser Gly Gly Pro Leu Val Cys
        195                 200                 205
Met Asp Ala Asn Asn Val Thr Tyr Val Trp Gly Val Val Ser Trp Gly
    210                 215                 220
Glu Asn Cys Gly Lys Pro Glu Phe Pro Gly Val Tyr Thr Lys Val Ala
225                 230                 235                 240
Asn Tyr Phe Asp Trp Ile Ser Tyr His Val Gly Arg Pro Phe Ile Ser
                245                 250                 255
Gln Tyr Asn Val
            260

<210> SEQ ID NO 13
<211> LENGTH: 7
<212> TYPE: PRT
<213> ORGANISM: Homo Sapiens

<400> SEQUENCE: 13

Met Asp Ala Asn Asn Val Thr
1               5

<210> SEQ ID NO 14
<211> LENGTH: 8
<212> TYPE: PRT
<213> ORGANISM: Homo Sapiens

<400> SEQUENCE: 14

Pro Phe Ile Ser Gln Tyr Asn Val
1               5

<210> SEQ ID NO 15
<211> LENGTH: 4
<212> TYPE: PRT
<213> ORGANISM: Homo Sapiens

<400> SEQUENCE: 15

Asp Gly Asn Lys
1

<210> SEQ ID NO 16
<211> LENGTH: 1135
<212> TYPE: PRT
<213> ORGANISM: Homo Sapiens

<400> SEQUENCE: 16

Lys Val Thr Tyr Thr Ser Gln Glu Asp Leu Val Glu Lys Lys Cys Leu
1               5                   10                  15
Ala Lys Lys Tyr Thr His Leu Ser Cys Asp Lys Val Phe Cys Gln Pro
            20                  25                  30
```

-continued

```
Trp Gln Arg Cys Ile Glu Gly Thr Cys Val Cys Lys Leu Pro Tyr Gln
         35                  40                  45
Cys Pro Lys Asn Gly Thr Ala Val Cys Ala Thr Asn Arg Arg Ser Phe
     50                  55                  60
Pro Thr Tyr Cys Gln Gln Lys Ser Leu Glu Cys Leu His Pro Gly Thr
 65                  70                  75                  80
Lys Phe Leu Asn Asn Gly Thr Cys Thr Ala Glu Gly Lys Phe Ser Val
                 85                  90                  95
Ser Leu Lys His Gly Asn Thr Asp Ser Glu Gly Ile Val Glu Val Lys
                100                 105                 110
Leu Val Asp Gln Asp Lys Thr Met Phe Ile Cys Lys Ser Ser Trp Ser
                115                 120                 125
Met Arg Glu Ala Asn Val Ala Cys Leu Asp Leu Gly Phe Gln Gln Gly
            130                 135                 140
Ala Asp Thr Gln Arg Arg Phe Lys Leu Ser Asp Leu Ser Ile Asn Ser
145                 150                 155                 160
Thr Glu Cys Leu His Val His Cys Arg Gly Leu Glu Thr Ser Leu Ala
                165                 170                 175
Glu Cys Thr Phe Thr Lys Arg Arg Thr Met Gly Tyr Gln Asp Phe Ala
            180                 185                 190
Asp Val Val Cys Tyr Thr Gln Lys Ala Asp Ser Pro Met Asp Asp Phe
            195                 200                 205
Phe Gln Cys Val Asn Gly Lys Tyr Ile Ser Gln Met Lys Ala Cys Asp
    210                 215                 220
Gly Ile Asn Asp Cys Gly Asp Gln Ser Asp Glu Leu Cys Cys Lys Ala
225                 230                 235                 240
Cys Gln Gly Lys Gly Phe His Cys Lys Ser Gly Val Cys Ile Pro Ser
                245                 250                 255
Gln Tyr Gln Cys Asn Gly Glu Val Asp Cys Ile Thr Gly Glu Asp Glu
            260                 265                 270
Val Gly Cys Ala Gly Phe Ala Ser Val Thr Gln Glu Glu Thr Glu Ile
        275                 280                 285
Leu Thr Ala Asp Met Asp Ala Glu Arg Arg Ile Lys Ser Leu Leu
    290                 295                 300
Pro Lys Leu Ser Cys Gly Val Lys Asn Arg Met His Ile Arg Arg Lys
305                 310                 315                 320
Arg Ile Val Gly Gly Lys Arg Ala Gln Leu Gly Asp Leu Pro Trp Gln
                325                 330                 335
Val Ala Ile Lys Asp Ala Ser Gly Ile Thr Cys Gly Gly Ile Tyr Ile
                340                 345                 350
Gly Gly Cys Trp Ile Leu Thr Ala Ala His Cys Leu Arg Ala Ser Lys
            355                 360                 365
Thr His Arg Tyr Gln Ile Trp Thr Thr Val Val Asp Trp Ile His Pro
    370                 375                 380
Asp Leu Lys Arg Ile Val Ile Glu Tyr Val Asp Arg Ile Ile Phe His
385                 390                 395                 400
Glu Asn Tyr Asn Ala Gly Thr Tyr Gln Asn Asp Ile Ala Leu Ile Glu
                405                 410                 415
Met Lys Lys Asp Gly Asn Lys Lys Asp Cys Glu Leu Pro Arg Ser Ile
                420                 425                 430
Pro Ala Cys Val Pro Trp Ser Pro Tyr Leu Phe Gln Pro Asn Asp Thr
            435                 440                 445
```

-continued

Cys Ile Val Ser Gly Trp Gly Arg Glu Lys Asp Asn Glu Arg Val Phe
450                 455                 460

Ser Leu Gln Trp Gly Glu Val Lys Leu Ile Ser Asn Cys Ser Lys Phe
465                 470                 475                 480

Tyr Gly Asn Arg Phe Tyr Glu Lys Glu Met Glu Cys Ala Gly Thr Tyr
            485                 490                 495

Asp Gly Ser Ile Asp Ala Cys Lys Gly Asp Ser Gly Gly Pro Leu Val
            500                 505                 510

Cys Met Asp Ala Asn Asn Val Thr Tyr Val Trp Gly Val Val Ser Trp
            515                 520                 525

Gly Glu Asn Cys Gly Lys Pro Glu Phe Pro Gly Val Tyr Thr Lys Val
530                 535                 540

Ala Asn Tyr Phe Asp Trp Ile Ser Tyr His Val Gly Arg Pro Phe Ile
545                 550                 555                 560

Ser Gln Tyr Asn Val Gly Ser Gly Gly Lys Val Thr Tyr Thr Ser
                565                 570                 575

Gln Glu Asp Leu Val Glu Lys Lys Cys Leu Ala Lys Lys Tyr Thr His
            580                 585                 590

Leu Ser Cys Asp Lys Val Phe Cys Gln Pro Trp Gln Arg Cys Ile Glu
            595                 600                 605

Gly Thr Cys Val Cys Lys Leu Pro Tyr Gln Cys Pro Lys Asn Gly Thr
            610                 615                 620

Ala Val Cys Ala Thr Asn Arg Arg Ser Phe Pro Thr Tyr Cys Gln Gln
625                 630                 635                 640

Lys Ser Leu Glu Cys Leu His Pro Gly Thr Lys Phe Leu Asn Asn Gly
            645                 650                 655

Thr Cys Thr Ala Glu Gly Lys Phe Ser Val Ser Leu Lys His Gly Asn
            660                 665                 670

Thr Asp Ser Glu Gly Ile Val Glu Val Lys Leu Val Asp Gln Asp Lys
            675                 680                 685

Thr Met Phe Ile Cys Lys Ser Ser Trp Ser Met Arg Glu Ala Asn Val
            690                 695                 700

Ala Cys Leu Asp Leu Gly Phe Gln Gln Gly Ala Asp Thr Gln Arg Arg
705                 710                 715                 720

Phe Lys Leu Ser Asp Leu Ser Ile Asn Ser Thr Glu Cys Leu His Val
            725                 730                 735

His Cys Arg Gly Leu Glu Thr Ser Leu Ala Glu Cys Thr Phe Thr Lys
            740                 745                 750

Arg Arg Thr Met Gly Tyr Gln Asp Phe Ala Asp Val Val Cys Tyr Thr
            755                 760                 765

Gln Lys Ala Asp Ser Pro Met Asp Asp Phe Phe Gln Cys Val Asn Gly
770                 775                 780

Lys Tyr Ile Ser Gln Met Lys Ala Cys Asp Gly Ile Asn Asp Cys Gly
785                 790                 795                 800

Asp Gln Ser Asp Glu Leu Cys Cys Lys Ala Cys Gln Gly Lys Gly Phe
            805                 810                 815

His Cys Lys Ser Gly Val Cys Ile Pro Ser Gln Tyr Gln Cys Asn Gly
            820                 825                 830

Glu Val Asp Cys Ile Thr Gly Glu Asp Glu Val Gly Cys Ala Gly Phe
            835                 840                 845

Ala Ser Val Thr Gln Glu Glu Thr Glu Ile Leu Thr Ala Asp Met Asp
850                 855                 860

Ala Glu Arg Arg Arg Ile Lys Ser Leu Leu Pro Lys Leu Ser Cys Gly

```
                    865                 870                 875                 880
Val Lys Asn Arg Met His Ile Arg Arg Lys Arg Ile Val Gly Gly Lys
                        885                 890                 895

Arg Ala Gln Leu Gly Asp Leu Pro Trp Gln Val Ala Ile Lys Asp Ala
            900                 905                 910

Ser Gly Ile Thr Cys Gly Gly Ile Tyr Ile Gly Gly Cys Trp Ile Leu
            915                 920                 925

Thr Ala Ala His Cys Leu Arg Ala Ser Lys Thr His Arg Tyr Gln Ile
        930                 935                 940

Trp Thr Thr Val Val Asp Trp Ile His Pro Asp Leu Lys Arg Ile Val
945                 950                 955                 960

Ile Glu Tyr Val Asp Arg Ile Ile Phe His Glu Asn Tyr Asn Ala Gly
                965                 970                 975

Thr Tyr Gln Asn Asp Ile Ala Leu Ile Glu Met Lys Lys Asp Gly Asn
            980                 985                 990

Lys Lys Asp Cys Glu Leu Pro Arg  Ser Ile Pro Ala Cys  Val Pro Trp
        995                 1000                1005

Ser Pro Tyr Leu Phe Gln Pro  Asn Asp Thr Cys Ile  Val Ser Gly
    1010                1015                1020

Trp Gly Arg Glu Lys Asp Asn  Glu Arg Val Phe Ser  Leu Gln Trp
    1025                1030                1035

Gly Glu Val Lys Leu Ile Ser  Asn Cys Ser Lys Phe  Tyr Gly Asn
    1040                1045                1050

Arg Phe Tyr Glu Lys Glu Met  Glu Cys Ala Gly Thr  Tyr Asp Gly
    1055                1060                1065

Ser Ile Asp Ala Cys Lys Gly  Asp Ser Gly Gly Pro  Leu Val Cys
    1070                1075                1080

Met Asp Ala Asn Asn Val Thr  Tyr Val Trp Gly Val  Val Ser Trp
    1085                1090                1095

Gly Glu Asn Cys Gly Lys Pro  Glu Phe Pro Gly Val  Tyr Thr Lys
    1100                1105                1110

Val Ala Asn Tyr Phe Asp Trp  Ile Ser Tyr His Val  Gly Arg Pro
    1115                1120                1125

Phe Ile Ser Gln Tyr Asn Val
    1130                1135

<210> SEQ ID NO 17
<211> LENGTH: 575
<212> TYPE: PRT
<213> ORGANISM: Homo Sapiens

<400> SEQUENCE: 17

Val Lys Asn Arg Met His Ile Arg Arg Lys Arg Ile Val Gly Gly Lys
1               5                   10                  15

Arg Ala Gln Leu Gly Asp Leu Pro Trp Gln Val Ala Ile Lys Asp Ala
            20                  25                  30

Ser Gly Ile Thr Cys Gly Gly Ile Tyr Ile Gly Gly Cys Trp Ile Leu
            35                  40                  45

Thr Ala Ala His Cys Leu Arg Ala Ser Lys Thr His Arg Tyr Gln Ile
        50                  55                  60

Trp Thr Thr Val Val Asp Trp Ile His Pro Asp Leu Lys Arg Ile Val
65                  70                  75                  80

Ile Glu Tyr Val Asp Arg Ile Ile Phe His Glu Asn Tyr Asn Ala Gly
                85                  90                  95
```

```
Thr Tyr Gln Asn Asp Ile Ala Leu Ile Glu Met Lys Lys Asp Gly Asn
                100                 105                 110

Lys Lys Asp Cys Glu Leu Pro Arg Ser Ile Pro Ala Cys Val Pro Trp
            115                 120                 125

Ser Pro Tyr Leu Phe Gln Pro Asn Asp Thr Cys Ile Val Ser Gly Trp
130                 135                 140

Gly Arg Glu Lys Asp Asn Glu Arg Val Phe Ser Leu Gln Trp Gly Glu
145                 150                 155                 160

Val Lys Leu Ile Ser Asn Cys Ser Lys Phe Tyr Gly Asn Arg Phe Tyr
                165                 170                 175

Glu Lys Glu Met Glu Cys Ala Gly Thr Tyr Asp Gly Ser Ile Asp Ala
            180                 185                 190

Cys Lys Gly Asp Ser Gly Gly Pro Leu Val Cys Met Asp Ala Asn Asn
        195                 200                 205

Val Thr Tyr Val Trp Gly Val Val Ser Trp Gly Glu Asn Cys Gly Lys
    210                 215                 220

Pro Glu Phe Pro Gly Val Tyr Thr Lys Val Ala Asn Tyr Phe Asp Trp
225                 230                 235                 240

Ile Ser Tyr His Val Gly Arg Pro Phe Ile Ser Gln Tyr Asn Val Gly
                245                 250                 255

Gly Gly Gly Gly Gly Gly Gly Lys Val Thr Tyr Thr Ser Gln
            260                 265                 270

Glu Asp Leu Val Glu Lys Lys Cys Leu Ala Lys Lys Tyr Thr His Leu
        275                 280                 285

Ser Cys Asp Lys Val Phe Cys Gln Pro Trp Gln Arg Cys Ile Glu Gly
    290                 295                 300

Thr Cys Val Cys Lys Leu Pro Tyr Gln Cys Pro Lys Asn Gly Thr Ala
305                 310                 315                 320

Val Cys Ala Thr Asn Arg Arg Ser Phe Pro Thr Tyr Cys Gln Gln Lys
                325                 330                 335

Ser Leu Glu Cys Leu His Pro Gly Thr Lys Phe Leu Asn Asn Gly Thr
            340                 345                 350

Cys Thr Ala Glu Gly Lys Phe Ser Val Ser Leu Lys His Gly Asn Thr
        355                 360                 365

Asp Ser Glu Gly Ile Val Glu Val Lys Leu Val Asp Gln Asp Lys Thr
    370                 375                 380

Met Phe Ile Cys Lys Ser Ser Trp Ser Met Arg Glu Ala Asn Val Ala
385                 390                 395                 400

Cys Leu Asp Leu Gly Phe Gln Gln Gly Ala Asp Thr Gln Arg Arg Phe
                405                 410                 415

Lys Leu Ser Asp Leu Ser Ile Asn Ser Thr Glu Cys Leu His Val His
            420                 425                 430

Cys Arg Gly Leu Glu Thr Ser Leu Ala Glu Cys Thr Phe Thr Lys Arg
        435                 440                 445

Arg Thr Met Gly Tyr Gln Asp Phe Ala Asp Val Val Cys Tyr Thr Gln
    450                 455                 460

Lys Ala Asp Ser Pro Met Asp Asp Phe Phe Gln Cys Val Asn Gly Lys
465                 470                 475                 480

Tyr Ile Ser Gln Met Lys Ala Cys Asp Gly Ile Asn Asp Cys Gly Asp
                485                 490                 495

Gln Ser Asp Glu Leu Cys Cys Lys Ala Cys Gln Gly Lys Gly Phe His
            500                 505                 510

Cys Lys Ser Gly Val Cys Ile Pro Ser Gln Tyr Gln Cys Asn Gly Glu
```

-continued

```
            515                 520                 525
Val Asp Cys Ile Thr Gly Glu Asp Glu Val Gly Cys Ala Gly Phe Ala
    530                 535                 540

Ser Val Thr Gln Glu Glu Thr Glu Ile Leu Thr Ala Asp Met Asp Ala
545                 550                 555                 560

Glu Arg Arg Arg Ile Lys Ser Leu Leu Pro Lys Leu Ser Cys Gly
                565                 570                 575

<210> SEQ ID NO 18
<211> LENGTH: 578
<212> TYPE: PRT
<213> ORGANISM: Homo Sapiens

<400> SEQUENCE: 18

Val Lys Asn Arg Met His Ile Arg Arg Lys Arg Ile Val Gly Gly Lys
1               5                   10                  15

Arg Ala Gln Leu Gly Asp Leu Pro Trp Gln Val Ala Ile Lys Asp Ala
                20                  25                  30

Ser Gly Ile Thr Cys Gly Gly Ile Tyr Ile Gly Gly Cys Trp Ile Leu
            35                  40                  45

Thr Ala Ala His Cys Leu Arg Ala Ser Lys Thr His Arg Tyr Gln Ile
    50                  55                  60

Trp Thr Thr Val Val Asp Trp Ile His Pro Asp Leu Lys Arg Ile Val
65                  70                  75                  80

Ile Glu Tyr Val Asp Arg Ile Ile Phe His Glu Asn Tyr Asn Ala Gly
                85                  90                  95

Thr Tyr Gln Asn Asp Ile Ala Leu Ile Glu Met Lys Lys Asp Gly Asn
            100                 105                 110

Lys Lys Asp Cys Glu Leu Pro Arg Ser Ile Pro Ala Cys Val Pro Trp
        115                 120                 125

Ser Pro Tyr Leu Phe Gln Pro Asn Asp Thr Cys Ile Val Ser Gly Trp
    130                 135                 140

Gly Arg Glu Lys Asp Asn Glu Arg Val Phe Ser Leu Gln Trp Gly Glu
145                 150                 155                 160

Val Lys Leu Ile Ser Asn Cys Ser Lys Phe Tyr Gly Asn Arg Phe Tyr
                165                 170                 175

Glu Lys Glu Met Glu Cys Ala Gly Thr Tyr Asp Gly Ser Ile Asp Ala
            180                 185                 190

Cys Lys Gly Asp Ser Gly Gly Pro Leu Val Cys Met Asp Ala Asn Asn
        195                 200                 205

Val Thr Tyr Val Trp Gly Val Val Ser Trp Gly Glu Asn Cys Gly Lys
    210                 215                 220

Pro Glu Phe Pro Gly Val Tyr Thr Lys Val Ala Asn Tyr Phe Asp Trp
225                 230                 235                 240

Ile Ser Tyr His Val Gly Arg Pro Phe Ile Ser Gln Tyr Asn Val Gly
                245                 250                 255

Gly Gly Gly Gly Gly Gly Gly Gly Gly Gly Lys Val Thr Tyr
            260                 265                 270

Thr Ser Gln Glu Asp Leu Val Glu Lys Lys Cys Leu Ala Lys Lys Tyr
        275                 280                 285

Thr His Leu Ser Cys Asp Lys Val Phe Cys Gln Pro Trp Gln Arg Cys
    290                 295                 300

Ile Glu Gly Thr Cys Val Cys Lys Leu Pro Tyr Gln Cys Pro Lys Asn
305                 310                 315                 320
```

```
Gly Thr Ala Val Cys Ala Thr Asn Arg Arg Ser Phe Pro Thr Tyr Cys
                325                 330                 335

Gln Gln Lys Ser Leu Glu Cys Leu His Pro Gly Thr Lys Phe Leu Asn
            340                 345                 350

Asn Gly Thr Cys Thr Ala Glu Gly Lys Phe Ser Val Ser Leu Lys His
            355                 360                 365

Gly Asn Thr Asp Ser Glu Gly Ile Val Glu Val Lys Leu Val Asp Gln
            370                 375                 380

Asp Lys Thr Met Phe Ile Cys Lys Ser Ser Trp Ser Met Arg Glu Ala
385                 390                 395                 400

Asn Val Ala Cys Leu Asp Leu Gly Phe Gln Gln Gly Ala Asp Thr Gln
            405                 410                 415

Arg Arg Phe Lys Leu Ser Asp Leu Ser Ile Asn Ser Thr Glu Cys Leu
            420                 425                 430

His Val His Cys Arg Gly Leu Glu Thr Ser Leu Ala Glu Cys Thr Phe
            435                 440                 445

Thr Lys Arg Arg Thr Met Gly Tyr Gln Asp Phe Ala Asp Val Val Cys
            450                 455                 460

Tyr Thr Gln Lys Ala Asp Ser Pro Met Asp Asp Phe Phe Gln Cys Val
465                 470                 475                 480

Asn Gly Lys Tyr Ile Ser Gln Met Lys Ala Cys Asp Gly Ile Asn Asp
            485                 490                 495

Cys Gly Asp Gln Ser Asp Glu Leu Cys Cys Lys Ala Cys Gln Gly Lys
            500                 505                 510

Gly Phe His Cys Lys Ser Gly Val Cys Ile Pro Ser Gln Tyr Gln Cys
            515                 520                 525

Asn Gly Glu Val Asp Cys Ile Thr Gly Glu Asp Glu Val Gly Cys Ala
            530                 535                 540

Gly Phe Ala Ser Val Thr Gln Glu Glu Thr Glu Ile Leu Thr Ala Asp
545                 550                 555                 560

Met Asp Ala Glu Arg Arg Arg Ile Lys Ser Leu Leu Pro Lys Leu Ser
                565                 570                 575

Cys Gly

<210> SEQ ID NO 19
<211> LENGTH: 575
<212> TYPE: PRT
<213> ORGANISM: Homo Sapiens

<400> SEQUENCE: 19

Val Lys Asn Arg Met His Ile Arg Arg Lys Arg Ile Val Gly Gly Lys
1               5                   10                  15

Arg Ala Gln Leu Gly Asp Leu Pro Trp Gln Val Ala Ile Lys Asp Ala
            20                  25                  30

Ser Gly Ile Thr Cys Gly Gly Ile Tyr Ile Gly Gly Cys Trp Ile Leu
            35                  40                  45

Thr Ala Ala His Cys Leu Arg Ala Ser Lys Thr His Arg Tyr Gln Ile
            50                  55                  60

Trp Thr Thr Val Val Asp Trp Ile His Pro Asp Leu Lys Arg Ile Val
65                  70                  75                  80

Ile Glu Tyr Val Asp Arg Ile Ile Phe His Glu Asn Tyr Asn Ala Gly
                85                  90                  95

Thr Tyr Gln Asn Asp Ile Ala Leu Ile Glu Met Lys Lys Asp Gly Asn
            100                 105                 110
```

```
Lys Lys Asp Cys Glu Leu Pro Arg Ser Ile Pro Ala Ser Val Pro Trp
            115                 120                 125

Ser Pro Tyr Leu Phe Gln Pro Asn Asp Thr Cys Ile Val Ser Gly Trp
        130                 135                 140

Gly Arg Glu Lys Asp Asn Glu Arg Val Phe Ser Leu Gln Trp Gly Glu
145                 150                 155                 160

Val Lys Leu Ile Ser Asn Cys Ser Lys Phe Tyr Gly Asn Arg Phe Tyr
                165                 170                 175

Glu Lys Glu Met Glu Cys Ala Gly Thr Tyr Asp Gly Ser Ile Asp Ala
            180                 185                 190

Cys Lys Gly Asp Ser Gly Gly Pro Leu Val Cys Met Asp Ala Asn Asn
            195                 200                 205

Val Thr Tyr Val Trp Gly Val Val Ser Trp Gly Glu Asn Cys Gly Lys
        210                 215                 220

Pro Glu Phe Pro Gly Val Tyr Thr Lys Val Ala Asn Tyr Phe Asp Trp
225                 230                 235                 240

Ile Ser Tyr His Val Gly Arg Pro Phe Ile Ser Gln Tyr Asn Val Gly
                245                 250                 255

Gly Gly Gly Gly Gly Gly Gly Gly Lys Val Thr Tyr Thr Ser Gln
            260                 265                 270

Glu Asp Leu Val Glu Lys Lys Cys Leu Ala Lys Lys Tyr Thr His Leu
        275                 280                 285

Ser Cys Asp Lys Val Phe Cys Gln Pro Trp Gln Arg Cys Ile Glu Gly
        290                 295                 300

Thr Cys Val Cys Lys Leu Pro Tyr Gln Cys Pro Lys Asn Gly Thr Ala
305                 310                 315                 320

Val Cys Ala Thr Asn Arg Arg Ser Phe Pro Thr Tyr Cys Gln Gln Lys
                325                 330                 335

Ser Leu Glu Cys Leu His Pro Gly Thr Lys Phe Leu Asn Asn Gly Thr
            340                 345                 350

Cys Thr Ala Glu Gly Lys Phe Ser Val Ser Leu Lys His Gly Asn Thr
            355                 360                 365

Asp Ser Glu Gly Ile Val Glu Val Lys Leu Val Asp Gln Asp Lys Thr
        370                 375                 380

Met Phe Ile Cys Lys Ser Ser Trp Ser Met Arg Glu Ala Asn Val Ala
385                 390                 395                 400

Cys Leu Asp Leu Gly Phe Gln Gln Gly Ala Asp Thr Gln Arg Arg Phe
                405                 410                 415

Lys Leu Ser Asp Leu Ser Ile Asn Ser Thr Glu Cys Leu His Val His
            420                 425                 430

Cys Arg Gly Leu Glu Thr Ser Leu Ala Glu Cys Thr Phe Thr Lys Arg
            435                 440                 445

Arg Thr Met Gly Tyr Gln Asp Phe Ala Asp Val Val Cys Tyr Thr Gln
        450                 455                 460

Lys Ala Asp Ser Pro Met Asp Asp Phe Phe Gln Cys Val Asn Gly Lys
465                 470                 475                 480

Tyr Ile Ser Gln Met Lys Ala Cys Asp Gly Ile Asn Asp Cys Gly Asp
                485                 490                 495

Gln Ser Asp Glu Leu Cys Cys Lys Ala Cys Gln Gly Lys Gly Phe His
            500                 505                 510

Cys Lys Ser Gly Val Cys Ile Pro Ser Gln Tyr Gln Cys Asn Gly Glu
            515                 520                 525

Val Asp Cys Ile Thr Gly Glu Asp Glu Val Gly Cys Ala Gly Phe Ala
```

```
                        530               535               540
Ser Val Thr Gln Glu Thr Glu Ile Leu Thr Ala Asp Met Asp Ala
545                         550               555               560

Glu Arg Arg Arg Ile Lys Ser Leu Leu Pro Lys Leu Ser Ser Gly
                        565               570               575

<210> SEQ ID NO 20
<211> LENGTH: 578
<212> TYPE: PRT
<213> ORGANISM: Homo Sapiens

<400> SEQUENCE: 20

Val Lys Asn Arg Met His Ile Arg Arg Lys Arg Ile Val Gly Gly Lys
1               5                   10                  15

Arg Ala Gln Leu Gly Asp Leu Pro Trp Gln Val Ala Ile Lys Asp Ala
                20                  25                  30

Ser Gly Ile Thr Cys Gly Gly Ile Tyr Ile Gly Gly Cys Trp Ile Leu
            35                  40                  45

Thr Ala Ala His Cys Leu Arg Ala Ser Lys Thr His Arg Tyr Gln Ile
        50                  55                  60

Trp Thr Thr Val Val Asp Trp Ile His Pro Asp Leu Lys Arg Ile Val
65                  70                  75                  80

Ile Glu Tyr Val Asp Arg Ile Ile Phe His Glu Asn Tyr Asn Ala Gly
                85                  90                  95

Thr Tyr Gln Asn Asp Ile Ala Leu Ile Glu Met Lys Lys Asp Gly Asn
            100                 105                 110

Lys Lys Asp Cys Glu Leu Pro Arg Ser Ile Pro Ala Ser Val Pro Trp
        115                 120                 125

Ser Pro Tyr Leu Phe Gln Pro Asn Asp Thr Cys Ile Val Ser Gly Trp
130                 135                 140

Gly Arg Glu Lys Asp Asn Glu Arg Val Phe Ser Leu Gln Trp Gly Glu
145                 150                 155                 160

Val Lys Leu Ile Ser Asn Cys Ser Lys Phe Tyr Gly Asn Arg Phe Tyr
                165                 170                 175

Glu Lys Glu Met Glu Cys Ala Gly Thr Tyr Asp Gly Ser Ile Asp Ala
            180                 185                 190

Cys Lys Gly Asp Ser Gly Gly Pro Leu Val Cys Met Asp Ala Asn Asn
        195                 200                 205

Val Thr Tyr Val Trp Gly Val Val Ser Trp Gly Glu Asn Cys Gly Lys
    210                 215                 220

Pro Glu Phe Pro Gly Val Tyr Thr Lys Val Ala Asn Tyr Phe Asp Trp
225                 230                 235                 240

Ile Ser Tyr His Val Gly Arg Pro Phe Ile Ser Gln Tyr Asn Val Gly
                245                 250                 255

Gly Gly Gly Gly Gly Gly Gly Gly Gly Gly Lys Val Thr Tyr
            260                 265                 270

Thr Ser Gln Glu Asp Leu Val Glu Lys Lys Cys Leu Ala Lys Lys Tyr
        275                 280                 285

Thr His Leu Ser Cys Asp Lys Val Phe Cys Gln Pro Trp Gln Arg Cys
    290                 295                 300

Ile Glu Gly Thr Cys Val Cys Lys Leu Pro Tyr Gln Cys Pro Lys Asn
305                 310                 315                 320

Gly Thr Ala Val Cys Ala Thr Asn Arg Arg Ser Phe Pro Thr Tyr Cys
                325                 330                 335
```

```
Gln Gln Lys Ser Leu Glu Cys Leu His Pro Gly Thr Lys Phe Leu Asn
                340                 345                 350

Asn Gly Thr Cys Thr Ala Glu Gly Lys Phe Ser Val Ser Leu Lys His
            355                 360                 365

Gly Asn Thr Asp Ser Glu Gly Ile Val Glu Val Lys Leu Val Asp Gln
        370                 375                 380

Asp Lys Thr Met Phe Ile Cys Lys Ser Ser Trp Ser Met Arg Glu Ala
385                 390                 395                 400

Asn Val Ala Cys Leu Asp Leu Gly Phe Gln Gln Gly Ala Asp Thr Gln
                405                 410                 415

Arg Arg Phe Lys Leu Ser Asp Leu Ser Ile Asn Ser Thr Glu Cys Leu
            420                 425                 430

His Val His Cys Arg Gly Leu Glu Thr Ser Leu Ala Glu Cys Thr Phe
        435                 440                 445

Thr Lys Arg Arg Thr Met Gly Tyr Gln Asp Phe Ala Asp Val Val Cys
    450                 455                 460

Tyr Thr Gln Lys Ala Asp Ser Pro Met Asp Asp Phe Phe Gln Cys Val
465                 470                 475                 480

Asn Gly Lys Tyr Ile Ser Gln Met Lys Ala Cys Asp Gly Ile Asn Asp
                485                 490                 495

Cys Gly Asp Gln Ser Asp Glu Leu Cys Cys Lys Ala Cys Gln Gly Lys
            500                 505                 510

Gly Phe His Cys Lys Ser Gly Val Cys Ile Pro Ser Gln Tyr Gln Cys
        515                 520                 525

Asn Gly Glu Val Asp Cys Ile Thr Gly Glu Asp Glu Val Gly Cys Ala
    530                 535                 540

Gly Phe Ala Ser Val Thr Gln Glu Glu Thr Glu Ile Leu Thr Ala Asp
545                 550                 555                 560

Met Asp Ala Glu Arg Arg Ile Lys Ser Leu Leu Pro Lys Leu Ser
                565                 570                 575

Ser Gly

<210> SEQ ID NO 21
<211> LENGTH: 1156
<212> TYPE: PRT
<213> ORGANISM: Homo Sapiens

<400> SEQUENCE: 21

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Cys Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
        50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125
```

```
Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
                180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
                260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
                340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
                420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
                500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
530                 535                 540

Lys Ala Val Met Asp Asp Phe Ala Ala Phe Val Glu Lys Cys Cys Lys
```

```
                                      -continued
545               550               555               560
Ala Asp Asp Lys Glu Thr Cys Phe Ala Glu Glu Gly Lys Lys Leu Val
              565               570               575

Ala Ala Ser Gln Ala Ala Leu Gly Leu Gly Gly Ser Ser Gly Gly Lys
              580               585               590

Val Thr Tyr Thr Ser Gln Glu Asp Leu Val Glu Lys Lys Cys Leu Ala
              595               600               605

Lys Lys Tyr Thr His Leu Ser Cys Asp Lys Val Phe Cys Gln Pro Trp
              610               615               620

Gln Arg Cys Ile Glu Gly Thr Cys Val Cys Lys Leu Pro Tyr Gln Cys
625               630               635               640

Pro Lys Asn Gly Thr Ala Val Cys Ala Thr Asn Arg Arg Ser Phe Pro
              645               650               655

Thr Tyr Cys Gln Gln Lys Ser Leu Glu Cys Leu His Pro Gly Thr Lys
              660               665               670

Phe Leu Asn Asn Gly Thr Cys Thr Ala Glu Gly Lys Phe Ser Val Ser
              675               680               685

Leu Lys His Gly Asn Thr Asp Ser Glu Gly Ile Val Glu Val Lys Leu
              690               695               700

Val Asp Gln Asp Lys Thr Met Phe Ile Cys Lys Ser Ser Trp Ser Met
705               710               715               720

Arg Glu Ala Asn Val Ala Cys Leu Asp Leu Gly Phe Gln Gln Gly Ala
              725               730               735

Asp Thr Gln Arg Arg Phe Lys Leu Ser Asp Leu Ser Ile Asn Ser Thr
              740               745               750

Glu Cys Leu His Val His Cys Arg Gly Leu Glu Thr Ser Leu Ala Glu
              755               760               765

Cys Thr Phe Thr Lys Arg Arg Thr Met Gly Tyr Gln Asp Phe Ala Asp
              770               775               780

Val Val Cys Tyr Thr Gln Lys Ala Asp Ser Pro Met Asp Asp Phe Phe
785               790               795               800

Gln Cys Val Asn Gly Lys Tyr Ile Ser Gln Met Lys Ala Cys Asp Gly
              805               810               815

Ile Asn Asp Cys Gly Asp Gln Ser Asp Glu Leu Cys Cys Lys Ala Cys
              820               825               830

Gln Gly Lys Gly Phe His Cys Lys Ser Gly Val Cys Ile Pro Ser Gln
              835               840               845

Tyr Gln Cys Asn Gly Glu Val Asp Cys Ile Thr Gly Glu Asp Glu Val
              850               855               860

Gly Cys Ala Gly Phe Ala Ser Val Thr Gln Glu Glu Thr Glu Ile Leu
865               870               875               880

Thr Ala Asp Met Asp Ala Glu Arg Arg Arg Ile Lys Ser Leu Leu Pro
              885               890               895

Lys Leu Ser Cys Gly Val Lys Asn Arg Met His Ile Arg Arg Lys Arg
              900               905               910

Ile Val Gly Gly Lys Arg Ala Gln Leu Gly Asp Leu Pro Trp Gln Val
              915               920               925

Ala Ile Lys Asp Ala Ser Gly Ile Thr Cys Gly Gly Ile Tyr Ile Gly
              930               935               940

Gly Cys Trp Ile Leu Thr Ala Ala His Cys Leu Arg Ala Ser Lys Thr
945               950               955               960

His Arg Tyr Gln Ile Trp Thr Thr Val Val Asp Trp Ile His Pro Asp
              965               970               975
```

Leu Lys Arg Ile Val Ile Glu Tyr Val Asp Arg Ile Ile Phe His Glu
            980                 985                 990

Asn Tyr Asn Ala Gly Thr Tyr Gln Asn Asp Ile Ala Leu Ile Glu Met
            995                 1000                1005

Lys Lys Asp Gly Asn Lys Lys Asp Cys Glu Leu Pro Arg Ser Ile
    1010                1015                1020

Pro Ala Cys Val Pro Trp Ser Pro Tyr Leu Phe Gln Pro Asn Asp
    1025                1030                1035

Thr Cys Ile Val Ser Gly Trp Gly Arg Glu Lys Asp Asn Glu Arg
    1040                1045                1050

Val Phe Ser Leu Gln Trp Gly Glu Val Lys Leu Ile Ser Asn Cys
    1055                1060                1065

Ser Lys Phe Tyr Gly Asn Arg Phe Tyr Glu Lys Glu Met Glu Cys
    1070                1075                1080

Ala Gly Thr Tyr Asp Gly Ser Ile Asp Ala Cys Lys Gly Asp Ser
    1085                1090                1095

Gly Gly Pro Leu Val Cys Met Asp Ala Asn Asn Val Thr Tyr Val
    1100                1105                1110

Trp Gly Val Val Ser Trp Gly Glu Asn Cys Gly Lys Pro Glu Phe
    1115                1120                1125

Pro Gly Val Tyr Thr Lys Val Ala Asn Tyr Phe Asp Trp Ile Ser
    1130                1135                1140

Tyr His Val Gly Arg Pro Phe Ile Ser Gln Tyr Asn Val
    1145                1150                1155

<210> SEQ ID NO 22
<211> LENGTH: 1376
<212> TYPE: PRT
<213> ORGANISM: Homo Sapiens

<400> SEQUENCE: 22

Met Glu Thr Asp Thr Leu Leu Leu Trp Val Leu Leu Leu Trp Val Pro
1               5                   10                  15

Gly Ser Thr Gly Asp Ala His Lys Ser Glu Val Ala His Arg Phe Lys
            20                  25                  30

Asp Leu Gly Glu Glu Asn Phe Lys Ala Leu Val Leu Ile Ala Phe Ala
        35                  40                  45

Gln Tyr Leu Gln Gln Cys Pro Phe Glu Asp His Val Lys Leu Val Asn
    50                  55                  60

Glu Val Thr Glu Phe Ala Lys Thr Cys Val Ala Asp Glu Ser Ala Glu
65                  70                  75                  80

Asn Cys Asp Lys Ser Leu His Thr Leu Phe Gly Asp Lys Leu Cys Thr
                85                  90                  95

Val Ala Thr Leu Arg Glu Thr Tyr Gly Glu Met Ala Asp Cys Cys Ala
            100                 105                 110

Lys Gln Glu Pro Glu Arg Asn Glu Cys Phe Leu Gln His Lys Asp Asp
        115                 120                 125

Asn Pro Asn Leu Pro Arg Leu Val Arg Pro Glu Val Asp Val Met Cys
    130                 135                 140

Thr Ala Phe His Asp Asn Glu Glu Thr Phe Leu Lys Lys Tyr Leu Tyr
145                 150                 155                 160

Glu Ile Ala Arg Arg His Pro Tyr Phe Tyr Ala Pro Glu Leu Leu Phe
                165                 170                 175

Phe Ala Lys Arg Tyr Lys Ala Ala Phe Thr Glu Cys Cys Gln Ala Ala

```
                180             185                 190
Asp Lys Ala Ala Cys Leu Leu Pro Lys Leu Asp Glu Leu Arg Asp Glu
            195                 200                 205
Gly Lys Ala Ser Ser Ala Lys Gln Arg Leu Lys Cys Ala Ser Leu Gln
            210                 215                 220
Lys Phe Gly Glu Arg Ala Phe Lys Ala Trp Ala Val Ala Arg Leu Ser
225                 230                 235                 240
Gln Arg Phe Pro Lys Ala Glu Phe Ala Glu Val Ser Lys Leu Val Thr
            245                 250                 255
Asp Leu Thr Lys Val His Thr Glu Cys Cys His Gly Asp Leu Leu Glu
            260                 265                 270
Cys Ala Asp Asp Arg Ala Asp Leu Ala Lys Tyr Ile Cys Glu Asn Gln
            275                 280                 285
Asp Ser Ile Ser Ser Lys Leu Lys Glu Cys Cys Glu Lys Pro Leu Leu
            290                 295                 300
Glu Lys Ser His Cys Ile Ala Glu Val Glu Asn Asp Glu Met Pro Ala
305                 310                 315                 320
Asp Leu Pro Ser Leu Ala Ala Asp Phe Val Glu Ser Lys Asp Val Cys
            325                 330                 335
Lys Asn Tyr Ala Glu Ala Lys Asp Val Phe Leu Gly Met Phe Leu Tyr
            340                 345                 350
Glu Tyr Ala Arg Arg His Pro Asp Tyr Ser Val Val Leu Leu Leu Arg
            355                 360                 365
Leu Ala Lys Thr Tyr Glu Thr Thr Leu Glu Lys Cys Cys Ala Ala Ala
            370                 375                 380
Asp Pro His Glu Cys Tyr Ala Lys Val Phe Asp Glu Phe Lys Pro Leu
385                 390                 395                 400
Val Glu Glu Pro Gln Asn Leu Ile Lys Gln Asn Cys Glu Leu Phe Glu
            405                 410                 415
Gln Leu Gly Glu Tyr Lys Phe Gln Asn Ala Leu Leu Val Arg Tyr Thr
            420                 425                 430
Lys Lys Val Pro Gln Val Ser Thr Pro Thr Leu Val Glu Val Ser Arg
            435                 440                 445
Asn Leu Gly Lys Val Gly Ser Lys Cys Cys Lys His Pro Glu Ala Lys
            450                 455                 460
Arg Met Pro Cys Ala Glu Asp Tyr Leu Ser Val Val Leu Asn Gln Leu
465                 470                 475                 480
Cys Val Leu His Glu Lys Thr Pro Val Ser Asp Arg Val Thr Lys Cys
            485                 490                 495
Cys Thr Glu Ser Leu Val Asn Arg Arg Pro Cys Phe Ser Ala Leu Glu
            500                 505                 510
Val Asp Glu Thr Tyr Val Pro Lys Glu Phe Asn Ala Glu Thr Phe Thr
            515                 520                 525
Phe His Ala Asp Ile Cys Thr Leu Ser Glu Lys Glu Arg Gln Ile Lys
            530                 535                 540
Lys Gln Thr Ala Leu Val Glu Leu Val Lys His Lys Pro Lys Ala Thr
545                 550                 555                 560
Lys Glu Gln Leu Lys Ala Val Met Asp Asp Phe Ala Ala Phe Val Glu
            565                 570                 575
Lys Cys Cys Lys Ala Asp Asp Lys Glu Thr Cys Phe Ala Glu Glu Gly
            580                 585                 590
Lys Lys Leu Val Ala Ala Ser Gln Ala Ala Leu Gly Leu Gly Gly Ser
            595                 600                 605
```

```
Ser Gly Gly Lys Val Thr Tyr Thr Ser Gln Glu Asp Leu Val Glu Lys
610                 615                 620

Lys Cys Leu Ala Lys Lys Tyr Thr His Leu Ser Cys Asp Lys Val Phe
625                 630                 635                 640

Cys Gln Pro Trp Gln Arg Cys Ile Glu Gly Thr Cys Val Cys Lys Leu
                645                 650                 655

Pro Tyr Gln Cys Pro Lys Asn Gly Thr Ala Val Cys Ala Thr Asn Arg
        660                 665                 670

Arg Ser Phe Pro Thr Tyr Cys Gln Gln Lys Ser Leu Glu Cys Leu His
    675                 680                 685

Pro Gly Thr Lys Phe Leu Asn Asn Gly Thr Cys Thr Ala Glu Gly Lys
690                 695                 700

Phe Ser Val Ser Leu Lys His Gly Asn Thr Asp Ser Glu Gly Ile Val
705                 710                 715                 720

Glu Val Lys Leu Val Asp Gln Asp Lys Thr Met Phe Ile Cys Lys Ser
                725                 730                 735

Ser Trp Ser Met Arg Glu Ala Asn Val Ala Cys Leu Asp Leu Gly Phe
                740                 745                 750

Gln Gln Gly Ala Asp Thr Gln Arg Arg Phe Lys Leu Ser Asp Leu Ser
            755                 760                 765

Ile Asn Ser Thr Glu Cys Leu His Val His Cys Arg Gly Leu Glu Thr
770                 775                 780

Ser Leu Ala Glu Cys Thr Phe Thr Lys Arg Arg Thr Met Gly Tyr Gln
785                 790                 795                 800

Asp Phe Ala Asp Val Val Cys Tyr Thr Gln Lys Ala Asp Ser Pro Met
                805                 810                 815

Asp Asp Phe Phe Gln Cys Val Asn Gly Lys Tyr Ile Ser Gln Met Lys
                820                 825                 830

Ala Cys Asp Gly Ile Asn Asp Cys Gly Asp Gln Ser Asp Glu Leu Cys
            835                 840                 845

Cys Lys Ala Cys Gln Gly Lys Gly Phe His Cys Lys Ser Gly Val Cys
850                 855                 860

Ile Pro Ser Gln Tyr Gln Cys Asn Gly Glu Val Asp Cys Ile Thr Gly
865                 870                 875                 880

Glu Asp Glu Val Gly Cys Ala Gly Phe Ala Ser Val Thr Gln Glu Glu
                885                 890                 895

Thr Glu Ile Leu Thr Ala Asp Met Asp Ala Glu Arg Arg Arg Ile Lys
                900                 905                 910

Ser Leu Leu Pro Lys Leu Ser Cys Gly Val Lys Asn Arg Met His Ile
            915                 920                 925

Arg Arg Lys Arg Ile Val Gly Gly Lys Arg Ala Gln Leu Gly Asp Leu
930                 935                 940

Pro Trp Gln Val Ala Ile Lys Asp Ala Ser Gly Ile Thr Cys Gly Gly
945                 950                 955                 960

Ile Tyr Ile Gly Gly Cys Trp Ile Leu Thr Ala Ala His Cys Leu Arg
                965                 970                 975

Ala Ser Lys Thr His Arg Tyr Gln Ile Trp Thr Thr Val Val Asp Trp
            980                 985                 990

Ile His Pro Asp Leu Lys Arg Ile Val Ile Glu Tyr Val Asp Arg Ile
    995                 1000                1005

Ile Phe His Glu Asn Tyr Asn Ala Gly Thr Tyr Gln Asn Asp Ile
    1010                1015                1020
```

| | | | | | | | | | | | |
|---|---|---|---|---|---|---|---|---|---|---|---|
| Ala | Leu | Ile | Glu | Met | Lys | Lys | Asp | Gly | Asn | Lys | Lys | Asp | Cys | Glu |
| 1025 | | | | | 1030 | | | | | 1035 | | | | |

Ala Leu Ile Glu Met Lys Lys Asp Gly Asn Lys Lys Asp Cys Glu
            1025                1030                1035

Leu Pro Arg Ser Ile Pro Ala Cys Val Pro Trp Ser Pro Tyr Leu
            1040                1045                1050

Phe Gln Pro Asn Asp Thr Cys Ile Val Ser Gly Trp Gly Arg Glu
            1055                1060                1065

Lys Asp Asn Glu Arg Val Phe Ser Leu Gln Trp Gly Glu Val Lys
            1070                1075                1080

Leu Ile Ser Asn Cys Ser Lys Phe Tyr Gly Asn Arg Phe Tyr Glu
            1085                1090                1095

Lys Glu Met Glu Cys Ala Gly Thr Tyr Asp Gly Ser Ile Asp Ala
            1100                1105                1110

Cys Lys Gly Asp Ser Gly Gly Pro Leu Val Cys Met Asp Ala Asn
            1115                1120                1125

Asn Val Thr Tyr Val Trp Gly Val Val Ser Trp Gly Glu Asn Cys
            1130                1135                1140

Gly Lys Pro Glu Phe Pro Gly Val Tyr Thr Lys Val Ala Asn Tyr
            1145                1150                1155

Phe Asp Trp Ile Ser Tyr His Val Gly Arg Pro Phe Ile Ser Gln
            1160                1165                1170

Tyr Asn Val Gly Gly Ser Gly Gly His Cys Gln Ala Pro
            1175                1180                1185

Asp His Phe Leu Phe Ala Lys Leu Lys Thr Gln Thr Asn Ala Ser
            1190                1195                1200

Asp Phe Pro Ile Gly Thr Ser Leu Lys Tyr Glu Cys Arg Pro Glu
            1205                1210                1215

Tyr Tyr Gly Arg Pro Phe Ser Ile Thr Cys Leu Asp Asn Leu Val
            1220                1225                1230

Trp Ser Ser Pro Lys Asp Val Cys Lys Arg Lys Ser Cys Lys Thr
            1235                1240                1245

Pro Pro Asp Pro Val Asn Gly Met Val His Val Ile Thr Asp Ile
            1250                1255                1260

Gln Val Gly Ser Arg Ile Asn Tyr Ser Cys Thr Thr Gly His Arg
            1265                1270                1275

Leu Ile Gly His Ser Ser Ala Glu Cys Ile Leu Ser Gly Asn Ala
            1280                1285                1290

Ala His Trp Ser Thr Lys Pro Pro Ile Cys Gln Arg Ile Pro Cys
            1295                1300                1305

Gly Leu Pro Pro Thr Ile Ala Asn Gly Asp Phe Ile Ser Thr Asn
            1310                1315                1320

Arg Glu Asn Phe His Tyr Gly Ser Val Val Thr Tyr Arg Cys Asn
            1325                1330                1335

Pro Gly Ser Gly Gly Arg Lys Val Phe Glu Leu Val Gly Glu Pro
            1340                1345                1350

Ser Ile Tyr Cys Thr Ser Asn Asp Asp Gln Val Gly Ile Trp Ser
            1355                1360                1365

Gly Pro Ala Pro Gln Cys Ile Ile
            1370                1375

<210> SEQ ID NO 23
<211> LENGTH: 603
<212> TYPE: PRT
<213> ORGANISM: Homo Sapiens

<400> SEQUENCE: 23

```
Met Lys Leu Ala His Leu Ser Leu Phe Leu Ala Leu His Leu Ser
1               5                   10                  15

Ser Ser Arg Ser Pro Ser Ala Ser Asp Leu Pro Gln Glu Glu Leu Val
            20                  25                  30

Asp Gln Lys Cys Leu Leu Gln Lys Tyr Thr His Arg Ser Cys Asn Lys
            35                  40                  45

Val Phe Cys Gln Pro Trp Gln Arg Cys Ile Glu Gly Thr Cys Ile Cys
    50                  55                  60

Lys Leu Pro Tyr Gln Cys Pro Arg Ala Gly Thr Pro Val Cys Ala Met
65                  70                  75                  80

Asn Gly Arg Ser Tyr Pro Thr Tyr Cys His Gln Lys Ser Phe Glu Cys
                85                  90                  95

Leu His Pro Glu Ile Lys Phe Ser His Asn Gly Thr Cys Ala Ala Glu
                100                 105                 110

Gly Lys Phe Asn Val Ser Leu Ile Tyr Gly Arg Thr Lys Thr Glu Gly
        115                 120                 125

Leu Val Gln Val Lys Leu Val Asp Gln Asp Glu Arg Met Phe Ile Cys
        130                 135                 140

Lys Asn Ser Trp Ser Met Ala Glu Ala Asn Val Ala Cys Val Asp Leu
145                 150                 155                 160

Gly Phe Pro Leu Gly Val Arg Asp Ile Gln Gly Ser Phe Asn Ile Ser
                165                 170                 175

Gly Asn Leu His Ile Asn Asp Thr Glu Cys Leu His Val His Cys Arg
                180                 185                 190

Gly Val Glu Thr Ser Leu Ala Glu Cys Ala Phe Thr Lys Arg Arg Thr
        195                 200                 205

Glu Leu Ser Asn Gly Leu Ala Gly Val Val Cys Tyr Lys Gln Asp Ala
        210                 215                 220

Asp Phe Pro Thr Ser Leu Ser Phe Gln Cys Val Asn Gly Lys His Ile
225                 230                 235                 240

Pro Gln Glu Lys Ala Cys Asn Gly Val Asn Asp Cys Gly Asp Gln Ser
                245                 250                 255

Asp Glu Leu Cys Cys Lys Gly Cys Arg Gly Asn Ala Ser Leu Cys Lys
                260                 265                 270

Ser Gly Val Cys Ile Pro Asp Gln Tyr Lys Cys Asn Gly Glu Val Asp
        275                 280                 285

Cys Ile Thr Gly Glu Asp Glu Ser Arg Cys Glu Glu Asp Arg Gln Gln
        290                 295                 300

Asn Ile Pro Lys Gly Leu Ala Arg Ser Ala Gln Gly Glu Ala Glu Ile
305                 310                 315                 320

Glu Thr Glu Glu Thr Glu Met Leu Thr Pro Gly Met Asp Asn Glu Arg
                325                 330                 335

Lys Arg Ile Lys Ser Leu Leu Pro Lys Leu Ser Cys Gly Val Lys Arg
                340                 345                 350

Asn Thr His Thr Arg Arg Lys Arg Val Ile Gly Gly Lys Pro Ala Asn
        355                 360                 365

Val Gly Asp Tyr Pro Trp Gln Val Ala Ile Lys Asp Gly Gln Arg Ile
        370                 375                 380

Thr Cys Gly Gly Ile Tyr Ile Gly Gly Cys Trp Ile Leu Thr Ala Ala
385                 390                 395                 400

His Cys Val Arg Pro Ser Arg Ala His Ser Tyr Gln Val Trp Thr Ala
                405                 410                 415
```

```
Leu Leu Asp Trp Leu Lys Pro Asn Ser Gln Leu Gly Ile Gln Thr Val
            420                 425                 430

Lys Arg Val Ile Val His Glu Lys Tyr Asn Gly Ala Thr Phe Gln Asn
        435                 440                 445

Asp Ile Ala Leu Ile Glu Met Lys Met His Thr Gly Lys Lys Glu Cys
450                 455                 460

Glu Leu Pro Asn Ser Val Pro Ala Cys Val Pro Trp Ser Pro Tyr Leu
465                 470                 475                 480

Phe Gln Pro Asn Asp Arg Cys Ile Ile Ser Gly Trp Gly Arg Gly Lys
                485                 490                 495

Asp Asn Gln Lys Val Tyr Ser Leu Arg Trp Gly Glu Val Asp Leu Ile
            500                 505                 510

Gly Asn Cys Ser Gln Phe Tyr Pro Asp Arg Tyr Tyr Glu Lys Glu Met
        515                 520                 525

Gln Cys Ala Gly Thr Arg Asp Gly Ser Ile Asp Ala Cys Lys Gly Asp
530                 535                 540

Ser Gly Gly Pro Leu Val Cys Glu Asp Ile Asn Asn Val Thr Tyr Val
545                 550                 555                 560

Trp Gly Ile Val Ser Trp Gly Glu Asn Cys Gly Lys Pro Glu Phe Pro
                565                 570                 575

Gly Val Tyr Thr Arg Val Ala Asn Tyr Phe Asp Trp Ile Ser Tyr His
            580                 585                 590

Val Gly Arg Ser Leu Val Ser Gln His Asn Val
        595                 600

<210> SEQ ID NO 24
<211> LENGTH: 20
<212> TYPE: PRT
<213> ORGANISM: Homo Sapiens

<400> SEQUENCE: 24

Glu Asp Val Pro Ala Ala Asp Leu Ser Asp Gln Val Pro Asp Thr Asp
1               5                   10                  15

Ser Glu Thr Arg
            20

<210> SEQ ID NO 25
<211> LENGTH: 12
<212> TYPE: PRT
<213> ORGANISM: Artificial Sequence
<220> FEATURE:
<223> OTHER INFORMATION: Linker Sequence

<400> SEQUENCE: 25

Gly Gly Gly Gly Gly Gly Gly Gly Gly Gly Gly Gly
1               5                   10

<210> SEQ ID NO 26
<211> LENGTH: 10
<212> TYPE: PRT
<213> ORGANISM: Artificial Sequence
<220> FEATURE:
<223> OTHER INFORMATION: Linker Sequence

<400> SEQUENCE: 26

Gly Gly Ser Ser Gly Gly Ser Ser Gly Gly
1               5                   10

<210> SEQ ID NO 27
<211> LENGTH: 9
```

```
<212> TYPE: PRT
<213> ORGANISM: Homo Sapiens

<400> SEQUENCE: 27

Arg Pro Phe Ile Ser Gln Tyr Asn Val
1               5

<210> SEQ ID NO 28
<211> LENGTH: 10
<212> TYPE: PRT
<213> ORGANISM: Homo Sapiens

<400> SEQUENCE: 28

Ser Glu Glu Thr Lys Gln Asn Glu Gly Phe
1               5                   10
```